United States Patent
Kawaguchi et al.

(10) Patent No.: US 10,975,091 B2
(45) Date of Patent: Apr. 13, 2021

(54) PYRIDINE DERIVATIVE

(71) Applicants: Astellas Pharma Inc., Tokyo (JP); KOTOBUKI PHARMACEUTICAL CO., LTD., Hanishina-gun (JP)

(72) Inventors: Kenichi Kawaguchi, Tokyo (JP); Akihiro Ishihata, Tokyo (JP); Yusuke Inagaki, Tokyo (JP); Kazuyuki Tsuchiya, Tokyo (JP); Tadaatsu Hanadate, Tokyo (JP); Akira Kanai, Tokyo (JP); Hiroyuki Kaizawa, Tokyo (JP); Junichi Kazami, Saitama (JP); Hiroshi Morikawa, Tokyo (JP); Masashi Hiramoto, Tokyo (JP); Kentaro Enjo, Ibaraki (JP); Hajime Takamatsu, Tokyo (JP)

(73) Assignees: Astellas Pharma Inc., Tokyo (JP); KOTOBUKI PHARMACEUTICAL CO., LTD., Hanishina-gun (JP)

( * ) Notice: Subject to any disclaimer, the term of this patent is extended or adjusted under 35 U.S.C. 154(b) by 0 days.

(21) Appl. No.: 16/544,245

(22) Filed: Aug. 19, 2019

(65) Prior Publication Data
US 2020/0055868 A1 Feb. 20, 2020

Related U.S. Application Data

(60) Continuation of application No. 16/041,117, filed on Jul. 20, 2018, now Pat. No. 10,421,762, which is a
(Continued)

(30) Foreign Application Priority Data

May 28, 2014 (JP) ................................. 2014-110432

(51) Int. Cl.
| | | |
|---|---|---|
| A61K 31/44 | (2006.01) |
| C07D 213/70 | (2006.01) |
| C07D 495/04 | (2006.01) |
| C07D 491/08 | (2006.01) |
| A61K 31/436 | (2006.01) |
| A61K 31/4355 | (2006.01) |
| A61K 31/437 | (2006.01) |
| A61K 31/439 | (2006.01) |
| A61K 31/443 | (2006.01) |
| A61K 31/4433 | (2006.01) |
| A61K 31/4436 | (2006.01) |
| A61K 31/4439 | (2006.01) |
| A61K 31/444 | (2006.01) |
| A61K 31/4545 | (2006.01) |
| A61K 31/4725 | (2006.01) |
| A61K 31/497 | (2006.01) |

(Continued)

(52) U.S. Cl.
CPC .......... *C07D 495/04* (2013.01); *A61K 31/436* (2013.01); *A61K 31/437* (2013.01); *A61K 31/439* (2013.01); *A61K 31/4355* (2013.01); *A61K 31/44* (2013.01); *A61K 31/443* (2013.01); *A61K 31/444* (2013.01); *A61K 31/4433* (2013.01); *A61K 31/4436* (2013.01); *A61K 31/4439* (2013.01); *A61K 31/4545* (2013.01); *A61K 31/4725* (2013.01); *A61K 31/497* (2013.01); *A61K 31/506* (2013.01); *A61K 31/5377* (2013.01); *C07D 213/68* (2013.01); *C07D 213/70* (2013.01); *C07D 213/74* (2013.01); *C07D 401/04* (2013.01); *C07D 401/06* (2013.01); *C07D 401/10* (2013.01); *C07D 401/12* (2013.01); *C07D 405/06* (2013.01); *C07D 405/12* (2013.01); *C07D 407/06* (2013.01); *C07D 407/12* (2013.01); *C07D 409/12* (2013.01); *C07D 471/04* (2013.01); *C07D 491/048* (2013.01); *C07D 491/056* (2013.01); *C07D 491/08* (2013.01)

(58) Field of Classification Search
CPC .............................. A61K 31/44; C07D 213/70
See application file for complete search history.

(56) References Cited

U.S. PATENT DOCUMENTS

2011/0212973 A1* 9/2011 Ishii ........................ A61P 13/00
514/253.1

OTHER PUBLICATIONS

Bundgaard, Design of Prodrugs, Chapter 1, p. 1, 1985.
(Continued)

*Primary Examiner* — Patricia L Morris
(74) *Attorney, Agent, or Firm* — Oblon, McClelland, Maier & Neustadt, L.L.P.

(57) ABSTRACT

The problem to be solved by the present invention is to provide a compound suitable for a pharmaceutical composition, specifically a pharmaceutically composition for treating nocturia.
The inventors have assumed that inhibition of nocturnal activity of placental leucine aminopeptidase (P-LAP), i.e. aminopeptidase that cleaves AVP, would maintain and/or increase an endogenous AVP level to enhance the antidiuretic effect, which would contribute to a decreased number of nocturnal voids, and have extensively studied compounds which inhibit P-LAP.
As a result, the inventors have found that (2R)-3-amino-2-{[4-(substituted pyridine)-2-yl]methyl}-2-hydroxy-propanoic acid derivatives have excellent P-LAP inhibitory activity. The inventors have evaluated antidiuretic effects in water-loaded rats and have found that the compounds increase endogenous AVP levels by inhibiting P-LAP and consequently reduce urine production. The present invention therefore provides compounds expected to be used as an agent for treating nocturia based on P-LAP inhibition.

1 Claim, 1 Drawing Sheet

Related U.S. Application Data division of application No. 15/313,712, filed as application No. PCT/JP2015/065344 on May 28, 2015, now Pat. No. 10,059,720.

(51) Int. Cl.

| | | |
|---|---|---|
| *A61K 31/506* | (2006.01) | |
| *A61K 31/5377* | (2006.01) | |
| *C07D 213/74* | (2006.01) | |
| *C07D 401/04* | (2006.01) | |
| *C07D 401/06* | (2006.01) | |
| *C07D 401/12* | (2006.01) | |
| *C07D 407/06* | (2006.01) | |
| *C07D 407/12* | (2006.01) | |
| *C07D 409/12* | (2006.01) | |
| *C07D 471/04* | (2006.01) | |
| *C07D 491/048* | (2006.01) | |
| *C07D 491/056* | (2006.01) | |
| *C07D 213/68* | (2006.01) | |
| *C07D 401/10* | (2006.01) | |
| *C07D 405/06* | (2006.01) | |
| *C07D 405/12* | (2006.01) | |

(56) References Cited

OTHER PUBLICATIONS

Silverman, Prodrugs and Drug Delivery Systems, The Organic chemistry of Drug Design and Drug action, Chapter 8, pp. 352-400,1992.
Banker et al., Prodrugs, Modern Pharmaceutics, 3 rd edition, Revised and Expanded, pp. 451 and 596, 1986.
Jordan, "Tamoxifen . . . " Nature Rev. v.2, p. 205-213 (2003).
Ettmayer et al., "Lessons Learned from Marketed and Investigational Prodrugs", J. Med. Chem., (2004), 47(10): 2393-2404.
Stella, Valentino, "Prodrugs as therapeutics", Expert Opin. Ther. Patents (2004), 14(3): 277-280.
Testa, "Prodrug researchL futile or fertile?" Biochemical Pharmacology, 868 (2004): 2097-2106.
Balant ed in Wolff et al., Burgers Medicinal Chemistry and Drug Discovery, 5th ed. vol. 1: Principles and Practice, pp. 949-982, 1996.

\* cited by examiner

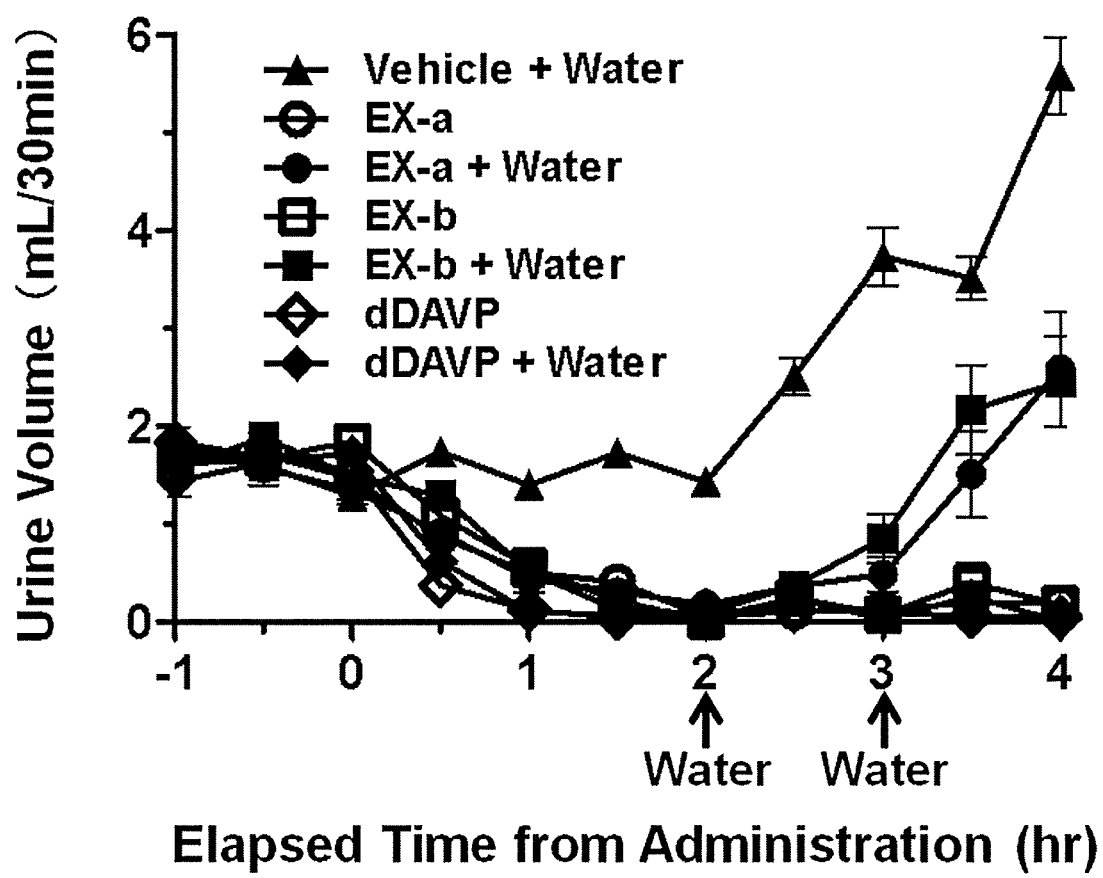

PYRIDINE DERIVATIVE

CROSS REFERENCE TO RELATED APPLICATIONS

This application is a divisional application of U.S. patent Ser. No. 16/041,117, filed on Jul. 20, 2018, which was a divisional application of U.S. patent application Ser. No. 15/313,712, filed on Nov. 23, 2016, which was a 371 of International Patent Application No. PCT/JP/2015/065344, filed on May 28, 2015 and claims priority to Japanese Patent Application No. 2014-110432, filed on May 28, 2014.

TECHNICAL FIELD

The present invention relates to a novel pyridine derivative or a salt thereof which is useful as a pharmaceutical, specifically a pharmaceutical for treating nocturia, and to a pharmaceutical containing such a compound as an active ingredient.

BACKGROUND ART

Nocturia is a lower urinary tract symptom defined as "the complaint that the individual has to wake at night one or more times to void" (Neurourol Urodyn 2002; 21: 167-178). Nocturia prevalence increases with age (J Urol 2010; 184: 440-446), and major patients with nocturia are older adults. It impairs quality of life (QOL) in that it disrupts sleep (Eur Urol 2010; 57: 488-498) and increases risk of fracture. Causes of nocturia are global polyuria, nocturnal polyuria, reduced bladder capacity, and sleep disorders, but in many patients nocturia is considered to be multifactorial (Eur Urol 2012; 62: 877-890). Nocturnal polyuria is defined as nocturnal urine volume greater than 33% of the 24-hour urine volume and is present in about 80% of the patients with nocturia (J Urol 2011; 186: 1358-1363).

Arginine-vasopressin (hereinafter, abbreviated as AVP) is an antidiuretic hormone that is biosynthesized and secreted in the hypothalamic-pituitary gland axis, and is a peptide consisting of nine amino acids. AVP receptors are classified into three subtypes: V1a, V1b, and V2. Known major pharmacological actions of AVP in the periphery are vasoconstriction through the V1a receptor, and antidiuresis through the V2 receptor. AVP acts on the renal tubules to promote renal water reabsorption, decreasing the urine volume. For this reason, decreased nocturnal AVP secretion with age is assumed to be a cause of increased nocturnal urine volume (J Int Med 1991; 229: 131-134, BJU Int 2004; 94: 571-575).

Stimulation of the V2 receptor is expected to improve nocturia. Desmopressin (hereinafter, abbreviated as dDAVP) is a selective V2 receptor agonist used for treating patients with nocturia, and is reported to decrease nocturnal urine volume and the number of nocturnal voids, resulting in an increased duration of initial undisturbed sleep (J Urol 2013; 190: 958-964, and J Urol 2013; 190: 965-972). Unfortunately, V2 receptor agonists theoretically induce fluid retention and increase risks of hyponatremia. It is reported that V2 receptor agonists should be administered with caution and monitoring of serum sodium level to older adults who are the majority of patients with nocturia (Neurourol urodyn 2004; 23: 302-305).

Placental leucine aminopeptidase (hereinafter, abbreviated as P-LAP) is an enzyme that degrades L-leucine-β-naphthylamide, oxytocin, and AVP (Arch Biochem Biophys 1992; 292: 388-392), and was cloned as an aminopeptidase by Rogi et al. in year 1996 (J Biol Chem 1996; 271: 56-61). The insulin-regulated aminopeptidase (hereinafter, abbreviated as IRAP) cloned by Keller et al. from rat epididymal fat pads has homology of 87% to human P-LAP. The IRAP is subsequently suggested to be an aminopeptidase that cleaves AVP and reported to be a rat homolog of human P-LAP (J Biol Chem 1995; 270: 23612-23618, Am J Physiol Endocrinol Metab 2007; 293: E1092-E1102). Angiotensin IV ($AT_4$) receptor isolated from bovine adrenal is also suggested to be an IRAP as a result of biochemical and pharmacological studies (J Biol Chem 2001; 276: 48623-48626).

Experiments using P-LAP knockout mice indicate that administration of AVP in wild type mice and P-LAP knockout mice results in much reduction of 24-h urine volume in P-LAP knockout mice, although no significant difference is observed in the 24-h urine volume between the wild type and P-LAP knockout mice. It suggests the possible involvement of P-LAP in regulation of the urine volume through degradation of AVP (NPL 1).

Compounds represented by Formula (A) below are reported to be IRAP inhibitors useful as a therapeutic agent for dementia and diabetes, and the like (PTLs 1 and 2).

[Formula 1]

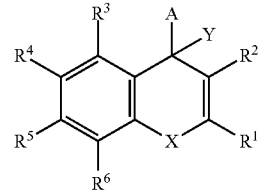

(A)

wherein X is O, NR' or S, and other symbols are defined as in PTLs 1 and 2.

Tripeptide analogs of $AT_4$ with 13- to 14-membered ring structure exhibits excellent IRAP inhibitory activity (NPL 2).

However, no antidiuretic agent or therapeutic agents for nocturia based on a mechanism mediated by P-LAP (or IRAP) has been reported.

Under such circumstances, there exists need for a safe antidiuretic agent that is suitable for treating nocturia.

CITATION LIST

Patent Literature

[PTL 1] WO 2006/026832
[PTL 2] WO 2009/065169

Non Patent Literature

[NPL 1] Life Sciences 84 (2009) 668-672
[NPL 2] J Med Chem 2011; 54; 3779-3792

SUMMARY OF INVENTION

Technical Problem

The present invention provides a compound useful as an active ingredient of a pharmaceutical composition, specifically a pharmaceutical composition for treating nocturia.

Solution to Problem

The inventors have assumed that inhibition of nocturnal activity of P-LAP, i.e. aminopeptidase that cleaves AVP, would maintain and/or increase an endogenous AVP level to enhance the antidiuretic effect, which would contribute to a decreased number of nocturnal voids, and have extensively studied compounds which inhibit P-LAP (including rat IRAP, a homolog of human P-LAP).

As a result, the inventors have found that a compound represented by Formula (I) below has excellent P-LAP inhibitory activity. The inventors have evaluated antidiuretic effects in water-loaded rats and have found that the compound represented by Formula (I) increases endogenous AVP levels by inhibiting P-LAP and consequently reduces urine production. Based on such findings, the inventors have accomplished the present invention.

The present invention relates to a compound represented by Formula (I) or a salt thereof, and a pharmaceutical composition comprising the compound represented by Formula (I) or a salt thereof and an excipient:

[Formula 2]

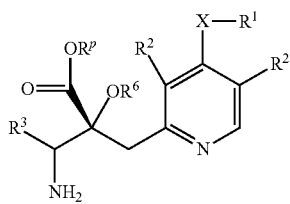

(I)

wherein, X is O, S or NR$^4$;

R$^4$ is H, lower alkyl which optionally has one to five substituents selected from the Group G$^1$, C$_{3-12}$ cycloalkyl which optionally has one to five substituents selected from the Group G$^2$, -(lower alkylene)-(C$_{3-12}$ cycloalkyl) which optionally has one to five substituents selected from the Group G$^2$, —C(O)-(lower alkyl which optionally has one to five substituents selected from the Group G$^1$), —C(O)—(C$_{3-12}$ cycloalkyl which optionally has one to five substituents selected from the Group G$^2$), or —C(O)-(lower alkylene)-(C$_{3-12}$ cycloalkyl which optionally has one to five substituents selected from the Group G$^2$), or R$^4$ forms together with neighboring —NR$^1$, as —NR$^1$R$^4$, a 4- to 8-membered nitrogen-containing saturated heterocyclic group, wherein the nitrogen-containing saturated heterocyclic group may be condensed with a benzene ring and optionally has one to five substituents selected from the Group G$^4$;

R$^1$ is H, C$_{1-10}$ alkyl which optionally has one to five substituents selected from the Group G$^1$, -(lower alkylene)-X$^{11}$-(lower alkyl which optionally has one to five substituents selected from the Group G$^1$), R$^{11}$, -(lower alkylene)-R$^{11}$, -(lower alkylene)-X$^{11}$—R$^{11}$, or -(lower alkylene)-X$^{11}$-(lower alkylene)-R$^{11}$;

R$^2$'s are the same or different from each other, and are H, lower alkyl which optionally has one to five substituents selected from the Group G$^1$, halogen, OH, SH, —O-(lower alkyl), —O-(lower alkylene)-aryl, —O-aryl, —S-(lower alkyl), —S-(lower alkylene)-aryl, —S-aryl, —O-(lower halogenoalkyl), —C(O)-(lower alkyl), —S(O)$_2$-(lower alkyl), —S(O)-(lower alkyl), NO$_2$, —NH$_2$, —NH-(lower alkyl), —N(lower alkyl)$_2$, —NH-aryl, —N(lower alkyl)-aryl, —C(O)OH, —C(O)O-(lower alkyl), —CHO, —C(O)NH$_2$, —C(O)NH-(lower alkyl), —C(O)N(lower alkyl)$_2$, CN, -(lower alkylene)-X$^{21}$-(lower alkyl which optionally has one to five substituents selected from the Group G$^1$), C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^5$, -(lower alkylene)-R$^{21}$, -(lower alkylene)-X$^{21}$—R$^{21}$, or -(lower alkylene)-X$^{21}$-(lower alkylene)-R$^{21}$;

R$^3$ is R$^{32}$, -(lower alkylene)-X$^{31}$—R$^{32}$, -(lower alkenylene)-X$^{31}$—R$^{32}$, R$^{31}$, -(lower alkylene)-R$^{31}$, -(lower alkylene)-X$^{31}$—R$^{31}$, -(lower alkylene)-X$^{31}$-(lower alkylene)-R$^{31}$, -(lower alkenylene)-R$^{31}$, -(lower alkynylene)-R$^{31}$, or —CH=(saturated monocyclic heterocycle);

X$^{11}$, X$^{21}$ and X$^{31}$ are the same or different from each other, and are O or S(O)$_n$, wherein n is 0, 1, or 2;

R$^{11}$, R$^{21}$, and R$^{31}$ are the same or different from each other, and are C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^5$, or mono- or bi-cyclic heterocyclic group which optionally has one to five substituents selected from the Group G$^5$;

R$^{32}$ is C$_{1-10}$ alkyl which optionally has one to five substituents selected from the Group G$^1$, lower alkenyl which optionally has one to five substituents selected from the Group G$^1$, or lower alkynyl which optionally has one to five substituents selected from the Group G$^1$;

R$^P$ is H or an ester group and R$^6$ is H; or R$^P$ and R$^6$ are linked to each other to form, together with —O—C(=O)—C—O— to which they are attached, 2,2-di(lower alkyl)-4-oxo-1,3-dioxolane-5,5-diyl;

if R$^3$ is C$_{1-10}$ alkyl which is optionally substituted by one to five halogens, —X—R$^1$ is optionally linked to any one of R$^2$'s attached to a pyridine ring to which —X—R$^1$ is also attached, to constitute a group represented by any one of foiinulae —X$^b$—(CH$_2$)$_m$—Y—, —X$^b$—CH=CH—, —X$^b$—CH=N—, and —X$^b$—N=CH—, and form a heterocycle condensed with the pyridine ring, wherein m is an integer of 1 to 3, X$^b$ is O, S or NH, Y is CH$_2$, O, S or NH, and the heterocycle optionally has one to four substituents selected from the group consisting of: C$_{3-12}$ cycloalkyl which optionally has one to five substituents selected from the Group G$^2$; -(lower alkylene)-(C$_{3-12}$ cycloalkyl which optionally has one to five substituents selected from the Group G$^2$); and the substituents defined in the Group G$^3$; in replacement of one or more H atoms attached to the ring atom(s) of the heterocycle;

—X—R$^1$ is optionally linked to R$^3$ to form a group represented by foimula —X—(C$_{5-15}$ carbon chain)-, wherein the C$_{5-15}$ carbon chain optionally has one to two O or S atoms in replacement of C atom(s), optionally has one to five unsaturated bonds, and optionally has one to five substituents selected from the Group G$^4$;

Group G$^1$ consists of halogen, OH, SH, —O-(lower alkyl), —O-(lower alkylene)-aryl, —O-aryl, —S-(lower alkyl), —S-(lower alkylene)-aryl, —S-aryl, —O-(lower halogenoalkyl), —C(O)-(lower alkyl), —C(O)-aryl, —S(O)$_2$-(lower alkyl), —S(O)-(lower alkyl), NO$_2$, —NH$_2$, —NH-(lower alkyl), —N(lower alkyl)$_2$, —NH-aryl, —N(lower alkyl)-aryl, —C(O)OH, —C(O)O-(lower alkyl), —CHO, —C(O)NH$_2$, —C(O)NH-(lower alkyl), —C(O)N (lower alkyl)$_2$, —C(O)NH-aryl, and CN;

Groups G$^2$ and G$^4$ consist of the substituents in the Group G$_1$, lower alkyl which optionally has one to five substituents selected from the Group G$^1$, —O—(C$_{2-3}$ alkylene)-O—, and —O—(C$_{3-4}$ alkylene)-;

Group G$^3$ consists of the substituents in the Group G$^1$ and lower alkyl which optionally has one to five substituents selected from the Group G$^1$; and Group G$^5$ consists of: i) the substituents in the Group G$^1$; ii) lower alkyl, lower alkenyl and lower alkynyl, each of which optionally has one to five substituents selected from the Group G$^1$; iii) -(lower alkylene)-O-(lower alkyl, lower alkenyl or lower alkynyl, which optionally has one to five substituents selected from the Group G$^1$); iv) C$_{3-12}$ cycloalkyl, and C$_{3-12}$ cycloalkenyl which may be condensed with a benzene ring optionally having one to four substituents selected from the Group G$^3$, the C$_{3-12}$ cycloalkyl and the C$_{3-12}$ cycloalkenyl optionally have one to five substituents selected from the Group G$^2$; v) aryl which optionally has one to five substituents selected from the Group G$^3$; vi) mono- or bi-cyclic heterocyclic group which optionally has one to five substituents selected from the Group G$^3$; vii) -(lower alkylene)-R$^G$; viii) -(lower alkylene)-O—R$^G$; ix) —C(O)—R$^G$; x) —C(O)—O—R$^G$; xi) —C(O)—O-(lower alkylene)-R$^G$; and xii) —S(O)$_2$—R$^G$, wherein R$^G$'s are the same or different from each other, and are C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^3$, or a mono- or bi-cyclic heterocyclic group which optionally has one to five substituents selected from the Group G$^3$.

As used herein, if a symbol used in a chemical formula is also used in other chemical formula, identical symbols have the same definition, unless otherwise specified.

The present invention also relates to a pharmaceutical composition comprising the compound represented by Formula (I) or a salt thereof. The pharmaceutical composition encompasses an agent for treating nocturia. The present invention also relates to a pharmaceutical composition comprising the compound represented by Formula (I) or a salt thereof and an excipient.

The present invention also relates to use of the compound represented by Formula (I) or a salt thereof for production of a pharmaceutical composition for treating nocturia, use of the compound represented by Formula (I) or a salt thereof for treating nocturia, the compound represented by Formula (I) or a salt thereof for treating nocturia, and a method of treating nocturia comprising administering to a subject an effective amount of the compound represented by Formula (I) or a salt thereof. As used herein, "subject" is a human or non-human animal in need of a preventive or therapeutic treatment, and in one embodiment, a human in need of the preventive or therapeutic treatment.

Advantageous Effects of Invention

The compound represented by Formula (I) or a salt thereof has inhibitory activity against P-LAP, i.e. the AVP-metabolizing enzyme, and maintains and/or increases an endogenous AVP level to reduce urine production. Such a compound thus is expected to be used as an agent for treating nocturia, and is also expected to be used as an agent for treating any other voiding dysfunction or polyuria associated with a decreased AVP level, such as pollakiuria, urinary incontinence, and nocturnal enuresis.

BRIEF DESCRIPTION OF DRAWINGS

FIG. 1 is a graph showing temporal changes in urine volumes of individual groups in the pharmacological test (4): antidiuresis test in continuously hydrated rats with additional water loading. The vertical axis represents urine volume (mL/30 min) and the horizontal axis represents elapsed time (hr) from the administration of the test compound. Groups represented by " . . . +Water" are water-loaded groups. The arrows in the horizontal axis represent the time points of additional water-loading.

DESCRIPTION OF EMBODIMENTS

Hereinafter, the present invention will be described in detail.

In the present specification, the "lower alkyl" is a straight or branched alkyl having one to ten carbon atoms (hereinafter, abbreviated as C$_{1-10}$). In one embodiment, the lower alkyl is a straight or branched C$_{1-6}$ alkyl, specifically, methyl, ethyl, n-propyl, isopropyl, n-butyl, isobutyl, sec-butyl, tert-butyl, isopentyl, isohexyl, isoheptyl, isooctyl, 3-ethylpentyl, 4-ethylhexyl, 4-ethylheptyl, n-hexyl, hexan-2-yl, 4-methylpentan-2-yl, 2,2-dimethylpropyl, 3,3-dimethylpentyl or 3,3-dimethylbutyl. The lower alkyl is, in one embodiment, a C$_{1-4}$ alkyl; in one embodiment, methyl, ethyl, n-propyl, isopropyl, n-butyl, isobutyl, sec-butyl or tert-butyl; and in one embodiment, methyl or ethyl.

The "C$_{1-10}$ alkyl" in the definition of R$^1$ and R$^3$ is a straight or branched C$_{1-10}$ alkyl in the above defined "lower alkyl". The "C$_{1-10}$ alkyl" of R$^1$ is, in one embodiment, methyl, n-hexyl, hexan-2-yl, 4-methylpentan-2-yl, 3,3-dimethylpentyl or 3,3-dimethylbutyl. The "C$_{1-10}$ alkyl" of R$^3$ is, in one embodiment, a branched C$_{1-10}$ alkyl; in one embodiment, isobutyl, isopentyl, isohexyl, 2,2-dimethylpropyl or 3-ethylpentyl; and in one embodiment, isobutyl.

The "lower alkenyl" is a straight or branched C$_{2-8}$ alkenyl; specifically, vinyl, propenyl, butenyl, pentenyl, 1-methylvinyl, 1-methyl-2-propenyl, 2-methyl-1-propenyl, 1,3-butadienyl, 3-methyl-1,3-butadienyl or 1,3-pentadienyl; in one embodiment, a C$_{2-6}$ alkenyl; in one embodiment, 2-methyl-1-propenyl or 3-methyl-1,3-butadienyl; and in one embodiment, 2-methyl-1-propenyl.

The "lower alkynyl" is a straight or branched C$_{2-6}$ alkynyl; specifically, ethynyl, propynyl, butynyl, pentynyl, 1-methyl-2-propynyl, 1,3-butadiynyl or 1,3-pentadiynyl; in one embodiment, a C$_{2-4}$ alkynyl; in one embodiment, ethynyl, 2-propynyl or 3-butynyl; and in one embodiment, 3-butynyl.

The "lower alkylene" is a straight or branched C$_{1-10}$ alkylene; specifically, methylene, ethylene, trimethylene, tetramethylene, pentamethylene, hexamethylene, heptamethylene, octamethylene, propylene, methylmethylene, ethylethylene, 1,2-dimethylethylene or 1,1,2,2-tetramethylethylene; in one embodiment, a C$_{1-6}$ alkylene; in one embodiment, a C$_{1-4}$ alkylene; in one embodiment, methylene, ethylene, trimethylene, propylene or methylmethylene; and in one embodiment, methylene or ethylene.

The "lower alkenylene" is a straight or branched C$_{2-6}$ alkenylene; specifically, vinylene, ethylidene, propenylene, butenylene, pentenylene, hexenylene, 1,3-butadienylene or 1,3-pentadienylene; in one embodiment, a $C_{2-4}$ alkenylene; in one embodiment, vinylene or ethylidene; and in one embodiment, vinylene.

The "lower alkynylene" is a straight or branched $C_{2-6}$ alkynylene; specifically, ethynylene, propynylene, butynylene, pentynylene, hexynylene, 1,3-butadiynylene or 1,3-pentadiynylene; in one embodiment, a $C_{2-4}$ alkynylene; and in one embodiment, ethynylene or propynylene.

The "halogen" is F, Cl, Br or I.

The "lower halogenoalkyl" is a straight or branched $C_{1-10}$ alkyl substituted by one or more halogens. The lower halogenoalkyl is, in one embodiment, a $C_{1-6}$ alkyl substituted by one to five halogens; in one embodiment, trifluoromethyl, trifluoroethyl, trifluoropropyl, 2-fluoro-2-methylpropyl, difluoromethyl, fluoromethyl or chloromethyl; and in one embodiment, trifluoromethyl.

The "$C_{3-12}$ cycloalkyl" is a $C_{3-12}$ saturated hydrocarbon ring group which is optionally cross-linked and optionally forms a spiro ring. The $C_{3-12}$ cycloalkyl is, specifically, cyclopropyl, cyclobutyl, cyclopentyl, cyclohexyl, cycloheptyl, cyclooctyl, bicyclo[2,2,1]heptyl, bicyclo[3,1,0]hexyl, bicyclo[3,1,1]heptyl, adamantyl, spiro[2,5]octyl, spiro[3,5]nonyl or spiro[4,5]decyl; in one embodiment, cyclohexyl, cycloheptyl, cyclooctyl, bicyclo[2,2,1]heptyl, bicyclo[3,1,0]hexyl, bicyclo[3,1,1]heptyl, adamantyl, spiro[2,5]octyl, spiro[3,5]nonyl or spiro[4,5]decyl; and in one embodiment, cyclopropyl, cyclobutyl, cyclopentyl or cyclohexyl. The "$C_{3-10}$ cycloalkyl" and the "$C_{3-8}$ cycloalkyl" is $C_{3-10}$ and $C_{3-8}$ saturated hydrocarbon ring groups, respectively, included in the above defined "$C_{3-12}$ cycloalkyl".

The "$C_{3-12}$ cycloalkenyl" is a $C_{3-12}$ hydrocarbon ring group having one or more unsaturated bonds, which is optionally cross-linked, and optionally forms a spiro-ring. The $C_{3-12}$ cycloalkenyl is, specifically, cyclopentenyl, cyclopentadienyl, cyclohexenyl or cyclohexadienyl. The "$C_{5-10}$ cycloalkenyl" is included in the above defined "$C_{3-12}$ cycloalkenyl". In the "$C_{3-12}$ cycloalkenyl which may be condensed with a benzene ring optionally having one to four substituents selected from the Group $G^3$", the "$C_{3-12}$ cycloalkenyl condensed with a benzene ring" is a $C_{3-12}$ cycloalkenyl having a benzene ring condensed therewith on the position of an unsaturated bond of the $C_{3-12}$ cycloalkenyl. The "$C_{3-12}$ cycloalkenyl condensed with a benzene ring" is, specifically, 1-tetrahydronaphthyl, 2-tetrahydronaphthyl, dihydroinden-1-yl, dihydroinden-2-yl, 1-indenyl, 2-indenyl or 9-fluorenyl. The "$C_{5-6}$ cycloalkenyl condensed with a benzene ring" is included in the above defined "$C_{3-12}$ cycloalkenyl condensed with a benzene ring"; in one embodiment, 1-tetrahydronaphthyl, 2-tetrahydronaphthyl, dihydroinden-1-yl or dihydroinden-2-yl; and in one embodiment, dihydroinden-2-yl.

The "aryl" is a $C_{6-14}$ mono-, bi- or tri-cyclic aromatic hydrocarbon ring group; specifically, phenyl or naphthyl; and in one embodiment, phenyl.

The "mono- or bi-cyclic heterocyclic group" is a 3- to 15-membered, in one embodiment 5- to 10-membered, mono- or bi-cyclic heterocyclic group having 1 to 4 heteroatoms selected from oxygen, sulfur and nitrogen, saturated, aromatic or partially hydrogenated heterocyclic group. A sulfur or nitrogen ring atom of the heterocyclic group is optionally oxidized to form an oxide or dioxide. The mono- or bi-cyclic heterocyclic group is, specifically, monocyclic heteroaryl such as pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl and the like; bicyclic heteroaryl such as indolyl, isoindolyl, benzimidazolyl, indazolyl, quinolyl, isoquinolyl, quinazolinyl, quinoxalinyl, phthalazinyl, benzothiazolyl, benzisothiazolyl, benzothiadiazolyl, benzoxazolyl, benzisoxazolyl, benzofuranyl, benzothienyl and the like; saturated or partially hydrogenated monocyclic heterocyclic group, such as azetidinyl, pyrrolidinyl, piperidyl, piperazinyl, azepanyl, diazepanyl, morpholinyl, thiomorpholinyl, tetrahydropyridinyl, dihydropyridinyl, oxetanyl, tetrahydrofuranyl, dihydrofuranyl, tetrahydrothienyl, dihydrothienyl, tetrahydropyranyl, dihydropyranyl, dioxolanyl, dioxanyl, tetrahydrothiopyranyl, dihydrothiopyranyl and the like; saturated or partially hydrogenated bicyclic heterocyclic group, such as indolinyl, isoindolinyl, tetrahydroquinolyl, tetrahydroisoquinolyl, dihydrobenzimidazolyl, tetrahydrobenzimidazolyl, tetrahydroquinoxalinyl, dihydroquinoxalinyl, dihydrobenzoxazolyl, dihydrobenzoxadinyl, dihydrobenzofuryl, chromanyl, chromenyl, methylenedioxyphenyl, ethylenedioxyphenyl and the like; or cross-linked heterocyclic group such as quinuclidinyl and the like. The mono- or bi-cyclic heterocyclic group is, in one embodiment, a 5- to 10-membered monocyclic heterocyclic group; in one embodiment, a 5- to 6-membered monocyclic heterocyclic group; in one embodiment, a 5- to 6-membered monocyclic heteroaryl; and in one embodiment, a 5- to 6-membered saturated or partially hydrogenated monocyclic heterocyclic group. The "mono- or bi-cyclic heterocyclic group" of $R^1$ is, in one embodiment, piperidyl, tetrahydropyranyl, thienyl, thiazolyl or pyrazolyl; and in one embodiment, piperidyl, tetrahydropyranyl, thienyl or pyrazolyl. The "mono- or bi-cyclic heterocyclic group" of $R^3$ is, in one embodiment, piperidyl, morpholinyl, tetrahydropyranyl, dihydropyranyl, pyridyl, pyrazinyl, pyrimidinyl or pyrazolyl; and in one embodiment, pyridyl, pyrazinyl, pyrimidinyl or pyrazolyl.

The "saturated monocyclic heterocyclic group" is a saturated and monocyclic heterocyclic group in the "mono- or bi-cyclic heterocyclic group" defined above; specifically, azetidinyl, pyrrolidinyl, piperidyl, piperazinyl, azepanyl, diazepanyl, morpholinyl, thiomorpholinyl, tetrahydrofuranyl, tetrahydrothienyl, tetrahydropyranyl, dioxolanyl, dioxanyl or tetrahydrothiopyranyl; and in one embodiment, tetrahydropyranyl. The "—CH=(saturated monocyclic heterocycle)" is a group in which CH is bonded to one ring carbon atom of the saturated monocyclic heterocycle by a double bond.

In the "$R^4$ forms together with neighboring —$NR^1$, as —$NR^1R^4$, a 4- to 8-membered nitrogen-containing saturated heterocyclic group, wherein the nitrogen-containing saturated heterocyclic group may be condensed with a benzene ring and optionally has one to five substituents selected from the Group $G^4$", the "4- to 8-membered nitrogen-containing saturated heterocyclic group" is a 4- to 8-membered monocyclic nitrogen-containing saturated heterocyclic group or such a heterocyclic group condensed with a benzene ring, in the "mono- or bi-cyclic heterocyclic group" defined above; specifically, 1-azetidinyl, 1-pyrrolidinyl, piperidino, 1-piperazinyl, 1-azepanyl, 1-diazepanyl, morpholino, indolin-1-yl, isoindolin-2-yl, tetrahydroquinolin-1-yl, tetrahydroisoquinolin-2-yl or tetrahydroquinoxalin-1-yl; in one embodiment, piperidino or 1,2,3,4-tetrahydroisoquinolin-2-yl; and in one embodiment, piperidino. Wherein the "4- to 8-membered nitrogen-containing saturated heterocyclic group" optionally has one to five substituents selected from the Group $G^4$ and the substituents are bonded to one or more ring atom(s) of the heterocycle (and/or the condensed benzene ring).

The "ester group" in the definition of $R^P$ is an ester group, such as lower alkyl, lower alkenyl, lower halogenoalkyl, $C_{3-8}$ cycloalkyl, (lower alkyl)-O-benzyl, nitrobenzyl, (lower alkyl)-O-benzhydryl, benzhydryl, -(lower alkylene)-O—C(O)-(lower alkyl), -(lower alkylene)-C(O)-(lower alkenyl), -(lower alkylene)-O—C(O)—O—($C_{3-8}$ cycloalkyl), -(lower alkylene)-O—C(O)-(lower alkenyl), -(lower alkylene)-O—C(O)-(lower alkylene)-O-(lower alkyl), -(lower alkylene)-O-(lower alkylene)-O-(lower alkyl), -(lower alkylene)-O-(lower alkylene)-O-(lower alkyl), -(lower alkylene)-O—C(O)—O-(lower alkyl), -(lower alkylene)-O—C(O)—O-(lower alkylene)-O-(lower alkyl), -(lower alkylene)-O-benzoyl, -(lower alkylene)-N(lower alkyl)$_2$, 2-oxotetrahydrofuran-5-yl, 2-oxo-5-alkyl-1,3-dioxolen-4-ylmethyl, tetrahydrofuranylcarbonyloxymethyl, or 3-phthalidyl. In one embodiment, the ester group is a lower alkyl group. A compound in which $R^P$ is an ester group may be a compound which can be converted into a corresponding carboxylic acid compound under physiological conditions. The present invention also encompasses such a compound.

The "$R^P$ and $R^6$ are linked to each other to form, together with —O—C(=O)—C—O— to which they are attached, 2,2-di(lower alkyl)-4-oxo-1,3-dioxolane-5,5-diyl" means that the compound represented by Formula (I) includes compounds represented by Formula (I-A):

[Formula 3]

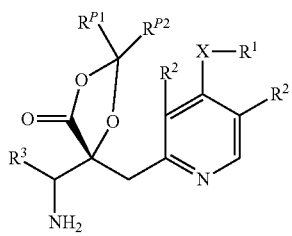
(I-A)

wherein, $R^{P1}$ and $R^{P2}$ are the same or different from each other, and are a lower alkyl. In one embodiment, both $R^{P1}$ and $R^{P2}$ represent methyl.

In the "—X—$R^1$ is optionally linked to any one of $R^2$'s attached to a pyridine ring to which —X—$R^1$ is also attached, to constitute a group represented by any one of formulae —$X^b$—(CH$_2$)$_m$—Y—, —$X^b$—CH=CH—, —$X^b$—CH=N—, and —$X^b$—N=CH—, and form a heterocycle condensed with the pyridine ring", the "heterocycle condensed with a pyridine ring" includes condensed rings represented by Formulae (i) to (iv) below. Such a condensed ring has a bond to —CH$_2$—C(OR$^6$)(COOR$^P$)—CH(NH$_2$)—$R^3$ at any one of carbon ring atoms neighboring the nitrogen ring atom of the pyridine ring (i.e. on the position 2 or 6 in the pyridine ring). Such a heterocycle optionally has one to five substituents selected from the Group G$^4$ in replacement of one or more H atoms attached to the ring atom(s) of the heterocycle.

[Formula 4]

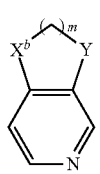
(i)

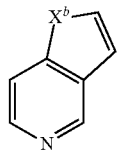
(ii)

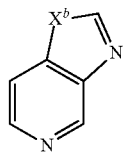
(iii)

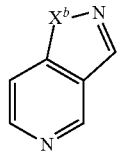
(iv)

wherein, $X^b$ is O, S or NH; m is an integer of 1 to 3; and Y is CH$_2$, O, S or NH.

In one embodiment, the "heterocycle condensed with a pyridine ring" is a condensed ring selected from the group consisting of the following rings:

[Formula 5]

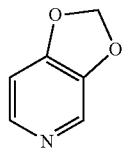
(a)

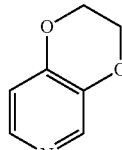
(b)

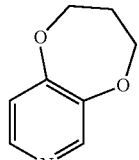
(c)

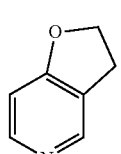
(d)

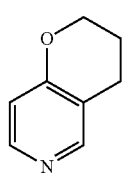
(e)

-continued (f)
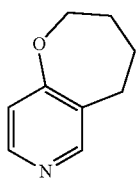

(g)
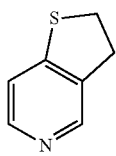

(h)
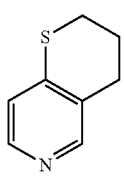

(j)
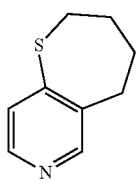

(k)
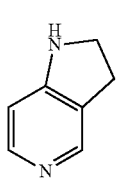

(m)
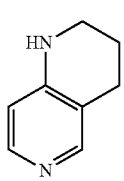

(n)
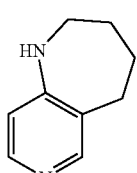

(o)
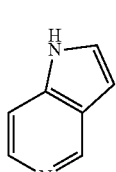

(p)
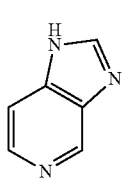

-continued (q)

(r)

(s)

(t)

(u)

(v)

(w)
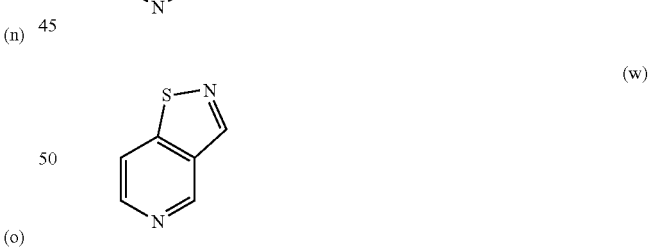

Among the above condensed rings, the heterocycle condensed with a pyridine ring is, in one embodiment, selected from the group consisting of the condensed rings (a), (b), (d), (e), (g), (h), (k), (m), (o), (p), (q), (r), (s), and (t); in one embodiment, selected from the group consisting of the condensed rings (b), (d), (o), (p), (q), and (r); in one embodiment, selected from the group consisting of the condensed rings (d) and (q); and in one embodiment, the condensed ring (q).

In one embodiment, the heterocycle condensed with a pyridine ring is selected from the group consisting of the following condensed rings:

[Formula 6]

(b-1)
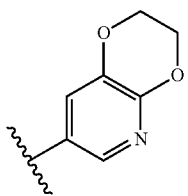

(d-1)
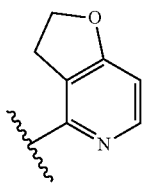

(o-1)
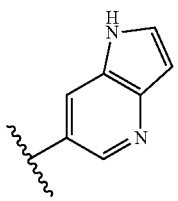

(p-1)
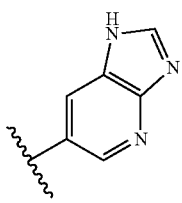

(q-1)
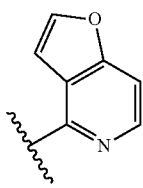

(r-1)
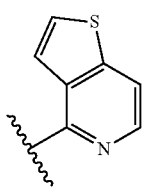

The heterocycle condensed with a pyridine ring is, in one embodiment, the condensed ring (d-1) or (q-1) among the above condensed rings; and in one embodiment, the condensed ring (q-1).

The "—X—R$^1$ is optionally linked to R$^3$ to form a group represented by formula —X—(C$_{5-15}$ carbon chain)-, wherein the C$_{5-15}$ carbon chain optionally has one to two O or S atoms in replacement of C atom(s), optionally has one to five unsaturated bonds" means that the C$_{5-15}$ carbon chain is a straight or branched alkylene having 5 to 15 carbon atoms, or a straight or branched alkenylene or alkynylene having 5 to 15 carbon atoms and 1 to 5 unsaturated bonds, and that 1 to 2 carbon atoms of the carbon chain may be replaced by O or S atom(s). The —X—(C$_{5-15}$ carbon chain)- is, specifically, —X—(C$_{5-15}$ alkylene)-, —X—(C$_{5-15}$ alkenylene)-, —X—(C$_{q1}$ alkylene)-O—(C$_{q2}$ alkylene)-, —X—(C$_{q1}$ alkylene)-S—(C$_{q2}$ alkylene)-, —X—(C$_{q1}$ alkenylene)-O—(C$_{q2}$ alkylene)-, alkenylene)-S—(C$_{q2}$ alkylene)-, —X—(C$_{q1}$ alkylene)-O—(C$_{q2}$ alkenylene)-, —X—(C$_{q1}$ alkylene)-S—(C$_{q2}$ alkenylene)-, —X—(C$_{r1}$ alkylene)-O—(C$_{r2}$ alkylene)-O—(C$_{r3}$ alkylene)-, —X—(C$_{r1}$ alkylene)-S—(C$_{r2}$ alkylene)-S—(C$_{r3}$ alkylene)-, —X—(C$_{r1}$ alkylene)-O—(C$_{r2}$ alkylene)-O—(C$_{r3}$ alkylene)-, —X—(C$_{r1}$ alkenylene)-S—(C$_{r2}$ alkylene)-S—(C$_{r3}$ alkylene)-, —X—(C$_{r1}$ alkylene)-O—(C$_{r2}$ alkenylene)-O—(C$_{r3}$ alkylene)- or —X—(C$_{r1}$ alkylene)-S—(C$_{r2}$ alkenylene)-S—(C$_{r3}$ alkylene)-. If the carbon chain is an alkylene, q1, q2, r1, r2, and r3 are each an integer of one or over, and if the carbon chain is an alkenylene, q1, q2, r1, r2, and r3 are each an integer of two or over, with the proviso that q1+q2=5 to 14 and r1+r2+r3=5 to 13. The —X—(C$_{5-15}$ carbon chain)- is, in one embodiment, —X—(C$_{q1}$ alkylene)-O—(C$_{q2}$ alkylene)- or —X—(C$_{q1}$ alkenylene)-O—(C$_{q2}$ alkylene)-; and in one embodiment, —X—(C$_{5-11}$ alkenylene)-O—(C$_{1-3}$ alkylene)- or —X—(C$_{5-11}$ alkylene)-O—(C$_{1-3}$ alkylene)-. In one embodiment, a compound in which —X—R$^1$ is linked to R$^3$ to form a group represented by formula —X—(C$_{5-15}$ carbon chain)- is represented by Formula (I-B) or (I-C):

[Formula 7]

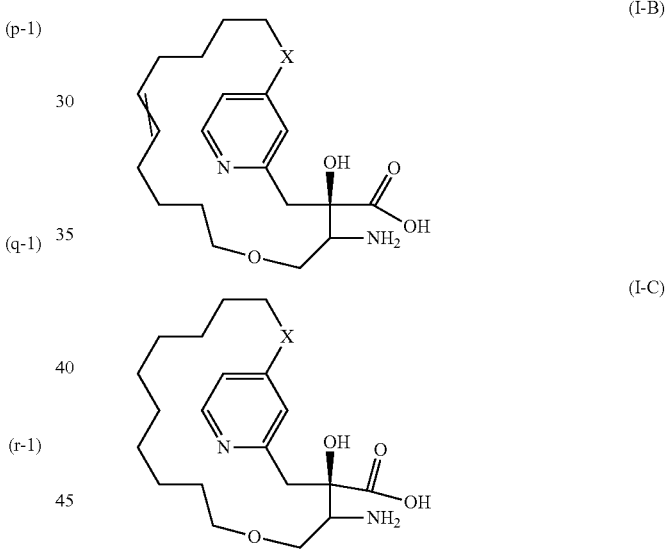

wherein, the double bond represented with two crossed lines indicates that the double bond forms an E isomer or Z isomer, or a mixture thereof.

The "—O—(C$_{2-3}$ alkylene)-O—" and the "—O—(C$_{3-4}$ alkylene)-" each represents a bivalent substituent group having two bonds to the same ring carbon atom. Specifically, "—O—(C$_{2-3}$ alkylene)-O—" is —O—(CH$_2$)$_2$—O— or —O—(CH$_2$)$_3$—O—, and "—O—(C$_{3-4}$ alkylene)-" is —O—(CH$_2$)$_3$— or —O—(CH$_2$)$_4$—.

In the present specification, the "optionally has one to five substituents" means that the specified group is unsubstituted or has one to five substituents. If the specified group has a plurality of substituents, the substituents may be the same or different from each other.

The compound represented by Formula (I) has at least two asymmetric carbon atoms. One asymmetric carbon atom attached to —C(O)OR$^P$ (position 2) has (R) configuration, and neighboring carbon atom attached to —NH$_2$ (position 3) may have either (R) or (S) configuration, and the compound represented by Formula (I) includes (R) or (S) isomer on position 3, and a mixture thereof. In one embodiment, the compound represented by Formula (I) is a compound represented by Formula (I') or a salt thereof:

[Formula 8]

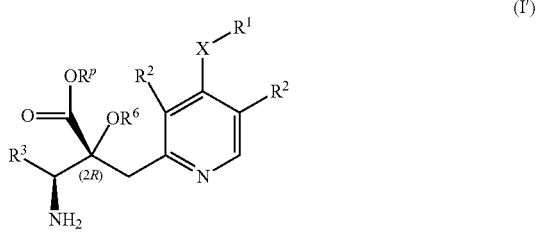

(I')

wherein, (2R) indicates that the carbon atom at position 2 has (R) configuration.

The compound represented by Formula (I) may have tautomers and geometric isomers, depending on the type of substituent groups. The compound represented by Formula (I) also includes separate tautomers and geometric isomers, and mixtures thereof.

The compound represented by Formula (I) may also have stereoisomers based on other asymmetric carbon atom than those described above, depending on the type of substituent groups. The compound represented by Formula (I) also includes separate stereoisomers and mixtures thereof.

The present invention also encompasses a pharmaceutically acceptable prodrug of the compound represented by Formula (I). A pharmaceutically acceptable prodrug is a compound having a group which can be converted into an amino group, a hydroxyl group, or a carboxyl group as a result of solvolysis or under physiological conditions. Examples of a group forming a prodrug are described in Prog. Med., 5, 2157-2161 (1985), "Iyakuhin no Kaihatsu (Pharmaceutical Research and Development)" (Hirokawa-Shoten Ltd.), 1990, Vol. 7, "Bunshi Sekkei (Drug Molecular Design)", pp. 163-198, and "Prodrugs and targeted delivery" (Wiley-VCH 2011) Methods and principles in medicinal chemistry, volume 47.

The salt of the compound represented by Formula (I) is a pharmaceutically acceptable salt of the compound represented by Formula (I). The compound represented by Formula (I) may form an acid addition salt or a salt with a base, depending on the type of substituent groups. Specific examples of the salt include acid addition salts with inorganic acids such as hydrochloric acid, hydrobromic acid, hydroiodic acid, sulfuric acid, nitric acid, and phosphoric acid; acid addition salts with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with inorganic bases such as sodium, potassium, magnesium, calcium, and aluminum; salts with organic bases such as methylamine, ethylamine, ethanolamine, lysine, and ornithine; salts with various amino acids and amino acid derivatives such as acetylleucine; and ammonium salts.

The present invention also encompasses various hydrates, solvates, and crystalline polymorphs of the compound represented by Formula (I) and a salt thereof. The present invention also encompasses various compounds labeled with a radioactive or nonradioactive isotope.

Some embodiments of the compound represented by Foiinula (I) are shown below.

(1-1) The compound or a salt thereof, in which X is O, S or $NR^4$; $R^4$ is H, lower alkyl which optionally has one to five substituents selected from the Group $G^1$, $C_{3-12}$ cycloalkyl which optionally has one to five substituents selected from the Group $G^2$, -(lower alkylene)-($C_{3-12}$ cycloalkyl which optionally has one to five substituents selected from the Group $G^2$), —C(O)-(lower alkyl which optionally has one to five substituents selected from the Group $G^1$), —C(O)—($C_{3-12}$ cycloalkyl which optionally has one to five substituents selected from the Group $G^2$), or —C(O)-(lower alkylene)-($C_{3-12}$ cycloalkyl which optionally has one to five substituents selected from the Group $G^2$); or $R^4$ forms together with neighboring —$NR^1$, as —$NR^1R^4$, a 4- to 8-membered nitrogen-containing saturated heterocyclic group, wherein the nitrogen-containing saturated heterocyclic group may be condensed with a benzene ring and optionally has one to five substituents selected from the Group $G^4$.

(1-2) The compound or a salt thereof, in which X is O, S or $NR^4$; $R^4$ is H; lower alkyl which optionally has one to five substituents selected from the group consisting of halogen, OH and —O-(lower alkyl); $C_{3-12}$ cycloalkyl which optionally has one to five substituents selected from the group consisting of lower alkyl, halogen, OH and —O-(lower alkyl); -(lower alkylene)-{$C_{3-12}$ cycloalkyl which optionally has one to five substituents selected from the group consisting of lower alkyl, halogen, OH and —O-(lower alkyl)}; —C(O)— {lower alkyl which optionally has one to five substituents selected from the group consisting of halogen, OH and —O-(lower alkyl)}; —C(O)—{$C_{3-12}$ cycloalkyl which optionally has one to five substituents selected from the group consisting of lower alkyl, halogen, OH and —O—(lower alkyl)}; or —C(O)-(lower alkylene)-{$C_{3-12}$ cycloalkyl which optionally has one to five substituents selected from the group consisting of lower alkyl, halogen, OH and —O-(lower alkyl)}; or $R^4$ forms together with neighboring —$NR^1$, as —$NR^1R^4$, a 4- to 8-membered nitrogen-containing saturated heterocyclic group, wherein the nitrogen-containing saturated heterocyclic group may be condensed with a benzene ring and optionally has one to three substituents selected from the group consisting of lower alkyl, halogen, OH and —O-(lower alkyl).

(1-3) The compound or a salt thereof, in which X is O, S or $NR^4$; $R^4$ is H, lower alkyl which is optionally substituted by one to five halogens, $C_{3-12}$ cycloalkyl, or —C(O)—($C_{3-12}$ cycloalkyl which is optionally substituted by one to five lower alkyls); or $R^4$ forms together with neighboring —$NR^1$, as —$NR^1R^4$, a 4- to 8-membered nitrogen-containing saturated heterocyclic group, wherein the nitrogen-containing saturated heterocyclic group may be condensed with a benzene ring and is optionally substituted by one to five lower alkyls.

(1-4) The compound or a salt thereof, in which X is O or S.

(1-5) The compound or a salt thereof, in which X is $NR^4$; $R^4$ is H, lower alkyl which is optionally substituted by one to five halogens, $C_{3-12}$ cycloalkyl, or —C(O)—($C_{3-12}$ cycloalkyl which is optionally substituted by one to five lower alkyls); or $R^4$ forms together with neighboring —$NR^1$, as —$NR^1R^4$, a 4- to 8-membered nitrogen-containing saturated heterocyclic group, wherein the nitrogen-containing saturated heterocyclic group may be condensed with a benzene ring and is optionally substituted by one to five lower alkyls.

(1-6) The compound or a salt thereof, in which X is O.

(1-7) The compound or a salt thereof, in which X is S.

(2-1) The compound or a salt thereof, in which:

(a) $R^1$ is H, $C_{1-10}$ alkyl which optionally has one to five substituents selected from the Group $G^1$, -(lower alkylene)-$X^{11}$-(lower alkyl which optionally has one to five substituents selected from the Group $G^1$), $R^{11}$, -(lower alkylene)-$R^{11}$, -(lower alkylene)-$X^{11}$—$R^{11}$, or -(lower alkylene)-$X^{11}$-(lower alkylene)-$R^{11}$; $R^{11}$ is $C_{3-12}$ cycloalkyl which optionally has one to five substituents selected from the Group $G^2$, $C_{3-12}$ cycloalkenyl which optionally has one to five substituents selected from the Group $G^2$ and which may be condensed with a benzene ring optionally having one to four substituents selected from the Group $G^3$, aryl which optionally has one to five substituents selected from the Group $G^5$, or mono- or bi-cyclic heterocyclic group which optionally has one to five substituents selected from the Group $G^5$; $X^{11}$ is O or $S(O)_m$, wherein n is 0, 1, or 2;

(b) $R^3$ is $C_{1-10}$ alkyl which is optionally substituted by one to five halogens; —X—$R^1$ is linked to any one of $R^2$'s attached to a pyridine ring to which —X—$R^1$ is also attached, to constitute a group represented by any one of formulae —$X^b$—$(CH_2)_m$—Y—, —$X^b$—CH=CH—, —$X^b$—CH=N—, and —$X^b$—N=CH—, and form a heterocycle condensed with the pyridine ring, wherein m is an integer of 1 to 3, $X^b$ is O, S or NH, Y is $CH_2$, O, S or NH, and the heterocycle optionally has one to four substituents selected from the group consisting of: $C_{3-12}$ cycloalkyl which optionally has one to five substituents selected from the Group $G^2$; -(lower alkylene)-($C_{3-12}$ cycloalkyl which optionally has one to five substituents selected from the Group $G^2$); and the substituents defined in the Group $G^3$; in replacement of one or more H atoms attached to the ring atom(s) of the heterocycle; or (c) —X—$R^1$ is linked to $R^3$ to form a group represented by formula —X—($C_{5-15}$ carbon chain)-, wherein the $C_{5-15}$ carbon chain optionally has one to two O or S atoms in replacement of C atom(s), optionally has one to five unsaturated bonds, and optionally has one to five substituents selected from the Group $G^4$.

(2-1a) The compound or a salt thereof according to (a) in (2-1).

(2-2) The compound or a salt thereof, in which:

(a) $R^1$ is H; $C_{1-10}$ alkyl which optionally has one to five substituents selected from the group consisting of halogen and OH; -(lower alkylene)-$X^{11}$-{lower alkyl which optionally has one to five substituents selected from the group consisting of halogen, OH, —O-(lower alkyl) and —O-(lower halogenoalkyl)}; $C_{3-12}$ cycloalkyl which optionally has one to five substituents selected from the group consisting of lower alkyl, halogen, lower halogenoalkyl, OH, —O— (lower alkyl), —O-(lower halogenoalkyl), —O— ($C_{2-3}$ alkylene)-O— and —O—($C_{3-4}$ alkylene)-; $C_{3-12}$ cycloalkenyl which optionally has one to five substituents selected from the group consisting of lower alkyl, halogen, lower halogenoalkyl, OH, —O-(lower alkyl) and —O-(lower halogenoalkyl), and which may be condensed with a benzene ring; aryl which optionally has one to five substituents selected from the group consisting of lower alkyl, halogen, lower halogenoalkyl, OH, —O-(lower alkyl) and —O-(lower halogenoalkyl); mono- or bi-cyclic heterocyclic group which optionally has one to five substituents selected from the group consisting of lower alkyl, halogen, lower halogenoalkyl, OH, —O-(lower alkyl), —O-(lower halogenoalkyl), —C(O)-(lower alkyl) and —C(O)—O-(lower alkylene)-aryl; -(lower alkylene)-$R^{11}$; -(lower alkylene)-$X^{11}$—$R^{11}$; or -(lower alkylene)-$X^{11}$-(lower alkylene)-$R^{11}$; $R^{11}$ is $C_{3-12}$ cycloalkyl which optionally has one to five substituents selected from the group consisting of lower alkyl, halogen, lower halogenoalkyl, OH, —O-(lower alkyl), —O-(lower halogenoalkyl), —O—($C_{2-3}$ alkylene)-O— and —O—($C_{3-4}$ alkylene)-; $C_{3-12}$ cycloalkenyl which optionally has one to five substituents selected from the group consisting of lower alkyl, halogen, lower halogenoalkyl, OH, —O-(lower alkyl) and —O-(lower halogenoalkyl), and which may be condensed with a benzene ring; aryl which optionally has one to five substituents selected from the group consisting of lower alkyl, halogen, lower halogenoalkyl, OH, —O-(lower alkyl) and —O-(lower halogenoalkyl); or mono- or bi-cyclic heterocyclic group which optionally has one to five substituents selected from the group consisting of lower alkyl, halogen, lower halogenoalkyl, OH, —O-(lower alkyl) and —O-(lower halogenoalkyl); $X^{11}$ is O or S;

(b) $R^3$ is $C_{1-10}$ alkyl which is optionally substituted by one to five halogens; —X—$R^1$ is linked to any one of $R^2$'s attached to a pyridine ring to which —X—$R^1$ is also attached, to constitute a group represented by any one of formulae —$X^b$—$(CH_2)_m$—Y—, —$X^b$—CH=CH—, —$X^b$—CH=N—, and —$X^b$—N=CH—, and form a heterocycle condensed with the pyridine ring, wherein m is an integer of 1 to 2, $X^b$ is O, S or NH, Y is $CH_2$, O, S or NH, and the heterocycle optionally has one to four substituents selected from the group consisting of: $C_{3-12}$ cycloalkyl which optionally has one to five substituents selected from the group consisting of lower alkyl, halogen, lower halogenoalkyl, OH, —O-(lower alkyl), —O-(lower halogenoalkyl), —O—($C_{2-3}$ alkylene)-O— and —O—($C_{3-4}$ alkylene)-; -(lower alkylene)-{$C_{3-12}$ cycloalkyl which optionally has one to five substituents selected from the group consisting of lower alkyl, halogen, lower halogenoalkyl, OH, —O-(lower alkyl), —O-(lower halogenoalkyl), —O—($C_{2-3}$ alkylene)-O— and —O—($C_{3-4}$ alkylene)-}; lower alkyl; halogen; lower halogenoalkyl; OH; —O-(lower alkyl); —O-(lower alkylene)-aryl; —O-aryl; —S-(lower alkyl); and —O-lower halogenoalkyl; in replacement of one or more H atoms attached to the ring atom(s) of the heterocycle; or (c) —X—$R^1$ is linked to $R^3$ to form —X—($C_{5-11}$ alkylene)-O—($C_{1-3}$ alkylene)- or —X—($C_{5-11}$ alkenylene)-O—($C_{1-3}$ alkylene)-.

(2-2a) The compound or a salt thereof according to (a) in (2-2).

(2-3) The compound or a salt thereof, in which:

(a) $R^1$ is H; $C_{1-10}$ alkyl; -(lower alkylene)-O-(lower alkyl); $C_{3-12}$ cycloalkyl which optionally has one to five substituents selected from the group consisting of lower alkyl, halogen and —O—($C_{3-4}$ alkylene)-; $C_{5-6}$ cycloalkenyl condensed with a benzene ring; aryl which optionally has one to five substituents selected from the group consisting of halogen and —O-(lower alkyl); 5- to 6-membered monocyclic heterocyclic group which optionally has one to five substituents selected from the group consisting of lower alkyl, —C(O)-(lower alkyl) and —C(O)—O-(lower alkylene)-aryl; -(lower alkylene)-$R^{11}$; -(lower alkylene)-O—($C_{3-12}$ cycloalkyl); -(lower alkylene)-O-aryl; or -(lower alkylene)-O-(lower alkylene)-aryl; $R^{11}$ is $C_{3-12}$ cycloalkyl which is optionally substituted by one to five lower alkyls; aryl which optionally has one to five substituents selected from the group consisting of halogen, lower halogenoalkyl, —O-(lower alkyl) and —O-(lower halogenoalkyl); or 5- to 6-membered monocyclic heterocyclic group which is optionally substituted by one to five lower alkyls;
(b) $R^3$ is $C_{10}$ alkyl which is optionally substituted by one to five halogens; —X—$R^1$ is linked to any one of $R^2$'s attached to a pyridine ring to which —X—$R^1$ is also attached, to constitute a group represented by any one of formulae —O—$CH_2$—$CH_2$—O—, —O—$CH_2$—$CH_2$—, —NH—CH=CH—, —NH—CH=N—, —O—CH=CH— and —S—CH=CH—, and form a heterocycle condensed with the pyridine ring, wherein the heterocycle condensed with the pyridine ring is selected from the group consisting of rings represented by Formulae (b-1), (d-1), (o-1), (p-1), (q-1), and (r-1):

[Formula 9]

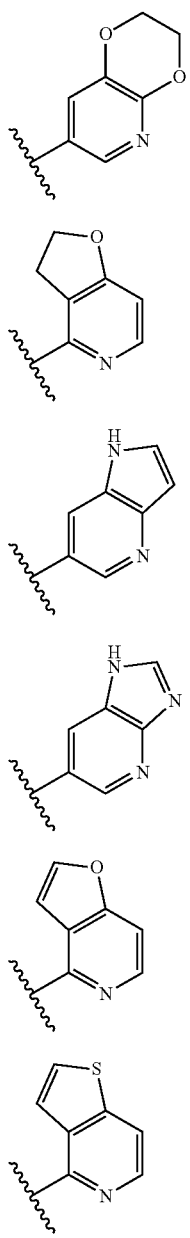

(b-1)

(d-1)

(o-1)

(p-1)

(q-1)

(r-1)

wherein the heterocycle has one to two substituents selected from the group consisting of -(lower alkylene)-($C_{3-12}$ cycloalkyl) and lower alkyl, in replacement of one or more H atoms attached to the ring atom(s) of the heterocycle; and the other $R^2$ is H; or (c) a compound represented by Formula (I-B1) or (I-C1) or a salt thereof:

[Formula 10]

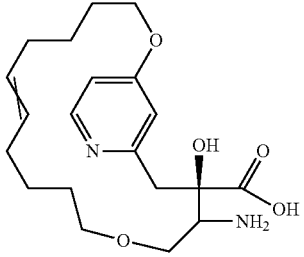

(I-B1)

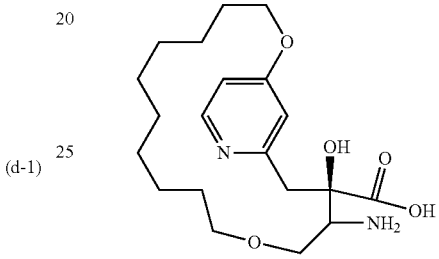

(I-C1)

in which the double bond represented with two crossed lines indicates that the double bond forms an E isomer, Z isomer or mixture thereof.

(2-4) The compound or a salt thereof according to (a) or (b) in (2-3).

(2-5) The compound or a salt thereof according to (a) in (2-3).

(2-6) The compound or a salt thereof according to (b) in (2-3).

(2-7) The compound or a salt thereof, in which $R^1$ is $C_{1-10}$ alkyl, $C_{3-10}$ cycloalkyl which is optionally substituted by one to three lower alkyls, -(lower alkylene)-($C_{3-10}$ cycloalkyl which is optionally substituted by one to three lower alkyls), or -(lower alkylene)-aryl.

(2-8) The compound or a salt thereof, in which $R^1$ is $C_{1-10}$ alkyl, $C_{3-10}$ cycloalkyl which is optionally substituted by lower alkyl, or -(lower alkylene)-($C_{3-10}$ cycloalkyl which is optionally substituted by lower alkyl).

(2-9) The compound or a salt thereof, in which $R^1$ is hexan-2-yl, 4-methylcyclohexyl, cyclohexyl, cycloheptyl, spiro[2,5]octyl, 2-(cyclopropyl)ethyl, 2-(1-methylcyclopropyl)ethyl or 3-(cyclopropyl)propyl.

(2-10) The compound or a salt thereof, in which $R^1$ is $C_{1-10}$ alkyl.

(2-11) The compound or a salt thereof, in which $R^1$ is $C_{3-10}$ cycloalkyl which is optionally substituted by one to three lower alkyls.

(2-12) The compound or a salt thereof, in which $R^1$ is cyclohexyl, cycloheptyl, 4-methylcyclohexyl or spiro[2,5]octyl.

(2-13) The compound or a salt thereof, in which $R^1$ is -(lower alkylene)-($C_{3-10}$ cycloalkyl which is optionally substituted by one to three lower alkyls).

(2-14) The compound or a salt thereof, in which $R^1$ is 2-(cyclopropyl)ethyl, 2-(1-methylcyclopropyl)ethyl or 3-(cyclopropyl)propyl.

(2-15) The compound or a salt thereof according to (2-6), wherein —X—R$^1$ is linked to any one of R$^2$'s attached to a pyridine ring to which —X—R$^1$ is also attached, to constitute a group represented by any one of formulae —O—CH$_2$—CH$_2$— and —O—CH=CH—, and form a heterocycle condensed with the pyridine ring as represented by Formula (d-1) or (q-1), and the heterocycle has -(lower alkylene)-(C$_{3-10}$ cycloalkyl) in replacement of one H atom attached to a ring atom of the heterocycle.

(2-16) The compound or a salt thereof according to (2-15), wherein —X—R$^1$ is linked to any one of R$^2$'s attached to a pyridine ring to which —X—R$^1$ is also attached, to constitute a group represented by formula —O—CH=CH—, and form a heterocycle condensed with the pyridine ring as represented by Formula (q-1), and the heterocycle has -(lower alkylene)-(C$_{3-10}$ cycloalkyl) in replacement of one H atom attached to a ring atom of the heterocycle.

(3-1) The compound or a salt thereof, in which R$^2$'s are the same or different from each other, and are H, lower alkyl which optionally has one to five substituents selected from the Group G$^1$, halogen, OH, SH, —O-(lower alkyl), —O-(lower alkylene)-aryl, —O-aryl, —S-(lower alkyl), —S-(lower alkylene)-aryl, —S-aryl, —S-(lower halogenoalkyl), —C(O)-(lower alkyl), —S(O)$_2$-(lower alkyl), —S(O)-(lower alkyl), NO$_2$, —NH$_2$, —NH-(lower alkyl), —N(lower alkyl)$_2$, —NH-aryl, —N(lower alkyl)-aryl, —C(O)OH, —C(O)O-(lower alkyl), —CHO, —C(O)NH$_2$, —C(O)NH-(lower alkyl), —C(O)N(lower alkyl)$_2$, CN, -(lower alkylene)-X$^{21}$-(lower alkyl which optionally has one to five substituents selected from the Group G$^1$), C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^5$, -(lower alkylene)-R$^{21}$, -(lower alkylene)-X$^{21}$—R$^{21}$, or -(lower alkylene)-X$^{21}$-(lower alkylene)-R$^{21}$; R$^{21}$ is C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^5$, or mono- or bi-cyclic heterocyclic group which optionally has one to five substituents selected from the Group G$^5$; and X$^{21}$ is O or S(O)$_n$, wherein n is 0, 1, or 2.

(3-2) The compound or a salt thereof, in which R$^2$'s are the same or different from each other, and are H, lower alkyl, lower halogenoalkyl, halogen, OH, —O-(lower alkyl), —O-(lower alkylene)-aryl, —O-aryl, —S-(lower alkyl), —O-(lower halogenoalkyl), -(lower alkylene)-O-(lower alkyl), C$_{3-12}$ cycloalkyl which optionally has one to five substituents selected from the group consisting of lower alkyl, lower halogenoalkyl and halogen, -(lower alkylene)-(C$_{3-12}$ cycloalkyl which optionally has one to five substituents selected from the group consisting of lower alkyl, lower halogenoalkyl and halogen), -(lower alkylene)-O—(C$_{3-12}$ cycloalkyl which optionally has one to five substituents selected from the group consisting of lower alkyl, lower halogenoalkyl and halogen), -(lower alkylene)-O-(lower alkylene)-(C$_{3-12}$ cycloalkyl which optionally has one to five substituents selected from the group consisting of lower alkyl, lower halogenoalkyl and halogen), -(lower alkylene)-(aryl which optionally has one to five substituents selected from the group consisting of lower alkyl, lower halogenoalkyl and halogen), -(lower alkylene)-O-(aryl which optionally has one to five substituents selected from the group consisting of lower alkyl, lower halogenoalkyl and halogen), or -(lower alkylene)-O-(lower alkylene)-(aryl which optionally has one to five substituents selected from the group consisting of lower alkyl, lower halogenoalkyl and halogen).

(3-3) The compound or a salt thereof, in which R$^2$'s are the same or different from each other, and are H, lower alkyl, halogen, -(lower alkylene)-aryl or -(lower alkylene)-O-(lower alkylene)-aryl.

(3-4) The compound or a salt thereof, in which R$^2$'s are the same or different from each other, and are H or lower alkyl.

(3-5) The compound or a salt thereof, in which R$^2$'s are H.

(4-1) The compound or a salt thereof, in which R$^3$ is R$^{32}$, -(lower alkylene)-X$^{31}$—R$^{32}$, -(lower alkenylene)-X$^{31}$—R$^{32}$, R$^{31}$, -(lower alkylene)-R$^{31}$, -(lower alkylene)-X$^{31}$—R$^{31}$, -(lower alkylene)-X$^{31}$-(lower alkylene)-R$^{31}$, -(lower alkenylene)-R$^{31}$, -(lower alkynylene)-R$^{31}$ or —CH=(saturated monocyclic heterocycle); R$^{31}$ is C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^5$, or mono- or bi-cyclic heterocyclic group which optionally has one to five substituents selected from the Group G$^5$; and X$^{31}$ is O or S(O)$_n$, wherein n is 0, 1, or 2.

(4-2) The compound or a salt thereof, in which R$^3$ is C$_{1-10}$ alkyl which optionally has one to five substituents selected from the group consisting of halogen and OH, lower alkenyl which optionally has one to five substituents selected from the group consisting of halogen and OH, lower alkynyl which optionally has one to five substituents selected from the group consisting of halogen and OH, -(lower alkylene)-X$^{31}$-{lower alkyl which optionally has one to five substituents selected from the group consisting of halogen, OH, —O-(lower alkyl) and —O-(lower halogenoalkyl)}, -(lower alkylene)-X$^{31}$-{lower alkenyl which optionally has one to five substituents selected from the group consisting of halogen, OH, —O-(lower alkyl) and —O-(lower halogenoalkyl)}, -(lower alkylene)-O-{lower alkynyl which optionally has one to five substituents selected from the group consisting of halogen, OH, —O-(lower alkyl) and —O-(lower halogenoalkyl)}, -(lower alkenylene)-O-{lower alkenyl which optionally has one to five substituents selected from the group consisting of halogen, OH, —O-(lower alkyl) and —O-(lower halogenoalkyl)}, -(lower alkenylene)-O-{lower alkyl which optionally has one to five substituents selected from the group consisting of halogen, OH, —O-(lower alkyl) and —O-(lower halogenoalkyl)}, R$^{31}$, -(lower alkylene)-R$^{31}$, -(lower alkylene)-X$^{31}$—R$^{31}$, -(lower alkylene)-X$^{31}$-(lower alkylene)-R$^{31}$, -(lower alkenylene)-R$^{31}$, or —CH=(saturated monocyclic heterocycle);

R$^{31}$ is C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^5$, or mono- or bi-cyclic heterocyclic group which optionally has one to five substituents selected from the Group G$^5$;

$X^{31}$ is O or $S(O)_n$, wherein n is 0, 1, or 2;

Group $G^2$ consists of lower alkyl, halogen, lower halogenoalkyl, OH, —O-(lower alkyl) and —O-(lower halogenoalkyl);

Group $G^5$ consists of: i) halogen, OH, SH, —O-(lower alkyl), —O-(lower alkylene)-aryl, —O-aryl, —S-(lower alkyl), —O-(lower halogenoalkyl), —C(O)-(lower alkyl), —S(O)$_2$-(lower alkyl) and CN; ii) lower alkyl, lower halogenoalkyl, lower alkenyl, and lower alkynyl; iii) -(lower alkylene)-O-(lower alkyl), -(lower alkylene)-O-(lower halogenoalkyl), and -(lower alkylene)-O-(lower alkyl substituted by one or more hydroxy groups); iv) $C_{3-12}$ cycloalkyl which optionally has one to five substituents selected from the Group $G^2$, and $C_{3-12}$ cycloalkenyl which may be condensed with a benzene ring; v) aryl which optionally has one to five substituents selected from the Group $G^3$; vi) mono- or bi-cyclic heterocyclic group which optionally has one to five substituents selected from the Group $G^3$; vii) -(lower alkylene)-$R^G$; viii) -(lower alkylene)-O—$R^G$; ix) —C(O)—$R^G$; and x) —S(O)$_2$—$R^G$, wherein $R^G$'s are the same or different from each other, and are $C_{3-12}$ cycloalkyl which optionally has one to five substituents selected from the Group $G^2$, $C_{3-12}$ cycloalkenyl which optionally has one to five substituents selected from the Group $G^2$ and may be condensed with a benzene ring optionally having one to four substituents selected from the Group $G^3$, aryl which optionally has one to five substituents selected from the Group $G^3$, or a mono- or bi-cyclic heterocyclic group which optionally has one to five substituents selected from the Group $G^3$; and Group $G^3$ consists of lower alkyl, halogen, lower halogenoalkyl, OH, —O-(lower alkyl), —O-(lower halogenoalkyl), —C(O)-(lower alkyl) and —S(O)$_2$-(lower alkyl).

(4-3) The compound or a salt thereof, in which $R^3$ is: $C_{1-10}$ alkyl which is optionally substituted by one to five halogens; -(lower alkylene)-O-(lower alkyl which optionally has one to five substituents selected from the group consisting of halogen and OH); -(lower alkylene)-O-(lower alkenyl); aryl which optionally has one to five substituents selected from the group consisting of halogen, CN, -(lower alkylene)-O-(lower alkyl), $C_{3-8}$ cycloalkyl, aryl which is optionally substituted by —S(O)$_2$-(lower alkyl), 5- to 6-membered monocyclic heterocyclic group, and —S(O)$_2$—($C_{3-8}$ cycloalkyl); -(lower alkylene)-($C_{3-8}$ cycloalkyl); -(lower alkylene)-(5- to 6-membered monocyclic heterocyclic group); -(lower alkylene)-O—($C_{3-8}$ cycloalkyl); -(lower alkylene)-O-{aryl which optionally has one to five substituents selected from the group consisting of halogen, —O-(lower alkyl), CN, and -(lower alkylene)-O-(lower alkyl)}; -(lower alkylene)-O-(5- to 6-membered monocyclic heterocyclic group which optionally has one to five substituents selected from the group consisting of halogen, lower alkyl and lower halogenoalkyl); -(lower alkylene)-O-(lower alkylene)-aryl; -(lower alkylene)-O-(lower alkylene)-($C_{3-8}$ cycloalkyl); -(lower alkylene)-S(O)$_n$-(lower alkyl), wherein n is 0, 1, or 2; -(lower alkylene)-S—($C_{3-8}$ cycloalkyl); -(lower alkylene)-S-(lower alkylene)-($C_{3-8}$ cycloalkyl); -(lower alkenylene)-aryl; or —CH=(saturated monocyclic heterocycle).

(4-4) The compound or a salt thereof, in which $R^3$ is: $C_{1-10}$ alkyl which is optionally substituted by one to five halogens; -(lower alkylene)-O-(lower alkyl which optionally has one to five substituents selected from the group consisting of halogen and OH); -(lower alkylene)-O-(lower alkenyl); -(lower alkylene)-($C_{3-8}$ cycloalkyl); -(lower alkylene)-O—($C_{3-8}$ cycloalkyl); -(lower alkylene)-O-(lower alkylene)-($C_{3-8}$ cycloalkyl); -(lower alkylene)-S-(lower alkyl); -(lower alkylene)-S—($C_{3-8}$ cycloalkyl); -(lower alkylene)-S-(lower alkylene)-($C_{3-8}$ cycloalkyl); -(lower alkylene)-O-{aryl which optionally has one to five substituents selected from the group consisting of halogen, —O-(lower alkyl), CN and -(lower alkylene)-O-(lower alkyl)}; or -(lower alkylene)-O-(5- to 6-membered monocyclic heterocyclic group which optionally has one to five substituents selected from the group consisting of halogen, lower alkyl and lower halogenoalkyl).

(4-5) The compound or a salt thereof, in which $R^3$ is $C_{1-10}$ alkyl, -(lower alkylene)-O-(lower alkenyl), -(lower alkylene)-($C_{3-8}$ cycloalkyl), -(lower alkylene)-O-(lower alkylene)-($C_{3-8}$ cycloalkyl), -(lower alkylene)-S-(lower alkyl), -(lower alkylene)-S-(lower alkylene)-($C_{3-8}$ cycloalkyl), or -(lower alkylene)-O-(pyridyl optionally substituted by one to five halogens).

(4-6) The compound or a salt thereof, in which $R^3$ is $C_{1-10}$ alkyl, -(lower alkylene)-($C_{3-8}$ cycloalkyl), -(lower alkylene)-S-(lower alkyl), or -(lower alkylene)-S-(lower alkylene)-($C_{3-8}$ cycloalkyl).

(4-7) The compound or a salt thereof, in which $R^3$ is isobutyl, isopentyl, 2,2-dimethylpropyl, 2-fluoro-2-methylpropyl, 3,3,3-trifluoropropyl, 2-(cyclopropyl)ethyl, 2-(cyclobutyl)ethyl, 2-(cyclopentyl)ethyl, 3-(cyclopropyl)propyl, 2-(cyclopropyl)ethyloxymethyl, methylthiomethyl, ethylthiomethyl, n-propylthiomethyl, isopropylthiomethyl, isobutylthiomethyl, cyclobutylthiomethyl, cyclopropylmethylthiomethyl, cyclobutylmethylthiomethyl, or 2-(cyclopropyl)ethylthiomethyl.

(4-8) The compound or a salt thereof, in which $R^3$ is $C_{1-10}$ alkyl, -(lower alkylene)-($C_{3-8}$ cycloalkyl), or -(lower alkylene)-S-(lower alkylene)-($C_{3-8}$ cycloalkyl).

(4-9) The compound or a salt thereof, in which $R^3$ is isobutyl, 2-(cyclobutyl)ethyl, or cyclopropylmethylthiomethyl.

(4-10) The compound or a salt thereof, in which $R^3$ is $C_{1-10}$ alkyl optionally substituted by one to five halogens.

(4-11) The compound or a salt thereof, in which $R^3$ is $C_{1-10}$ alkyl.

(4-12) The compound or a salt thereof, in which $R^3$ is isobutyl.

(4-13) The compound or a salt thereof, in which $R^3$ is -(lower alkylene)-($C_{3-8}$ cycloalkyl).

(4-14) The compound or a salt thereof, in which $R^3$ is -(lower alkylene)-S-(lower alkylene)-($C_{3-8}$ cycloalkyl).

(4-15) The compound or a salt thereof, in which $R^3$ is cyclopropylmethylthiomethyl.

(4-16) The compound or a salt thereof, in which $R^3$ is -(lower alkylene)-S-(lower alkyl).

(4-17) The compound or a salt thereof, in which $R^3$ is methylthiomethyl or ethylthiomethyl.

(5-1) The compound or a salt thereof, in which $R^P$ is H or an ester group and $R^6$ is H; or $R^P$ and $R^6$ are linked to each other to form, together with —O—C(=O)—C—O— to which they are attached, 2,2-di(lower alkyl)-4-oxo-1,3-dioxolane-5,5-diyl.

(5-2) The compound or a salt thereof, in which $R^P$ is H, or an ester group selected from the group consisting of: lower alkyl, lower alkenyl, lower halogenoalkyl, $C_{3-8}$ cycloalkyl, (lower alkyl)-O-benzyl, nitrobenzyl, (lower alkyl)-O-benzhydryl, benzhydryl, -(lower alkylene)-O—C(O)-(lower alkyl), -(lower alkylene)-C(O)-(lower alkenyl), -(lower alkylene)-O—C(O)—O—($C_{3-8}$ cycloalkyl), -(lower alkylene)-O—C(O)-(lower alkenyl), -(lower alkylene)-O—C(O)-(lower alkylene)-O-(lower alkyl), -(lower alkylene)-O-(lower alkylene)-O-(lower alkylene)-O-(lower alkyl), -(lower alkylene)-O—C(O)—O-(lower alkyl), -(lower alkylene)-O—C(O)—O-(lower alkylene)-O-(lower alkyl), -(lower alkylene)-O-benzoyl, -(lower alkylene)-N(lower alkyl)$_2$, 2-oxotetrahydrofuran-5-yl, 2-oxo-5-alkyl-1,3-dioxolen-4-ylmethyl, tetrahydrofuranyl-carbonyloxymethyl and 3-phthalidyl, and R$^6$ is H; or R$^P$ and R$^6$ are linked to each other to form, together with —O—C(=O)—C—O— to which they are attached, 2,2-di(lower alkyl)-4-oxo-1,3-dioxolane-5,5-diyl.

(5-3) The compound or a salt thereof, in which R$^P$ is H or lower alkyl, and R$^6$ is H; or R$^P$ and R$^6$ are linked to each other to faun, together with —O—C(=O)—C—O— to which they are attached, 2,2-dimethyl-4-oxo-1,3-dioxolane-5,5-diyl.

(5-4) The compound or a salt thereof, in which R$^P$ is H or an ester group set forth in (5-2), and R$^6$ is H.

(5-5) The compound or a salt thereof, in which R$^P$ is H or lower alkyl, and R$^6$ is H.

(5-6) The compound or a salt thereof, in which R$^P$ is H and R$^6$ is H.

(6) The compound or a salt thereof, according to a combination of any one of the embodiments (1-1) to (1-7), any one of the embodiments (2-1) to (2-16), any one of the embodiments (3-1) to (3-5), any one of the embodiments (4-1) to (4-17), and any one of the embodiments (5-1) to (5-6). Specific examples thereof include the following embodiments, but are not limited to:

(6-1) The compound or a salt thereof, according to a combination of the embodiments (1-2), (2-2), (3-2), (4-2), and (5-2).

(6-1a) The compound or a salt thereof, according to a combination of the embodiments (1-2), (2-2a), (3-2), (4-2), and (5-2).

(6-2) The compound or a salt thereof, according to a combination of the embodiments (1-3), (2-3), (3-3), (4-3), and (5-3).

(6-2a) The compound or a salt thereof, according to a combination of the embodiments (1-3), (2-5), (3-3), (4-3), and (5-3).

(6-3) The compound or a salt thereof, according to a combination of the embodiments (1-4), (2-4), (3-4), (4-4), and (5-5).

(6-4) The compound or a salt thereof, which is a combination of the embodiments (1-4), (2-2a), (3-4), (4-2), and (5-6).

(6-5) The compound or a salt thereof, which is a combination of the embodiments (2-6) and (5-6).

(6-6) The compound or a salt thereof, according to a combination of the embodiments (1-4), (2-7), (3-5), (4-5), and (5-6).

(6-7) The compound or a salt thereof, according to a combination of the embodiments (1-6), (2-8), (3-5), (4-6), and (5-6).

(6-8) The compound or a salt thereof, according to a combination of the embodiments (1-6), (2-9), (3-5), (4-7), and (5-6).

(6-9) The compound or a salt thereof, according to a combination of the embodiments (1-6), (2-8), (3-5), (4-8), and (5-6).

(6-10) The compound or a salt thereof, according to a combination of the embodiments (1-6), (2-9), (3-5), (4-9), and (5-6).

(6-11) The compound or a salt thereof, according to a combination of the embodiments (2-15), (4-11), and (5-6).

(6-12) The compound or a salt thereof, according to a combination of the embodiments (1-7), (2-7), (3-5), (4-5), and (5-6).

(6-13) The compound or a salt thereof, according to a combination of the embodiments (1-6), (2-5), (3-2), (4-2), and (5-5).

(6-14) The compound or a salt thereof, according to a combination of the embodiments (1-6), (2-11), (3-2), (4-2), and (5-5).

(6-15) The compound or a salt thereof, according to a combination of the embodiments (1-6), (2-13), (3-2), (4-2), and (5-5).

(6-16) The compound or a salt thereof, according to a combination of the embodiments (1-4), (2-5), (3-2), (4-10), and (5-5).

(6-17) The compound or a salt thereof, according to a combination of the embodiments (1-6), (2-10), (3-5), (4-11), and (5-6).

(6-18) The compound or a salt thereof, according to a combination of the embodiments (1-6), (2-11), (3-5), (4-11), and (5-6).

(6-19) The compound or a salt thereof, according to a combination of the embodiments (1-6), (2-11), (3-5), (4-14), and (5-6).

(6-20) The compound or a salt thereof, according to a combination of the embodiments (1-6), (2-13), (3-5), (4-11), and (5-6).

(6-21) The compound or a salt thereof, according to a combination of the embodiments (1-6), (2-13), (3-5), (4-13), and (5-6).

(6-22) The compound or a salt thereof, according to a combination of the embodiments (2-16), (4-11), and (5-6).

(6-23) The compound or a salt thereof, according to a combination of the embodiments (1-6), (2-11), (3-5), (4-16), and (5-6).

In one embodiment, the compound represented by Formula (I) is a compound represented by Formula (I') according to any one of the embodiments (6-1) to (6-23).

In one embodiment, the compound represented by Formula (I) or a salt thereof is a compound selected from the group consisting of the following compounds, or a salt thereof:

(2R,3 S)-3-amino-2-{[4-(2-cyclopropylethoxy)pyridin-2-yl]methyl}-2-hydroxy-5-methylhexanoic acid;

(2R,3S)-3-amino-2-{[4-(cyclohexyloxy)pyridin-2-yl]methyl}-2-hydroxy-5-methylhexanoic acid;

(2R,3 S)-3-amino-2-hydroxy-5-methyl-2-{[4-(spiro[2.5]oct-6-yloxy)pyridin-2-yl]methyl}hexanoic acid;

(2R,3R)-3-amino-4-[(cyclopropylmethyl)sulfanyl]-2-hydroxy-2-({4-[(trans-4-methylcyclohexyl)oxy]pyridin-2-yl}methyl)butanoic acid;

(2R,3S)-3-amino-2-hydroxy-5-methyl-2-({4-[(trans-4-methylcyclohexyl)oxy]pyridin-2-yl}methyl)hexanoic acid;

(2R,3S)-3-amino-5-cyclobutyl-2-{[4-(2-cyclopropylethoxy)pyridin-2-yl]methyl}-2-hydroxypentanoic acid;

(2R,3S)-3-amino-2-hydroxy-5-methyl-2-({4-[2-(1-methylcyclopropypethoxy]pyridin-2-yl}methyl)hexanoic acid;

(2R,3 S)-3-amino-2-{[4-(3-cyclopropylpropoxy)pyridin-2-yl]methyl}-2-hydroxy-5-methylhexanoic acid;

(2R,3 S)-3-amino-2-{[4-(cycloheptyloxy)pyridin-2-yl]methyl}-2-hydroxy-5-methylhexanoic acid; and (2R,3S)-3-amino-2-({4-[(2R)-hexan-2-yloxy]pyridin-2-yl}methyl)-2-hydroxy-5-methylhexanoic acid.

The compound represented by Formula (I) or a salt thereof is, in one embodiment, a compound selected from the group consisting of the compounds described above and the following compounds, or a salt thereof:

(2R,3R)-3-amino-4-(ethylsulfanyl)-2-hydroxy-2-({4-[(trans-4-methylcyclohexyl)oxy]pyridin-2-yl}methyl)butanoic acid; and (2R,3R)-3-amino-2-hydroxy-2-({4-[(trans-4-methylcyclohexyl)oxy]pyridin-2-yl}methyl)-4-(methylsulfanyl)butanoic acid.

In other embodiments, the compound represented by Formula (I) or a salt thereof is (2R,3 S)-3-amino-2-{[2-(2-cyclopropylethyl)furo[3,2-c]pyridin-4-yl]methyl}-2-hydroxy-5-methylhexanoic acid or a salt thereof.

(Preparation Methods)

The compound represented by the formula (I) or a salt thereof can be prepared using the characteristics based on the basic structure or the type of substituents and by applying various known synthesis methods. During the preparation, replacement of the functional group with a suitable protective group (a group that can be easily converted into the functional group) at the stage from starting material to an intermediate may be effective depending on the type of functional groups in the production technology in some cases. Such a protective group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

Hereinbelow, the representative preparation methods for the compound represented by the formula (I) will be described. Each of the production processes may also be carried out with reference to the References appended in the present description. Further, the preparation methods of the present invention are not limited to the examples as shown below.

(Production Process 1)

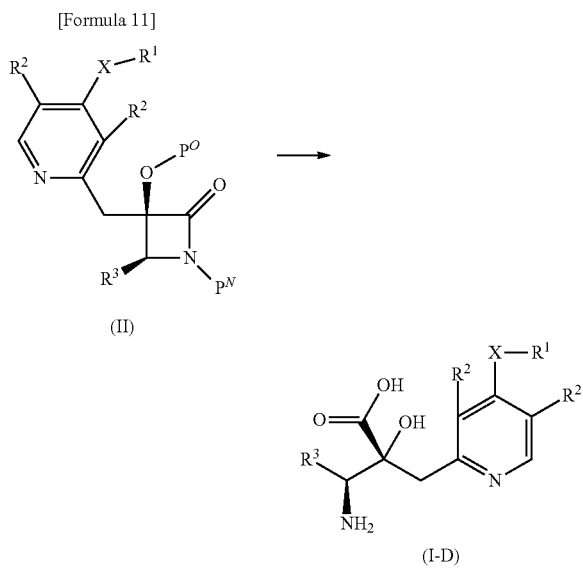

[Formula 11]

(II)

(I-D)

In the formula, $P^O$ represents a protective group for a hydroxyl group, and $P^N$ represents a protective group for an amino group.

The compound (I-D) can be produced by ring-opening and deprotection of the compound (II).

In this reaction, the compound (II) and a hydrolytic reagent in equivalent amounts, or either thereof in an excess amount, are used, and the mixture is stirred for usually 0.1 hour to five days in a solvent which is inert to the reaction under from cooling to heating with reflux. Examples of the solvent used herein are not particularly limited, but include alcohols such as methanol, ethanol and propanol; halogenated hydrocarbons such as dichloromethane, 1,2-dichloroethane and chloroform; 1,4-dioxane; N,N-dimethylformamide; tetrahydrofuran and the like. In some cases, a mixed solvent of such a solvent and water is preferably used for the reaction. Examples of the hydrolytic reagent used herein are not particularly limited, but include bases such as aqueous sodium hydroxide solution and aqueous potassium hydroxide solution; and acids such as hydrochloric acid and trifluoroacetic acid. In some cases, it is preferred to treat the compound (II) with a base and then with an acid, or to treat it with an acid and then with a base.

Examples of $P^O$, the protective group for a hydroxyl group, include methoxymethyl, benzyloxymethyl and the like. Examples of $P^N$, the protective group for an amino group, include methoxymethyl, benzyloxymethyl and the like.

(Production Process 2)

[Formula 12]

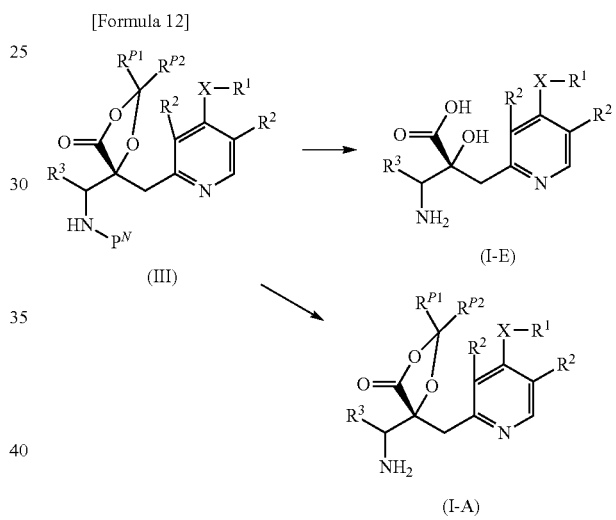

(III)

(I-E)

(I-A)

The compound (I-E) can be prepared by deprotection of the compound (III).

In this reaction, the compound (III) and a deprotecting reagent in equivalent amounts, or either thereof in an excess amount, are used, and the mixture is stirred for usually 0.1 hour to five days in a solvent which is inert to the reaction or in the absence of a solvent, under from cooling to heating with reflux. Examples of the solvent used herein are not particularly limited, but include alcohols such as methanol, ethanol and propanol; halogenated hydrocarbons such as dichloromethane, 1,2-dichloroethane and chloroform; 1,4-dioxane; N,N-dimethylformamide; tetrahydrofuran and the like. In some cases, a mixed solvent of such a solvent and water is preferably used for the reaction. Examples of the deprotecting reagent are not particularly limited, but include bases such as aqueous sodium hydroxide solution and aqueous potassium hydroxide solution; and acids such as hydrochloric acid and trifluoroacetic acid. In some cases, it is preferred to treat the compound (III) with a base and then with an acid, or to treat it with an acid and then with a base.

Examples of $P^N$, the protective group for an amino group, include tert-butoxycarbonyl, methoxymethyl, benzyloxymethyl and the like.

The compound (I-A) can also be prepared from the compound (III) under selected reaction conditions. For example, the compound (I-A) can be prepared by using tert-butoxycarbonyl as the protective group P$^N$ and treating with hydrogen chloride, trifluoroacetic acid and the like, in a solvent such as 1,4-dioxane or toluene.

(Production Process 3)

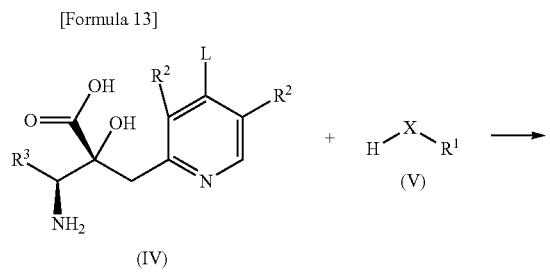

In the formula, L represents a leaving group.

The compound (I-D) can be prepared by reacting the compound (IV) with the compound (V). Examples of the leaving group L include halogen, methanesulfonyloxy, trifluoromethanesulfonyloxy and p-toluenesulfonyloxy groups.

In this reaction, the compounds (IV) and (V) in equivalent amounts, or either thereof in an excess amount, are used, the mixture is stirred for usually 0.1 hour to five days in a solvent which is inert to the reaction in the presence of a base under from cooling to heating with reflux, preferably at a temperature of 0 to 180° C. The reaction may be carried out under microwave irradiation. Examples of the solvent used herein are not particularly limited, but include aromatic hydrocarbons such as benzene, toluene and xylene; ethers such as diethylether, tetrahydrofuran, 1,4-dioxane and 1,2-dimethoxyethane; halogenated hydrocarbons such as dichloromethane, 1,2-dichloroethane and chloroform; N,N-dimethylformamide; dimethylsulfoxide; ethyl acetate; acetonitrile; and a mixture thereof. Examples of the base include organic bases such as triethylamine, diisopropylethylamine, potassium hexamethyldisilazide, 1,8-diazabicyclo[5.4.0]-undec-7-ene, n-butyllithium and potassium tert-butoxide; and inorganic bases such as sodium carbonate, potassium carbonate, cesium carbonate and sodium hydride. In some cases, the reaction is advantageously carried out in the presence of a phase transfer catalyst, such as tetra-n-butylammonium chloride.

[References]

"Organic Functional Group Preparations" written by S. R. Sandler and W. Karo, 2nd edition, Vol. 1, Academic Press Inc., 1991

"Courses in Experimental Chemistry (5th edition)" edited by The Chemical Society of Japan, Vol. 14 (2005) (Maruzen)

(Other Production Process)

A compound of Formula (I) prepared by the respective production processes can be used as a starting material and is subjected to a chemical modification reaction generally used by those skilled in the art, such as cyanation, hydrogenation and esterification, to produce other compounds represented by Formula (I).

(Synthesis of Starting Material 1)

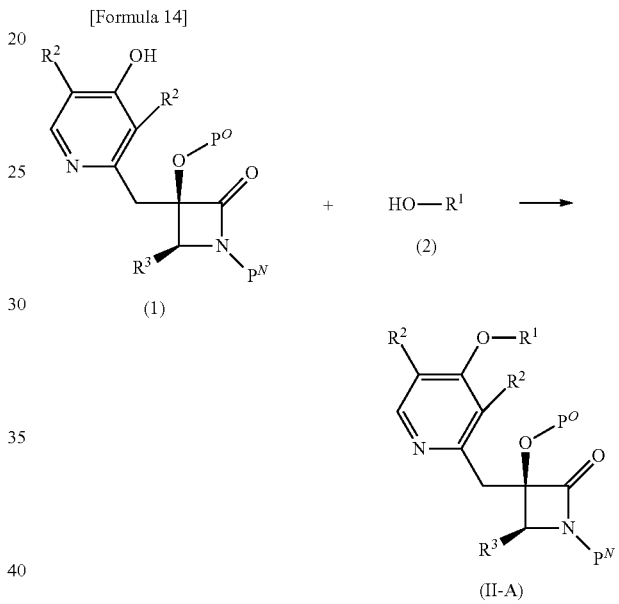

The compound (II-A) can be prepared by Mitsunobu reaction of the compounds (1) and (2).

In this reaction, the compounds (1) and (2) in equivalent amounts, or either thereof in an excess amount, are used, the mixture of the compounds and a Tsunoda reagent is stirred for useally 0.1 hour to five days in a solvent which is inert to the reaction under from cooling to heating with reflux, preferably at a temperature of 0 to 180° C. The reaction may be carried out under microwave irradiation. In some cases, the reaction may be preferably carried out under argon or nitrogen atmosphere and/or under anhydrous conditions. Examples of the Tsunoda reagent used herein include (cyanomethylene)tri-n-butylphosphorane (CMBP) and (cyanomethylene)trimethylphosphorane (CMMP). Examples of the solvent used herein are not particularly limited, but include aromatic hydrocarbons such as benzene, toluene and xylene, and a mixture thereof.

[References]

Tetsuto Tsunoda and Sho Ito, Journal of Synthetic Organic Chemistry, Japan, 1997, 55(7), 631-641

T. Tsunoda et al, Tetrahedron letters, 1996, 37(14), 2459-2462

(Synthesis of Starting Material 2)

[Formula 15]

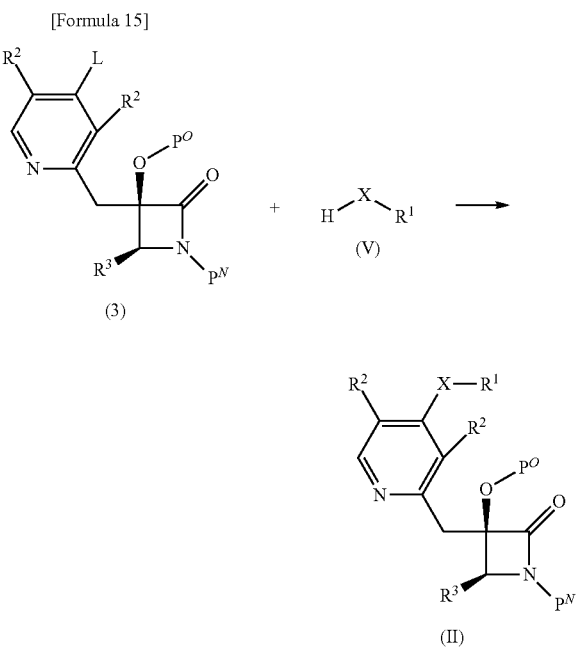

The compound (II) can be prepared by reacting the compound (3) with the compound (V).

This reaction can be carried out by the same method as in the Production Process 3 described above.

(Synthesis of Starting Material 3)

(Step 1)

The compound (5) can be prepared through introduction of protective groups in the compound (4). The $P^O$ and $P^N$ may be the same, and are specifically methoxymethyl or benzyloxymethyl.

(Step 2)

The compound (7) can be prepared through iodination of the compound (6) by Finkelstein reaction.

[Reference]

Chirality, 2011, 23(1), 24-33

(Step 3)

The compound (8) can be prepared by reacting the compound (5) with the compound (7).

In this reaction, the compounds (5) and (7) in equivalent amounts, or either thereof in an excess amount, are used, the mixture is stirred for usually 0.1 hour to five days in a solvent which is inert to the reaction in the presence of a base under from cooling to heating, preferably under cooling. Examples of the solvent used herein are not particularly limited, but include aromatic hydrocarbons such as benzene, toluene and xylene; ethers such as diethylether, tetrahydrofuran, 1,4-dioxane and 1,2-dimethoxyethane; hexane; and a mixture thereof. Examples of the base include organic bases such as lithium diisopropylamide, triethylamine, diisopropylethylamine, potassium hexamethyldisilazide, 1,8-diazabicyclo[5.4.0]-undec-7-ene and n-butyllithium; and inorganic bases such as sodium carbonate, potassium carbonate, cesium carbonate, sodium hydride and potassium tert-butoxide.

[References]

Journal of Organic Chemistry, 1990, 55(20), 5525-5528

Tetrahedron Letters, 2000, 41(33), 6523-6526

(Step 4)

The compound (1) can be prepared by catalytic hydrogenation reaction of the compound (8).

[Formula 16]

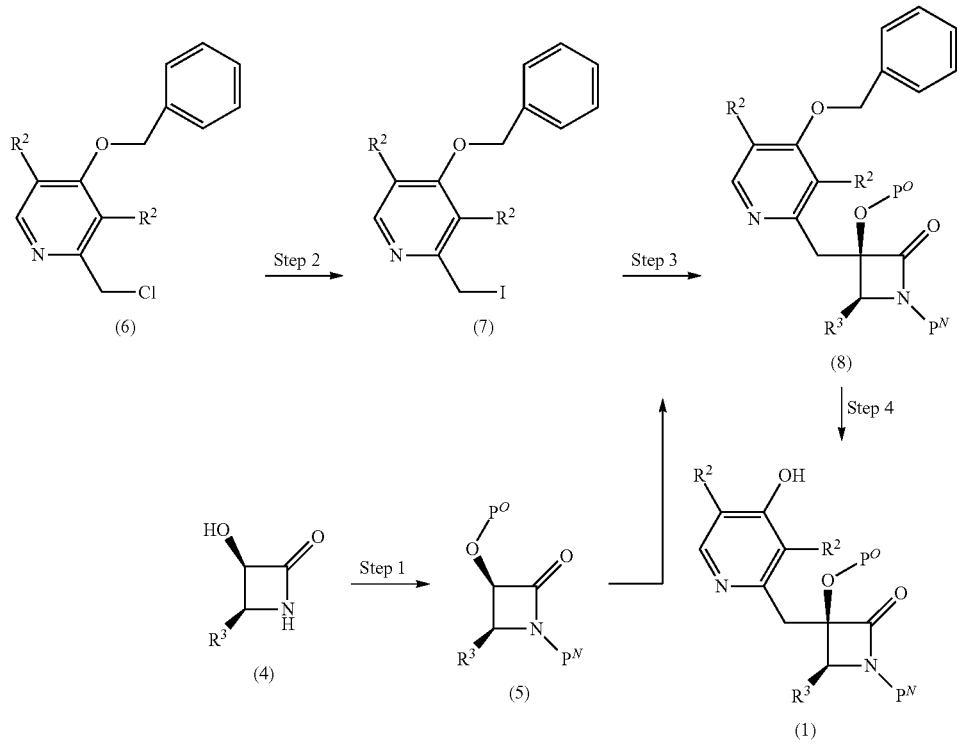

In this reaction, the compound (8) is stirred for one hour to five days in a solvent which is inert to the reaction, such as methanol, ethanol and the like, in the presence of a metal catalyst under hydrogen atmosphere and under from cooling to heating, preferably at a room temperature. Preferred examples of the metal catalyst include palladium catalysts such as palladium on carbon and palladium black; platinum catalysts such as platinum plate and platinum oxide; and nickel catalysts such as reduced nickel and Raney nickel.

[References]

"Organic Functional Group Preparations" written by S. R. Sandler and W. Karo, 2nd edition, Vol. 1, Academic Press Inc., 1991

"Courses in Experimental Chemistry (5th edition)" edited by The Chemical Society of Japan, Vol. 14 (2005) (Maruzen)

(Synthesis of Starting Material 4)

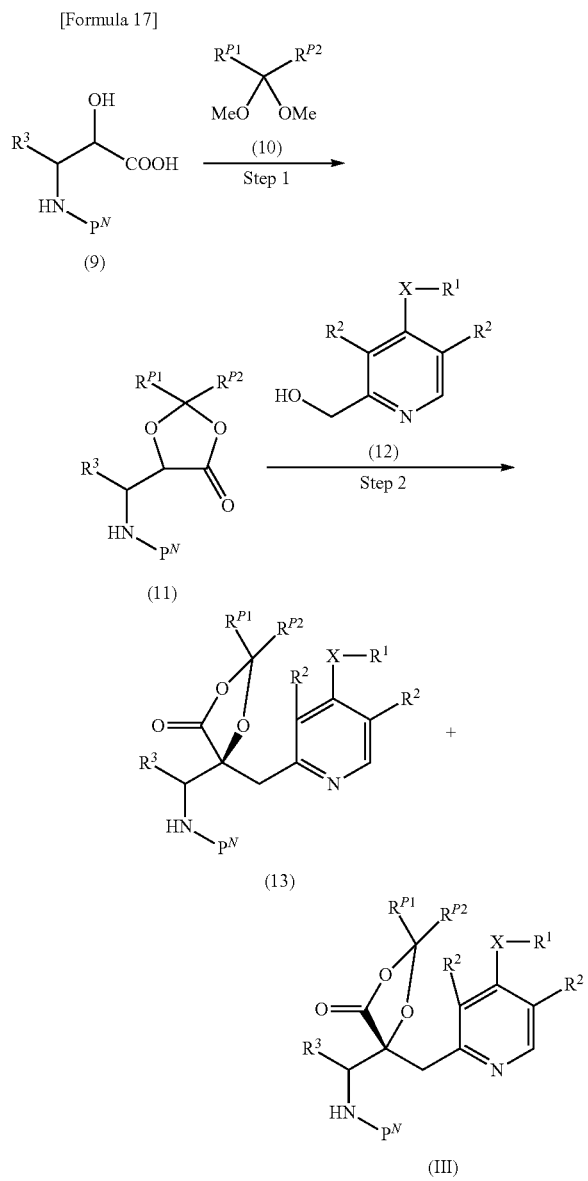

(Step 1)

The compound (11) can be prepared by reacting the compound (9) with the compound (10) in the presence of pyridinium p-toluenesulfonate. In this reaction, a mixture of the compounds (9) and (10) is stirred for one hour to five days in a solvent which is inert to the reaction in the presence of pyridinium p-toluenesulfonate under from cooling to heating, preferably at a temperature of from 40 to 120° C. Examples of the solvent include aromatic hydrocarbons such as benzene, toluene and xylene; ethers such as diethylether, tetrahydrofuran, 1,4-dioxane and 1,2-dimethoxyethane; and halogenated hydrocarbons such as dichloromethane, 1,2-dichloroethane and chloroform.

Examples of $P^N$, the protective group for an amino group, include tert-butoxycarbonyl, methoxymethyl, benzyloxymethyl and the like.

(Step 2)

In this step, the compounds (III) and (13) are prepared by reacting the compound (11) with the compound (12). In this reaction, the compound (11) is treated with lithium diisopropylamide under argon atmosphere. The compound (12) is brominated with $PBr_3$ and is then added to the treated compound (11) to cause a reaction. In this reaction, a mixture of the compounds is stirred for one hour to five days in a solvent which is inert to a reaction under from cooling to heating, preferably under cooling. Examples of the solvent include aromatic hydrocarbons such as benzene, toluene and xylene; ethers such as diethylether, tetrahydrofuran, 1,4-dioxane and 1,2-dimethoxyethane; and halogenated hydrocarbons such as dichloromethane, 1,2-dichloroethane and chloroform.

A compound (III) having a desired configuration can be produced from a starting compound (9) in which the asymmetric carbon attached to —$NHP^N$ has a specific configuration. In some cases, it is preferred to add trimethylchlorosilane at the time of reaction of the compounds (11) and (12), depending on the configuration of the asymmetric carbon attached to —$NHP^N$.

[References]

Molecules, 2004, 9(5), 365-372

Tetrahedron Asymmetry, 1991, 2(7), 705-720

(Synthesis of the Starting Material 5)

[Formula 18]

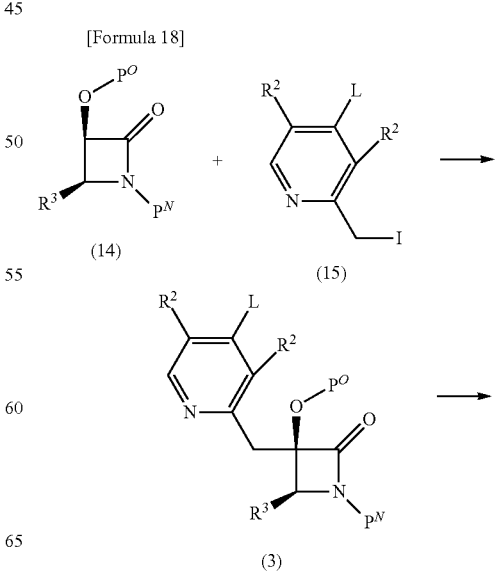

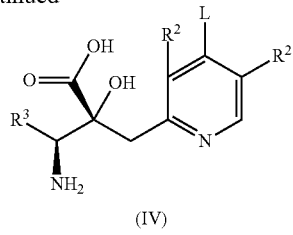

(IV)

The compound (3) can be prepared by reacting the compound (14) with the compound (15). The reaction can be carried out by the same method as in the step 3 of the synthesis of the starting material 3. The compound (3) is subjected to ring-opening and deprotection to produce the compound (IV). The reaction can be carried out by the same method as in the production process 1.

(Synthesis of Other Starting Materials)

A desired starting compound can be produced using any other method known to those skilled in the art. For example, the methods shown in the reaction scheme below can be used to produce the compounds (5-A), (5-B), (1-A), (3-A), (II-D) and (II-E):

[Formula 19]

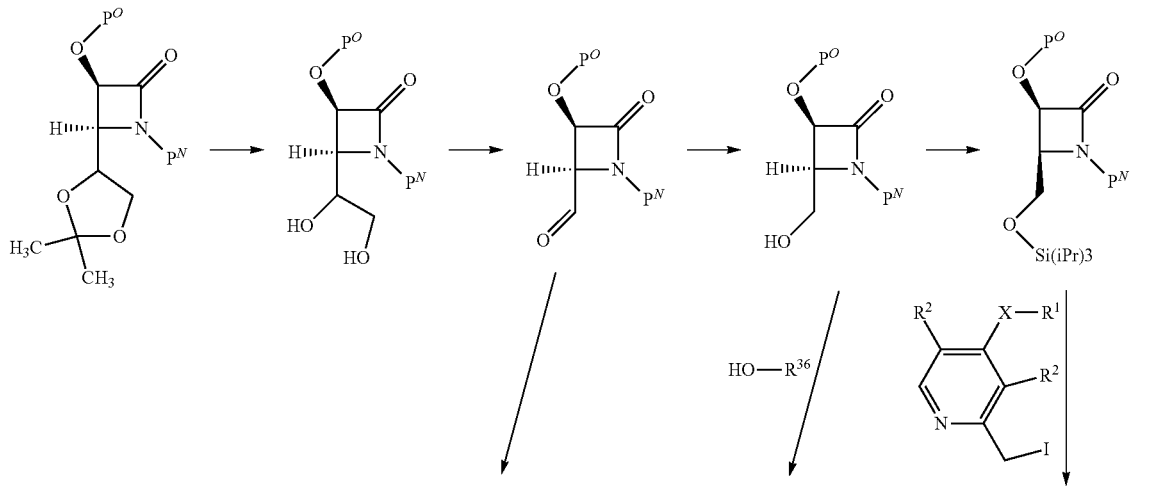

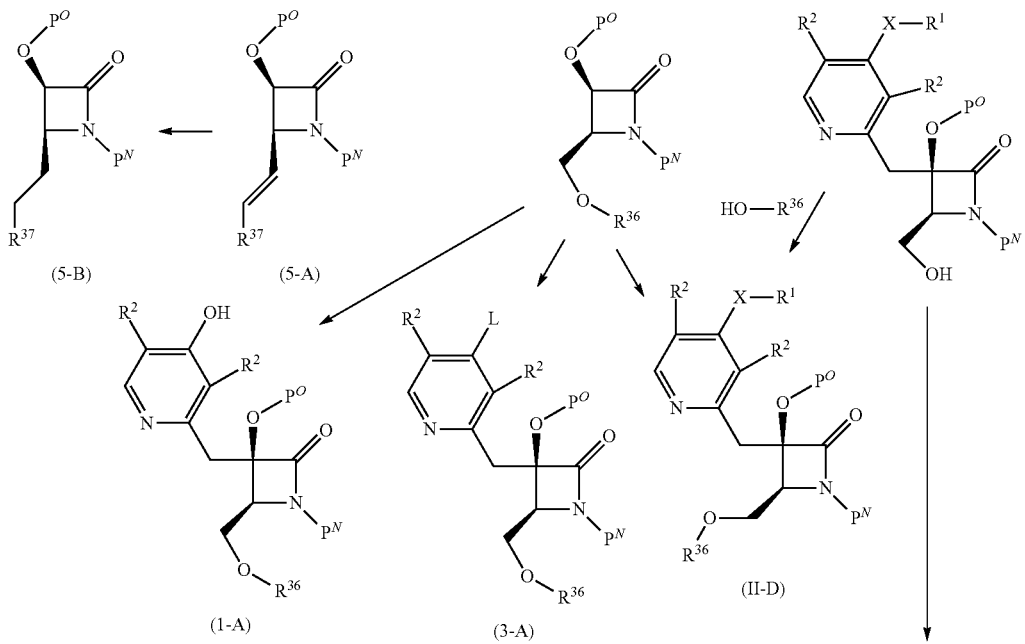

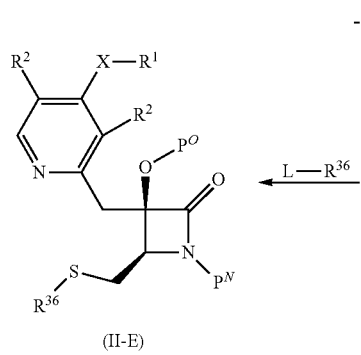

(II-E)

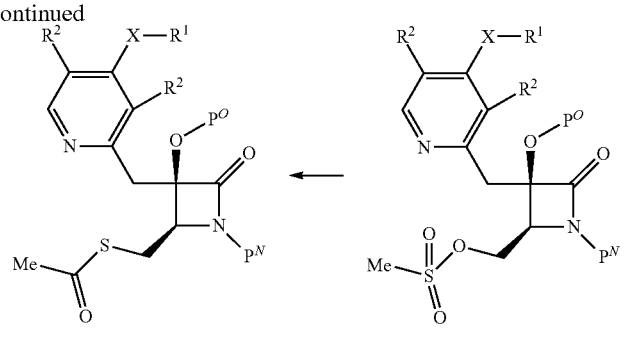

wherein $R^{36}$ is $R^{32}$, $R^{31}$ or -(lower alkylene)-$R^{31}$; and $R^{37}$ is lower alkyl which optionally has one to five substituents selected from the Group $G^1$, -(lower alkylene)-$X^{31}$-(lower alkyl which optionally has one to five substituents selected from the Group $G^1$), $R^{31}$, -(lower alkylene)-$R^{31}$, -(lower alkylene)-$X^{31}$—$R^{31}$, or -(lower alkylene)-$X^{31}$-(lower alkylene)-$R^{31}$.

The compounds represented by Formula (I) are isolated and purified as free compounds, or salts, hydrates, solvates or crystalline polymorphs thereof. Salts of the compound represented by Formula (I) can also be produced by a conventional salt forming reaction.

Isolation and purification is carried out by a general chemical procedure such as extraction, fractional crystallization, and various types of fractional chromatography.

Various isomers can be produced by selection of appropriate starting compounds, or can be separated based on differences in physicochemical properties among the isomers. For example, optical isomers can be prepared by a general optical resolution technique of racemic products (for example, fractional crystallization that converts the compound into diastereomer salts with optically active bases or acids, or chromatography using a chiral column), or can also be produced from appropriate optically active starting compounds.

Pharmacological effects of the compounds represented by Formula (I) were confirmed by the tests described below. Doses of individual test compounds described herein are indicated as corresponding weights of free compounds.

(1) Inhibition of IRAP Activity

Rat epididymal fat pads were homogenized and subjected to ultracentrifugation at 100,000×g for 30 minutes to obtain microsomes containing IRAP. The microsomes (with a total protein content of 55 μg/well) were mixed with a solvent (dimethyl sulfoxide; hereinafter, abbreviated as DMSO (final concentration: 0.1%)) or with each test compound (common ratio: 3; maximum concentration: 10 μM). AVP was then added to the solution to a final concentration of 25 μM, and the resulting solution was allowed to react for one hour at 37° C. An aqueous trifluoroacetic acid (hereinafter, abbreviated as TFA) solution was then added to the solution (final concentration: 1%) to stop the enzymatic reaction. Residual AVP was then determined by mass spectrometry (MALDI-MS). Based on the results, $IC_{50}$ values (nM), i.e. concentrations required for 50% inhibition of decrease in AVP level in the solvent control group, of the individual test compounds were calculated by the logistic regression to evaluate inhibition of IRAP activity. As comparative examples, similar tests were performed with the compounds of the Reference Examples 1 and 2 described below: (2S,3S)-3-amino-2-hydroxy-5-methyl-2-({4-[(trans-4-methylcyclohexyl)oxy]pyridin-2-yl}methyl)hexanoic acid dihydrochloride; and (2S,3R)-3-amino-2-hydroxy-5-methyl-2-({4-[(trans-4-methylcyclohexyl)oxy]pyridin-2-yl}methyl)hexanoic acid hydrochloride, respectively.

The results are shown in Tables 1 and 2, and indicate that the example compounds effectively inhibit AVP degradation by IRAP, i.e. a rat homolog of human P-LAP. The compounds of the Reference Examples 1 and 2 have (2S) configuration, i.e. (S) configuration in position 2, while the compounds represented by Formula (I) have (2R) configuration, i.e. (R) configuration in position 2. The results indicate that the compounds of Reference Examples 1 and 2 have less effect of inhibiting AVP degradation by IRAP in comparison with the example compounds, and suggest that the configuration in position 2 influences on the effect of inhibiting AVP degradation.

(2) Inhibition of Human P-LAP (hP-LAP) Activity

HEK293 cells forced to transiently express hP-LAP (J Biol Chem 1996; 271: 56-61) were prepared by lipofection, homogenized, and then subjected to ultracentrifugation at 100,000×g for 30 minutes. Microsomes containing hP-LAP were thereby prepared. The microsomes (with a total protein content of 0.5 to 1.5 μg/well) were mixed with a solvent (DMSO; final concentration: 0.1%) or with each test compound (common ratio: 3; maximum concentration: 10 μM). AVP was then added to the solution into a final concentration of 25 μM, and the resulting solution was allowed to react for one hour at 37° C. An aqueous TFA solution was then added to the solution (final concentration: 1%) to stop the enzymatic reaction. Residual AVP was then determined by mass spectrometry (MALDI-MS). Based on the results, $IC_{50}$ values (nM), i.e. concentrations required for 50% inhibition of decrease in AVP level in the solvent control group, of the individual test compounds were calculated by logistic regression to evaluate inhibition of human P-LAP (hP-LAP) activity. The results are shown in Tables 1 and 2 and indicate that the example compounds effectively inhibit AVP degradation by hP-LAP.

In the Tables 1 and 2 below, numerals in the column "Ex" indicate Example numbers related to the respective test compounds; "-" indicates an unadministered test; "S-1" indicates the compound of Reference Example 1; and "S-2" indicates the compound of Reference Example 2. The value with the symbol "*" represents a value measured using a dihydrochloride salt of the compound of the Example.

TABLE 1

| Ex | IRAP $IC_{50}$(nM) | hP-LAP $IC_{50}$(nM) |
|---|---|---|
| 1 | 1.5 | 3.2 |
| 2(1) | 1.8 | 4.6 |
| 2(2) | 6.0 | 6.8 |

TABLE 1-continued

| Ex | IRAP IC$_{50}$(nM) | hP-LAP IC$_{50}$(nM) |
|---|---|---|
| 3 | 1.6 | 2.5 |
| 4 | 1.7 | 2.4 |
| 5 | 2.3 | 7.2 |
| 6 | 1.2 | 1.3 |
| 7(1) | 8.9 | 4.5 |
| 7(2) | 200 | — |
| 8 | 170 | — |
| 9 | 1.7 | 8.5 |
| 10 | 4.9 | 16 |
| 11 | 23 | 52 |
| 12 | 30 | 21 |
| 13 | 1.3 | 1.0 |
| 14 | 1.5 | 3.1 |
| 15 | 11 | 7.2 |
| 16 | 8.6 | 14 |
| 17(2) | 11 | 8.6 |
| 18 | 11 | 5.6 |
| 19 | 20 | 34 |
| 20 | 2.4 | 10 |
| 21 | 4.0 | 11 |
| 22 | 250 | — |
| 23 | 8.2 | 13 |
| 24 | 6.2 | 4.0 |
| 25 | 2.7 | 1.8 |
| 26 | 5.2 | 1.9 |
| 27 | 9.5 | 8.9 |
| 28 | 1.2 | 2.9 |
| 29 | 2.2 | 4.1 |
| 30 | 11 | 2.7 |
| 31 | 27 | 20 |
| 32 | 120 | 200 |
| 33 | 2.5 | 1.5 |
| 34 | 48 | 33 |
| 35 | 10 | 15 |
| 36 | 4.9 | 2.6 |
| 37 | 2.9 | 7.8 |
| 38 | 4.1 | 10 |
| 39 | 33 | 17 |
| 40 | 8.0 | 3.0 |
| 41 | 1.8 | 4.2 |
| 42 | 3.8 | 3.8 |
| 43 | 1.9 | 2.8 |
| 44 | 1.9 | 1.8 |
| 45 | 0.42 | 0.89 |
| 46 | 12 | 4.0 |
| 47 | 2.0 | 1.5 |
| 48 | 5.2 | 1.6 |
| 49 | 4.1 | 2.9 |
| 50 | 14 | 13 |
| 51 | 13 | 16 |
| 52 | 8.8 | 4.0 |
| 53 | 290 | — |
| 54 | 10 | 10 |
| 55 | 1.9 | 2.1 |
| 56 | 1.8 | 2.0 |
| 57 | 130 | — |
| 58 | 1.3 | 3.0 |
| 59 | 1.7 | 4.4 |
| 60 | 2.0 | 1.6 |
| 61 | 1.9 | 1.8 |
| 62 | 290 | — |
| 63 | 34 | 63 |
| 64 | 7.6 | 4.6 |
| 65 | 39 | 22 |
| 66 | 1.9 | 2.3 |
| 67 | 1.9 | 1.8 |
| 68 | 5.4 * | 22 * |
| 69 | 7.3 | 8.6 |
| 70 | 13 | 17 |
| 71 | 15 | 45 |
| 72 | 0.77 | 0.94 |
| 73 | 1.1 | 1.6 |
| 74 | 5.3 | 9.8 |
| 75 | 1.2 | 2.3 |
| 76 | 4.9 | 17 |

TABLE 1-continued

| Ex | IRAP IC$_{50}$(nM) | hP-LAP IC$_{50}$(nM) |
|---|---|---|
| 77 | 8.8 | 2.6 |
| 78 | 6.7 | 4.0 |
| 79 | 33 | 30 |
| 80 | 6.4 | 6.5 |
| 81 | 6.5 | 3.8 |
| 82 | 1.9 | 3.6 |
| 83 | 4.3 | 24 |
| 84 | 2.7 | 3.7 |
| 85 | 110 | — |
| 86 | 6.6 | 5.9 |
| 87 | 1.4 | 1.3 |
| 88 | 2.4 | 12 |
| 89 | 12 | 9.0 |
| 90 | 1.0 | 0.95 |
| 91 | 15 | 16 |
| 92 | 1.1 | 1.2 |
| 93 | 4.1 | 5.2 |
| 94 | 6.8 | 9.1 |
| 95 | 1.5 | 1.5 |
| 96 | 8.7 | 6.9 |
| 97 | 2.8 | 3.0 |
| 98 | 4.9 | 3.2 |
| 99 | 7.4 | 43 |
| 100 | 2.0 | 3.0 |
| 101 | 200 | — |
| 102 | 6.5 | 7.2 |

TABLE 2

| Ex | IRAP IC$_{50}$(nM) | hP-LAP IC$_{50}$(nM) |
|---|---|---|
| 103 | 1.0 | 1.4 |
| 104 | 21 | 26 |
| 105 | 0.62 | 1.9 |
| 106 | 2.5 | 8.7 |
| 107 | 1.7 | 4.5 |
| 108 | 2.1 | 4.5 |
| 109 | 35 | 74 |
| 110 | 9.8 | 46 |
| 111 | 3.2 | 17 |
| 112 | 26 | 49 |
| 113 | 12 | 32 |
| 114 | 13 | 84 |
| 115 | 8.1 | 38 |
| 116 | 4.0 | 21 |
| 117 | 15 | 7.9 |
| 118 | 35 | 120 |
| 119 | 3.3 | 13 |
| 120 | 3.7 | 9.7 |
| 121 | 1.6 | 13 |
| 122 | 4.8 | 26 |
| 123 | 6.1 | 35 |
| 124 | 0.92 | 2.9 |
| 125 | 0.90 | 5.2 |
| 126 | 1.5 | 4.2 |
| 127 | 2.0 | 10 |
| 128 | 6.5 | 6.0 |
| 129 | 55 | 98 |
| 130 | 3.3 | 51 |
| 131 | 0.91 | 4.9 |
| 132 | 1.8 | 5.2 |
| 133 | 1.0 | 7.1 |
| 134 | 19 | 27 |
| 135 | 15 | 31 |
| 136 | 4.8 | 5.5 |
| 137 | 3.8 | 13 |
| 138 | 14 | 18 |
| 139 | 8.5 | 15 |
| 140 | 3.0 | 14 |
| 141 | 2.0 | 21 |
| 142 | 2.6 | 21 |
| 143 | 1.9 | 13 |
| 144 | 2.9 | 21 |

TABLE 2-continued

| Ex | IRAP IC$_{50}$(nM) | hP-LAP IC$_{50}$(nM) |
|---|---|---|
| 145 | 0.77 | 1.3 |
| 146 | 19 | 24 |
| S-1 | 2,400 | — |
| S-2 | 5,200 | — |

(3) Antidiuresis Test in Water-Loaded Rats (Oral Administration)

Individual test compounds were dissolved in a vehicle (containing 10% N,N-dimethylformamide, 10% propylene glycol, and 80% distilled water), and the resulting solution was orally administered to the rats. Rats in a vehicle control group were administered only with the vehicle. One hour after the administration, 30 ml/kg of distilled water was orally administered to the rats. One hour after the water loading, the urine volume was measured (urine volumes less than 0.3 ml were considered as 0 ml) to calculate the ratio of the urine volume (urinary excretion rate) to the amount of water load.

The inhibition of urination (%) in the compound-administered group in comparison with the vehicle control group was calculated in accordance with the following expression (each group consisted of four to five rats):

Inhibition of urination (%)={[(urinary excretion rate in the vehicle control group)−(urinary excretion rate in the compound-administered group]/(urinary excretion rate in the vehicle control group)}×100

Table 3 shows inhibition of urination (%) observed when some example compounds included in compounds of Formula (I) were respectively administered in the amount of 3 mg/kg. The value with a symbol "*" represents inhibition (%) observed when 1 mg/kg of the corresponding compound was administered.

TABLE 3

| Ex | Inhibition (%) |
|---|---|
| 1 | 88 |
| 3 | 59 |
| 4 | 93 |
| 5 | 90 |
| 6 | 96 |
| 9 | 82 |
| 18 | 52 |
| 20 | 94 |
| 28 | 92 |
| 29 | 93 |
| 41 | 55 |
| 55 | 91 |
| 83 | 80 |
| 84 | 64 |
| 88 | 89 |
| 92 | 61 |
| 103 | 92* |
| 105 | 98 |
| 110 | 57 |
| 111 | 57 |
| 119 | 97 |
| 139 | 90 |
| 143 | 100 |

The results shown above suggest that the compounds represented by Formula (I) inhibit P-LAP (IRAP), i.e. an aminopeptidase that cleaves AVP, to inhibit degradation of endogenous AVP, which results in a reduced urine production.

(4) Antidiuresis Test in Continuously Hydrated Rats with Additional Water Loading (Oral Administration)

Male Wistar rats were used in the test. Initially, water load with 15 mL/kg of distilled water was forcedly administered to the rats. Every 30 minutes after loading water, urine volume collected during 30 minutes was measured and distilled water was forcedly administered to the rats in an amount equal to the urine volume excreted during the last 30 minutes. This water load procedure was repeated to the termination of the test to maintain the diuretic state. After the urine volume every 30 minutes became stable, individual example compounds included in compounds of Formula (I) (EX-a: 100 mg/kg of the compound of Example 17(1); or EX-b: 30 mg/kg of the compound of Example 105) or dDAVP (30 µg/kg) dissolved in a vehicle (containing 10% N,N-dimethylformamide, 10% propylene glycol, and 80% distilled water; 3 mL/kg) or in distilled water was orally administered. The individual groups were further divided into two subgroups, and additional distilled water of 15 mL/kg load was forcedly administered to one of the subgroups two times, i.e. at two hours and three hours after the administration. For comparison, the Vehicle group administered only with the vehicle was also subjected to the additional administrations of water load. Blood was collected from a half of the rats in each group subjected to additional administrations of water load, at three hours after the administration (immediately before the second additional water load) and from the other half at four hours after the administration, and plasma sodium levels were measured with an automatic electrolyte analyzer to determine the plasma sodium levels at three hours and four hours after the administration, respectively (each group consisted of seven to eight rats). Changes in the urine volume in individual groups are shown in FIG. 1, and the plasma sodium levels of the group administered with additional water loads are shown in Table 4.

TABLE 4

|  | 3 hours after administration | 4 hours after administration |
|---|---|---|
| Vehicle group | 140.6 ± 0.4 mmol/L | 139.6 ± 0.2 mmol/L |
| EX-a group | 134.9 ± 0.4 mmol/L | 133.2 ± 0.7 mmol/L |
| EX-b group | 140.4 ± 0.4 mmol/L | 139.2 ± 0.5 mmol/L |
| dDAVP group | 132.0 ± 0.4 mmol/L | 128.0 ± 0.3 mmol/L |

In EX-a, EX-b, and dDAVP groups without additional water loads, urine production was rapidly reduced after administration of the test compound and was almost stopped after two hours of the administration, and such an effect was maintained until four hours after the administration. In contrast, in the EX-a and EX-b groups with additional water loads, urine production was reduced as a result of administration of the individual test compounds but was resumed after administration of the additional water loads. After four hours of the administration of the test material, urine volumes were recovered up to an approximately half amount of that of the Vehicle group, while urine production was not resumed in the groups administered with dDAVP even after administration of the additional water loads (see FIG. 1).

In the Vehicle, EX-a and EX-b groups, the plasma sodium levels slightly decreased after three hours and four hours of the administration, while more significant decreases in the plasma sodium level were observed in the dDAVP group in comparison with the Vehicle, EX-a and EX-b groups. It is assumed that such a result reflects the decreased plasma sodium level due to the body fluid retention caused by the additional water loads (see Table 4).

The plasma AVP level is strictly regulated by plasma osmolality. It is known that an excessive water intake reduces AVP production and secretion to cause diuresis. The results indicate that the example compounds have an antidiuretic effect based on P-LAP inhibition by endogenous AVP and suggest that such compounds have a low impact on a plasma sodium level, even in a case of an excessive water intake, because decreased endogenous AVP level reduces the antidiuretic effect. Therefore, the compound represented by Foiinula (I) is expected to involve lower risks of hyponatremia, unlike V2 receptor agonists.

A pharmaceutical composition containing one or more compounds represented by Formula (I) or salts thereof as an active ingredient can be prepared by a common method using an excipient generally used in the art, that is, an excipient or a carrier for a phallnaceutical.

Such a pharmaceutical composition can be administered in any form, such as oral administration of tablets, pills, capsules, granules, powder, or liquid, and parental administration by intraarticular, intravenous, or intramuscular injection, suppositories, transdermal liquid, transdermal patches, transmucosal liquid, transmucosal patches, or inhalations.

A solid composition for oral administration may be in a form of, for example, a tablet, powder, and granules. Such a solid composition contains one or more active ingredients mixed with at least one inactive excipient. The composition may contain an inactive additive, for example, a lubricant, a disintegrating agent, a stabilizing agent, and a solubilizing agent, in accordance with conventional techniques. Tablets or pills may be coated with sugar or a film of gastric or enteric soluble material, if necessary.

A liquid composition for oral administration includes a pharmaceutically acceptable emulsion, solution, suspension, syrup, and elixir, and contains a common inactive diluent, for example, purified water or ethanol. The liquid composition may contain an additive such as a solubilizing agent, a moisturizer, and a suspending agent; a sweetening agent; a flavoring agent; an aromatic agent; and a preservative, in addition to the inactive diluent.

An injection for parenteral administration contains aqueous or non-aqueous sterile solvent, suspension, or emulsion. Examples of the aqueous solvent include distilled water for injection and physiological saline. Examples of the non-aqueous solvent include alcohols such as ethanol. The composition may further contain a tonicity agent, a preservative, a moisturizer, an emulsifier, a dispersant, a stabilizer, or a solubilizing agent. These components are sterilized by filtration through a bacteria retentive filter, blending a bactericide, or irradiation, for example. These components may also be formulated into a sterile solid composition to be dissolved or suspended in a sterile solvent for injection before use.

If the compound represented by Formula (I) is orally administered, an appropriate daily dose is approximately 0.001 to 100 mg/kg, preferably 0.1 to 30 mg/kg, more preferably 0.1 to 10 mg/kg, per body weight, and is administered daily in a single dose or in two to four separate doses. If the compound is intravenously administered, an appropriate daily dose is approximately 0.0001 to 10 mg/kg per body weight, and is administered daily in a single dose or in separate doses. If the compound is transmucosally administered, an appropriate daily dose is approximately 0.001 to 100 mg/kg per body weight, and is administered daily in a single dose or in separate doses. The dose is appropriately determined depending on, for example, the symptom, age, and sex of individual patient. If the compound represented by Formula (I) is used for prevention or treatment of nocturia, it may be preferably administered once daily after supper or before going to bed, for example.

The pharmaceutical composition of the present invention contains one or more compounds represented by Formula (I) or salts thereof in an amount of 0.01 to 100% by weight, in one embodiment 0.01 to 50% by weight, as an active ingredient, while the amount may vary depending on a route of administration, dosage form, site of administration, and the type of excipient or additive.

The compound represented by Formula (I) may be used in combination with various therapeutic agents or preventive agents for diseases to which the compound of Formula (I) is assumed to be effective. The compound represented by Formula (I) and the agent to be used in combination therewith may be administered simultaneously, sequentially or at desired time intervals. The preparation to be simultaneously administered may be combined with the compound of Formula (I) or formulated as a separate preparation.

EXAMPLES

Hereinbelow, the production processes for the compound represented by Formula (I) will be described in more details with reference to Examples. The present invention is not limited to the compounds described in the Examples. Production processes for starting compounds will be described in Production Examples and production processes for comparative compounds will be described in Reference Examples. The production process for the compound represented by Formula (I) should not be limited to the processes described in the specific Examples below, but the compound represented by Formula (I) can be prepared by a combination of such production processes or by any method obvious to those skilled in the art.

As used herein, the unit "mol/L" for a concentration is abbreviated as "M" for expediency. For example, "1 M aqueous sodium hydroxide solution" refers to 1 mol/L aqueous sodium hydroxide solution.

In the Examples, Production Examples and Tables below, the following abbreviations may be used:

DMF: N,N-dimethylformamide; AcOEt: ethyl acetate; AcOH: acetic acid; THF: tetrahydrofuran; MeCN: acetonitrile; EtOH: ethanol; MeOH: methanol; DOX: 1,4-dioxane; DMSO: dimethylsulfoxide; Et$_3$N: triethylamine; DIPEA: diisopropylethylamine; Pd(OAc)$_2$: palladium acetate; Pd/C: palladium on carbon; NaBH$_4$: sodium borohydride; LDA: lithium diisopropylamide; CMBP: (cyanomethylene)tri-n-butylphosphorane; CMMP: (cyanomethylene)trimethylphosphorane; ODS: octadecylsilyl; PEx: Production Example number; Ex: Example number; REx: Reference Example number; PSyn: the Production Example number in which a compound is prepared by the same method; Syn: Example number in which a compound is prepared by the same method; Str: chemical structural formula (Me: methyl, Et: ethyl, cHex: cyclohexyl, Boc: tert-butoxycarbonyl, Ph: phenyl, Bn: benzyl, tBu: tert-butyl, TIPS: triisopropylsilyl, TBDMS: tert-butyl(dimethyl)silyl); DATA: physicochemical data, ESI+: m/z value in mass spectrometry (electrospray ionization (ESI); representing [M+H]$^+$ unless otherwise specified); APCI/ESI+: APCI/ESI-MS (atmospheric-pressure chemical ionization (APCI); APCI/ESI indicates simultaneous measurement by APCI and ESI; representing [M+H]$^+$ unless otherwise specified); EI: m/z value in mass spectrometry (electron ionization (EI); representing [M]$^+$ unless otherwise specified); and CI+: m/z value in mass spectrometry (chemical ionization (CI); representing [M+H]+ unless otherwise specified).

The symbol "*" in a chemical structural formula indicates that the corresponding compound is a single isomer having the indicated configuration. The symbol "#" indicates that the corresponding compound has the indicated steric configuration and is a mixture of isomers which have (R) and (S) configurations, respectively, in an asymmetric carbon with the steric configuration not indicated. The symbol "#2" indicates that the corresponding compound has the indicated configuration and is a mixture of isomers which have (R) and (S) configurations, respectively, in the sulfoxide moiety. The symbol "$" indicates that the corresponding compound has the indicated configuration and is a mixture of exo-diastereomers in the bicyclo[2.2.1]hept-2-yl moiety. "HCl" in a structural formula indicates that the compound is a monohydrochloride, "2 HCl" indicates that the compound is a dihydrochloride, and "3 HCl" indicates that the compound is a trihydrochloride. A double bond represented with two crossed lines in a chemical formula indicates that the double bond forms an E isomer or Z isomer, or a mixture thereof.

In the present specification, a nomenclature software such as ACD/Name (registered trademark, Advanced Chemistry Development, Inc.) may be used for nomenclature of compounds in some cases.

RINT-TTRII was used in the measurement of powder X-ray diffraction described herein. The diffractometry was carried out under the following conditions: X-ray tube: Cu; tube current: 300 mA; tube voltage: 50 kV; sampling width: 0.020°; scanning speed: 4°/min; wavelength: 1.54056 Å; range of diffraction angle in measurement (2θ): 2.5 to 40°. In powder X-ray diffraction, the crystal lattice distance and the entire pattern are important for the identification of crystals in view of the characteristics of the data. A diffraction angle and intensity may slightly vary depending on the direction of crystal growth, the particle size, and the measuring conditions, and should not be interpreted strictly. As used herein, the diffraction angle (2θ) in the powder X-ray diffraction pattern is interpreted with a margin of error generally acceptable in the measurement, for example, a margin of error of ±0.2°.

Example 1

Under argon atmosphere, CMBP (0.353 ml) was added to a mixture of (3R,4S)-3-[(4-hydroxypyridin-2-yl)methyl]-4-isobutyl-3-(methoxymethoxy)-1-(methoxymethyl)azetidin-2-one (150 mg), 2-cyclopropylethanol (116 mg) and toluene (1.5 ml) and the mixture was stirred at 150° C. for 1 hour under microwave irradiation. The resulting reaction mixture was allowed to cool to room temperature and subsequently purified by silica gel column chromatography (hexane/AcOEt). 6 M Aqueous sodium hydroxide solution (1.5 ml) was added to a mixture of the obtained compound and MeOH (1.5 ml) and the mixture was stirred at 50° C. for 2 hours. The resulting reaction mixture was allowed to cool to room temperature and subsequently concentrated under reduced pressure. A mixture of the resulting residue and DOX (1.5 ml) was cooled with an ice-water bath, subsequently 9 M hydrochloric acid (1.5 ml) was added thereto and the mixture was stirred at 50° C. for 1 hour. The resulting reaction mixture was allowed to cool to room temperature and subsequently concentrated under reduced pressure. The resulting residue was purified by ODS column chromatography (MeCN/0.1% aqueous formic acid solution). After adding MeOH and MeCN to the obtained compound, the solvent was distilled off from the obtained mixture to give (2R,3S)-3-amino-2-{[4-(2-cyclopropylethoxy)pyridin-2-yl]methyl}-2-hydroxy-5-methylhexanoic acid (27 mg) as a solid.

Example 2

6 M Hydrochloric acid (1.1 ml) was added to a mixture of (3R,4S)-3-{[4-(2-cyclopropylethoxy)pyridin-2-yl]methyl}-4-[(3-cyclopropylpropoxy)methyl]-3-(methoxymethoxy)-1-(methoxymethyl)azetidin-2-one (121 mg) and THF (5 ml) and the mixture was stirred at 60° C. for 1 hour. The resulting reaction mixture was allowed to cool to room temperature and subsequently concentrated under reduced pressure. The resulting residue was purified by ODS column chromatography (MeCN/0.1% aqueous formic acid solution) to give (1) (2R,3S)-3-amino-4-[(4-chlorohexyl)oxy]-2-{[4-(2-cyclopropylethoxy)pyridin-2-yl]methyl}-2-hydroxybutanoic acid (26.8 mg) and (2) (2R,3S)-3-amino-2-{[4-(2-cyclopropylethoxy)pyridin-2-yl]methyl}-2-hydroxy-4-[(4-hydroxyhexyl)oxy]butanoic acid (31.7 mg) each as a solid.

Example 3

6 M Aqueous sodium hydroxide solution (1.2 ml) was added to a mixture of (3R,4S)-3-{[4-(cyclohexyloxy)pyridin-2-yl]methyl}-4-isobutyl-3-(methoxymethoxy)-1-(methoxymethyl)azetidin-2-one (85 mg) and MeOH (1.2 ml) and the mixture was stirred at 70° C. for 4.5 hours. After cooling the resulting reaction mixture with an ice-water bath, concentrated hydrochloric acid (1 ml) was added thereto. The resulting reaction mixture was stirred at room temperature for 13 hours and subsequently at 50° C. for 1.5 hours. The resulting reaction mixture was concentrated under reduced pressure, and the residue was purified by ODS column chromatography (MeCN/0.1% aqueous formic acid solution). The obtained compound was dissolved in a mixture of MeCN and an excess amount of 1 M hydrochloric acid, the solvent was distilled off under reduced pressure to give (2R,3S)-3-amino-2-{[4-(cyclohexyloxy)pyridin-2-yl]methyl}-2-hydroxy-5-methylhexanoic acid dihydrochloride (54.6 mg) as a solid.

Example 4

6 M Aqueous sodium hydroxide solution (0.5 ml) was added to a mixture of (3R,4 S)-4-isobutyl-3-(methoxymethoxy)-1-(methoxymethyl)-3-{[4-(spiro[2.5]octa-6-yloxy)pyridin-2-yl]methyl}azetidin-2-one (40 mg) and MeOH (0.5 ml) and the mixture was stirred at 70° C. for 5 hours. After cooling the resulting reaction mixture with an ice-water bath, 6 M hydrochloric acid (0.5 ml) was added thereto and concentrated under reduced pressure. 1 M Hydrochloric acid (1 ml) and MeCN (0.5 ml) were added to the resulting residue and the mixture was stirred at room temperature for 16 hours. The obtained mixture was purified by ODS column chromatography (MeCN/0.1% aqueous formic acid solution) to give (2R,3S)-3-amino-2-hydroxy-5-methyl-2-{[4-(spiro[2.5]octa-6-yloxy)pyridin-2-yl]methyl}hexanoic acid (8.2 mg) as a solid.

Example 5

Trifluoroacetic acid (0.5 ml) was added to a mixture of (3R,4R)-4-{[(cyclopropylmethyl)sulfanyl]methyl}-3-

(methoxymethoxy)-1-(methoxymethyl)-3-({4-[(trans-4-methylcyclohexyl)oxy]pyridin-2-yl}methyl)azetidin-2-one (39.7 mg) and CH$_2$Cl$_2$ (0.5 ml) and the mixture was stirred at room temperature overnight. The resulting reaction mixture was concentrated under reduced pressure, MeOH (1.5 ml) and 6 M aqueous sodium hydroxide solution (1.5 ml) were added to the residue and the mixture was stirred at room temperature overnight. 1 M Hydrochloric acid was added to the resulting reaction mixture to adjust pH to about 7 and the mixture was concentrated under reduced pressure. The resulting residue was purified by ODS column chromatography (MeCN/0.1% aqueous formic acid solution) to give (2R,3R)-3-amino-4-[(cyclopropylmethypsulfanyl)-2-hydroxy-2-({4-[(trans-4-methylcyclohexyl)oxy]pyridin-2-yl}methyl)butanoic acid (18.4 mg) as a solid.

Example 6

6 M Hydrochloric acid (1 ml) was added to (3R,4S)-4-isobutyl-3-(methoxymethoxy)-1-(methoxymethyl)-3-({4-[trans-4-methylcyclohexypoxy]pyridin-2-yl}methyl)azetidin-2-one (30 mg) and the mixture was stirred at 60° C. for 3 hours. The resulting reaction mixture was concentrated under reduced pressure, and the residue was purified by ODS column chromatography (MeCN/0.1% aqueous formic acid solution). An excess amount of 1 M hydrochloric acid was added to the obtained compound and the solvent was distilled off under reduced pressure to give (2R,3S)-3-amino-2-hydroxy-5-methyl-2-({4-[(trans-4-methylcyclohexyl)oxy]pyridin-2-yl}methyl)hexanoic acid dihydrochloride (25 mg) as a solid.

Example 7

6 M Aqueous sodium hydroxide solution (2 ml) was added to a mixture of (3R,4S)-4-isobutyl-3-(methoxymethoxy)-1-(methoxymethyl)-3-{[4-(1-phenylethoxy)pyridin-2-yl]methyl}azetidin-2-one (93 mg) and MeOH (4 ml) and the mixture was stirred at 60° C. for 6 hours. The resulting reaction mixture was concentrated under reduced pressure. DOX (4 ml) and 1 M hydrochloric acid (20 ml) were added to the resulting residue and the mixture was stirred at room temperature overnight. The resulting reaction mixture was concentrated under reduced pressure and the residue was purified by ODS column chromatography (MeCN/0.1% aqueous formic acid solution) to give (1) (2R,3S)-3-amino-2-hydroxy-5-methyl-2-{[4-(1-phenylethoxy)pyridin-2-yl]methyl}hexanoic acid (20.4 mg) and (2) (2R,3S)-3-amino-2-hydroxy-2-[(4-hydroxypyridin-2-yl)methyl]-5-methylhexanoic acid (13.3 mg) each as a solid.

Example 8

Hydrogen chloride (4 M DOX solution, 0.6 ml) was added to a mixture of tert-butyl {(1S)-1-[(4R)-2,2-dimethyl-4-({4-[(trans-4-methylcyclohexyl)oxy]pyridin-2-yl}methyl)-5-oxo-1,3-dioxolan-4-yl]-3-methylbutyl}carbamate (100 mg) and DOX (1 ml) and the mixture was stirred at room temperature for 4.5 hours. The resulting reaction mixture was concentrated under reduced pressure and the residue was purified by ODS column chromatography (MeCN/0.1% aqueous formic acid solution). CH$_2$Cl$_2$ (1 ml) and hydrogen chloride (4 M DOX solution, 0.2 ml) were added to the obtained compound. The solvent was distilled off from the obtained mixture under reduced pressure to give (5R)-5-[(1S)-1-amino-3-methylbutyl]-2,2-dimethyl-5-({4-[(trans-4-methylcyclohexyl)oxy]pyridin-2-yl}methyl)-1,3-dioxolan-4-one dihydrochloride (72 mg) as a solid.

Example 9

A mixture of (3R,4S)-4-(2-cyclobutylethyl)-3-{[4-(2-cyclopropylethoxy)pyridin-2-yl]methyl}-3-(methoxymethoxy)-1-(methoxymethyl)azetidin-2-one (212 mg), THF (5 ml) and 6 M hydrochloric acid (1 ml) was stirred at 60° C. for 1 hour. The resulting reaction mixture was allowed to cool to room temperature and subsequently concentrated under reduced pressure. The resulting residue was purified by ODS column chromatography (MeCN/0.1% aqueous formic acid solution) to give (2R,3S)-3-amino-5-cyclobutyl-2-{[4-(2-cyclopropylethoxy)pyridin-2-yl]methyl}-2-hydroxypentanoic acid (124 mg) as a solid.

Example 10

Under argon atmosphere, a mixture of (2R,3S)-3-amino-3-(4-bromophenyl)-2-{[4-(cyclohexyloxy)pyridin-2-yl]methyl}-2-hydroxypropanoic acid (191 mg), zinc cyanide (250 mg), bis(tri-tert-butylphosphine)palladium (0) (87 mg), zinc (5 mg) and N,N-dimethylacetamide (3.8 ml) was stirred at 95° C. overnight. After cooling the resulting reaction mixture to room temperature, water was added thereto and the mixture was extracted twice with CH$_2$Cl$_2$. The obtained organic layer was combined, washed sequentially with water and a saturated aqueous sodium chloride solution and dried over anhydrous magnesium sulfate. The solvent was distilled off under reduced pressure. Water was added to the resulting residue, and the insoluble materials were removed by filtration and the filtrate was purified by ODS column chromatography (MeCN/0.1% aqueous formic acid solution). An excess amount of 1 M hydrochloric acid was added to the obtained compound and the solvent was distilled off under reduced pressure to give (2R,3S)-3-amino-3-(4-cyanophenyl)-2-{[4-(cyclohexyloxy)pyridin-2-yl]methyl}-2-hydroxypropanoic acid dihydrochloride (76 mg) as a solid.

Example 11

Under argon atmosphere, a mixture of (2R,3S)-3-amino-4-(2-bromophenoxy)-2-{[4-(cyclohexyloxy)pyridin-2-yl]methyl}-2-hydroxybutanoic acid (141 mg), zinc cyanide (345 mg), bis(tri-tert-butylphosphine)palladium (0) (150 mg), zinc (19 mg) and N,N-dimethylacetamide (2.8 ml) was stirred at 95° C. for 8 hours. Water was added to the resulting reaction mixture and the mixture was extracted twice with CH$_2$Cl$_2$. The obtained organic layers were combined, dried over anhydrous magnesium sulfate and the solvent was distilled off under reduced pressure. 1 M Hydrochloric acid and AcOEt were added to the resulting residue. The organic layer and the aqueous layer were separated and the obtained aqueous layer was purified by ODS column chromatography (MeCN/0.1% aqueous formic acid solution) to give (2R,3S)-3-amino-4-(2-cyanophenoxy)-2-{[4-(cyclohexyloxy)pyridin-2-yl]methyl}-2-hydroxybutanoic acid (58 mg) as a solid.

Example 12

A mixture of (15S,16R)-15-amino-16-hydroxy-2,13-dioxa-19-azabicyclo[16.3.1]docosa-1(22),7,18,20-tetraene-16-carboxylic acid dihydrochloride (30 mg), EtOH (10 ml) and 10% Pd/C (50% water content, 50 mg) was stirred at room temperature for 3 hours under hydrogen atmosphere of 3 atm. Celite was added to the resulting reaction mixture, and the insoluble materials were removed by filtration. The obtained filtrate was concentrated under reduced pressure and the residue was purified by ODS column chromatography (MeCN/0.1% aqueous folinic acid solution). An excess amount of 1 M hydrochloric acid was added to the obtained compound and the solvent was distilled off under reduced pressure to give (15S,16R)-15-amino-16-hydroxy-2,13-dioxa-19-azabicyclo[16.3.1]docosa-1(22),18,20-toriene-16-carboxylic acid dihydrochloride (18 mg) as a solid.

Example 13

Piperidine (0.11 ml) was added to a mixture of (2R,3S)-3-amino-2-[(4-chloropyridin-2-yl)methyl]-2-hydroxy-5-methylhexanoic acid (30 mg) and water (0.6 ml) and the mixture was stirred at 130° C. for 1 hour under microwave irradiation. The resulting reaction mixture was cooled with an ice-water bath, subsequently 1 M hydrochloric acid (1.2 ml) was added thereto and purified by ODS column chromatography (MeCN/0.1% aqueous formic acid solution). An excess amount of 1 M hydrochloric acid was added to the obtained compound and the solvent was distilled off under reduced pressure to give (2R,3S)-3-amino-2-hydroxy-5-methyl-2-{[4-(piperidin-1-yppyridin-2-yl]methyl}hexanoic acid dihydrochloride (25.6 ml) as a solid.

Example 14

CMBP (0.23 ml) was added to a mixture of (3R,4S)-3-[(4-hydroxypyridin-2-yl)methyl]-4-isobutyl-3-(methoxymethoxy)-1-(methoxymethyl)azetidin-2-one (100 mg), 1-naphthylmethanol (140 mg) and toluene (2 ml) and the mixture was stirred at 110° C. overnight. The resulting reaction mixture was concentrated under reduced pressure. DOX (1 ml) and 6 M hydrochloric acid (1 ml) were added to the resulting residue and the mixture was stirred at 60° C. overnight. Water was added to the resulting reaction mixture and the mixture was washed with AcOEt. The obtained aqueous layer was concentrated under reduced pressure. The resulting residue was purified by ODS column chromatography (MeCN/0.1% aqueous formic acid solution). After adding an excess amount of 1 M hydrochloric acid to the obtained compound, the solvent was distilled off under reduced pressure to give (2R,3S)-3-amino-2-hydroxy-5-methyl-2-{[4-(1-naphthylmethoxy)pyridin-2-yl]methyl}hexanoic acid dihydrochloride (55.6 mg) as a solid.

Example 15

CMBP (0.35 ml) was added to a mixture of (3R,4S)-3-[(4-hydroxypyridin-2-yl)methyl]-4-isobutyl-3-(methoxymethoxy)-1-(methoxymethyl)azetidin-2-one (150 mg), 2-(1-methyl-1H-pyrazol-4-yl)ethanol (170 mg) and toluene (3 ml) and the mixture was stirred at 90° C. overnight. The resulting reaction mixture was allowed to cool to room temperature and subsequently concentrated under reduced pressure. DOX (1 ml) and 6 M hydrochloric acid (3 ml) were added to the resulting residue and the mixture was stirred at 60° C. for 3 hours. After cooling the resulting reaction mixture to room temperature, water was added thereto and the mixture was washed with AcOEt. The obtained aqueous layer was concentrated under reduced pressure and the residue was purified by ODS column chromatography (MeCN/0.1% aqueous formic acid solution) to give (2R,3S)-3-amino-2-hydroxy-5-methyl-2-({4-[2-(1-methyl-1H-pyrazol-4-yl)ethoxy]pyridin-2-yl}methyl) hexanoic acid (65 mg) as a solid.

Example 16

Under nitrogen atmosphere, CMMP (100 mg) was added to a mixture of (3R,4S)-3-[(4-hydroxypyridin-2-yl)methyl]-4-isobutyl-3-(methoxymethoxy)-1-(methoxymethyl)azetidin-2-one (200 mg), (1S,2S,3S,5R)-2,6,6-trimethylbicyclo[3.1.1]heptan-3-ol (135 mg) and toluene (4 ml) and the mixture was stirred at 170° C. for 1 hour under microwave irradiation. The resulting reaction mixture was allowed to cool to room temperature and subsequently concentrated under reduced pressure. DOX (1.33 ml) and 6 M hydrochloric acid (4 ml) were added to the resulting residue and the mixture was stirred at 60° C. overnight. After cooling the resulting reaction mixture to room temperature, water was added thereto, and the mixture was washed with AcOEt. The obtained aqueous layer was concentrated under reduced pressure and the residue was purified by ODS column chromatography (MeCN/0.1% aqueous formic acid solution). An excess amount of 1 M hydrochloric acid was added to the obtained compound and the solvent was distilled off under reduced pressure to give (2R,3S)-3-amino-2-hydroxy-5-methyl-2-[(4-{[(1S,2S,3R,5R)-2,6,6-trimethylbicyclo[3.1.1]hepta-3-yl]oxy}pyridin-2-yl)methyl]hexanoic acid dihydrochloride (15 mg) as a solid.

Example 17

(1) 0.2 M Phosphate buffer (30 ml) adjusted pH to 7.7 was added to (2R,3S)-3-amino-2-hydroxy-5-methyl-2-({4-[(trans-4-methylcyclohexypoxy]pyridin-2-yl}methyl) hexanoic acid dihydrochloride (625 mg), subsequently 1 M aqueous sodium hydroxide solution was added to adjust a pH of the reaction mixture to about 7.7 and the mixture was then stirred at room temperature for 2 hours. The precipitate was collected by filtration to give (2R,3S)-3-amino-2-hydroxy-5-methyl-2-({4-[(trans-4-methylcyclohexypoxy] pyridin-2-yl}methyl)hexanoic acid (509 mg) as a solid. The obtained solid (100 mg) was used for the reaction (2) to be described later. The remaining solid was combined with a solid of a same compound separately prepared in the same manner (total 5.27 g). To the solid of the compound was added EtOH (28.5 ml) and water (19 ml), and the mixture was heated to 80° C. and stirred until the solid was dissolved. The obtained solution was gradually allowed to cool to room temperature and stirred for 16 hours. The precipitate was collected by filtration to give (2R,3S)-3-amino-2-hydroxy-5-methyl-2-({4-[(trans-4-methylcyclohexypoxy] pyridin-2-yl}methyl)hexanoic acid (4.29 g) as a crystal. The obtained crystal had a powder X-ray diffraction pattern having peaks at about 2θ (°) 5.2, 10.2, 10.4, 13.6, 17.0, 17.5, 18.5, 20.4, 20.9, 21.2 and 23.1.

(2) A mixture of (2R,3S)-3-amino-2-hydroxy-5-methyl-2-({4-[(trans-4-methylcyclohexypoxy]pyridin-2-yl}methyphexanoic acid (100 mg) and MeOH (2 ml) was cooled with an ice-water bath and subsequently thionyl chloride (0.5 ml) was added thereto with stirring. The resulting reaction mixture was stirred at room temperature for 3 days and subsequently concentrated under reduced pressure. The resulting residue was purified by amino-silica gel column chromatography (hexane/AcOEt). An excess amount of 1 M hydrochloric acid was added to the obtained compound and the solvent was distilled off under reduced pressure to give methyl (2R,3S)-3-amino-2-hydroxy-5- methyl-2-({4-[(trans-4-methylcyclohexyl)oxy]pyridin-2-yl}methyl) hexanoate dihydrochloride (48 mg) as a solid.

Example 18 n-Butanthiol (0.11 ml) was added to a mixture of (2R, 3S)-3-amino-2-[(4-chloropyridin-2-yl)methyl]-2-hydroxy-5-methylhexanoic acid (100 mg), DIPEA (0.12 ml), potassium carbonate (150 mg) and DMF (3 ml) and the mixture was stirred at 120° C. for 3 hours under microwave irradiation. After cooling the resulting reaction mixture to room temperature, water was added thereto. The obtained mixture was purified by ODS column chromatography (MeCN/0.1% aqueous formic acid solution) to give (2R,3S)-3-amino-2-{[4-(butylsulphanyl)pyridin-2-yl]methyl}-2-hydroxy-5-methylhexanoic acid (15 mg) as a solid.

Example 19

A mixture of (2R,3S)-3-amino-2-[(4-chloropyridin-2-yl) methyl]-2-hydroxy-5-methylhexanoic acid (50 mg), 2-naphthol (126 mg), cesium carbonate (284 mg) and N,N-dimethylacetamide (1.5 ml) was stirred at 150° C. for 2 hours under microwave irradiation. The resulting reaction mixture was allowed to cool to room temperature, subsequently diluted with water and washed twice with diethyl ether. 1 M Hydrochloric acid (1.9 ml) was added to the obtained aqueous layer and subsequently purified by ODS column chromatography (MeCN/0.1% aqueous formic acid solution). MeCN and an excess amount of 1 M hydrochloric acid were added to the obtained compound and the solvent was distilled off under reduced pressure to give (2R,3S)-3-amino-2-hydroxy-5-methyl-2-{[4-(2-naphthyloxy)pyridin-2-yl]methyl}hexanoic acid dihydrochloride (10.4 mg) as a solid.

Example 20

1 M Aqueous sodium hydroxide solution (0.25 ml) was added to a mixture of tert-butyl {(1S)-1-[(4R)-4-{[2-(2-cyclopropylethyl)furo[3,2-c]pynidin-4-yl]methyl}-2,2-dimethyl-5-oxo-1,3-dioxolan-4-yl]-3-methylbutyl}carbamate (10 mg), DOX (0.25 ml) and MeOH (0.25 ml) and the mixture was stirred at 50° C. for 5 hours. The resulting reaction mixture was allowed to cool to room temperature and subsequently concentrated under reduced pressure. After adding DOX (0.25 ml) to the resulting residue, hydrogen chloride (4 M DOX solution, 0.25 ml) was added thereto under ice-bath cooling and subsequently the mixture was stirred at room temperature for 1 hour. The resulting reaction mixture was cooled again with an ice-water bath, 1 M aqueous sodium hydroxide solution (0.5 ml) and DOX were added thereto and the mixture was concentrated under reduced pressure. The resulting residue was purified by ODS column chromatography (MeCN/0.1% aqueous formic acid solution) to give (2R,3S)-3-amino-2-{[2-(2-cyclopropylethyl)furo[3,2-c]pyridin-4-yl]methyl}-2-hydroxy-5-methylhexanoic acid (5 mg) as a solid.

Examples 21 to 101

Example compounds shown in Tables to be described later were produced in the same manner as in the method described in the above Examples.

Example 102

Under argon atmosphere, a mixture of (3R,4S)-3-[(4-chloropyridin-2-yl)methyl]-4-[(4-fluorophenoxy)methyl]-3-(methoxymethoxy)-1-(methoxymethyl)azetidin-2-one (300 mg), N-(2,2,2-trifluoroethyl)cyclohexaneamine hydrochloride (270 mg), tris(dibenzylideneacetone)dipalladium (129 mg), 2-(dicyclohexylphosphino)-2',4',6'-triisopropyl-1,1'-biphenyl (135 mg), sodium tert-butoxide (390 mg) and toluene (12 ml) was stirred at 120° C. for 1 hour under microwave irradiation. The resulting reaction mixture was allowed to cool to room temperature and subsequently purified by silica gel column chromatography (hexane/AcOEt) to give (3R, 4S)-3-({4-[cyclohexyl(2,2,2-trifluoroethypamino]pyridin-2-yl}methyl)-4-[(4-fluorophenoxy)methyl]-3-(methoxymethoxy)-1-(methoxymethypazetidin-2-one (150 mg) as an oily product. (2R,3S)-3-Amino-2-({4-[cyclohexyl (2,2,2-trifluoroethyl)amino]pyridin-2-yl}methyl)-4-(4-fluorophenoxy)-2-hydroxy butanoic acid dihydrochloride (15 mg) was prepared as a solid from the above oily product (80 mg) in the same manner as in the method described in Example 6.

Example 103

A mixture of S-{[(2R,3R)-3-(methoxymethoxy)-1-(methoxymethyl)-3-({4-[(trans-4-methylcyclohexyl)oxy]pyridin-2-yl}methyl)-4-oxoazetidin-2-yl]methyl}thioacetate (200 mg), MeOH (2 ml), DMF (2 ml), methyl iodide (0.08 ml) and potassium carbonate (180 mg) was stirred at room temperature for 2 hours. Water was added to the resulting reaction mixture. The mixture was extracted with AcOEt and subsequently concentrated under reduced pressure. MeOH (2 ml) and 6 M aqueous sodium hydroxide solution (1 ml) were added to the resulting residue and the mixture was stirred at 60° C. overnight. After cooling the resulting reaction mixture to room temperature, the mixture was concentrated under reduced pressure. DOX (2 ml) and 6 M hydrochloric acid (3 ml) were added to the resulting residue under ice-bath cooling. The resulting reaction mixture was stirred at room temperature for 5 hours and subsequently concentrated under reduced pressure. The resulting residue was purified by ODS column chromatography (MeCN/0.1% aqueous formic acid solution) to give (2R,3R)-3-amino-2-hydroxy-2-({4-[(trans-4-methylcyclohexyl)oxy]pyridin-2-yl}methyl)-4-(methylsulfanyl)butanoic acid (100 mg) as a solid.

Example 104

A mixture of S-{[(2R,3R)-3-({4-[(2R)-hexan-2-yloxy] pyridin-2-yl}methyl)-3-(methoxymethoxy)-1-(methoxymethyl)-4-oxoazetidin-2-yl]methyl}thioacetate (100 mg), MeOH (1 ml), DMF (1 ml), 1-iodo-2-methylpropane (0.08 ml) and potassium carbonate (100 mg) was stirred at room temperature overnight. Water was added to the resulting reaction mixture. The mixture was extracted with AcOEt and subsequently concentrated under reduced pressure. MeOH (1 ml) and 6 M aqueous sodium hydroxide solution (1 ml) were added to the resulting residue and the resulting reaction mixture was stirred at 60° C. for 3 hours. The resulting reaction mixture was allowed to cool to room temperature and subsequently concentrated under reduced pressure. DOX (1 ml) and 6 M hydrochloric acid (3 ml) were added to the resulting residue and the resulting reaction mixture was stirred at room temperature overnight and subsequently concentrated under reduced pressure. The resulting residue was purified by ODS column chromatography (MeCN/0.1% aqueous formic acid solution). An excess amount of 1 M hydrochloric acid was added to the obtained compound and the solvent was distilled off under reduced pressure to give (2R,3R)-3-amino-2-({4-[(2R)-hexan-2-yloxy]pyridin-2-yl}methyl)-2-hydroxy-4-(isobutylsulfanyl)butanoic acid dihydrochloride (48 mg) as a solid.

Example 105

3 M Hydrochloric acid (6 ml) was added to a mixture of (3R,4R)-4-[(ethylsulfanyl)methyl]-3-(methoxymethoxy)-1-(methoxymethyl)-3-({4-[(trans-4-methylcyclohexyl)oxy]pyridin-2-yl}methyl)azetidin-2-one (598 mg) and DOX (1.5 ml) and the mixture was stirred at 60° C. for 2 hours. After adding 6 M aqueous sodium hydroxide solution (1.5 ml) to the resulting reaction mixture under ice-bath cooling, the mixture was concentrated under reduced pressure. The resulting residue was dissolved in water (10 ml) and a pH of the solution was adjusted to about 2.0 with 6 M aqueous sodium hydroxide solution. After adding EtOH (3 ml), a pH of the solution was adjusted to about 7.0 with 6 M aqueous sodium hydroxide solution and 1 M hydrochloric acid. The obtained mixture was stirred at room temperature for 15 hours. The precipitate was collected by filtration and washed with water to give (2R,3R)-3-amino-4-(ethylsulfanyl)-2-hydroxy-2-({4-[(trans-4-methylcyclohexyl)oxy]pyridin-2-yl}methyl)butanoic acid (417 mg) as a crystal. The obtained crystal had a powder X-ray diffraction pattern having peaks at about 2θ (°) 5.1, 13.8, 17.6, 18.2, 18.5, 18.7, 19.1, 20.3, 20.7, 23.4, 24.3 and 25.2.

Examples 106-146

Example compounds shown in Tables to be described later were produced in the same manner as in the method described in the above Examples.
Tables to be described later show the structure, physicochemical data and production method of the Example compounds.

Production Example 1

A mixture of (3R,4S)-3-[(4-hydroxypyridin-2-yl)methyl]-4-isobutyl-3-(methoxymethoxy)-1-(methoxymethyl)azetidin-2-one (200 mg), cis-4-methyl cyclohexanol (0.224 ml), CMBP (0.467 ml) and toluene (4 ml) was stirred at 90° C. overnight. The resulting reaction mixture was allowed to cool to room temperature and subsequently concentrated under reduced pressure. The resulting residue was purified by silica gel column chromatography (hexane/AcOEt) to give (3R,4S)-4-isobutyl-3-(methoxymethoxy)-1-(methoxymethyl)-3-({4-[(trans-4-methylcyclohexyl)oxy]pyridin-2-yl}methyl)azetidin-2-one (35 mg) as an oily product.

Production Example 2

Under nitrogen atmosphere, CMMP (65 mg) was added to a mixture of (3R,4S)-3-[(4-hydroxypyridin-2-yl)methyl]-4-isobutyl-3-(methoxymethoxy)-1-(methoxymethyl)azetidin-2-one (160 mg), (5r,8s)-1-oxaspiro[4.5]decan-8-ol (78 mg) and toluene (2 ml) and the mixture was stirred at 140° C. for 1.5 hours under microwave irradiation. The resulting reaction mixture was allowed to cool to room temperature and subsequently concentrated under reduced pressure. The resulting residue was purified by silica gel column chromatography (hexane/AcOEt/MeOH) to give (3R,4S)-4-isobutyl-3-(methoxymethoxy)-1-(methoxymethyl)-3-({4-[(5s,8r)-1-oxaspiro [4.5]deca-8-yloxy]pyridin-2-yl}methyl)azetidin-2-one (63 mg) as an oily product.

Production Example 3

Under argon atmosphere, to a mixture of (3R,4S)-3-hydroxy-4-isobutylazetidin-2-one (38.9 g), chloro(methoxy)methane (90 ml) and THF (778 ml) was added NaH (60% mineral oil dispersion, total 26 g) portionwise (ca. 5 g×5 times) over a period of 1 hour under ice-bath cooling. After stirring the resulting reaction mixture for 1 hour under ice-bath cooling, 5% aqueous ammonium chloride solution was added thereto. After separating the organic layer, the aqueous layer was extracted 3 times with AcOEt. The organic layers were combined and washed sequentially with a saturated aqueous sodium hydrogen carbonate solution and a saturated aqueous sodium chloride solution. The organic layer was dried over anhydrous magnesium sulfate and concentrated under reduced pressure. The resulting residue was purified by silica gel column chromatography (hexane/AcOEt) to give (3R,4S)-4-isobutyl-3-(methoxymethoxy)-1-(methoxymethyl)azetidin-2-one (57.89 g) as an oily product.

Production Example 4

Potassium hexamethyldisilazide (1.0 M THF solution, 1.5 ml) was added to a mixture of (3R,4S)-4-[(4S)-2,2-dimethyl-1,3-dioxolan-4-yl]-3-(methoxymethoxy)azetidin-2-one (302 mg), chloro(methoxy)methane (0.15 ml), tetra-n-butylammonium iodide (500 mg) and THF (9 ml) under ice-bath cooling, the mixture was stirred for 1 hour and then stirred at room temperature overnight. Water was added to the resulting reaction mixture and the mixture was extracted with AcOEt. The obtained organic layer was dried over anhydrous magnesium sulfate and concentrated under reduced pressure. The resulting residue was purified by silica gel column chromatography (hexane/AcOEt) to give (3R,4S)-4-[(4S)-2,2-dimethyl-1,3-dioxolan-4-yl]-3-(methoxymethoxy)-1-(methoxymethyl)azetidin-2-one (247 mg) as an oily product.

Production Example 5

A saturated aqueous sodium hydrogen carbonate solution was added to a mixture of 4-(benzyloxy)-2-(chloromethyl)pyridine hydrochloride (17.5 g) and CHCl$_3$. After separating the organic layer from the obtained mixture, the aqueous layer was extracted with CHCl$_3$. The obtained organic layers were combined, dried over anhydrous magnesium sulfate and concentrated under reduced pressure. Sodium iodide (20 g) was added to a mixture of the obtained oily product, THF (100 ml) and acetone (100 ml) at room temperature. After stirring at room temperature for 1 hour, the mixture was diluted with toluene. The resulting mixture was concentrated to about 50 ml under reduced pressure and toluene and anhydrous magnesium sulfate were added to the obtained mixture. The insoluble material was removed by filtration and the obtained filtrate was concentrated again to about 50 ml under reduced pressure (mixture A).
Under argon atmosphere, LDA (1.12 M hexane-THF solution, 60 ml) was added dropwise with stirring to a mixture of (3R,4S)-4-isobutyl-3-(methoxymethoxy)-1-(methoxymethyl)azetidin-2-one (10 g) and THF (200 ml) at −78° C. The resulting reaction mixture was stirred at the same temperature for 30 minutes and subsequently the mixture A was added dropwise at the same temperature. The mixture was stirred at the same temperature for 3 hours and subsequently allowed to warm up to room temperature. After cooling the resulting reaction mixture to 0° C., water was added thereto and the mixture was extracted with AcOEt. The obtained organic layer was dried over anhydrous magnesium sulfate. The obtained organic layer was concentrated under reduced pressure and the residue was purified by silica gel column chromatography (hexane/AcOEt) to give (3R,4S)-3-{ [4-(benzyloxy)pyridin-2-yl]methyl}-4-isobutyl-3-(methoxymethoxy)-1-(methoxymethyl)azetidin-2-one (14.5 g) as an oily product.

Production Example 6

Under ice-bath cooling, thionyl chloride (17 ml) was added to a mixture of [4-(benzyloxy)pyridin-2-yl]methanol (23.6 g) and $CH_2Cl_2$ (500 ml). The resulting reaction mixture was allowed to warm up to room temperature and stirred overnight. The resulting reaction mixture was concentrated under reduced pressure and toluene was added to the residue. The obtained mixture was concentrated under reduced pressure and the resulting residue was washed with diisopropyl ether to give 4-(benzyloxy)-2-(chloromethyl)pyridine hydrochloride (24.9 g) as a solid.

Production Example 7

Under argon atmosphere, 10% Pd/C (50% water content, 1.45 g) was added to a mixture of (3R,4S)-3-{[4-(benzyloxy)pyridin-2-yl]methyl}-4-isobutyl-3-(methoxymethoxy)-1-(methoxymethyl)azetidin-2-one (14.5 g) and MeOH (200 ml) and subsequently the mixture was stirred overnight under hydrogen atmosphere. The resulting reaction mixture was filtered through Celite and the filtrate was concentrated under reduced pressure. The resulting residue was purified by silica gel column chromatography ($CHCl_3$/MeOH) to give (3R,4S)-3-[(4-hydroxypyridin-2-yl)methyl]-4-isobutyl-3-(methoxymethoxy)-1-(methoxymethyl)azetidin-2-one (9.8 g) as an oily product.

Production Example 8

Under argon atmosphere, a mixture of (3R,4S)-3-{[4-(cyclohexyloxy)pyridin-2-yl]methyl}-4-(hydroxymethyl)-3-(methoxymethoxy)-1-(methoxymethyl)azetidin-2-one (250 mg), CMBP (280 mg), 2-bromophenol (220 mg) and toluene (6 ml) was stirred at 90° C. for 8 hours. The resulting reaction mixture was concentrated under reduced pressure and the residue was purified by silica gel column chromatography (hexane/AcOEt) to give (3R,4S)-4-[(2-bromophenoxy)methyl]-3-{[4-(cyclohexyloxy)pyridin-2-yl]methyl}-3-(methoxymethoxy)-1-(methoxymethyl)azetidin-2-one (338 mg) as a solid.

Production Example 9

NaH (60% mineral oil dispersion, 3.0 g) was added to a mixture of 2-cyclopropylethanol (5.04 g) and DMF (90 ml) under ice-bath cooling and the mixture was stirred for 30 minutes. A solution of 4-chloropyridine-2-carbonitrile (8.6 g) in DMF (10 ml) was added to the resulting reaction mixture and the mixture was stirred at room temperature for 2 hours. Water was added to the resulting reaction mixture under ice-bath cooling and the mixture was extracted with AcOEt. The obtained organic layer was washed with a saturated aqueous sodium chloride solution and subsequently dried over anhydrous magnesium sulfate. The organic layer was concentrated under reduced pressure and the resulting residue was purified by silica gel column chromatography (hexane/AcOEt) to give 4-(2-cyclopropylethoxy)pyridine-2-carbonitrile (6.76 g) as a solid.

Production Example 10

Sodium methoxide (28% MeOH solution, 7.2 ml) was added to a mixture of 4-(2-cyclopropylethoxy)pyridine-2-carbonitrile (6.76 g) and MeOH (140 ml) under ice-bath cooling and the mixture was stirred at room temperature for 3 hours. 1 M Hydrochloric acid (120 ml) was added to the resulting reaction mixture and the mixture was stirred for 1 hour. The resulting reaction mixture was concentrated under reduced pressure and AcOEt and a saturated aqueous sodium hydrogen carbonate solution were added to the resulting residue. The organic layer was separated from the obtained mixture and the aqueous layer was extracted with AcOEt. The obtained organic layer was washed with a saturated aqueous sodium chloride solution and subsequently dried over anhydrous sodium sulfate. The organic layer was concentrated under reduced pressure, $NaBH_4$ (4.0 g) was added to a mixture of the resulting residue and MeOH (150 ml) under ice-bath cooling and the mixture was stirred at room temperature overnight. The resulting reaction mixture was concentrated under reduced pressure and a saturated aqueous ammonium chloride solution was added to the residue and the mixture was extracted with AcOEt. The organic layer was washed with a saturated aqueous sodium chloride solution and subsequently dried over anhydrous magnesium sulfate. The obtained organic layer was concentrated under reduced pressure and the resulting residue was purified by silica gel column chromatography ($CHCl_3$/MeOH) to give [4-(2-cyclopropylethoxy)pyridin-2-yl]methanol (5.89 g) as an oily product.

Production Example 11

Under argon atmosphere, cyclopropylmethylbromide (0.03 ml) was added to a mixture of (3R,4R)-3-(methoxymethoxy)-1-(methoxymethyl)-3-({4-[(trans-4-methylcyclohexyl)oxy]pyridin-2-yl}methyl)-4-(sulfanylmethyl)azetidin-2-one (120 mg), potassium carbonate (50 mg), sodium iodide (100 mg) and DMF (5 ml) and the mixture was stirred at room temperature overnight. A saturated aqueous sodium chloride solution was added to the resulting reaction mixture and the mixture was extracted with AcOEt. The obtained organic layer was washed with a saturated aqueous sodium chloride solution, dried over anhydrous magnesium sulfate and concentrated under reduced pressure. The resulting residue was purified by silica gel column chromatography (hexane/AcOEt) to give (3R,4R)-4-{[(cyclopropylmethyl)sulphanyl]methyl}-3-(methoxymethoxy)-1-(methoxymethyl)-3-({4-[(trans-4-methylcyclohexyl)oxy]pyridin-2-yl}methyl)azetidin-2-one (39.7 mg) as an oily product.

Production Example 12

AcOH (0.0176 ml) and N-[(dimethylamino)(3H-[1,2,3]triazolo[4,5-b]pyridin-3-yloxy)methylene]-N-methylmethaneaminium hexafluorophosphate (71 mg) were added under ice-bath cooling to a mixture of (3R,4S)-4-isobutyl-3-(methoxymethoxy)-1-(methoxymethyl)-3-{[4-(piperidin-4-yloxy)pyridin-2-yl]methyl}azetidin-2-one (65 mg) and DMF (1 ml). After stirring the resulting reaction mixture at room temperature for 1 hour, water was added thereto and the mixture was extracted twice with $CHCl_3$. The obtained organic layer was dried over anhydrous sodium sulfate and concentrated under reduced pressure. The resulting residue was purified by silica gel column chromatography (CHCl$_3$/MeOH) to give (3R,4S)-3-({4-[(1-acetylpiperidin-4-yl)oxy]pyridin-2-yl}methyl)-4-isobutyl-3-(methoxymethoxy)-1-(methoxymethyl)azetidin-2-one (49 mg) as an oily product.

Production Example 13

Under nitrogen atmosphere, a mixture of (3R,4S)-3-[(4-chloropyridin-2-yl)methyl]-4-isobutyl-3-(methoxymethoxy)-1-(methoxymethyl)azetidin-2-one (200 mg), trans-4-methylcyclohexanecarboxamide (90 mg), (9,9-dimethyl-9H-xanthene-4,5-diyl)bis(diphenylphosphine) (65 mg), tris(dibenzylideneacetone)dipalladium (50 mg), cesium carbonate (200 mg) and DOX (4 ml) was stirred at 110° C. for 20 hours. The resulting reaction mixture was concentrated under reduced pressure and the residue was purified by silica gel column chromatography (hexane/AcOEt) to give trans-N-(2-{[(2S,3R)-2-isobutyl-3-(methoxymethoxy)-1-(methoxymethyl)-4-oxoazetidin-3-yl]methyl}pyridin-4-yl)-4-methylcyclohexanecarboxamide (137 mg) as an oily product.

Production Example 14

A mixture of 2,5-dimethyl-4-nitropyridine 1-oxide (2 g), benzyl alcohol (6.7 ml), potassium carbonate (3.3 g), benzyltri-n-butylammonium chloride (700 mg) and water (10.5 ml) was stirred at 160° C. for 1 hour under microwave irradiation. After cooling the resulting reaction mixture to room temperature, water was added thereto and the mixture was extracted three times with CHCl$_3$. The obtained organic layer was dried over anhydrous magnesium sulfate and subsequently concentrated under reduced pressure. The resulting residue was purified by silica gel column chromatography (CHCl$_3$/MeOH) to give 4-(benzyloxy)-2,5-dimethylpyridin 1-oxide (1.9 g) as a solid.

Production Example 15

A mixture of 4-(benzyloxy)-2,5-dimethylpyridin 1-oxide (4.3 g) and acetic anhydride (80 ml) was stirred at 80° C. for 1 hour. The resulting reaction mixture was allowed to cool to room temperature and subsequently concentrated under reduced pressure. MeOH (70 ml) and potassium carbonate (6 g) were added to the resulting residue and the mixture was stirred at room temperature for 1 hour. Water was added to the resulting reaction mixture and the mixture was extracted with CHCl$_3$. The organic layer was dried over anhydrous magnesium sulfate and subsequently concentrated under reduced pressure. The resulting residue was purified by amino-silica gel column chromatography (hexane/AcOEt) to give [4-(benzyloxy)-5-methylpyridin-2-yl]methanol (1.94 g) as a solid. The obtained compound was combined with a same compound separately prepared in the same manner. Thionyl chloride (2.4 ml) was added with stirring under ice-bath cooling to a mixture of the obtained [4-(benzyloxy)-5-methylpyridin-2-yl]methanol (3.56 g) and CH$_2$Cl$_2$ (70 ml) and the mixture was stirred at room temperature for 2 hours. The resulting reaction mixture was concentrated under reduced pressure and toluene was added to the residue. The solvent was distilled off from the obtained mixture under reduced pressure to give 4-(benzyloxy)-2-(chloromethyl)-5-methylpyridine hydrochloride (4.41 g) as a solid.

Production Example 16

After cooling a mixture of 5-[(benzyloxy)methyl]-4-methoxy-2-methylpyridine (500 mg) and CH$_2$Cl$_2$ (10 ml) with an ice-water bath, m-chloroperbenzoic acid (about 25% water content, 532 mg) was added thereto and the mixture was stirred at room temperature for 2 hours. Aqueous sodium thiosulfate solution was added to the resulting reaction mixture and the mixture was stirred at room temperature for 15 minutes. After separating the aqueous layer from the organic layer, the organic layer was washed sequentially with water and a saturated aqueous sodium chloride solution. The obtained organic layer was dried over anhydrous magnesium sulfate and subsequently concentrated under reduced pressure. AcOH (1 ml) and acetic anhydride (1 ml) were added to the resulting residue and the mixture was stirred at 100° C. for 3 hours. The resulting reaction mixture was allowed to cool to room temperature and subsequently concentrated under reduced pressure. MeOH (5.0 ml) and 6 M aqueous sodium hydroxide solution (1 ml) were added to the resulting residue and the mixture was stirred at room temperature overnight. Water was added to the resulting reaction mixture and the mixture was extracted with CHCl$_3$. The obtained organic layer was dried over anhydrous magnesium sulfate and subsequently concentrated under reduced pressure. The resulting residue was purified by silica gel column chromatography (CHCl$_3$/MeOH) to give {5-[(benzyloxy)methyl]-4-methoxypyridin-2-yl}methanol (380 mg) as an oily product.

Production Example 17

A mixture of 4-[(2-{[(2S,3R)-2-isobutyl-3-(methoxymethoxy)-1-(methoxymethyl)-4-oxoazetidin-3-yl]methyl}pyridin-4-yl)oxy]piperidine-1-benzyl carboxylate (216 mg), 10% Pd/C (50% water content, 22 mg) and EtOH (5 ml) was stirred at room temperature for 4 hours under hydrogen atmosphere. Insoluble material was removed by filtration from the resulting reaction mixture and subsequently the filtrate was concentrated under reduced pressure. MeOH (5 ml) and 10% Pd/C (50% water content, 49 mg) were added to the resulting residue and the mixture was stirred at room temperature for 3 hours under hydrogen atmosphere. Insoluble material was removed by filtration from the resulting reaction mixture and subsequently the filtrate was concentrated under reduced pressure to give (3R,4S)-4-isobutyl-3-(methoxymethoxy)-1-(methoxymethyl)-3-{[4-(piperidin-4-yloxy)pyridin-2-yl]methyl}azetidin-2-one (157 mg) as an oily product.

Production Example 18

A mixture of 2,3,5-trimethyl-4-(2-phenylethoxy)pyridin 1-oxide (510 mg), 4-methylbenzenesulfonyl chloride (570 mg) and MeCN (8 ml) was stirred at 40° C. for 1 hour. Et$_3$N (0.43 ml) was added to the reaction mixture with stirring and the mixture was stirred at 40° C. for 3 hours. After cooling the resulting reaction mixture to room temperature, a saturated aqueous sodium hydrogen carbonate solution was added thereto and the mixture was extracted with CHCl$_3$. The obtained organic layer was washed with a saturated aqueous sodium chloride solution, dried over anhydrous magnesium sulfate and subsequently concentrated under reduced pressure. The resulting residue was purified by silica gel column chromatography (hexane/AcOEt) to give 2-(chloromethyl)-3,5-dimethyl-4-(2-phenylethoxy)pyridine (370 mg) as an oily product.

Production Example 19

A mixture of (4-methoxy-6-methylpyridin-3-yl)methanol (2.4 g) and DMF (20 ml) was cooled with an ice-water bath, subsequently NaH (55% mineral oil dispersion, 750 mg) was added thereto and the mixture was stirred at the same temperature for 1 hour. A mixture of benzyl bromide (4 ml) and DMF (4 ml) was added to the reaction mixture and the mixture was stirred at room temperature overnight. Water was added to the resulting reaction mixture and the mixture was extracted with $CHCl_3$. The obtained organic layer was dried over anhydrous magnesium sulfate and subsequently concentrated under reduced pressure. The resulting residue was purified by silica gel column chromatography ($CHCl_3$/MeOH) to give 5-[(benzyloxy)methyl]-4-methoxy-2-methylpyridine (1 g) as an oily product.

Production Example 20

Under nitrogen atmosphere, $NaBH_4$ (270 mg) was added under ice-bath cooling to a mixture of 1-(2-cyclohexylethyl)-1H-imidazo[4,5-c]pyridine-6-methyl carboxylate (640 mg) and MeOH (9 ml) and the mixture was stirred at the same temperature for 30 minutes. The resulting reaction mixture was allowed to warm up to room temperature and stirred overnight. The resulting reaction mixture was cooled with an ice-water bath. A saturated aqueous ammonium chloride solution was added thereto and the mixture was extracted three times with $CH_2Cl_2$. The obtained organic layer was washed with a saturated aqueous sodium chloride solution and dried over anhydrous sodium sulfate. The solvent was distilled off under reduced pressure to give [1-(2-cyclohexylethyl)-1H-imidazo[4,5-c]pyridin-6-yl]methanol (560 mg) as an oily product.

Production Example 21

A mixture of (2S,3R)-3-[(tert-butoxycarbonyl)amino]-2-hydroxy-5-methylhexanoic acid (4 g), 1,2-dichloroethane (20 ml), 2,2-dimethoxypropane (20 ml) and pyridinium p-toluenesulfonate (385 mg) was stirred at 80° C. overnight. After cooling the resulting reaction mixture to room temperature, a saturated aqueous sodium hydrogen carbonate solution was added thereto and the mixture was extracted with AcOEt. The obtained organic layer was dried over anhydrous magnesium sulfate and subsequently concentrated under reduced pressure. EtOH and water were added to the resulting residue and the mixture was heated to 60° C. The obtained mixture was allowed to cool to room temperature and subsequently the precipitate was collected by filtration and washed with water to give tert-butyl {(1R)-1-[(4S)-2,2-dimethyl-5-oxo-1,3-dioxolan-4-yl]-3-methylbutyl}carbamate (3.4 g) as a solid.

Production Example 22

After cooling a mixture of {4-[(trans-4-methylcyclohexyl)oxy]pyridin-2-yl}methanol (9.3 g) and THF (70 ml) with an ice-water bath, a mixture of $PBr_3$ (4.2 ml) and THF (20 ml) was added dropwise and the mixture was stirred at room temperature for 3 hours. The resulting reaction mixture was cooled with an ice-water bath. MeOH (46.5 ml) was added dropwise and the mixture was stirred at room temperature for 30 minutes. Activated carbon (1 g) was added to the reaction mixture and the mixture was stirred at room temperature for 30 minutes. Celite was added to the reaction mixture and the insoluble material was removed by filtration through Celite. The obtained filtrate was concentrated under reduced pressure. AcOEt was added to the resulting residue and the mixture was stirred at room temperature for 1 hour. Diisopropyl ether was added dropwise to the obtained mixture and the mixture was stirred at room temperature for 5 hours. The precipitate was collected by filtration and rinsed with a mixture of AcOEt-diisopropyl ether (2:1) and diisopropyl ether to give 2-(bromomethyl)-4-[(trans-4-methylcyclohexyl)oxy]pyridine hydrobromate (13.8 g) as a solid.

Production Example 23

A mixture of 2-(bromomethyl)-4-[(trans-4-methylcyclohexyl)oxy]pyridine hydrobromate (7.5 g) and THF (35 ml) was cooled to −78° C., lithium hexamethyldisilazide (1.3 M hexane solution, 16 ml) was added dropwise thereto under argon atmosphere and the mixture was stirred at the same temperature for 30 minutes. The resulting reaction mixture was warmed up to 0° C. and stirred for 30 minutes (mixture A).

Under argon atmosphere, a mixture of (3R,4S)-3-(methoxymethoxy)-1-(methoxymethyl)-4-{[(triisopropylsilyl)oxy]methyl}azetidin-2-one (7 g) and THF (28 ml) was cooled to −78° C., LDA (1.09 M hexane-THF solution, 37 ml) was added dropwise thereto and the mixture was stirred for 30 minutes. The mixture A was added to the resulting reaction mixture and the mixture was stirred for 2 hours. A mixture of AcOH (2.1 ml) and THF (7 ml) was added to the resulting reaction mixture at −78° C. and the mixture was stirred for 15 minutes. The resulting reaction mixture was warmed up to 0° C. Dimethylamine (2 M THF solution, 19.4 ml) was added thereto and the mixture was stirred for 30 minutes. The resulting reaction mixture was poured into a mixture of water and AcOEt and the oraganic layer was separated. The obtained organic layer was washed sequentially with 1 M hydrochloric acid, a saturated aqueous sodium hydrogen carbonate solution and a saturated aqueous sodium chloride solution, dried over anhydrous magnesium sulfate and subsequently concentrated under reduced pressure. The resulting residue was purified by silica gel column chromatography (hexane/AcOEt) to give (3R,4S)-3-(methoxymethoxy)-1-(methoxymethyl)-3-({4-[(trans-4-methylcyclohexyl)oxy]pyridin-2-yl}methyl)-4-{[(triisopropylsilyl)oxy]methyl}azetidin-2-one (7.1 g) as an oily product.

Production Example 24

A solution of $PBr_3$ (1.17 ml) in $CH_2Cl_2$ (10 ml) was added dropwise under ice-bath cooling to a solution of {4-[(trans-4-methylcyclohexypoxy]pyridin-2-yl}methanol (3.44 g) in $CH_2Cl_2$ (42 ml). The reaction mixture was stirred at room temperature for 1.5 hours and subsequently added to an ice-cooled mixture of a saturated aqueous sodium hydrogen carbonate solution and $CH_2Cl_2$. The obtained mixture was stirred at room temperature for 20 minutes and subsequently extracted with $CH_2Cl_2$. The obtained organic layer was washed with a saturated aqueous sodium chloride solution, subsequently dried over anhydrous magnesium sulfate, diluted with toluene and concentrated under reduced pressure to about 20 ml. The obtained mixture was diluted again with toluene and concentrated again under reduced pressure to about 25 ml (mixture A).

Under nitrogen atmosphere, a solution of tert-butyl {(1S)-1-[(4S)-2,2-dimethyl-5-oxo-1,3-dioxolan-4-yl]-3-methylbutyl}carbamate (3.12 g) in THF (62 ml) was cooled with a dry ice-acetone bath and LDA (1.09 M hexane—THF solution, 22 ml) was added dropwise thereto. The resulting reaction mixture was stirred for 40 minutes while cooled with the dry ice-acetone bath. The mixture A was added dropwise and the mixture was further stirred for 2 hours. AcOH was added to the resulting reaction mixture. The mixture was allowed to warm up to room temperature and AcOEt was added thereto. The obtained mixture was washed with a saturated aqueous sodium carbonate solution and a saturated aqueous sodium chloride solution, subsequently dried over anhydrous magnesium sulfate and concentrated under reduced pressure. The resulting residue was purified by silica gel column chromatography (hexane/AcOEt) to give tert-butyl {(1S)-1-[(4R)-2,2-dimethyl-4-({4-[(trans-4-methylcyclohexyl)oxy]pyridin-2-yl}methyl)-5-oxo-1,3-dioxolan-4-yl]-3-methylbutyl}carbamate (3.63 g) as a foamy solid.

Production Example 25

1H-Benzotriazole-1-methanol (35 mg) was added to a mixture of (3R,4S)-4-isobutyl-3-(methoxymethoxy)-1-(methoxymethyl)-3-{[4-(piperidin-4-yloxy)pyridin-2-yl]methyl}azetidin-2-one (65 mg) and MeCN (1 ml) and the mixture was stirred at room temperature for 10 minutes. Triacetoxysodium borohydride (50 mg) was added to the resulting reaction mixture and the mixture was further stirred at room temperature for 50 minutes. A saturated aqueous ammonium chloride solution was added to the resulting reaction mixture under ice-bath cooling and the mixture was extracted three times with $CHCl_3$-MeOH (5:1). The organic layer was dried over anhydrous sodium sulfate and concentrated under reduced pressure. The resulting residue was purified by silica gel column chromatography ($CHCl_3$/MeOH) to give (3R,4S)-4-isobutyl-3-(methoxymethoxy)-1-(methoxymethyl)-3-({4-[(1-methylpiperidin-4-yl)oxy]pyridin-2-yl}methyl) azetidin-2-one (56 mg) as an oily product.

Production Example 26

(2R,3S)-3-amino-2-[(4-chloropyridin-2-yl)methyl]-2-hydroxy-5-methylhexanoic acid (198 mg) was prepared as a solid from (3R,4S)-3-[(4-chloropyridin-2-yl)methyl]-4-isobutyl-3-(methoxymethoxy)-1-(methoxymethyl)azetidin-2-one (382 mg) in the same manner as in the method described in Example 9.

Production Example 27

A mixture of (3R,4S)-4-(2-cyclobutylethyl)-3-(methoxymethoxy)azetidin-2-one (517 mg), 1,2-dichloroethane (13 ml), chloro(methoxy)methane (0.8 ml) and DIPEA (2 ml) was stirred at 90° C. for 12 hours. The resulting reaction mixture was allowed to cool to room temperature. Chloro(methoxy)methane (0.35 ml) and DIPEA (0.83 ml) were added thereto and the mixture was stirred at 90° C. for 5 hours. The resulting reaction mixture was allowed to cool to room temperature. A saturated aqueous sodium hydrogen carbonate solution was added thereto and the mixture was extracted with AcOEt. The obtained organic layer was washed with a saturated aqueous sodium chloride solution and dried over anhydrous magnesium sulfate. The organic layer was concentrated under reduced pressure and the resulting residue was purified by silica gel column chromatography (hexane/AcOEt) to give (3R,4S)-4-(2-cyclobutylethyl)-3-(methoxymethoxy)-1-(methoxymethyl)azetidin-2-one (512 mg) as an oily product.

Production Example 28

Ammonium cerium (IV) nitrate (4.7 g) was added to a mixture of (3R,4S)-4-(2-cyclobutylethyl)-3-(methoxymethoxy)-1-(4-methoxyphenyl)azetidin-2-one (960 mg), MeCN (24 ml) and water (12 ml) under ice-bath cooling and the mixture was stirred for 30 minutes. Water and a saturated aqueous sodium hydrogen carbonate solution were added to the resulting reaction mixture with stirring and subsequently a 2% aqueous sodium hydrogen sulfite solution was added thereto. The resulting reaction mixture was filtered through Celite and the filtrate was extracted with $CHCl_3$. The obtained organic layer was washed with a saturated aqueous sodium chloride solution, dried over anhydrous magnesium sulfate and subsequently concentrated under reduced pressure. The resulting residue was purified by silica gel column chromatography (hexane/AcOEt) to give (3R,4S)-4-(2-cyclobutylethyl)-3-(methoxymethoxy)azetidin-2-one (459 mg) as a solid.

Production Example 29

A mixture of (3R,4S)-4-[(4S)-2,2-dimethyl-1,3-dioxolan-4-yl]-3-(methoxymethoxy)-1-(4-methoxyphenyl)azetidin-2-one (3.2 g), AcOH (50 ml) and water (13 ml) was stirred at 50° C. for 4 hours. The resulting reaction mixture was allowed to cool to room temperature and subsequently concentrated under reduced pressure. The resulting residue was purified by silica gel column chromatography ($CHCl_3$/MeOH) to give (3R,4S)-4-[(1S)-1,2-dihydroxyethyl]-3-(methoxymethoxy)-1-(4-methoxyphenyl)azetidin-2-one (2.6 g) as an oily product.

Production Example 30

Sodium periodate (2.3 g) was added to a mixture of (3R,4S)-4-[(1S)-1,2-dihydroxyethyl]-3-(methoxymethoxy)-1-(4-methoxyphenyl)azetidin-2-one (2.1 g), $CH_2Cl_2$ (40 ml) and a saturated aqueous sodium hydrogen carbonate solution (1 ml) and the mixture was stirred at room temperature for 1 hour. Anhydrous magnesium sulfate was added to the resulting reaction mixture and the mixture was stirred for 30 minutes. The resulting reaction mixture was filtered through Celite and the solvent was distilled off from the filtrate under reduced pressure to give (2R,3R)-3-(methoxymethoxy)-1-(4-methoxyphenyl)-4-oxoazetidin-2-carbaldehyde (1.8 g) as a solid.

Production Example 31

$NaBH_4$ (1.2 g) was added to a mixture of (2R,3R)-3-(methoxymethoxy)-1-(methoxymethyl)-4-oxoazetidin-2-carbaldehyde (5.1 g) and THF (50 ml) under ice-bath cooling and the mixture was stirred for 30 minutes. After adding water (5 ml) to the resulting reaction mixture, anhydrous magnesium sulfate was added thereto and the mixture was stirred at room temperature for 30 minutes. The resulting reaction mixture was filtered and subsequently the filtrate was concentrated under reduced pressure. The resulting residue was purified by silica gel column chromatography ($CHCl_3$/MeOH) to give (3R,4S)-4-(hydroxymethyl)-3-(methoxymethoxy)-1-(methoxymethyl)azetidin-2-one (4.4 g) as an oily product.

Production Example 32

A mixture of (3R,4S)-4-(hydroxymethyl)-3-(methoxymethoxy)-1-(methoxymethyl)azetidin-2-one (100 mg), triisopropylchlorosilane (0.21 ml), imidazole (140 mg) and DMF (2 ml) was stirred at room temperature overnight. The resulting reaction mixture was added to water and the mixture was extracted with AcOEt. The obtained organic layer was washed with a saturated aqueous sodium chloride solution, dried over anhydrous magnesium sulfate and subsequently concentrated under reduced pressure. The resulting residue was purified by silica gel column chromatography (hexane/AcOEt) to give (3R,4S)-3-(methoxymethoxy)-1-(methoxymethyl)-4-{[(triisopropylsilypoxy]methyl}azetidin-2-one (137 mg) as an oily product.

Production Example 33

After cooling a mixture of (3R,4S)-3-(methoxymethoxy)-1-(methoxymethyl)-3-({4-[(trans-4-methylcyclohexyl)oxy]pyridin-2-yl}methyl-4-{[(triisopropylsilyl)oxy]methyl}azetidin-2-one (7.1 g) and THF (100 ml) with an ice-water bath, tetra-n-butylammonium fluoride (1 M THF solution, 19 ml) was added thereto and the mixture was stirred for 30 minutes. The reaction mixture was added to a saturated aqueous ammonium chloride solution and the mixture was extracted with AcOEt. The obtained organic layer was washed with a saturated aqueous sodium chloride solution, dried over anhydrous magnesium sulfate and subsequently concentrated under reduced pressure. The resulting residue was purified by silica gel column chromatography ($CHCl_3$/MeOH) to give (3R,4S)-4-(hydroxymethyl)-3-(methoxymethoxy)-1-(methoxymethyl)-3-({4-[(trans-4-methylcyclohexypoxy]pyridin-2-yl}methypazetidin-2-one (4.7 g) as an oily product.

Production Example 34

A mixture of (3R,4S)-4-(2-hydroxyethyl)-3-(methoxymethoxy)-1-(methoxymethyl)-3-({4-[(trans-4-methylcyclohexypoxy]pyridin-2-yl}methyl)azetidin-2-one (200 mg), 1-iodo-2-methylpropane (2 ml) and $Ag_2O$ (1 g) was stirred at 90° C. overnight. The resulting reaction mixture was allowed to cool to room temperature. Insoluble material was removed by filtration and the filtrate was concentrated under reduced pressure. The resulting residue was purified by silica gel column chromatography (hexane/AcOEt) to give (3R,4S)-4-(2-isobutoxyethyl)-3-(methoxymethoxy)-1-(methoxymethyl)-3-({4-[(trans-4-methylcyclohexyl)oxy]pyridin-2-yl}methypazetidin-2-one (80 mg) as an oily product.

Production Example 35

Methanesulfonyl chloride (0.085 ml) was added to a mixture of (3R,4S)-4-(hydroxymethyl)-3-(methoxymethoxy)-1-(methoxymethyl)-3-({4-[(trans-4-methylcyclohexyl)oxy]pyridin-2-yl}methyl)azetidin-2-one (222 mg), pyridine (0.175 ml) and $CH_2Cl_2$ (4 ml) and the mixture was stirred at room temperature overnight. $CH_2Cl_2$ was added to the resulting reaction mixture, and the mixture was washed sequentially with 0.5 M hydrochloric acid, a saturated aqueous sodium hydrogen carbonate solution and a saturated aqueous sodium chloride solution. The obtained organic layer was dried over anhydrous magnesium sulfate and the solvent was distilled off under reduced pressure to give methanesulfonic acid [(2S,3R)-3-(methoxymethoxy)-1-(methoxymethyl)-3-({4-[(trans-4-methylcyclohexyl)oxy]pyridin-2-yl}methyl)-4-oxoazetidin-2-yl]methyl (247 mg) as an oily product.

Production Example 36

A mixture of [(2S,3R)-3-(methoxymethoxy)-1-(methoxymethyl)-3-({4-[(trans-4-methylcyclohexyl)oxy]pyridin-2-yl}methyl)-4-oxoazetidin-2-yl]methyl methanesulfonate (247 mg), sodium iodide (457 mg) and acetone (10 ml) was refluxed overnight. Sodium iodide (2 g) was added to the resulting reaction mixture and the mixture was refluxed for 13 hours. After cooling the resulting reaction mixture to room temperature, water was added thereto and the mixture was extracted twice with $CH_2Cl_2$. The obtained organic layers were combined, washed with a saturated aqueous sodium chloride solution, dried over anhydrous magnesium sulfate and subsequently the solvent was distilled off under reduced pressure to give (3R,4R)-4-(iodomethyl)-3-(methoxymethoxy)-1-(methoxymethyl)-3-({4-[(trans-4-methylcyclohexyl)oxy]pyridin-2-yl}methyl)azetidin-2-one (250 mg) as an oily product.

Production Example 37

Under argon atmosphere, a sodium hydrosulfide hydrate (48 mg) was added to a mixture of (3R,4R)-4-(iodomethyl)-3-(methoxymethoxy)-1-(methoxymethyl)-3-({4-[(trans-4-methylcyclohexyl)oxy]pyridin-2-yl}methyl)azetidin-2-one (147 mg) and DMF (2 ml) under ice-bath cooling and the mixture was stirred for 30 minutes. AcOH was added to the resulting reaction mixture to acidify. Water was added thereto and the mixture was extracted with AcOEt. The obtained organic layer was dried over anhydrous magnesium sulfate and the solvent was distilled off under reduced pressure to give (3R,4R)-3-(methoxymethoxy)-1-(methoxymethyl)-3-({4-[(trans-4-methylcyclohexyl)oxy]pyridin-2-yl}methyl)-4-(sulfanylmethyl)azetidin-2-one (120 mg) as an oily product.

Production Example 38

A mixture of (2R,3R)-3-(methoxymethoxy)-1-(methoxymethyl)-4-oxoazetidine-2-carbaldehyde (3.3 g), (triphenylphosphoranyliden)acetaldehyde (5.5 g) and $CH_2Cl_2$ (88 ml) was stirred at room temperature overnight. The reaction mixture was concentrated under reduced pressure and the resulting residue was purified by silica gel column chromatography (hexane/AcOEt) to give a mixture of 3-[(3R)-3-(methoxymethoxy)-1-(methoxymethyl)-4-oxoazetidin-2-yl]acrylaldehyde and triphenylphosphineoxide in a ratio of about 1:1 (3.7 g).

Production Example 39

A mixture of 5-[(cyclobutylmethyl) sulfonyl]-1-phenyl-1H-tetrazole (2.04 g) and THF (40 ml) was cooled to −78° C., potassium hexamethyldisilazide (1.0 M THF solution, 8.4 ml) was added thereto and the mixture was stirred for 30 minutes. A solution of (2R,3R)-3-(methoxymethoxy)-1-(4-methoxyphenyl)-4-oxoazetidine-2-carbaldehyde (1.85 g) in THF (30 ml) was added to the resulting reaction mixture and the mixture was stirred at the same temperature for 30 minutes. The resulting reaction mixture was allowed to warm up to room temperature. A saturated aqueous ammonium chloride solution was added to the mixture and the mixture was extracted with AcOEt. The obtained organic layer was washed with a saturated aqueous sodium chloride solution and dried over anhydrous magnesium sulfate. The organic layer was concentrated under reduced pressure and the resulting residue was purified by silica gel column chromatography (hexane/AcOEt) to give (3R)-4-(2-cyclobutylvinyl)-3-(methoxymethoxy)-1-(4-methoxyphenyl)azetidin-2-one (1.25 g) as an oily product.

Production Example 40

(1,5-Cyclooctadiene)(pyridine)(tricyclohexylphosphine)iridium (I) hexafluorophosphate (270 mg) was added to a mixture of (3R)-4-(2-cyclobutylvinyl)-3-(methoxymethoxy)-1-(4-methoxyphenyl)azetidin-2-one (1.06 g) and $CH_2Cl_2$ (24 ml) and the mixture was stirred at room temperature overnight under hydrogen atmosphere. The resulting reaction mixture was concentrated under reduced pressure and the resulting residue was purified by silica gel column chromatography (hexane/AcOEt) to give (3R,4S)-4-(2-cyclobutylethyl)-3-(methoxymethoxy)-1-(4-methoxyphenyl)azetidin-2-one (960 mg) as an oily product.

Production Example 41

A mixture of 4-methylpentanal (1.1 g), (2R,5R)-2,5-dimethylpyrrolidine-1-amine (1.29 g), $CH_2Cl_2$ (21.9 ml) and anhydrous magnesium sulfate (3.97 g) was stirred at room temperature for 2 hours. Insoluble material was removed by filtration from the resulting reaction mixture and the filtrate was concentrated under reduced pressure. The resulting residue was purified by silica gel column chromatography (hexane/AcOEt) to give (2R,5R)-2,5-dimethyl-N-[(1E)-4-methylpentylidene]pyrrolidin-1-amine (1.63 g) as an oily product.

Production Example 42

1-Chloro-N,N,2-trimethylpropenylamine (5.7 g) was added at room temperature to a mixture of (methoxymethoxy)acetic acid (5.13 g) and toluene (105 ml) and the mixture was stirred at room temperature for 1 hour under nitrogen atmosphere (mixture A). A mixture of (2R, 5R)—N-[(E)-(4-bromophenyl) methylene]-2,5-dimethylpyrrolidin-1-amine (3.0 g), $Et_3N$ (11.9 ml) and toluene (51 ml) was stirred at 100° C. while the mixture A was added dropwise thereto over a period of 30 minutes. The resulting reaction mixture was stirred at 100° C. for 5 hours. Water was added to the resulting reaction mixture and the mixture was extracted with AcOEt. The obtained organic layer was washed with a saturated aqueous sodium chloride solution and dried over anhydrous magnesium sulfate. The solvent was distilled off under reduced pressure and the resulting residue was purified by silica gel column chromatography (hexane/AcOEt) to give (3R,4S)-4-(4-bromophenyl)-1-[(2R,5R)-2,5-dimethylpyrrolidin-1-yl]-3-(methoxymethoxy)azetidin-2-one (3.1 g) as a solid.

Production Example 43

A mixture of (3R,4S)-3-(benzyloxy)-1-[(2R,5R)-2,5-dimethylpyrrolidin-1-yl]-4-(3-methylbutyl)azetidin-2-one (470 mg), MeOH (15.5 ml) and magnesium monoperoxyphthalate hexahydrate (about 80% purity, 1.3 g) was stirred at room temperature for 2 hours. Water was added to the resulting reaction mixture and the mixture was extracted with $CHCl_3$. The obtained organic layer was dried over anhydrous magnesium sulfate and subsequently concentrated under reduced pressure. The resulting residue was purified by silica gel column chromatography (hexane/AcOEt) to give (3R,4S)-3-(benzyloxy)-4-(3-methylbutyl)azetidin-2-one (188 mg) as a solid.

Production Example 44 m-Chloroperbenzoic acid (about 25% water content, 555 mg) was added under ice-bath cooling to a mixture of 2-(2-cyclopropylethyl)furo[3,2-c]pyridine (300 mg) and $CHCl_3$ (6 ml). After stirring the resulting reaction mixture at room temperature for 8 hours, the mixture was cooled with an ice-water bath and m-chloroperbenzoic acid (about 25% water content, 300 mg) was added again thereto. The resulting reaction mixture was further stirred at room temperature for 16 hours. After cooling the resulting reaction mixture with an ice-water bath, a saturated aqueous sodium hydrogen carbonate solution and a 5% aqueous sodium sulfite solution were added thereto and the mixture was extracted three times with $CHCl_3$. The obtained organic layer was dried over anhydrous sodium sulfate and subsequently concentrated under reduced pressure. The resulting residue was purified by silica gel column chromatography ($CHCl_3$/MeOH) to give 2-(2-cyclopropylethyl)furo[3,2-c]pyridine 5-oxide (190 mg) as an oily product.

Production Example 45

Under nitrogen atmosphere, CMBP (0.9 ml) was added to a mixture of (3R,4S)-4-(hydroxymethyl)-3-(methoxymethoxy)-1-(methoxymethyl)azetidin-2-one (500 mg), 4-fluorophenol (350 mg) and toluene (10 ml) and the mixture was stirred at 150° C. for 1 hour under microwave irradiation. The resulting reaction mixture was allowed to cool to room temperature, and subsequently purified by silica gel column chromatography (hexane/AcOEt) to give (3R,4S)-4-[(4-fluorophenoxy)methyl]-3-(methoxymethoxy)-1-(methoxymethyl) azetidin-2-one (620 mg) as an oily product.

Production Example 46

Under nitrogen atmosphere, CMMP (120 mg) was added to a mixture of (3R,4S)-4-(hydroxymethyl)-3-(methoxymethoxy)-1-(methoxymethyl)-3-({4-[(trans-4-methylcyclohexyl)oxy]pyridin-2-yl}methyl)azetidin-2-one (200 mg), pyrimidin-2-ol (100 mg) and toluene (2 ml) and the mixture was stirred at 130° C. for 1 hour under microwave irradiation. The resulting reaction mixture was allowed to cool to room temperature and subsequently concentrated under reduced pressure. The resulting residue was purified by silica gel column chromatography (hexane/AcOEt) to give (3R,4S)-3-(methoxymethoxy)-1-(methoxymethyl)-3-({4-[(trans-4-methylcyclohexyl)oxy]pyridin-2-yl}methyl)-4-[(pyrimidin-2-yloxy)methyl]azetidin-2-one (120 mg) as an oily product.

Production Example 47

A mixture of (3R,4S)-4-(4-bromophenyl)-3-{[4-(cyclohexyloxy)pyridin-2-yl]methyl}-3-(methoxymethoxy)-1-(methoxymethyl)azetidin-2-one (250 mg), sodium cyclopropanesulfinate (185 mg), CuI (138 mg), N,N'-dimethylethylenediamine (0.155 ml) and DMF (5 ml) was stirred at 130° C. for 1 hour under microwave irradiation. Water was added to the resulting reaction mixture and the mixture was extracted twice with AcOEt. The obtained organic layer was washed with a saturated aqueous sodium chloride solution, dried over anhydrous magnesium sulfate and the solvent was distilled off under reduced pressure. The resulting residue was purified by silica gel column chromatography (hexane/AcOEt) to give (3R,4S)-3-{[4-(cyclohexyloxy)pyridin-2-yl]methyl}-4-[4-(cyclopropylsulfonyl)phenyl]-3-(methoxymethoxy)-1-(methoxymethyl)azetidin-2-one (246 mg) as an oily product.

Production Example 48

Under argon atmosphere, a mixture of (3R,4S)-4-(4-bromophenyl)-3-{[4-(cyclohexyloxy)pyridin-2-yl]methyl}-3-(methoxymethoxy)-1-(methoxymethyl)azetidin-2-one (300 mg), Pd(OAc)$_2$ (13 mg), cesium carbonate (565 mg), dicyclohexyl(2',6'-diisopropoxybiphenyl-2-yl)phosphine (54 mg), potassium trifluoro(methoxymethyl)borate (263 mg), toluene (6 ml) and water (1.3 ml) was stirred at 100° C. overnight. Pd(OAc)$_2$ (13 mg), dicyclohexyl(2',6'-diisopropoxybiphenyl-2-yl)phosphine (54 mg) and potassium trifluoro(methoxymethyl)borate (263 mg) were added to the resulting reaction mixture and the mixture was stirred at 100° C. overnight under argon atmosphere. Water was added to the resulting reaction mixture and the mixture was extracted twice with AcOEt. The obtained organic layer was washed with a saturated aqueous sodium chloride solution, and dried over anhydrous magnesium sulfate. The solvent was distilled off under reduced pressure. The resulting residue was purified by amino-silica gel column chromatography (hexane/AcOEt) to give (3R,4S)-3-{[4-(cyclohexyloxy)pyridin-2-yl]methyl}-3-(methoxymethoxy)-1-(methoxymethyl)-4-[4-(methoxymethyl)phenyl]azetidin-2-one (101 mg) as an oily product.

Production Example 49

A mixture of (3R,4S)-3-{[4-(cyclohexyloxy)pyridin-2-yl]methyl}-4-(hydroxymethyl)-3-(methoxymethoxy)-1-(methoxymethyl)azetidin-2-one (200 mg), Ag$_2$O (360 mg), benzyl bromide (0.19 ml), tetra-n-butylammonium iodide (18 mg) and CH$_2$Cl$_2$ (2 ml) was stirred at room temperature overnight. Ag$_2$O (600 mg) and benzyl bromide (0.3 ml) were added to the resulting reaction mixture and the mixture was stirred at room temperature for 2 days. The resulting reaction mixture was filtered and the filtrate was concentrated under reduced pressure. The resulting residue is purified by silica gel column chromatography (hexane/AcOEt) to give (3R,4S)-4-[(benzyloxy)methyl]-3-{[4-(cyclohexyloxy)pyridin-2-yl]methyl}-3-(methoxymethoxy)-1-(methoxymethyl)azetidin-2-one (94 mg) as an oily product.

Production Example 50

Under argon atmosphere, a mixture of (3R,4S)-4-[(hex-5-en-1-yloxy)methyl]-3-{[4-(hex-5-en-1-yloxy)pyridin-2-yl]methyl}-3-(methoxymethoxy)-1-(methoxymethyl)azetidin-2-one (340 mg), dichloro[1,3-bis(mesitypimidazolidin-2-ylidene](benzylidene)(tricyclohexylphosphoranylidene)ruthenium (VIII) (60 mg) and CH$_2$Cl$_2$ (170 ml) was stirred at room temperature overnight. The resulting reaction mixture was concentrated under reduced pressure and the resulting residue was purified by silica gel column chromatography (hexane/AcOEt) to give (3R,6S)-3-(methoxymethoxy)-5-(methoxymethyl)-8,19-dioxa-5,23-diazatricyclo[18.3.1.0$^{3,6}$]tetracosa-1(24),13,20,22-tetraen-4-one (148 mg) as an oily product.

Production Example 51

A mixture of (3R,4S)-4-[(1S)-2-{[tert-butyl(dimethyl)silyl]oxy}-1-hydroxyethyl]-3-(methoxymethoxy)-1-(methoxymethyl)azetidin-2-one (4 g), THF (50 ml) and 1,1'-thiocarbonyldiimidazole (6.2 g) was stirred at 80° C. overnight. The resulting reaction mixture was allowed to cool to room temperature and subsequently concentrated under reduced pressure. The resulting residue was purified by silica gel column chromatography (hexane/AcOEt) to give O-{(1S)-2-{[tert-butyl(dimethyl)silyl]oxy}-1-[(2S,3R)-3-(methoxymethoxy)-1-(methoxymethyl)-4-oxoazetidin-2-yl]ethyl}1H-imidazol-1-carbothioate (5.2 g) as an oily product.

Production Example 52

Under argon atmosphere, a mixture of O-{(1S)-2-{[tert-butyl(dimethyl)silyl]oxy}-1-[(2S,3R)-3-(methoxymethoxy)-1-(methoxymethyl)-4-oxoazetidin-2-yl]ethyl}1H-imidazol-1-carbothioate (5.2 g), benzene (26 ml) and tri-n-butyltin hydride (6.2 ml) was stirred at 100° C. for 5 minutes. 2,2'-Azobis (isobutyronitrile) (500 mg) was added to the resulting reaction mixture and the mixture was stirred at 100° C. for 2 hours. The resulting reaction mixture was allowed to cool to room temperature and concentrated under reduced pressure. The resulting residue was purified by silica gel column chromatography (hexane/AcOEt) to give (3R,4S)-4-(2-{[tert-butyl(dimethyl)silyl]oxy}ethyl)-3-(methoxymethoxy)-1-(methoxymethyl)azetidin-2-one (3 g) as an oily product.

Production Example 53

Under nitrogen atmosphere, a mixture of 1H-imidazo[4,5-c]pyridine-6-methyl carboxylate (1 g), 2-cyclohexylethanol (2 ml), CMBP (2 ml) and toluene (10 ml) was stirred at 90° C. overnight. The resulting reaction mixture was concentrated under reduced pressure and purified by silica gel column chromatography (hexane/AcOEt) to give (1) 1-(2-cyclohexylethyl)-1H-imidazo[4,5-c]pyridine-6-methyl carboxylate (640 mg) and (2) 3-(2-cyclohexylethyl)-3H-imidazo[4,5-c]pyridine-6-methyl carboxylate (450 mg) each as an oily product.

Production Example 54

1-Hexyl-1H-pyrrolo[3,2-c]pyridine-6-carbonitrile (367 mg) was prepared as a foamy solid from 6-chloro-1-hexyl-1H-pyrrolo[3,2-c]pyridine (700 mg) in the same manner as in the method described in Example 11.

Production Example 55

A mixture of sodium hydrogen carbonate (218 mg) and water (13 ml) was added to a mixture of 6-(chloromethyl)-1-(2-cyclohexylethyl)-1H-imidazo[4,5-c]pyridine hydrochloride (320 mg) and CH$_2$Cl$_2$ (13 ml) and the mixture was stirred at room temperature for 5 minutes. The organic layer and the aqueous layer of the resulting reaction mixture were separated and the aqueous layer was extracted with CH$_2$Cl$_2$. The obtained organic layers were combined and washed with a saturated aqueous sodium chloride solution. The obtained organic layer was dried over anhydrous magnesium sulfate and concentrated under reduced pressure. Acetone (13 ml) and sodium iodide (800 mg) were added to the resulting residue and the mixture was stirred at room temperature for 3 hours under nitrogen atmosphere. After adding THF (13 ml) and toluene (30 ml) to the resulting reaction mixture, the mixture was concentrated under reduced pressure to about 2 ml. Insoluble material was removed by filtration from the obtained mixture and toluene (30 ml) was added again to the filtrate The reaction mixture was concentrated under reduced pressure to about 1 ml (mixture A).

Under argon atmosphere, a mixture of tert-butyl {(1S)-1-[(4S)-2,2-dimethyl-5-oxo-1,3-dioxolan-4-yl]-3-methylbutyl}carbamate (261 mg) and THF (5 ml) was cooled to −78° C. with stirring, LDA (1.12 M hexane-THF solution, 2.5 ml) was added dropwise and the mixture was stirred at the same temperature for 30 minutes. The mixture A was added dropwise at −78° C. to the resulting reaction mixture under argon atmosphere and the mixture was stirred at the same temperature for 1 hour. The resulting reaction mixture was allowed to warm up to room temperature, a saturated aqueous ammonium chloride solution and AcOEt were added thereto. The organic layer and the aqueous layer were separated and the aqueous layer was extracted with AcOEt. The obtained organic layers were combined and washed with a saturated aqueous sodium chloride solution. The obtained mixture was dried over anhydrous magnesium sulfate and the solvent was distilled off under reduced pressure. The resulting residue was purified by silica gel column chromatography (hexane/AcOEt) to give tert-butyl {(1S)-1-[(4R)-4-{[1-(2-cyclohexylethyl)-1H-imidazo[4,5-c]piridin-6-yl]methyl}-2,2-dimethyl-5-oxo-1,3-dioxolan-4-yl]-3-methylbutyl}carbamate (150 mg) as an oily product.

Production Example 56

Under nitrogen atmosphere, a mixture of 1-oxaspiro[4.5]decan-8-one (500 mg) and CH$_2$Cl$_2$ (5 ml) was cooled with a dry ice-acetone bath and diisobutylaluminium hydride (1.04 M hexane solution, 3.5 ml) was slowly added thereto. The reaction mixture was stirred for 10 minutes while cooled in the dry ice-acetone bath and subsequently MeOH and sodium sulfate decahydrate were added thereto. The obtained mixture was allowed to warm up to room temperature and stirred for 6 hours. Anhydrous sodium sulfate was added thereto and the mixture was further stirred for 14 hours. The obtained mixture was filtered through Celite and the filtrate was concentrated under reduced pressure. The resulting residue was purified by silica gel column chromatography (hexane/AcOEt) to give an oily product (258 mg). The obtained oily product (144 mg) was dissolved in toluene (4 ml) and 4-methoxybenzoic acid (210 mg), tri-n-butylphosphine (0.34 ml) and (E)-N,N,N',N'-tetramethyldiazene-1,2-dicarboxamide (238 mg) were added thereto under ice-bath cooling. The mixture was stirred for 10 minutes under ice-bath cooling and subsequently stirred at 60° C. for 24 hours. The obtained mixture was allowed to cool to room temperature. Insoluble material was removed by filtration and the filtrate was concentrated under reduced pressure. The resulting residue was purified by silica gel column chromatography (hexane/AcOEt) to give (1) (5s,8r)-1-oxaspiro[4.5]deca-8-yl4-methoxybenzoate (20.7 mg) and (2) (5r,8s)-1-oxaspiro[4.5]deca-8-yl 4-methoxybenzoate (182 mg) each as an oily product.

Production Example 57

A solution of tert-butyl {(1S)-1-[(4R)-4-{[2-(2-cyclopropylethyl)furo[3,2-c]pyridin-4-yl]methyl}-2,2-dimethyl-5-oxo-1,3-dioxolan-4-yl]-3-methylbutyl}carbamate (75 mg) in EtOH (3 ml) was subjected to a reaction with a continuous-flow hydrogenation reactor (H-Cube Pro (registered tradename); manufactured by ThalesNano) and CatCart (registered tradename) 10% Pd/C (manufactured by ThalesNano, 70×4 mm) as a cartridge catalyst under the conditions of a flow rate of 1.0 ml/min, a pressure of 1 bar and a temperature of 25° C. The resulting reaction mixture was concentrated under reduced pressure, and a solution of the residue in EtOH (3 ml) was subjected to a reaction again with a continuous-flow hydrogenation reactor (H-Cube Pro (registered tradename); manufactured by ThalesNano) and CatCart (registered tradename) 10% Pd/C (manufactured by ThalesNano, 70×4 mm) as a cartridge catalyst under the conditions of a flow rate of 1.0 ml/min, a pressure of 50 bar and a temperature of 60° C. The resulting reaction mixture was concentrated under reduced pressure, and a solution of the residue in EtOH (3 ml) was subjected to a reaction again with a continuous-flow hydrogenation reactor (H-Cube Pro (registered tradename); manufactured by ThalesNano) and CatCart (registered tradename) 10% Pd/C (manufactured by ThalesNano, 70×4 mm) as a cartridge catalyst under the conditions of a flow rate of 1.0 ml/min, a pressure of 50 bar and a temperature of 60° C. The resulting reaction mixture was concentrated under reduced pressure to give tert-butyl {(1S)-1-[(4R)-4-{[2-(2-cyclopropylethyl)-2,3-dihydrofuro[3,2-c]pyridin-4-yl]methyl}-2,2-dimethyl-5-oxo-1,3-dioxolan-4-yl]-3-methylbutyl}carbamate (65.7 mg) as an oily product.

Production Example 58

1 M Aqueous sodium hydroxide solution (2 ml) was added to a mixture of (5r,8s)-1-oxaspiro[4.5]deca-8-yl 4-methoxybenzoate (175 mg), MeOH (1 ml) and THF (2 ml) and the mixture was stirred at 50° C. for 16 hours. The resulting reaction mixture was allowed to cool to room temperature and concentrated under reduced pressure. The resulting residue was extracted with diethyl ether. The organic layer was washed with a saturated aqueous sodium hydrogen carbonate solution and a saturated aqueous sodium chloride solution, subsequently dried over anhydrous magnesium sulfate and concentrated under reduced pressure (residue A). The aqueous layer was extracted three times with AcOEt, the organic layer was dried over anhydrous magnesium sulfate and concentrated under reduced pressure (residue B). The residue B was purified by amino-silica gel column chromatography (hexane/AcOEt). The obtained compound was mixed with the residue A to give (5r,8s)-1-oxaspiro[4.5]decan-8-ol (79.6 mg) as an oily product.

Production Example 59

A mixture of {4-[(trans-4-methylcyclohexyl)oxy]pyridin-2-yl}methanol (5 g) and CH$_2$Cl$_2$ (18 ml) was cooled with an ice-water bath. PBr$_3$ (0.43 ml) was added and the mixture was stirred at room temperature for 2 hours. After cooling the resulting reaction mixture with an ice-water bath, a saturated aqueous sodium hydrogen carbonate solution was added thereto and the mixture was stirred at room temperature for 30 minutes. CHCl$_3$ and a saturated aqueous sodium chloride solution were added to the reaction mixture. The organic layer was separated, dried over anhydrous magnesium sulfate and subsequently concentrated under reduced pressure. Toluene (5 ml) was added to the resulting residue (mixture A).

A mixture of tert-butyl {(1R)-1-[(4S)-2,2-dimethyl-5-oxo-1,3-dioxolan-4-yl]-3-methylbutyl}carbamate (1.13 g) and THF (18 ml) was cooled to −78° C., LDA (1.09 M hexane-THF solution, 3.5 ml) was added under argon atmosphere and the mixture was stirred for 30 minutes. Trimethylchlorosilane (0.5 ml) was added to the reaction mixture, and the reaction mixture was allowed to warm up to 0° C. and subsequently stirred for 30 minutes. The resulting reaction mixture was cooled to −78° C. LDA (1.09 M hexane-THF solution, 7 ml) was added thereto and the mixture was stirred for 30 minutes. The mixture A was added to the resulting reaction mixture at −78° C. and the mixture was stirred for 2 hours. Water was added to the resulting reaction mixture. The reaction mixture was allowed to warm up to room temperature and extracted with $CHCl_3$. The obtained organic layer was dried over anhydrous magnesium sulfate and subsequently concentrated under reduced pressure. The resulting residue was purified by silica gel column chromatography (hexane/AcOEt) to give (1) tert-butyl {(1R)-1-[(4S)-2,2-dimethyl-4-({4-[(trans-4-methylcyclohexyl)oxy]pyridin-2-yl}methyl)-5-oxo-1,3-dioxolan-4-yl]-3-methylbutyl}carbamate (0.97 g) and (2) tert-butyl {(1R)-1-[(4R)-2,2-dimethyl-4-({4-[(trans-4-methylcyclohexyl)oxy]pyridin-2-yl}methyl)-5-oxo-1,3-dioxolan-4-yl]-3-methylbutyl}carbamate (0.45 g) each as an oily product.

Production Example 60

Hydrogen peroxide (30% aqueous solution, 7 ml) and ammonium molybdate tetrahydrate (2.4 g) were added to a mixture of 5-[(2-methoxyethyl)sulfanyl]-1-phenyl-1H-tetrazole (2.33 g) and EtOH (46 ml) and the mixture was stirred at 65° C. for 3 hours. The resulting reaction mixture was allowed to cool to room temperature and subsequently filtered through Celite. After adding water to the filtrate, the mixture was concentrated under reduced pressure until most of the EtOH was removed. After adding AcOEt to the residue and the mixture was extracted. The organic layer was washed with a saturated aqueous sodium thiosulfate solution. The obtained organic layer was dried over anhydrous magnesium sulfate and subsequently concentrated under reduced pressure. The produced solid was washed using a mixed solvent of diisopropyl ether-MeOH to give 5-[(2-methoxyethyl)sulfonyl]-1-phenyl-1H-tetrazole (2.14 g) as a solid.

Production Example 61

A mixture of (2R,5R)-2,5-dimethyl-N-[(1E)-4-methylpentylidene]pyrrolidin-1-amine (1.62 g), $Et_3N$ (9.2 ml) and toluene (48 ml) was heated to 80° C. and benzyloxy acetyl chloride (0.4 M toluene solution, 83 ml) was added thereto with stirring over a period of 4 hours. The reaction mixture was allowed to cool to room temperature, subsequently a saturated aqueous sodium hydrogen carbonate solution was added thereto and the mixture was extracted with AcOEt. The obtained organic layer was dried over anhydrous magnesium sulfate and subsequently concentrated under reduced pressure. The resulting residue was purified by silica gel column chromatography (hexane/AcOEt) to give (3R,4S)-3-(benzyloxy)-1-[(2R,5R)-2,5-dimethylpyrrolidin-1-yl]-4-(3-methylbutyl)azetidin-2-one (2.02 g) as an oily product.

Production Example 62

Under nitrogen atmosphere, a mixture of (3R,4S)-4-(4-bromophenyl)-3-{[4-(cyclohexyloxy)pyridin-2-yl]methyl}-3-(methoxymethoxy)-1-(methoxymethyl)azetidin-2-one (200 mg), cyclopropylboronic acid (99 mg), $Pd(OAc)_2$ (17 mg), dicyclohexyl(2',6'-dimethoxybiphenyl-2-yl)phosphine (63 mg), tripotassium phosphate (327 mg), toluene (4 ml) and water (0.1 ml) was stirred at 90° C. for 15 hours. Water was added to the resulting reaction mixture and the mixture was extracted with AcOEt. The obtained organic layer was washed with a saturated aqueous sodium chloride solution, dried over anhydrous magnesium sulfate and the solvent was distilled off under reduced pressure. The resulting residue was purified by silica gel column chromatography (hexane/AcOEt) to give (3R,4S)-3-{[4-(cyclohexyloxy)pyridin-2-yl]methyl}-4-(4-cyclopropylphenyl)-3-(methoxymethoxy)-1-(methoxymethyl)azetidin-2-one (126 mg) as an oily product.

Production Example 63

Under nitrogen atmosphere, a mixture of tert-butyl dimethylchlorosilane (2.4 g), imidazole (2.2 g), 4-(dimethylamino)pyridine (140 mg) and $CH_2Cl_2$ (18 ml) was added under ice-bath cooling to a mixture of (3R,4S)-4-[(1S)-1,2-dihydroxyethyl]-3-(methoxymethoxy)-1-(methoxymethyl) azetidin-2-one (3.7 g) and $CH_2Cl_2$ (74 ml) and the mixture was stirred at room temperature overnight. Water was added to the resulting reaction mixture and the mixture was extracted twice with $CH_2Cl_2$. The obtained organic layers were combined, washed with a saturated aqueous sodium chloride solution and dried over anhydrous magnesium sulfate. The obtained organic layer was concentrated under reduced pressure to give (3R,4S)-4-[(1S)-2-{[tert-butyl(dimethyl)silyl]oxy}-1-hydroxyethyl]-3-(methoxymethoxy)-1-(methoxymethyl)azetidin-2-one (4.8 g) as an oily product.

Production Example 64

NaH (60% mineral oil dispersion, 327 mg) was added under ice-bath cooling to a mixture of indan-2-ol (1 g) and DMF (5.04 ml) and the mixture was stirred for 1 hour. A mixture of 4-chloropyridine-2-carbonitrile (600 mg) and DMF (0.96 ml) was added to the resulting reaction mixture and the mixture was stirred for 1.5 hours. The resulting reaction mixture was poured into ice cooled water and the mixture was extracted twice with AcOEt. The obtained organic layers were combined, washed with a saturated aqueous sodium chloride solution and dried over anhydrous sodium sulfate. The obtained organic layer was concentrated under reduced pressure, MeOH (20 ml) was added to the residue and cooled with an ice-water bath, subsequently sodium methoxide (28% MeOH solution, 0.9 ml) was added thereto and the mixture was stirred at room temperature for 3 hours. 1 M Hydrochloric acid (14 ml) was added to the resulting reaction mixture and the mixture was stirred at room temperature for 1 hour. The resulting reaction mixture was concentrated under reduced pressure, a saturated aqueous sodium hydrogen carbonate solution was added to the residue and the mixture was extracted with AcOEt. The obtained organic layer was washed with a saturated aqueous sodium chloride solution, dried over anhydrous sodium sulfate and subsequently concentrated under reduced pressure. MeOH (20 ml) was added to the resulting residue and cooled with an ice-water bath, subsequently $NaBH_4$ (720 mg) was added thereto and the mixture was stirred at room temperature for 15 hours. After cooling the resulting reaction mixture with an ice-water bath, a saturated aqueous sodium chloride solution was added thereto and the mixture was concentrated under reduced pressure. Water was added to the resulting residue and the mixture was extracted with $CHCl_3$. The obtained organic layer was dried over anhydrous sodium sulfate and subsequently concentrated under reduced pressure. The resulting residue was purified by silica gel column chromatography (CHCl$_3$/MeOH) to give [4-(2,3-dihydro-1H-inden-2-yloxy)pyridin-2-yl]methanol (300 mg) as an oily product.

Production Example 65

CMBP (0.31 ml) was added to a mixture of (3R,4S)-3-[(4-hydroxypyridin-2-yl)methyl]-4-isobutyl-3-(methoxymethoxy)-1-(methoxymethyl)azetidin-2-one (200 mg), 3,3-dimethyl-1-pentanol (141 mg) and toluene (2 ml) and the mixture was stirred at 150° C. for 30 minutes under microwave irradiation. The resulting reaction mixture was allowed to cool to room temperature and subsequently concentrated under reduced pressure. The resulting residue was purified by silica gel column chromatography (hexane/AcOEt) to give (3R,4S)-3-({4-[(3,3-dimethylpentyl)oxy]pyridin-2-yl}methyl)-4-isobutyl-3-(methoxymethoxy)-1-(methoxymethyl)azetidin-2-one (123 mg) as an oily product.

Production Example 66

Under nitrogen atmosphere, CMMP (100 mg) was added to a mixture of (3R,4S)-3-[(4-hydroxypyridin-2-yl)methyl]-4-isobutyl-3-(methoxymethoxy)-1-(methoxymethyl)azetidin-2-one (200 mg), (S)-4-methyl-2-pentanol (0.11 ml) and toluene (2 ml) and the mixture was stirred at 100° C. for 1 hour under microwave irradiation. The resulting reaction mixture was allowed to cool to room temperature and subsequently concentrated under reduced pressure. The resulting residue was purified by silica gel column chromatography (hexane/AcOEt) to give (3R,4S)-4-isobutyl-3-(methoxymethoxy)-1-(methoxymethyl)-3-[(4-{[(2R)-4-methylpentan-2-yl]oxy}pyridin-2-yl}methyl)azetidin-2-one (131 mg) as an oily product.

Production Example 67

Under nitrogen atmosphere, trimethylsilylcyanide (0.183 ml) was added to a mixture of 2-(2-cyclopropylethyl)furo[3,2-c]pyridine 5-oxide (190 mg), Et$_3$N (0.33 ml) and MeCN (4 ml) and the mixture was stirred at 85° C. for 16 hours. After cooling the resulting reaction mixture to room temperature, Et$_3$N (0.65 ml) and trimethylsilylcyanide (0.35 ml) were added thereto. The reaction mixture was stirred again at 85° C. for 3.5 hours and subsequently allowed to cool to room temperature. AcOEt was added to the resulting reaction mixture and washed sequentially with a saturated aqueous sodium hydrogen carbonate solution and a saturated aqueous sodium chloride solution. The obtained organic layer was dried over anhydrous magnesium sulfate and concentrated under reduced pressure. The resulting residue was purified by silica gel column chromatography (hexane/AcOEt) to give 2-(2-cyclopropylethyl)furo[3,2-c]pyridine-4-carbonitrile (148 mg) as an oily product.

Production Example 68

Under nitrogen atmosphere, sodium iodide (6.8 g), which was dried in advance at 30° C. for 7 hours and at room temperature for 5 days under reduced pressure, was added to a mixture of 4-chloro-2-(chloromethyl)pyridine (7 g) and THF (100 ml) and the mixture was stirred at room temperature for 4 hours. Anhydrous sodium sulfate (dried at 50° C. for 4 hours under reduced pressure, 3 g) was added to the reaction mixture and the mixture was further stirred for 30 minutes (mixture A).

Under nitrogen atmosphere, to a solution of (3R,4S)-4-isobutyl-3-(methoxymethoxy)-1-(methoxymethyl)azetidin-2-one (5 g) in THF (50 ml), LDA (1.12 M hexane-THF solution, 25 ml) was slowly added at −78° C. The reaction mixture was stirred at −78° C. for 30 minutes, subsequently the mixture A was added dropwise thereto and the mixture was further stirred for 30 minutes. A saturated aqueous ammonium chloride solution was added to the resulting reaction mixture, subsequently the mixture was allowed to warm up to room temperature and extracted twice with AcOEt. The obtained organic layer was dried over anhydrous sodium sulfate and concentrated under reduced pressure. The resulting residue was purified by silica gel column chromatography (hexane/AcOEt) to give (3R,4S)-3-[(4-chloropyridin-2-yl)methyl]-4-isobutyl-3-(methoxymethoxy)-1-(methoxymethyl)azetidin-2-one (5.32 g) as an oily product.

Production Example 69

PBr$_3$ (0.1 ml) was added to a mixture of (1-hexyl-1H-pyrrolo[3,2-c]pyridin-6-yl)methanol (220 mg) and CH$_2$Cl$_2$ (5 ml) under ice-bath cooling, subsequently allowed to warm up to room temperature and the mixture was stirred for 2 hours. The resulting reaction mixture was poured into a saturated aqueous sodium hydrogen carbonate solution and the mixture was stirred for 1 hour. The obtained mixture was filtered through Celite and the Celite pad was washed with toluene. The organic layer was separated from the obtained filtrate and washed with a saturated aqueous sodium chloride solution. The obtained organic layer was dried over anhydrous sodium sulfate and concentrated under reduced pressure to about 2 ml (mixture A).

Under nitrogen atmosphere, a mixture of (3R,4S)-4-isobutyl-3-(methoxymethoxy)-1-(methoxymethyl)azetidin-2-one (200 mg) and THF (2 ml) was cooled with a dry ice-acetone bath, LDA (1.09 M hexane-THF solution, 1 ml) was added and the mixture was stirred for 30 minutes. The mixture A was slowly added to the reaction mixture, subsequently the mixture was stirred for 30 minutes under dry ice-acetone bath cooling. A saturated aqueous ammonium chloride solution was added to the resulting reaction mixture, and the mixture was allowed to warm up to room temperature and extracted with AcOEt. The obtained organic layer was dried over anhydrous magnesium sulfate and concentrated under reduced pressure. The resulting residue was purified by silica gel column chromatography (CHCl$_3$/MeOH) to give (3R,4S)-3-[(1-hexyl-1H-pyrrolo[3,2-c]pyridin-6-yl)methyl]-4-isobutyl-3-(methoxymethoxy)-1-(methoxymethyl)azetidin-2-one (324 mg) as an oily product.

Production Example 70

10% Pd/C (50% water content, 1.5 g) was added to a mixture of (3R,4S)-3-{[4-(benzyloxy)-5-methylpyridin-2-yl]methyl}-4-isobutyl-3-(methoxymethoxy)-1-(methoxymethyl)azetidin-2-one (3.46 g) and MeOH (150 ml) and the mixture was stirred at room temperature for 2 hours under hydrogen atmosphere of 4 atm. The reaction mixture was filtered through Celite and the filtrate was concentrated under reduced pressure. The resulting residue was purified by silica gel column chromatography (CHCl$_3$/MeOH) to give (3R,4S)-3-[(4-hydroxy-5-methylpyridin-2-yl)methyl]-4-isobutyl-3-(methoxymethoxy)-1-(methoxymethyl)azetidin-2-one (1.82 g) as a foamy solid.

Production Example 71

Under nitrogen atmosphere, a mixture of (3R,4S)-4-(4-bromophenyl)-3-{[4-(cyclohexyloxy)pyridin-2-yl]methyl}-

3-(methoxymethoxy)-1-(methoxymethyl)azetidin-2-one (200 mg), morpholine (0.066 ml), 2-(dicyclohexylphosphino)-2',4',6'-triisopropyl-1,1'-biphenyl (37 mg), tripotassium phosphate (163 mg), bis(dibenzylideneacetone)palladium (11 mg) and toluene (2 ml) was stirred at 100° C. overnight. Water was added to the resulting reaction mixture and the mixture was extracted with AcOEt. The obtained organic layer was washed with a saturated aqueous sodium chloride solution, dried over anhydrous magnesium sulfate and the solvent was distilled off under reduced pressure. The resulting residue was purified by silica gel column chromatography (hexane/AcOEt) to give (3R,4S)-3-{[4-(cyclohexyloxy)pyridin-2-yl]methyl}-3-(methoxymethoxy)-1-(methoxymethyl)-4-[4-(morpholin-4-yl)phenyl]azetidin-2-one (138 mg) as an oily product.

Production Example 72

Under argon atmosphere, a mixture of (3R,4S)-3-[(5-bromo-4-methoxypyridin-2-yl)methyl]-4-isobutyl-3-(methoxymethoxy)-1-(methoxymethyl)azetidin-2-one (125 mg), 2-benzyl-4,4,5,5-tetramethyl-1,3,2-dioxaborolane (0.13 ml), bis(tricyclohexylphosphine)palladium (II) dichloride (44 mg), tripotassium phosphate (125 mg), DOX (2.5 ml) and water (0.35 ml) was stirred at 90° C. overnight. The resulting reaction mixture was allowed to cool to room temperature and subsequently a saturated aqueous sodium hydrogen carbonate solution was added thereto. The obtained mixture was extracted with AcOEt and the organic layer was dried over anhydrous magnesium sulfate and concentrated under reduced pressure. The resulting residue was purified by silica gel column chromatography (hexane/AcOEt) to give (3R,4S)-3-[(5-benzyl-4-methoxypyridin-2-yl)methyl]-4-isobutyl-3-(methoxymethoxy)-1-(methoxymethyl)azetidin-2-one (27 mg) as an oily product.

Production Example 73

A mixture of (3R,4S)-4-(hydroxymethyl)-3-(methoxymethoxy)-1-(methoxymethyl)-3-({4-[(trans-4-methylcyclohexyl)oxy]pyridin-2-yl}methyl)azetidin-2-one (530 mg), cyclopropylmethyliodide (8.39 g) and Ag$_2$O (3 g) was stirred at 90° C. overnight. Ag$_2$O (3 g) was added to the resulting reaction mixture and the mixture was further stirred at 90° C. overnight. Insoluble material was removed by filtration from the resulting reaction mixture and the obtained filtrate was concentrated under reduced pressure. The resulting residue was purified by silica gel column chromatography (hexane/AcOEt) to give (3R,4S)-4-[(but-3-en-1-yloxy)methyl]-3-(methoxymethoxy)-1-(methoxymethyl)-3-({4-[(trans-4-methylcyclohexyl)oxy]pyridin-2-yl}methyl)azetidin-2-one (84.6 mg) as an oily product.

Production Example 74

Under nitrogen atmosphere, a mixture of trimethylsilylacetylene (320 mg) and THF (1.6 ml) was cooled at −78° C. and n-butyl lithium (1.58 M hexane solution, 2.6 ml) was added dropwise. The resulting reaction mixture was stirred for 10 minutes under ice-bath cooling and subsequently cooled again to −78° C. N,N,N',N',N'',N''-Hexamethylphosphoric acid triamide (0.86 ml) was added to the resulting reaction mixture, and the mixture was stirred at the same temperature for 30 minutes and subsequently (2-bromoethyl)cyclopropane (500 mg) was added thereto. The resulting reaction mixture was allowed to warm up to room temperature and stirred overnight. Water was added to the resulting reaction mixture and the organic layer was separated. The obtained organic layer was washed three times with water and twice with a saturated aqueous sodium chloride solution. The obtained organic layer was dried over anhydrous sodium sulfate and subsequently concentrated under reduced pressure to give (4-cyclopropylbut-1-yn-1-yl)(trimethyl)silane (506 mg) as an oily product.

Production Example 75

Under argon atmosphere, tetra-n-butylammonium fluoride (1 M THF solution, 8.8 ml) was added to a mixture of 3-bromopyridin-4(1H)-one (500 mg), (4-cyclopropylbut-1-yn-1-yl)(trimethyl)silane (1.44 g), Et$_3$N (2.8 ml) and DMF (5 ml). The obtained mixture was irradiated with supersonic wave for 30 seconds, subsequently bis(triphenylphosphine)palladium (II) dichloride (420 mg) was added thereto and the mixture was stirred at 110° C. for 1 hour under microwave irradiation. AcOEt and silica gel were added to the resulting reaction mixture and the mixture was concentrated under reduced pressure. The resulting residue was purified by silica gel column chromatography (hexane/AcOEt) to give 2-(2-cyclopropylethyl)furo[3,2-c]pyridine (302 mg) as an oily product.

Production Examples 76 to 194

Production Example compounds shown in Tables to be described later were produced in the same manner as in the method described in the above Production Examples.

Production Example 195

A mixture of (3R,4S)-3-(methoxymethoxy)-4-(3,3,3-trifluoropropyl)azetidin-2-one (628 mg), 1,2-dichloroethane (20 ml), chloro(methoxy)methane (1.5 ml) and DIPEA (3.5 ml) was stirred at 90° C. for 12 hours. The resulting reaction mixture was allowed to cool to room temperature. A saturated aqueous sodium hydrogen carbonate solution was added thereto and the mixture was extracted with AcOEt. The obtained organic layer was washed with a saturated aqueous sodium chloride solution and dried over anhydrous magnesium sulfate. The organic layer was concentrated under reduced pressure and the resulting residue was purified by silica gel column chromatography (hexane/AcOEt) to give (1) (3R,4S)-3-(methoxymethoxy)-1-(methoxymethyl)-4-(3,3,3-trifluoropropyl)azetidin-2-one (129 mg) as a solid, and (2) (3R,4S)-3-(methoxymethoxy)-1-[(methoxymethoxy)methyl]-4-(3,3,3-trifluoropropyl)azetidin-2-one (474 mg) as an oily product.

Production Example 196

Under argon atmosphere, a mixture of tert-butyl [(1S)-1-{(4R)-4-[(4-chloropyridin-2-yl)methyl]-2,2-dimethyl-5-oxo-1,3-dioxolan-4-yl}-3-methylbutyl]carbamate (1.03 g), 2-(trimethylsilyl)ethanethiol (0.4 ml), (9,9-dimethyl-9H-xanthene-4,5-diyl)bis(diphenylphosphine) (700 mg), tris(dibenzylideneacetone)dipalladium (550 mg), DIPEA (0.85 ml) and DOX (16 ml) was stirred at 120° C. for 2 hours under microwave irradiation. After cooling the resulting reaction mixture to room temperature, AcOEt was added thereto, and the insoluble materials were removed by filtration. The filtrate was concentrated under reduced pressure and the residue was purified by silica gel column chromatography (hexane/AcOEt) to give tert-butyl [(1S)-1-{(4R)-2,2-dimethyl-5-oxo-4-[(4-{[2-(trimethylsilyl)ethyl]

sulfanyl}pyridin-2-yl)methyl]-1,3-dioxolan-4-yl}-3-methylbutyl]carbamate (1.1 g) as a foamy solid.

Production Example 197

Under nitrogen atmosphere, 2,2,6,6-tetramethylpiperidinyl-magnesium chloride-lithium chloride complex (1 M THF-toluene solution, 91 ml) was added dropwise at −20° C. over a period of 2 hours to a mixture of methyl N-(tert-butoxycarbonyl)-O-(2-cyclopropylethyl)-L-serinate (6.5 g), dibromomethane (8.0 g) and THF (22 ml) while maintaining an internal temperature below −11° C. and subsequently stirred at −15° C. for 2 hours. The resulting reaction mixture was poured into a cold mixture of 5% aqueous citric acid solution and AcOEt (cooled with ice-water bath) and subsequently stirred for 10 minutes. The organic layer was separated, and washed with 5% aqueous citric acid solution 3 times and a saturated aqueous sodium chloride solution. The obtained organic layer was dried over anhydrous sodium sulfate, and subsequently concentrated under reduced pressure to give the residue (10.7 g) containing tert-butyl [(2S)-4,4-dibromo-1-(2-cyclopropylethoxy)-3-oxobutan-2-yl]carbamate as an oily product.

Production Example 198

2 M Aqueous sodium hydroxide solution (57 ml) was added dropwise under ice-bath cooling to a mixture of tert-butyl [(2S)-4,4-dibromo-1-(2-cyclopropylethoxy)-3-oxobutan-2-yl]carbamate (9.6 g) and toluene (76 ml) over a period of 15 minutes and the mixture was subsequently stirred at room temperature for 2 hours. Toluene and water were added to the resulting reaction mixture and subsequently the organic layer and the aqueous layer were separated. The organic layer was extracted twice with water, combined with the aqueous layer obtained first and subsequently AcOEt was added thereto. After cooling the obtained mixture with an ice-water bath, 2 M hydrochloric acid was added to adjust a pH of the aqueous layer to about 1.5. The organic layer and the aqueous layer of the resulting reaction mixture were separated and the aqueous layer was extracted 3 times with AcOEt. The obtained organic layers were combined and dried over anhydrous sodium sulfate. The obtained organic layer was concentrated under reduced pressure to give (3S)-3-[(tert-butoxycarbonyl)amino]-4-(2-cyclopropylethoxy)-2-hydroxybutanoic acid (4.53 g) as an oily product.

Production Example 199

Trifluoroacetic acid (12 ml) was added to a solution of ethyl (2S)-2-[(tert-butoxycarbonyl)amino]-4-methylpenta-4-enoate (5.7 g) in CH$_2$Cl$_2$ (40 ml) and the mixture was stirred at room temperature for 1 hour. The resulting reaction mixture was concentrated under reduced pressure, THF (60 ml), benzyl chloroformate (3.2 ml), sodium hydrogen carbonate (4.3 g) and water (60 ml) were added to the residue and the mixture was stirred at room temperature for 1 hour. The resulting reaction mixture was extracted with AcOEt, the organic layer was washed with a saturated aqueous sodium chloride solution and subsequently dried over anhydrous magnesium sulfate. The resulting residue was purified by silica gel column chromatography (hexane/AcOEt) to give ethyl (2S)-2-{[(benzyloxy)carbonyl]amino}-4-methylpenta-4-enoate (4.2 g) as an oily product.

Production Example 200

Under nitrogen atmosphere, a mixture of trifluoroacetic acid (4.5 ml) and CH$_2$Cl$_2$ (35 ml) was added dropwise under ice-bath cooling to a mixture of diethyl zinc (1.09 M hexane solution, 55 ml) and CH$_2$Cl$_2$ (75 ml). The resulting reaction mixture was stirred for 30 minutes under ice-bath cooling and subsequently diiodomethane (4.8 ml) was added thereto at the same temperature. After stirring the reaction mixture for 30 minutes under ice-bath cooling, a mixture of ethyl (2S)-2-{[(benzyloxy) carbonyl]amino}-4-methylpenta-4-enoate (4.2 g) and CH$_2$Cl$_2$ (35 ml) was added dropwise at the same temperature. After stirring the resulting reaction mixture at room temperature overnight, 1 M hydrochloric acid (50 ml) was added under ice-bath cooling. The obtained mixture was extracted with CHCl$_3$, the organic layer was washed with a saturated aqueous sodium hydrogen carbonate solution, subsequently dried over anhydrous magnesium sulfate and concentrated under reduced pressure. The resulting residue was purified by silica gel column chromatography (hexane/AcOEt) to give ethyl N-[(benzyloxy)carbonyl]-3-(1-methylcyclopropyl)-L-alaninate (3.8 g) as an oily product.

Production Example 201

10% Pd/C (50% water content, 0.95 g) was added to a solution of ethyl N-[(benzyloxy)carbonyl]-3-(1-methylcyclopropyl)-L-alaninate (3.8 g) in EtOH (76 ml) and the mixture was stirred at room temperature for 1.5 hours under hydrogen atmosphere. Insoluble material was removed by filtration from the resulting reaction mixture and subsequently the filtrate was concentrated under reduced pressure. Di-tert-butyl dicarbonate (2.85 g) and DIPEA (2.3 ml) were added under ice-bath cooling to a solution of the resulting residue in THF (76 ml) and the mixture was stirred at room temperature for 2 hours. The resulting reaction mixture was poured into a saturated aqueous ammonium chloride solution and the mixture was extracted with AcOEt. The obtained organic layer was dried over anhydrous sodium sulfate and subsequently concentrated under reduced pressure. The resulting residue was purified by silica gel column chromatography (hexane/AcOEt) to give ethyl N-(tert-butoxycarbonyl)-3-(1-methylcyclopropyl)-L-alaninate (3.2 g) as an oily product.

Production Example 202

Under nitrogen atmosphere, to a mixture of N-(tert-butoxycarbonyl)-L-serine (20 g) and DMF (480 ml) was added NaH (60% mineral oil dispersion, 8.6 g) in five portions while maintaining an internal temperature below 5° C. under ice-bath cooling and subsequently the mixture was stirred for 1 hour under ice-bath cooling. (2-Iodoethyl) cyclopropane (24 g) was added to the resulting reaction mixture and the mixture was stirred at room temperature for 14 hours. After cooling the resulting reaction mixture with an ice-water bath, water and 1 M hydrochloric acid were added to adjust a pH to 2 to 3. The resulting reaction mixture was extracted three times with AcOEt and subsequently the organic layer was washed with a saturated aqueous sodium chloride solution. The obtained organic layer was dried over anhydrous sodium sulfate and concentrated under reduced pressure. MeOH (140 ml) and CH$_2$Cl$_2$ (420 ml) were added to the resulting residue, (diazomethyl)(trimethyl)silane (2 M hexane solution, 62 ml) was added dropwise under ice-bath cooling while maintaining an internal temperature below 6° C. and subsequently the mixture was stirred for 10 minutes under ice-bath cooling and at room temperature for 1 hour. AcOH was added to the resulting reaction mixture to decompose an excess amount of (diazomethyl)(trimethyl)silane and subsequently the reaction mixture was concentrated under reduced pressure. The resulting residue was purified by silica gel column chromatography (hexane/AcOEt) to give methyl N-(tert-butoxycarbonyl)-O-(2-cyclopropylethyl)-L-serinate (6.51 g) as an oily product.

Production Example 203

A mixture of tert-butyl [(1R)-1-[(4R)-2,2-dimethyl-4-({4-[(trans-4-methylcyclohexyl)oxy]pyridin-2-yl}methyl)-5-oxo-1,3-dioxolan-4-yl]-2-(ethylsulfanyl)ethyl]carbamate (203 mg) and $CH_2Cl_2$ (4 ml) was cooled with an ice-water bath, subsequently m-chloroperbenzoic acid (about 25% water content, 89.5 mg) was added thereto and the mixture was stirred at the same temperature for 1 hour. 10% Aqueous sodium thiosulfate solution was added to the resulting reaction mixture and the mixture was stirred for 10 minutes. After separating the aqueous layer and the organic layer, the organic layer was washed twice with a saturated aqueous sodium hydrogen carbonate solution. The obtained organic layer was dried over anhydrous magnesium sulfate and subsequently concentrated under reduced pressure. The resulting residue was purified by silica gel column chromatography ($CHCl_3$/MeOH) to give tert-butyl [(1R)-1-[(4R)-2,2-dimethyl-4-({4-[(trans-4-methylcyclohexyl)oxy]pyridin-2-yl}methyl)-5-oxo-1,3-dioxolan-4-yl]-2-ethylsulfinyl)ethyl]carbamate (172 mg) as a solid.

Production Example 204

A mixture of tert-butyl [(1R)-1-[(4R)-2,2-dimethyl-4-({4-[(trans-4-methylcyclohexyl)oxy]pyridin-2-yl}methyl)-5-oxo-1,3-dioxolan-4-yl]-2-ethylsulfanyl)ethyl]carbamate (103 mg) and $CH_2Cl_2$ (6 ml) was cooled with an ice-water bath, subsequently m-chloroperbenzoic acid (about 25% water content, 91 mg) was added thereto and the mixture was stirred at the same temperature for 1 hour and then at room temperature for 1 hour. The resulting reaction mixture was cooled again with an ice-water bath, m-chloroperbenzoic acid (about 25% water content, 9 mg) was added thereto and the mixture was stirred at room temperature for 30 minutes. 10% Aqueous sodium thiosulfate solution was added to the resulting reaction mixture and the mixture was stirred for 10 minutes. After separating the aqueous layer and the organic layer, the organic layer was washed twice with a saturated aqueous sodium hydrogen carbonate solution. The obtained organic layer was dried over anhydrous magnesium sulfate and subsequently concentrated under reduced pressure. The resulting residue was purified by silica gel column chromatography ($CHCl_3$/AcOEt) to give tert-butyl [(1R)-1-[(4R)-2,2-dimethyl-4-({4-[(trans-4-methylcyclohexyl)oxy]pyridin-2-yl}methyl)-5-oxo-1,3-dioxolan-4-yl]-2-(ethylsulfonyl)ethyl]carbamate (81 mg) as a solid.

Production Example 205

A mixture of [(2S,3R)-3-(methoxymethoxy)-1-(methoxymethyl)-3-({4-[(trans-4-methylcyclohexyl)oxy]pyridin-2-yl}methyl)-4-oxoazetidin-2-yl]methyl methanesulfonate (1.19 g), DMF (25 ml) and potassium thioacetate (560 mg) was stirred at 60° C. overnight. Water was added to the resulting reaction mixture and the mixture was extracted with AcOEt. The obtained organic layer was washed sequentially with a saturated aqueous sodium hydrogen carbonate solution and a saturated aqueous sodium chloride solution and dried over anhydrous magnesium sulfate. The obtained organic layer was concentrated under reduced pressure and the residue was purified by silica gel column chromatography (hexane/AcOEt) to give S-{[(2R,3R)-3-(methoxymethoxy)-1-(methoxymethyl)-3-({4-[(trans-4-methylcyclohexyl)oxy]pyridin-2-yl}methyl)-4-oxoazetidin-2-yl]methyl}thioacetate (700 mg) as an oily product.

Production Example 206

A saturated aqueous sodium hydrogen carbonate solution was added to a mixture of 2-(bromomethyl)-4-[(trans-4-methylcyclohexyl)oxy]pyridine hydrobromate (766 mg) and $CH_2Cl_2$ (25 ml) and the mixture was stirred at room temperature for 10 minutes. After separating the organic layer from the obtained mixture, the aqueous layer was extracted with $CH_2Cl_2$. The obtained organic layers were combined, dried over anhydrous magnesium sulfate and diluted with toluene. The obtained mixture was concentrated under reduced pressure to about 20 ml. Toluene was added again to the obtained mixture and the mixture was concentrated to about 10 ml (mixture A).

Under nitrogen atmosphere, LDA (1.09 M hexane-THF solution, 2.2 ml) was slowly added at −78° C. with stirring to a mixture of (3R,4R)-4-[(ethylsulfanyl)methyl]-3-(methoxymethoxy)-1-(methoxymethyl)azetidin-2-one (407 mg) and THF (6 ml). The resulting reaction mixture was stirred at the same temperature for 30 minutes and subsequently the mixture A was added dropwise thereto. After stirring at the same temperature for 1.5 hours, a saturated aqueous ammonium chloride solution was added thereto and the mixture was allowed to warm up to room temperature. The obtained mixture was extracted with AcOEt. The obtained organic layer was dried over anhydrous magnesium sulfate and concentrated under reduced pressure. The resulting residue was purified by silica gel column chromatography ($CHCl_3$/AcOEt) and subsequently purified again with silica gel column chromatography (hexane/AcOEt) to give (3R,4R)-4-[(ethylsulfanyl)methyl]-3-(methoxymethoxy)-1-(methoxymethyl)-3-({4-[(trans-4-methylcyclohexyl)oxy]pyridin-2-yl}methyl)azetidin-2-one (599 mg) as an oily product.

Production Example 207

Under argon atmosphere, tetra-n-butylammonium fluoride (1 M THF solution, 1.2 ml) was added to a mixture of 2-ethylhexyl 3-[(3-bromo-2-cyanopyridin-4-yl)sulfanyl}propanoate (200 mg), (4-cyclopropylbut-1-yn-1-yl)(trimethyl)silane (170 mg), $Et_3N$ (0.49 ml) and DMF (1.5 ml). The obtained mixture was irradiated with supersonic wave for 30 seconds, subsequently bis(triphenylphosphine) palladium (II) dichloride (70 mg) was added thereto and the mixture was stirred at 110° C. for 30 minutes under microwave irradiation. AcOEt was added to the resulting reaction mixture and the mixture was washed with a saturated aqueous sodium chloride solution. The obtained organic layer was dried over anhydrous magnesium sulfate and subsequently concentrated under reduced pressure. The resulting residue was purified by silica gel column chromatography (hexane/AcOEt) to give 2-(2-cyclopropylethyl)thieno[3,2-c]pyridin-4-carbonitrile (12 mg) as an oily product.

Production Example 208

2-Ethylhexyl 3-sulfanylpropanoate (2.4 ml) was added under ice-bath cooling to a mixture of 3-bromo-4-chloropyridin-2-carbonitrile (2 g), Et₃N (2.6 ml) and DMF (20 ml) and the mixture was stirred at the same temperature for 10 minutes and then at room temperature for 11 hours. Water and AcOEt were added to the resulting reaction mixture and the organic layer was separated. The obtained organic layer was washed with a saturated aqueous sodium chloride solution and dried over anhydrous magnesium sulfate. The obtained organic layer was concentrated under reduced pressure and the residue was purified by silica gel column chromatography (hexane/AcOEt) to give 2-ethylhexyl 3-[(3-bromo-2-cyanopyridin-4-yl)sulfanyl]propanoate (2.7 g) as an oily product.

Production Example 209

Hydrogen fluoride-pyridine (25 g) was cooled to −10° C. (MeOH-ice bath) and ethyl (2S)-2-amino-4-methylpenta-4-enoate mono {[(1R,4S)-7,7-dimethyl-2-oxobicyclo[2.2.1]hepta-1-yl]methanesulfonic acid}salt (7.5 g) was slowly added so that an internal temperature was kept below −5° C. The resulting reaction mixture was stirred at room temperature for 3 hours, subsequently cooled again in the MeOH-ice bath and a saturated aqueous ammonium acetate solution was added thereto. Subsequently, 28% aqueous ammonia solution was added to adjust a pH of the reaction mixture to about 9.5. The obtained mixture was extracted three times with methyl-tert-butyl ether. The obtained organic layer was dried over anhydrous magnesium sulfate and concentrated under reduced pressure. THF (50 ml) was added to the resulting residue, DIPEA (3.3 ml) and di-tert-butyl dicarbonate (3.86 ml) were added thereto at room temperature and the mixture was stirred for 4 hours. The resulting reaction mixture was concentrated under reduced pressure and water was added to the residue and the mixture was extracted with AcOEt. The organic layer was dried over anhydrous magnesium sulfate and subsequently concentrated under reduced pressure. The resulting residue was purified by silica gel column chromatography (hexane/AcOEt) to give ethyl N-(tert-butoxycarbonyl)-4-fluoro-L-leucinate (2.65 g) as an oily product.

Production Example 210

PtO₂ (61 mg) was added to a solution of (3R)-4-(2-cyclopropylvinyl)-3-(methoxymethoxy)-1-(4-methoxyphenyl)azetidin-2-one (831 mg) in toluene (25 ml) and the mixture was stirred at 0° C. for 6 hours under hydrogen atmosphere. Insoluble material was removed by filtration from the resulting reaction mixture and subsequently the filtrate was concentrated under reduced pressure. The resulting residue was purified by silica gel column chromatography (hexane/AcOEt) to give (3R,4S)-4-(2-cyclopropylethyl)-3-(methoxymethoxy)-1-(4-methoxyphenyl)azetidin-2-one (574 mg) as an oily product.

Production Example 211

Under nitrogen atmosphere, diisopropyl azodicarboxylate (1.2 ml) was added dropwise under ice-bath cooling to a mixture of (3R,4S)-4-(hydroxymethyl)-3-(methoxymethoxy)-1-(methoxymethyl)azetidin-2-one (300 mg), THF (12 ml), thioacetic acid (0.32 ml) and triphenyl phosphine (1.6 g) and the mixture was stirred at room temperature overnight. Water was added to the resulting reaction mixture and the mixture was extracted with CHCl₃. The obtained organic layer was dried over anhydrous magnesium sulfate and subsequently concentrated under reduced pressure. Diisopropyl ether was added to the resulting residue, and the insoluble materials were removed by filtration. The obtained filtrate was concentrated under reduced pressure and the residue was purified by silica gel column chromatography (hexane/AcOEt) to give S-{[(2R,3R)-3-(methoxymethoxy)-1-(methoxymethyl)-4-oxoazetidin-2-yl]methyl}thioacetate (300 mg) as an oily product.

Production Example 212

1-Bromo-2-methylpropane (0.3 ml) and sodium iodide (435 mg) were added to a mixture of S-{[(2R,3R)-3-(methoxymethoxy)-1-(methoxymethyl)-4-oxoazetidin-2-yl]methyl}thioacetate (150 mg), DMF (1.5 ml), MeOH (1.5 ml), and potassium carbonate (420 mg) and the mixture was stirred at 40° C. overnight. Water was added to the resulting reaction mixture and the mixture was extracted with AcOEt. The obtained organic layer was washed with a saturated aqueous sodium chloride solution and dried over anhydrous magnesium sulfate. The obtained organic layer was concentrated under reduced pressure and the residue was purified by silica gel column chromatography (hexane/AcOEt) to give (3R,4R)-4-[(isobutylsulfanyl)methyl]-3-(methoxymethoxy)-1-(methoxymethyl)azetidin-2-one (125 mg) as an oily product.

Production Example 213

Methanesulfonyl chloride (2.1 ml) was added under ice-bath cooling to a mixture of (3R,4S)-4-(hydroxymethyl)-3-(methoxymethoxy)-1-(methoxymethyl)azetidin-2-one (2.7 g), pyridine (4.3 ml) and CH₂Cl₂ (30 ml) and the mixture was stirred at room temperature for 18 hours. CHCl₃ was added to the resulting reaction mixture and washed sequentially with 0.5 M hydrochloric acid, a saturated aqueous sodium hydrogen carbonate solution and a saturated aqueous sodium chloride solution. The obtained organic layer was dried over anhydrous magnesium sulfate and concentrated under reduced pressure. The resulting residue was purified by silica gel column chromatography (hexane/AcOEt) to give a solid (3.4 g). Sodium ethanethiolate (575 mg) was added under ice-bath cooling to a mixture of the obtained solid (1 g) and DMF (10 ml) and the mixture was stirred at the same temperature for 1 hour. AcOEt was added to the resulting reaction mixture and the mixture was washed sequentially with water, a saturated aqueous sodium hydrogen carbonate solution and a saturated aqueous sodium chloride solution and dried over anhydrous magnesium sulfate. The obtained organic layer was concentrated under reduced pressure and the residue was purified by silica gel column chromatography (hexane/AcOEt) to give (3R,4R)-4-[(ethylsulfanyl)methyl]-3-(methoxymethoxy)-1-(methoxymethyl)azetidin-2-one (300 mg) as an oily product.

Production Examples 214 to 294

Production Example compounds shown in Tables to be described later were produced in the same manner as in the method described in the above Production Examples.

Tables to be described later show the structure, physicochemical data and production method of the Production Example compounds.

Reference Example 1

6 M Hydrochloric acid (1 ml) was added to tert-butyl {(1S)-1-[(4S)-2,2-dimethyl-4-({4-[(trans-4-methylcyclohexyl)oxy]pyridin-2-yl}methyl)-5-oxo-1,3-dioxolan-4-yl]-3-methylbutyl}carbamate (75.2 mg) and the mixture was stirred at 80° C. overnight. The resulting reaction mixture was allowed to cool to room temperature and subsequently concentrated under reduced pressure. The resulting residue was purified by ODS column chromatography (MeCN/0.1% aqueous formic acid solution). MeCN and an excess amount of 1 M hydrochloric acid were added to the obtained compound and the solvent was distilled off to give (2S,3S)-3-amino-2-hydroxy-5-methyl-2-({4-[(trans-4-methylcyclohexyl)oxy]pyridin-2-yl}methyl)hexanoic acid dihydrochloride (50 mg) as a solid.

Reference Example 2

6 M Hydrochloric acid (30 ml) was added to tert-butyl {(1R)-1-[(4S)-2,2-dimethyl-4-({4-[(trans-4-methylcyclohexyl)oxy]pyridin-2-yl}methyl)-5-oxo-1,3-dioxolan-4-yl]-3-methylbutyl}carbamate (3.7 g) and the mixture was stirred at 80° C. overnight. After cooling the resulting reaction mixture with an ice-water bath, 6 M aqueous sodium hydroxide solution was added thereto to adjust a pH of the reaction mixture to about 1.5. The produced insoluble material was collected by filtration to give (2S,3R)-3-amino-2-hydroxy-5-methyl-2-({4-[(trans-4-methylcyclohexyl)oxy]pyridin-2-yl}methyl)hexanoic acid hydrochloride (1.2 g) as a solid.

Tables to be described later show the structure and physicochemical data of Reference Example compounds.

TABLE 5

| Ex | Str |
|---|---|
| 1 | 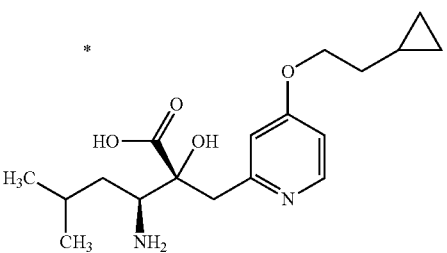 [SMILES: CC(C)C[C@H](N)[C@](O)(Cc1cc(OCCC2CC2)ccn1)C(=O)O] |
| 2(1) | 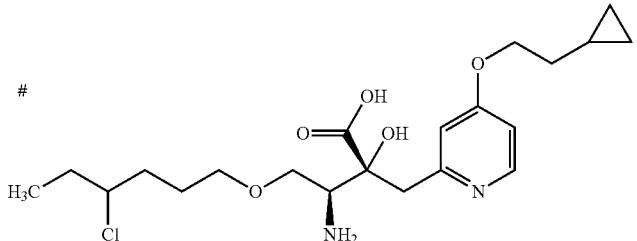 |
| 2(2) | 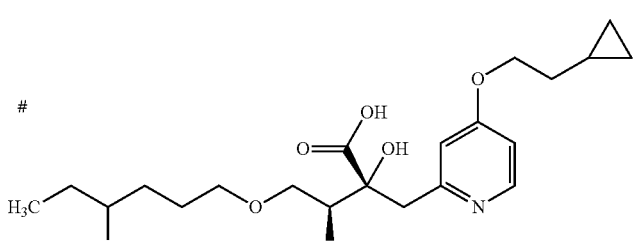 |
| 3 | 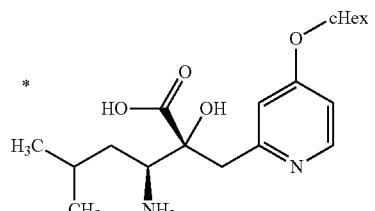 |

TABLE 5-continued

| Ex | Str |
|---|---|
| 4 | (structure) |
| 5 | (structure) |
| 6 | (structure) 2HCl |
| 7(1) | (structure) |
| 7(2) | (structure) |

TABLE 5-continued

| Ex | Str |
|---|---|
| 8 | (structure) 2HCl |
| 9 | (structure) |
| 10 | (structure) 2HCl |
| 11 | (structure) |
| 12 | (structure) 2HCl |
| 13 | (structure) 2HCl |

TABLE 5-continued

| Ex | Str |
|---|---|
| 14 | (structure: (S)-2-amino-2-hydroxy-5-methyl-2-((4-(naphthalen-1-ylmethoxy)pyridin-2-yl)methyl)hexanoic acid · 2HCl) |
| 15 | (structure: (S)-2-amino-2-hydroxy-5-methyl-2-((4-(2-(1-methyl-1H-pyrazol-4-yl)ethoxy)pyridin-2-yl)methyl)hexanoic acid) |
| 16 | (structure: pyridine with pinanyloxy substituent; leucine-derived core · 2HCl) |
| 17(1) | (structure: (S)-2-amino-2-hydroxy-5-methyl-2-((4-((trans-4-methylcyclohexyl)oxy)pyridin-2-yl)methyl)hexanoic acid) |
| 17(2) | (structure: methyl ester analog of 17(1) · 2HCl) |

TABLE 5-continued
| Ex | Str |
|---|---|
| 18 | 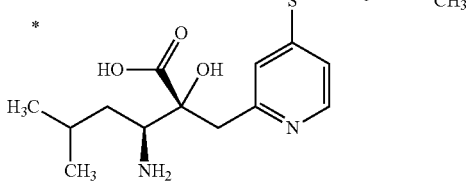 |
| 19 | 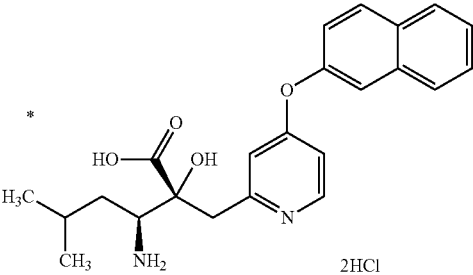 [SMILES: CC(C)C[C@H](N)[C@](O)(Cc1cc(Oc2ccc3ccccc3c2)ccn1)C(=O)O] 2HCl |
| 20 | 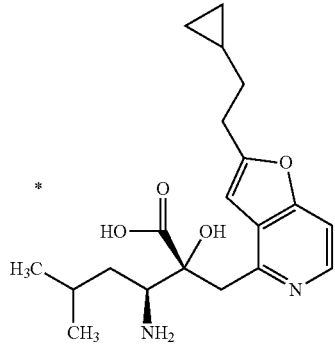 [SMILES: CC(C)C[C@H](N)[C@](O)(Cc1nccc2oc(CCC3CC3)cc12)C(=O)O] |
| 21 | 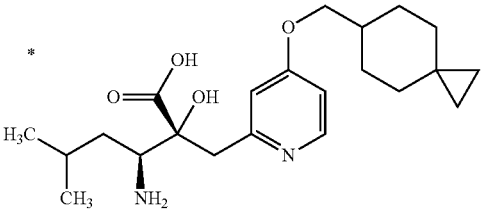 [SMILES: CC(C)C[C@H](N)[C@](O)(Cc1cc(OCC2CCC3(CC2)CC3)ccn1)C(=O)O] |
| 22 | 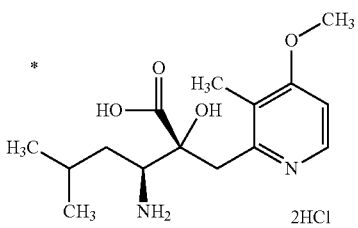 [SMILES: COc1ccnc(C[C@](O)(C(=O)O)[C@@H](N)CC(C)C)c1C] 2HCl |
| 23 | 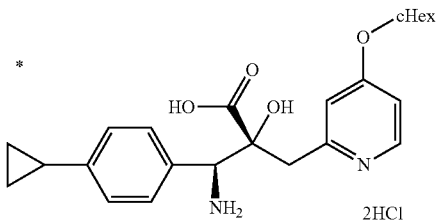 2HCl |

TABLE 5-continued

| Ex | Str |
|---|---|
| 24 | (structure: 2HCl salt) |
| 25 | (structure: 2HCl salt) |
| 26 | (structure) |
| 27 | (structure) |
| 28 | (structure) |
| 29 | (structure) |

TABLE 5-continued

| Ex | Str |
|---|---|
| 30 | |
| 31 | |
| 32 | |
| 33 | |
| 34 | |
| 35 | |

TABLE 5-continued

| Ex | Str |
|---|---|
| 36 | (structure: 3-amino-2-hydroxy-3-(4-phenylphenyl)-2-[(4-cyclohexyloxy-pyridin-2-yl)methyl]propanoic acid, 2HCl) |
| 37 | (structure: 3-amino-2-hydroxy-5-methyl-2-[(4-((1-methylpiperidin-4-yl)oxy)pyridin-2-yl)methyl]hexanoic acid, 3HCl) |
| 38 | (structure: 3-amino-2-[(4-((1-acetylpiperidin-4-yl)oxy)pyridin-2-yl)methyl]-2-hydroxy-5-methylhexanoic acid, 2HCl) |
| 39 | (structure: 3-amino-2-[(4-(benzyloxy)pyridin-2-yl)methyl]-2-hydroxy-5-methylhexanoic acid, 2HCl) |
| 40 | (structure: 3-amino-2-[(4-cyclohexyloxy-pyridin-2-yl)methyl]-2-hydroxy-5-phenyl-pent-4-enoic acid, 2HCl) |

TABLE 5-continued
| Ex | Str |
|---|---|
| 41 | 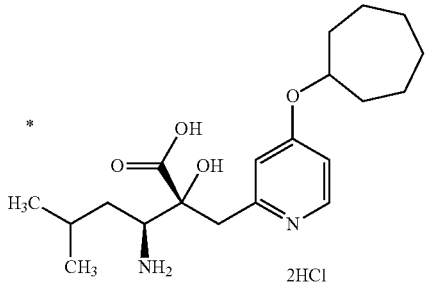 [SMILES: CC(C)C[C@H](N)[C@](O)(Cc1cc(OC2CCCCCC2)ccn1)C(=O)O] |
| 42 | 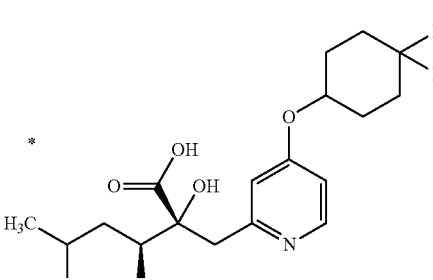 |
| 43 | 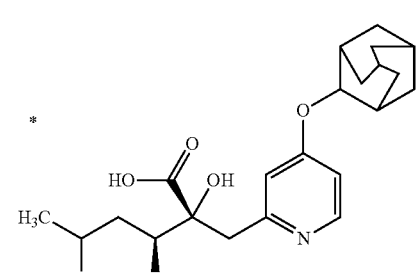 |
| 44 | 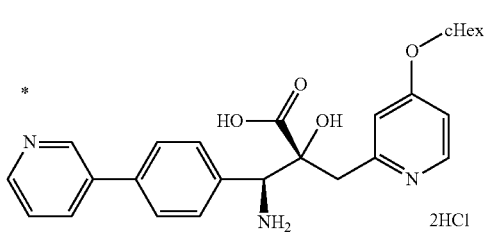 |
| 45 | 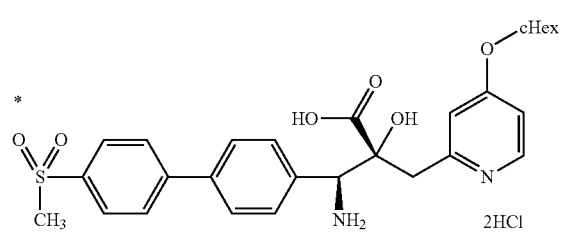 |

TABLE 5-continued

| Ex | Str |
|---|---|
| 46 | (structure) 2HCl |
| 47 | (structure) 2HCl |
| 48 | (structure) 3HCl |
| 49 | (structure) 2HCl |
| 50 | (structure) 2HCl |
| 51 | (structure) 2HCl |

TABLE 5-continued

| Ex | Str |
|---|---|
| 52 | (structure: 4-methoxy-5-benzyl pyridine derivative, 2HCl) |
| 53 | (structure: 4-methoxy-5-bromo pyridine derivative, 2HCl) |
| 54 | (structure: 4-[(2-trifluoromethylbenzyl)oxy]pyridine derivative, 2HCl) |
| 55 | (structure: 4-[(R)-hexan-2-yloxy]pyridine derivative, 2HCl) |
| 56 | (structure: 4-(trans-4-methylcyclohexyloxy)pyridine derivative, 2HCl) |
| 57 | (structure: 4-methoxy-5-(benzyloxymethyl)pyridine derivative, 2HCl) |

TABLE 5-continued
| Ex | Str |
|---|---|
| 58 | 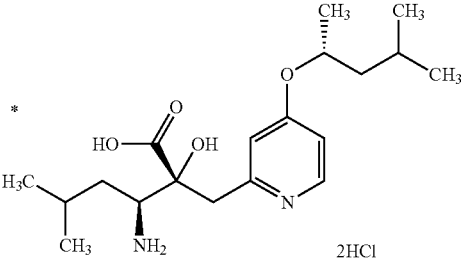 [SMILES: CC(C)C[C@@H](C)Oc1ccnc(C[C@](O)(C(=O)O)[C@@H](N)CC(C)C)c1] 2HCl |
| 59 | 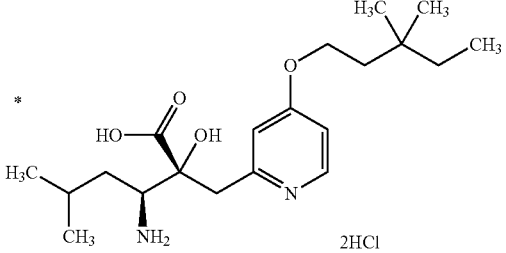 [SMILES: CCC(C)(C)CCOc1ccnc(C[C@](O)(C(=O)O)[C@@H](N)CC(C)C)c1] 2HCl |
| 60 | 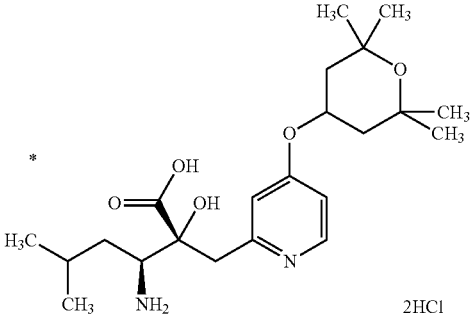 [SMILES: CC(C)C[C@H](N)[C@](O)(Cc1cc(OC2CC(C)(C)OC(C)(C)C2)ccn1)C(=O)O] 2HCl |
| 61 | 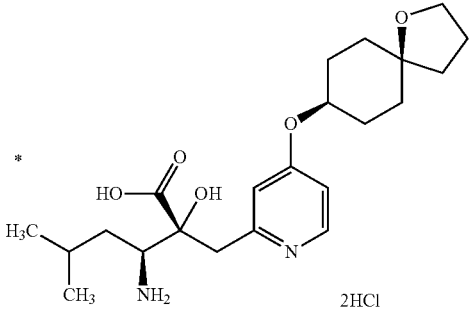 [SMILES: CC(C)C[C@H](N)[C@](O)(Cc1cc(O[C@H]2CC[C@]3(CCCO3)CC2)ccn1)C(=O)O] 2HCl |
| 62 | 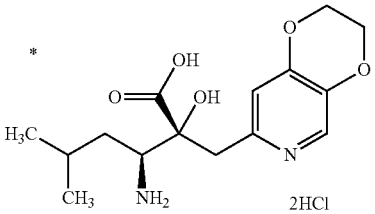 [SMILES: CC(C)C[C@H](N)[C@](O)(Cc1cc2c(cn1)OCCO2)C(=O)O] 2HCl |

TABLE 5-continued

| Ex | Str |
|---|---|
| 63 | |
| 64 | |
| 65 | |
| 66 | |
| 67 | |
| 68 | |

TABLE 5-continued
| Ex | Str |
|---|---|
| 69 | 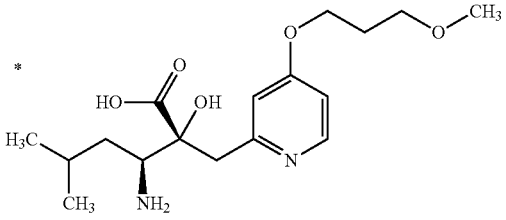 [SMILES: COCCCOc1ccnc(C[C@](O)(C(=O)O)[C@@H](N)CC(C)C)c1] |
| 70 | 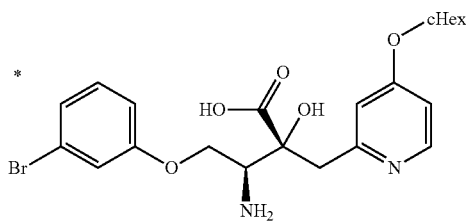 |
| 71 | 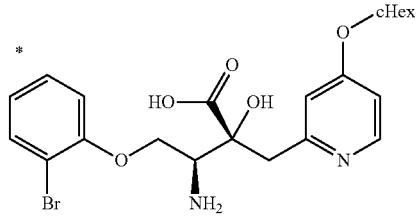 |
| 72 | 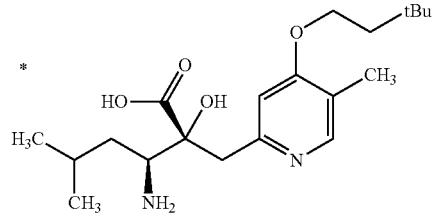 [SMILES: Cc1cnc(C[C@](O)(C(=O)O)[C@@H](N)CC(C)C)cc1OCCC(C)(C)C] |
| 73 | 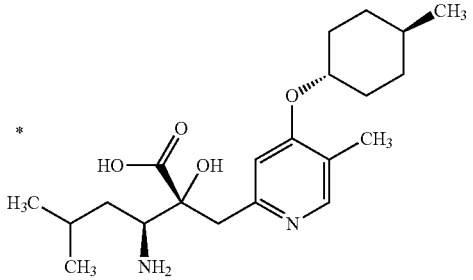 [SMILES: Cc1cnc(C[C@](O)(C(=O)O)[C@@H](N)CC(C)C)cc1O[C@H]1CC[C@H](C)CC1] |
| 74 | 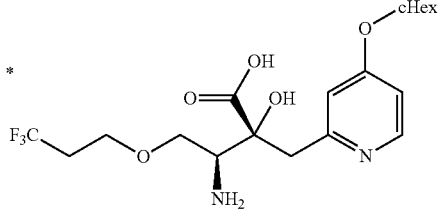 |

TABLE 5-continued

| Ex | Str |
| --- | --- |
| 75 | (structure) |
| 76 | (structure) |
| 77 | (structure) |
| 78 | (structure) |
| 79 | (structure) |
| 80 | (structure) |

TABLE 5-continued
| Ex | Str |
|---|---|
| 81 | 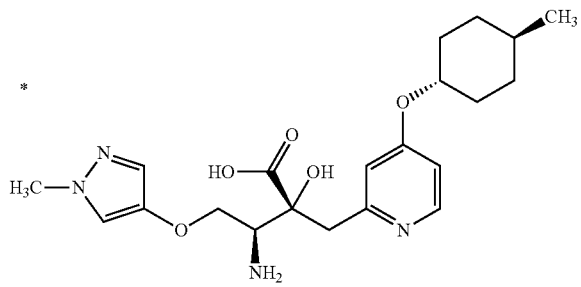 |
| 82 | 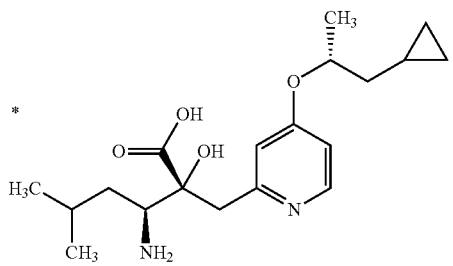 [SMILES: CC(C)C[C@H](N)[C@](O)(Cc1cc(O[C@H](C)CC2CC2)ccn1)C(=O)O] |
| 83 | 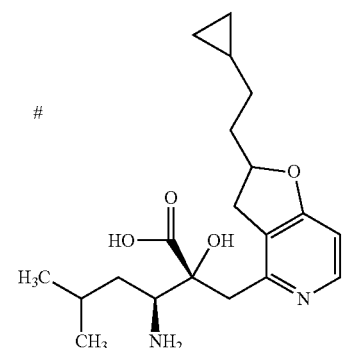 |
| 84 | 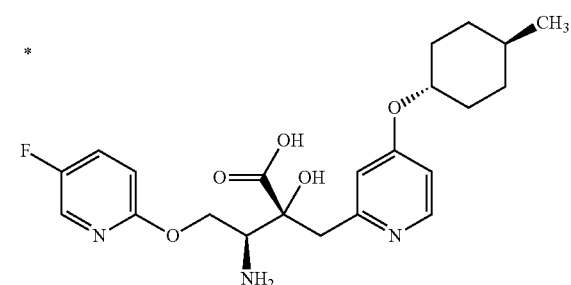 |
| 85 | 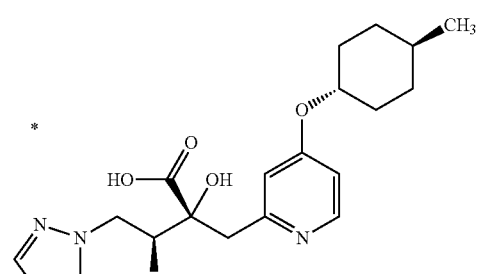 |

TABLE 5-continued

| Ex | Str |
|---|---|
| 86 | (structure) |
| 87 | (structure) |
| 88 | (structure) |
| 89 | (structure) |
| 90 | (structure) |

TABLE 5-continued

| Ex | Str |
|---|---|
| 91 | (structure) |
| 92 | (structure) |
| 93 | (structure) |
| 94 | (structure) |
| 95 | (structure) |

TABLE 5-continued
| Ex | Str |
|---|---|
| 96 | 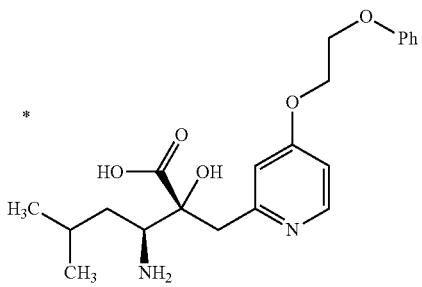 [SMILES: CC(C)C[C@H](N)[C@](O)(Cc1cc(OCCOc2ccccc2)ccn1)C(=O)O] |
| 97 | 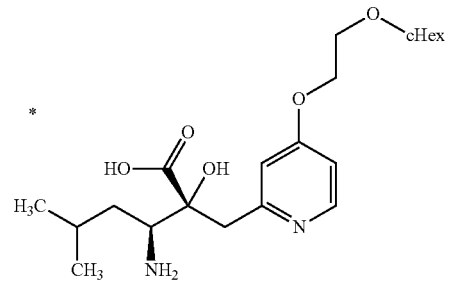 |
| 98 | 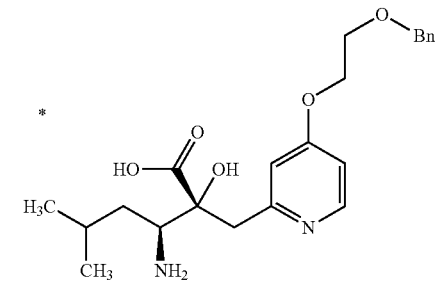 [SMILES: CC(C)C[C@H](N)[C@](O)(Cc1cc(OCCOCc2ccccc2)ccn1)C(=O)O] |
| 99 | 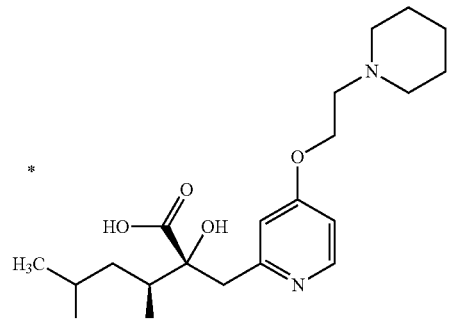 |
| 100 | 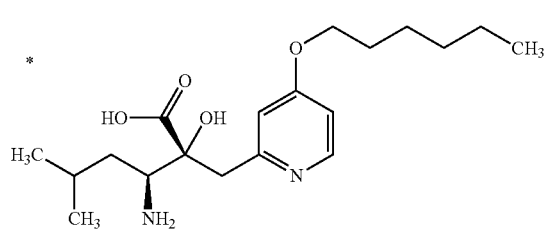 [SMILES: CCCCCCOc1ccnc(C[C@](O)(C(=O)O)[C@@H](N)CC(C)C)c1] |

TABLE 5-continued
| Ex | Str |
|---|---|
| 101 | 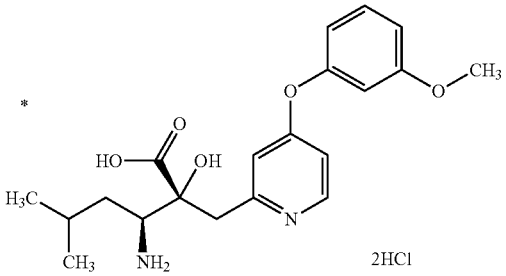 [SMILES: COc1cccc(Oc2ccnc(C[C@](O)(C(=O)O)[C@@H](N)CC(C)C)c2)c1] 2HCl |
| 102 | 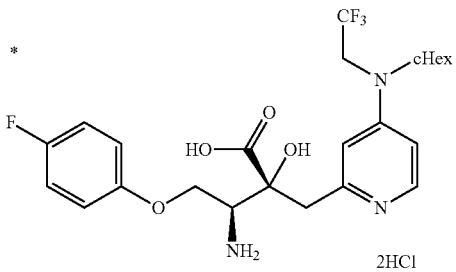 2HCl |
| 103 | 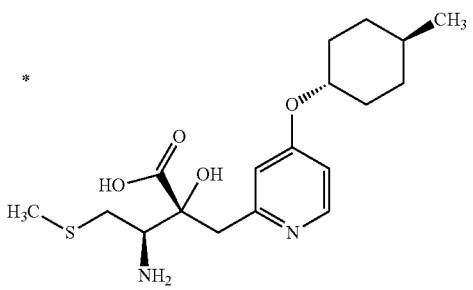 |
| 104 | 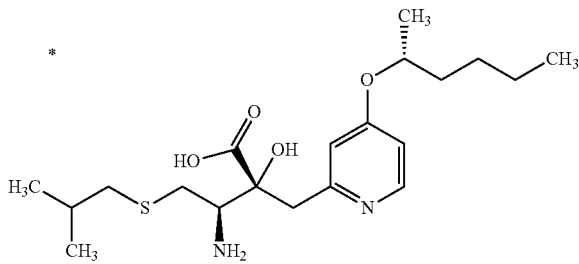 [SMILES: CCCC[C@@H](C)Oc1ccnc(C[C@](O)(C(=O)O)[C@@H](N)CSCC(C)C)c1] |
| 105 | 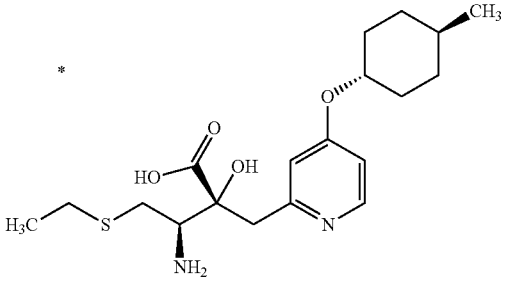 [SMILES: CCSC[C@H](N)[C@](O)(Cc1cc(O[C@H]2CC[C@H](C)CC2)ccn1)C(=O)O] |

TABLE 5-continued
| Ex | Str |
|---|---|
| 106 | 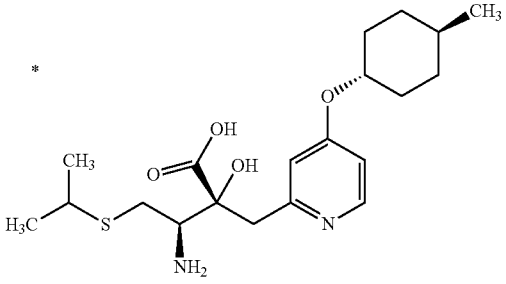 [SMILES: CC(C)SC[C@H](N)[C@](O)(Cc1cc(O[C@H]2CC[C@H](C)CC2)ccn1)C(=O)O] |
| 107 | 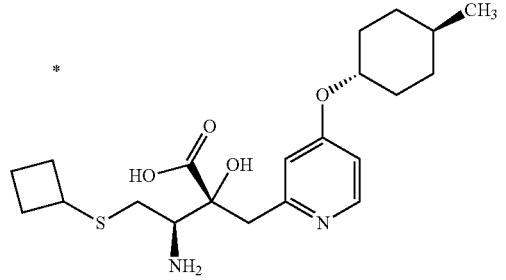 [SMILES: C[C@H]1CC[C@H](Oc2ccnc(C[C@](O)(C(=O)O)[C@@H](N)CSC3CCC3)c2)CC1] |
| 108 | 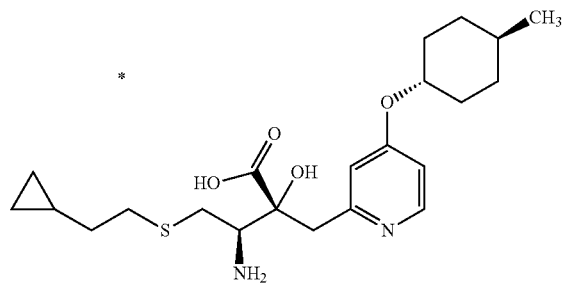 [SMILES: C[C@H]1CC[C@H](Oc2ccnc(C[C@](O)(C(=O)O)[C@@H](N)CSCCC3CC3)c2)CC1] |
| 109 | 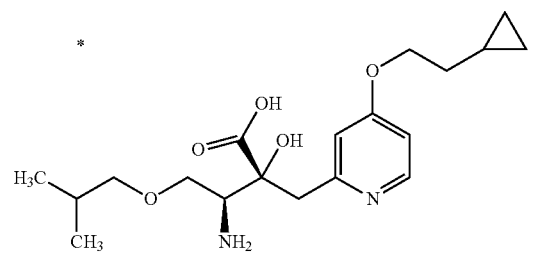 [SMILES: CC(C)COC[C@H](N)[C@](O)(Cc1cc(OCCC2CC2)ccn1)C(=O)O] |
| 110 | 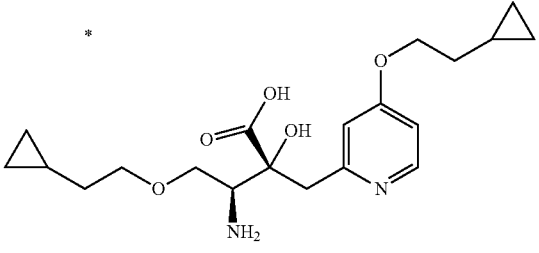 [SMILES: N[C@@H](COCCC1CC1)[C@](O)(Cc1cc(OCCC2CC2)ccn1)C(=O)O] |

TABLE 5-continued

| Ex | Str |
|---|---|
| 111 | (structure) |
| 112 | (structure) |
| 113 | (structure) |
| 114 | (structure) |
| 115 | (structure) |
| 116 | (structure) |

TABLE 5-continued
| Ex | Str |
|---|---|
| 117 | 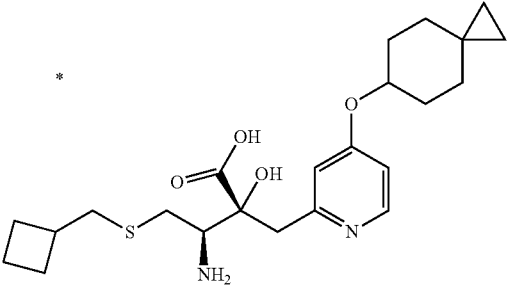 [SMILES: N[C@@H](CSCC1CCC1)[C@](O)(Cc1cc(OC2CCC3(CC2)CC3)ccn1)C(=O)O] |
| 118 | 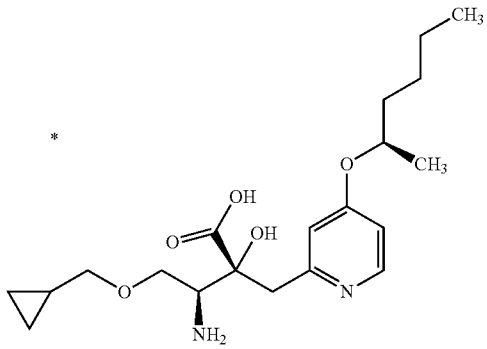 [SMILES: CCCC[C@@H](C)Oc1ccnc(C[C@](O)(C(=O)O)[C@@H](N)COCC2CC2)c1] |
| 119 | 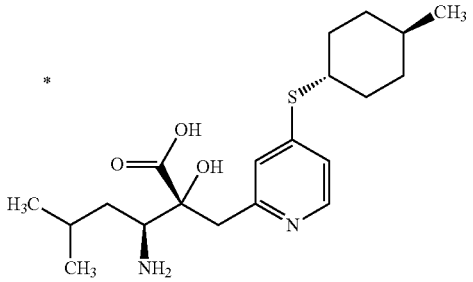 [SMILES: CC(C)C[C@H](N)[C@](O)(Cc1cc(S[C@H]2CC[C@H](C)CC2)ccn1)C(=O)O] |
| 120 | 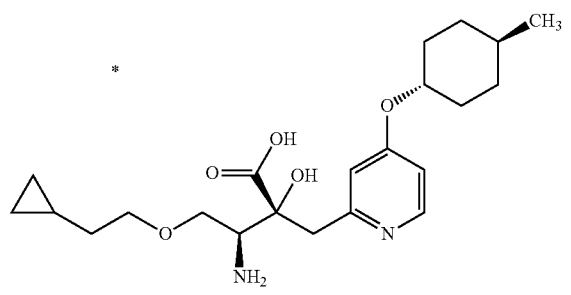 [SMILES: C[C@H]1CC[C@H](Oc2ccnc(C[C@](O)(C(=O)O)[C@@H](N)COCCC3CC3)c2)CC1] |
| 121 | 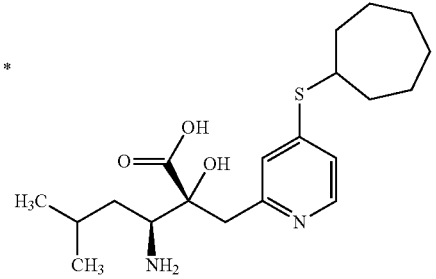 [SMILES: CC(C)C[C@H](N)[C@](O)(Cc1cc(SC2CCCCCC2)ccn1)C(=O)O] |

TABLE 5-continued
| Ex | Str |
|---|---|
| 122 | 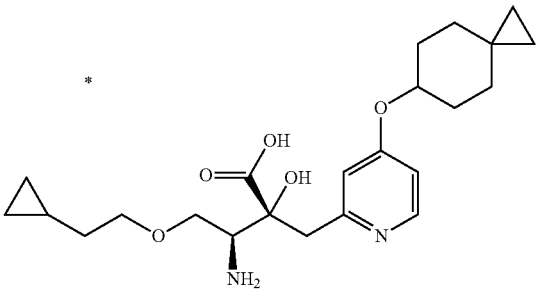 [SMILES: N[C@@H](COCCC1CC1)[C@](O)(Cc1cc(OC2CCC3(CC2)CC3)ccn1)C(=O)O] |
| 123 | 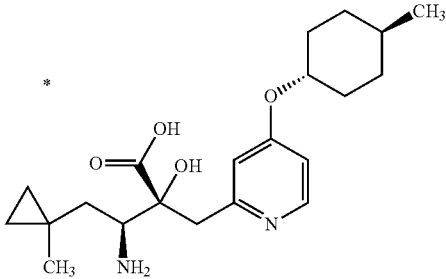 [SMILES: CC1(C[C@H](N)[C@](O)(Cc2cc(O[C@H]3CC[C@H](C)CC3)ccn2)C(=O)O)CC1] |
| 124 | 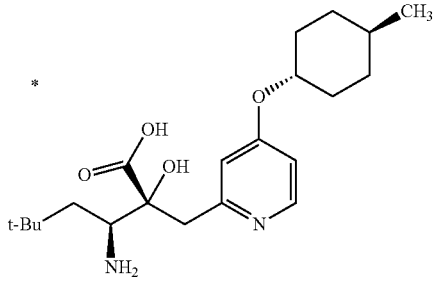 [SMILES: CC(C)(C)C[C@H](N)[C@](O)(Cc1cc(O[C@H]2CC[C@H](C)CC2)ccn1)C(=O)O] |
| 125 | 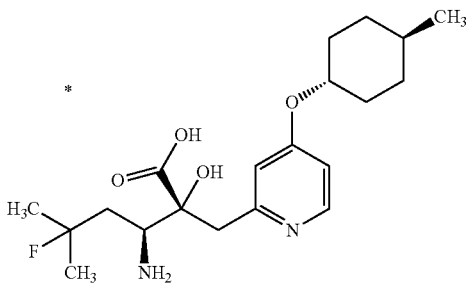 [SMILES: CC(C)(F)C[C@H](N)[C@](O)(Cc1cc(O[C@H]2CC[C@H](C)CC2)ccn1)C(=O)O] |
| 126 | 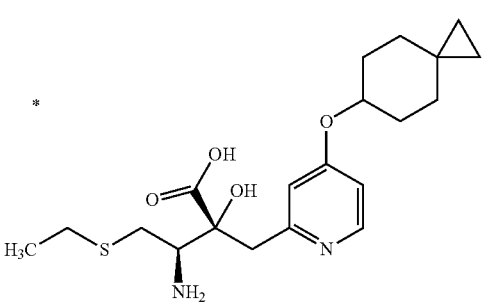 [SMILES: CCSC[C@H](N)[C@](O)(Cc1cc(OC2CCC3(CC2)CC3)ccn1)C(=O)O] |

TABLE 5-continued
| Ex | Str |
|---|---|
| 127 | 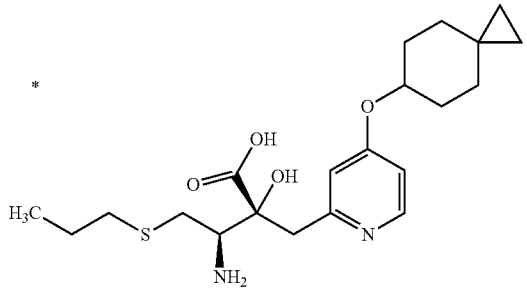 [SMILES: CCCSC[C@H](N)[C@](O)(Cc1cc(OC2CCC3(CC2)CC3)ccn1)C(=O)O] |
| 128 | 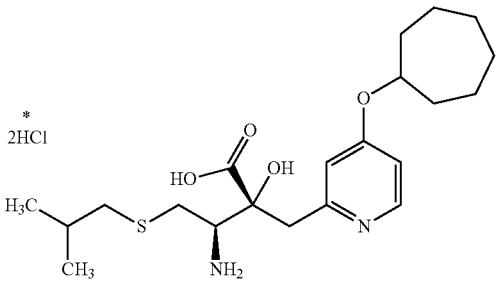 [SMILES: CC(C)CSC[C@H](N)[C@](O)(Cc1cc(OC2CCCCCC2)ccn1)C(=O)O] |
| 129 | 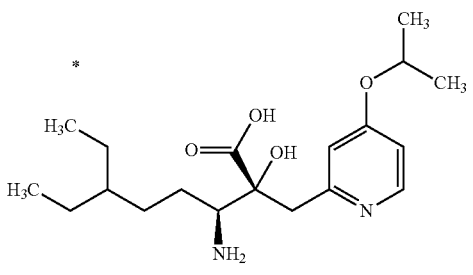 [SMILES: CCC(CC)CC[C@H](N)[C@](O)(Cc1cc(OC(C)C)ccn1)C(=O)O] |
| 130 | 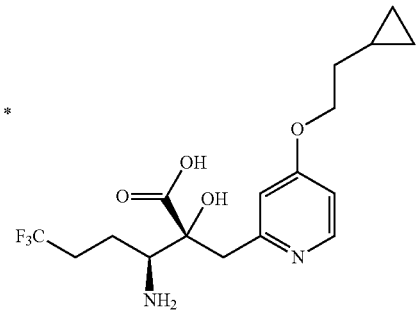 [SMILES: N[C@@H](CCC(F)(F)F)[C@](O)(Cc1cc(OCCC2CC2)ccn1)C(=O)O] |
| 131 | 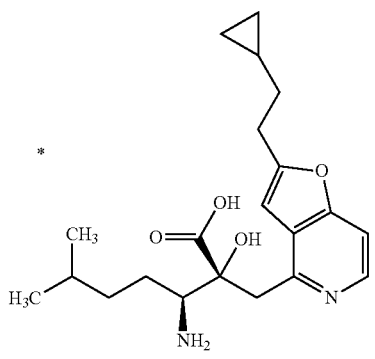 [SMILES: CC(C)CC[C@H](N)[C@](O)(Cc1nccc2oc(CCC3CC3)cc12)C(=O)O] |

TABLE 5-continued

| Ex | Str |
|---|---|
| 132 | |
| 133 | |
| 134 | |
| 135 #2 | |
| 136 | |

TABLE 5-continued
| Ex | Str |
|---|---|
| 137 | 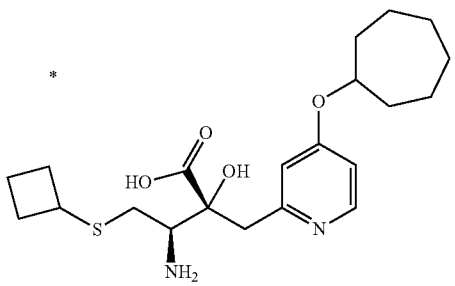 [SMILES: N[C@@H](CSC1CCC1)[C@](O)(Cc1cc(OC2CCCCCC2)ccn1)C(=O)O] |
| 138 | 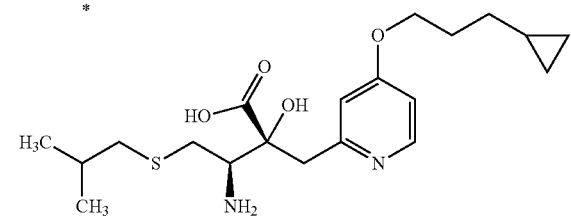 [SMILES: CC(C)CSC[C@H](N)[C@](O)(Cc1cc(OCCCC2CC2)ccn1)C(=O)O] |
| 139 | 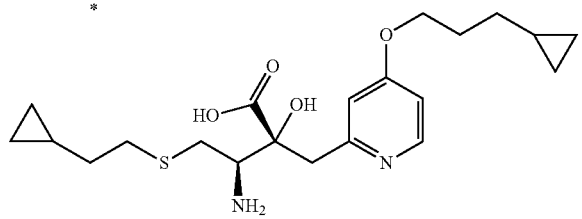 [SMILES: N[C@@H](CSCCC1CC1)[C@](O)(Cc1cc(OCCCC2CC2)ccn1)C(=O)O] |
| 140 | 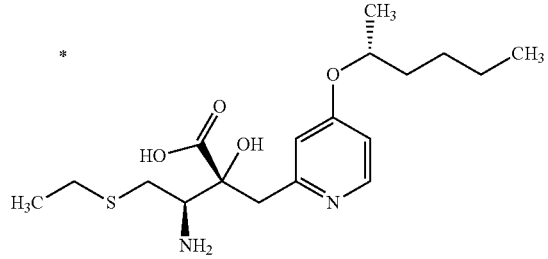 [SMILES: CCCC[C@@H](C)Oc1ccnc(C[C@](O)(C(=O)O)[C@@H](N)CSCC)c1] |
| 141 | 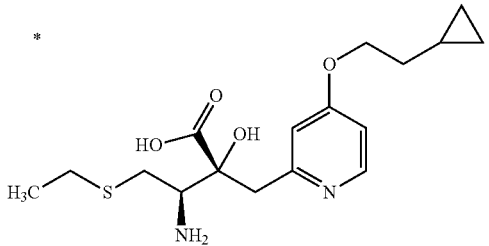 [SMILES: CCSC[C@H](N)[C@](O)(Cc1cc(OCCC2CC2)ccn1)C(=O)O] |
| 142 | 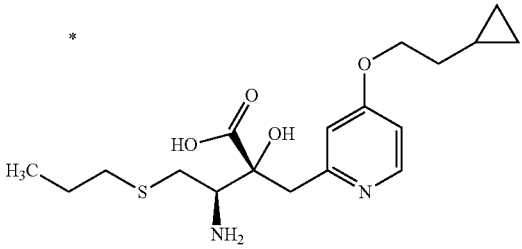 [SMILES: CCCSC[C@H](N)[C@](O)(Cc1cc(OCCC2CC2)ccn1)C(=O)O] |

TABLE 5-continued

| Ex | Str |
|---|---|
| 143 | (structure) |
| 144 | (structure) |
| 145 | (structure) |
| 146 | 2HCl (structure) |

TABLE 6

| Ex | Syn | DATA |
|---|---|---|
| 1 | — | ESI+: 337.3<br>$^1$H NMR (400 MHz, DMSO-d$_6$) δ ppm:<br>0.09-0.16 (2 H, m), 0.40-0.48 (2 H, m), 0.70 (3 H, d, J = 6.6 Hz), 0.75-0.87 (4 H, m), 1.22 (1 H, ddd, J = 14.2, 9.9, 4.0 Hz), 1.37-1.47 (1 H, m), 1.63 (2 H, dt, J = 6.6, 6.6 Hz), 1.68-1.82 (1 H, m), 2.83-2.91 (2 H, m), 3.11 (1 H, d, J = 13.7 Hz), 4.08 (2 H, t, J = 6.6 Hz), 6.82-6.86 (2 H, m), 8.24-8.28 (1 H, m) |
| 2(1) | — | ESI+: 429.2, 431.2 |
| 2(2) | — | ESI+: 411.3 |
| 3 | — | ESI+: 351.2<br>$^1$H NMR (400 MHz, MeOH-d$_4$) δ ppm:<br>1.00 (3 H, d, J = 6.4 Hz), 1.06 (3 H, d, J = 6.4 Hz), 1.34-1.46 (1 H, m), 1.46-1.58 (2 H, m), 1.58-1.72 (5 H, m), 1.75-1.90 (3 H, m), 1.99-2.13 (2 H, m), 3.27 (1 H, d, J = 13.7 Hz), 3.52 (1 H, d, J = 13.7 Hz), 3.62 (1 H, dd, J = 9.2, 3.9 Hz), 4.74-4.82 (1 H, m), 7.38 (1 H, d, J = 2.7 Hz), 7.42 (1 H, dd, J = 7.0, 2.7 Hz), 8.50 (1 H, d, J = 7.0 Hz) |
| 4 | — | ESI+: 377.3<br>$^1$H NMR (400 MHz, MeOH-d$_4$) δ ppm:<br>0.26-0.36 (4 H, m), 0.85 (3 H, d, J = 6.2 Hz), 0.95 (3 H, d, J = 6.2 Hz), 1.31-1.42 (2 H, m), 1.43-1.58 (3 H, m), 1.59-1.80 (4 H, m), 1.94-2.05 (2 |

TABLE 6-continued

| Ex | Syn | DATA |
|---|---|---|
| | | H, m), 3.04-3.13 (2 H, m), 3.20 (1 H, d, J = 15.0 Hz), 4.57-4.66 (1 H, m), 6.89 (1 H, dd, J = 6.1, 2.5 Hz), 6.96 (1 H, d, J = 2.5 Hz), 8.26 (1 H, d, J = 6.1 Hz) |
| 5 | — | ESI+: 409.3<br>$^1$H NMR (400 MHz, MeOH-d$_4$) δ ppm:<br>0.14-0.27 (2 H, m), 0.45-0.60 (2 H, m), 0.90-1.01 (4 H, m), 1.09-1.30 (2 H, m), 1.36-1.56 (3 H, m), 1.81 (2 H, d, J = 13.3 Hz), 2.13 (2 H, brs.), 2.39-2.61 (3 H, m), 3.14-3.29 (4 H, m), 4.40-4.51 (1 H, m), 6.95 (1 H, dd, J = 6.2, 2.3 Hz), 7.00 (1 H, d, J = 2.2), 8.28 (1 H, d, J = 6.3 Hz) |
| 6 | — | ESI+: 365.3<br>$^1$H NMR (400 MHz, DMSO-d$_6$) δ ppm:<br>0.85 (3 H, d, J = 6.4 Hz), 0.88-0.97 (6 H, m), 1.01-1.21 (2 H, m), 1.31-1.53 (4 H, m), 1.62 (1 H, ddd, J = 14.2, 10.6, 3.2 Hz), 1.70-1.87 (3 H, m), 2.03-2.13 (2 H, m), 3.29-3.56 (3 H, m), 4.58-4.75 (1 H, m), 7.33 (1 H, d, J = 2.4 Hz), 7.44 (1 H, dd, J = 6.8, 2.4 Hz), 8.33 (2 H, brs), 8.62 (1 H, d, J = 6.8 Hz) |
| 7(1) | — | ESI+: 373.3 |
| 7(2) | — | ESI+: 269.2 |
| 8 | — | ESI+: 405.3 |
| 9 | — | ESI+: 363.3<br>$^1$H NMR (400 MHz, MeOH-d$_4$) δ ppm:<br>0.08-0.21 (2 H, m), 0.41-0.58 (2 H, m), 0.79-0.95 (1 H, m), 1.32-1.51 (2 H, m), 1.57-1.73 (5 H, m), 1.79-1.94 (3 H, m), 1.97-2.11 (2 H, m), 2.18-2.34 (1 H, m), 2.98-3.07 (1 H, m), 3.13 (1 H, d, J = 13.7 Hz), 3.20 (1 H, d, J = 13.7 Hz), 4.10-4.29 (2 H, m), 6.92-6.99 (1 H, m), 6.99-7.06 (1 H, m), 8.30 (1 H, d, J = 5.9 Hz) |
| 10 | — | ESI+: 396.3 |
| 11 | — | ESI+: 426.3 |
| 12 | — | ESI+: 381.3 |
| 13 | — | ESI+: 336.1 |
| 14 | — | ESI+: 409.1 |
| 15 | — | ESI+: 377.3 |
| 16 | — | ESI+: 405.4 |
| 17(1) | — | ESI+: 365.2<br>$^1$H NMR (400 MHz, DMSO-d$_6$) δ ppm:<br>0.69 (3 H, d, J = 6.4 Hz), 0.83 (3 H, d, J = 6.6 Hz), 0.89 (3 H, d, J = 6.6 Hz), 1.03-1.17 (2 H, m), 1.22 (1 H, ddd, J = 14.2, 9.9, 3.9 Hz), 1.30-1.47 (4 H, m), 1.67-1.79 (3 H, m), 2.00-2.09 (2 H, m), 2.82-2.91 (2 H, m), 3.09 (1 H, d, J = 13.7 Hz), 4.35 (1 H, dddd, J = 10.6, 10.6, 4.2, 4.2 Hz), 6.80-6.83 (2 H, m), 8.23 (1 H, dd, J = 4.6, 1.5 Hz) |
| 17(2) | — | ESI+: 379.4 |
| 18 | — | ESI+: 341.3<br>$^1$H NMR (400 MHz, DMSO-d$_6$) δ ppm:<br>0.71 (3 H, d, J = 6.5 Hz), 0.84 (3 H, d, J = 6.5 Hz), 0.91 (3 H, t, J = 7.4 Hz), 1.21 (1 H, ddd, J = 14.1, 9.9, 3.7 Hz), 1.35-1.50 (3 H, m), 1.56-1.66 (2 H, m), 1.68-1.81 (1 H, m), 2.85-2.97 (2 H, m), 2.99-3.11 (3 H, m), 7.10 (1 H, dd, J = 5.4, 1.7 Hz), 7.13 (1 H, d, J = 1.7 Hz), 8.25 (1 H, d, J = 5.4 Hz) |
| 19 | — | ESI+: 395.3 |
| 20 | — | ESI+: 361.1<br>$^1$H NMR (400 MHz, MeOH-d$_4$) δ ppm:<br>0.05-0.11 (2 H, m), 0.41-0.49 (2 H, m), 0.73-0.86 (4 H, m), 0.92 (3 H, d, J = 6.4 Hz), 1.47 (1 H, ddd, J = 14.1, 9.8, 3.7 Hz), 1.58-1.80 (4 H, m), 2.89-2.95 (2 H, m), 3.03 (1 H, dd, J = 9.8, 2.6 Hz), 3.42 (2 H, s), 6.73 (1 H, d, J = 0.9 Hz), 7.38 (1 H, dd, J = 5.7, 0.9 Hz), 8.29 (1 H, d, J = 5.7 Hz) |
| 21 | 1 | ESI+: 391.3 |
| 22 | 3 | ESI+: 297.3 |
| 23 | 3 | ESI+: 411.3 |
| 24 | 3 | ESI+: 475.3 |
| 25 | 3 | ESI+: 376.3 |
| 26 | 4 | ESI+: 349.3 |
| 27 | 4 | ESI+: 389.3 |
| 28 | 4 | ESI+: 351.3<br>$^1$H NMR (400 MHz, MeOH-d$_4$) δ ppm:<br>0.25-0.35 (2 H, m), 0.35-0.41 (2 H, m), 0.84 (3 H, d, J = 6.3 Hz), 0.95 (3 H, d, J = 6.3 Hz), 1.12 (3 H, s), 1.46 (1 H, ddd, J = 13.9, 9.8, 3.4 Hz), 1.63-1.81 (4 H, m), 3.06 (1 H, dd, J = 9.8, 2.5 Hz), 3.08 (1 H, d, J = 14.4 Hz), 3.22 (1 H, d, J = 14.4 Hz), 4.14-4.26 (2 H, m), 6.86 (1 H, dd, J = 6.0, 2.4 Hz), 6.95 (1 H, d, J = 2.4 Hz), 8.27 (1 H, d, J = 6.0 Hz) |
| 29 | 4 | ESI+: 351.3<br>$^1$H NMR (400 MHz, MeOH-d$_4$) δ ppm:<br>0.01-0.07 (2 H, m), 0.41-0.48 (2 H, m), 0.66-0.80 (1 H, m), 0.84 (3 H, d, J = 6.4 Hz), 0.95 (3 H, d, J = 6.4 Hz), 1.34-1.51 (3 H, m), 1.61-1.81 (2 H, m), 1.86-1.95 (2 H, m), 3.05 (1 H, dd, J = 9.8, 2.8 Hz), 3.07 (1 H, d, J = 13.9 Hz), 3.22 (1 H, d, J = 13.9 Hz), 4.07-4.17 (2 H, m), 6.84 (1 H, dd, J = 6.0, 2.4 Hz), 6.93 (1 H, d, J = 2.4 Hz), 8.26 (1 H, d, J = 6.0 Hz) |
| 30 | 4 | ESI+: 445.1 |
| 31 | 4 | ESI+: 449.3 |
| 32 | 4 | ESI+: 417.3 |

TABLE 6-continued

| Ex | Syn | DATA |
|---|---|---|
| 33 | 4 | ESI+: 403.3 |
| 34 | 5 | ESI+: 392.2 |
| 35 | 5 | ESI+: 393.2 |
| 36 | 6 | ESI+: 447.4 |
| 37 | 6 | ESI+: 366.3 |
| 38 | 6 | ESI+: 394.3 |
| 39 | 6 | ESI+: 359.1 |
| 40 | 6 | ESI+: 397.3 |
| 41 | 6 | ESI+: 365.4<br>$^1$H NMR (400 MHz, MeOH-d$_4$) δ ppm:<br>1.00 (3 H, d, J = 6.5 Hz), 1.06 (3 H, d, J = 6.5 Hz), 1.51-1.96 (13 H, m), 2.07-2.17 (2 H, m), 3.26 (1 H, d, J = 13.8 Hz), 3.51 (1 H, d, J = 13.8 Hz), 3.56-3.69 (1 H, m), 4.89-4.97 (1 H, m), 7.34 (1 H, d, J = 2.6 Hz), 7.38 (1 H, dd, J = 7.1, 2.6 Hz), 8.50 (1 H, d, J = 7.1 Hz) |
| 42 | 6 | ESI+: 387.3 |
| 43 | 6 | ESI+: 403.2 |
| 44 | 6 | ESI+: 448.4 |
| 45 | 6 | ESI+: 525.3 |
| 46 | 6 | ESI+: 401.3 |
| 47 | 6 | ESI+: 363.4 |
| 48 | 6 | ESI+: 456.3 |
| 49 | 6 | ESI+: 385.3 |
| 50 | 6 | ESI+: 415.4 |
| 51 | 6 | ESI+: 415.1 |
| 52 | 6 | ESI+: 373.3 |
| 53 | 6 | ESI+: 361.2 |
| 54 | 6 | ESI+: 427.3 |
| 55 | 6 | ESI+: 353.1<br>$^1$H NMR (400 MHz, MeOH-d$_4$) δ ppm:<br>0.89-0.97 (3 H, m), 1.00 (3 H, d, J = 6.4 Hz), 1.06 (3 H, d, J = 6.4 Hz), 1.31-1.52 (7 H, m), 1.63-1.90 (5 H, m), 3.25 (1 H, d, J = 13.7 Hz), 3.50 (1 H, d, J = 13.7 Hz), 3.61 (1 H, dd, J = 7.5, 5.5 Hz), 4.80-4.90 (1 H, m), 7.36 (1 H, d, J = 2.8 Hz), 7.41 (1 H, dd, J = 7.0, 2.8 Hz), 8.50 (1 H, d, J = 7.0 Hz) |
| 56 | 6 | ESI+: 365.3 |
| 57 | 6 | ESI+: 403.1 |
| 58 | 6 | ESI+: 353.3 |
| 59 | 6 | ESI+: 367.3 |
| 60 | 6 | ESI+: 409.4 |
| 61 | 6 | ESI+: 407.3 |
| 62 | 6 | ESI+: 311.2 |
| 63 | 6 | ESI+: 365.2 |
| 64 | 6 | ESI+: 379.2 |
| 65 | 19 | ESI+: 423.0, 425.0 |
| 66 | 9 | ESI+: 365.3 |
| 67 | 9 | ESI+: 391.3 |
| 68 | 9 | ESI+: 451.2 |
| 69 | 9 | ESI+: 341.3 |
| 70 | 9 | ESI+: 481.0 |
| 71 | 9 | ESI+: 479.0, 481.0 |
| 72 | 9 | ESI+: 367.3 |
| 73 | 9 | ESI+: 379.4 |
| 74 | 9 | ESI+: 421.3 |
| 75 | 9 | ESI+: 395.3 |
| 76 | 9 | ESI+: 379.4 |
| 77 | 9 | ESI+: 416.3 |
| 78 | 9 | ESI+: 456.2 |
| 79 | 9 | ESI+: 393.3 |
| 80 | 9 | ESI+: 417.4 |
| 81 | 9 | ESI+: 419.4 |
| 82 | 1 | ESI+: 351.1 |
| 83 | 20 | ESI+: 363.2<br>$^1$H NMR (400 MHz, MeOH-d$_4$) δ ppm:<br>0.02-0.12 (2 H, m), 0.39-0.51 (2 H, m), 0.67-0.80 (1 H, m), 0.83 (3 H, d, J = 6.4 Hz), 0.94 (3 H, d, J = 6.4 Hz), 1.27-1.53 (3 H, m), 1.57-1.67 (1 H, m), 1.68-1.80 (1 H, m), 1.80-2.03 (2 H, m), 3.00-3.23 (4 H, m), 3.33-3.43 (1 H, m), 4.95-5.08 (1 H, m), 6.74 (1 H, d, J = 5.9 Hz), 8.18 (1 H, d, J = 5.9 Hz) |
| 84 | 9 | ESI+: 434.2<br>$^1$H NMR (400 MHz, MeOH-d$_4$) δ ppm:<br>0.95 (3 H, d, J = 6.7 Hz), 1.09-1.24 (2 H, m), 1.38-1.55 (3 H, m), 1.77-1.85 (2 H, m), 2.08-2.19 (2 H, m), 3.20-3.28 (2 H, m), 3.64 (1 H, dd, J = 8.4, 3.3 Hz), 4.40-4.51 (2 H, m), 4.76 (1 H, dd, J = 11.7, 3.1 Hz), 6.87-6.93 (1 H, m), 6.97 (1 H, dd, J = 6.3, 2.7 Hz), 7.04 (1 H, d, J = 2.3 Hz), 7.54 (1 H, ddd, J = 9.0, 7.8, 3.1 Hz), 8.00 (1 H, d, J = 3.1 Hz), 8.29 (1 H, d, J = 6.3 Hz) |

TABLE 6-continued

| Ex | Syn | DATA |
|---|---|---|
| 85 | 9 | ESI+: 389.3 |
| 86 | 9 | ESI+: 409.4 |
| 87 | 9 | ESI+: 486.4 |
| 88 | 9 | ESI+: 393.3<br>$^1$H NMR (400 MHz, MeOH-d$_4$) δ ppm:<br>0.94 (3 H, d, J = 6.6 Hz), 1.04-1.21 (2 H, m), 1.39-1.53 (3 H, m), 1.74-<br>1.87 (2 H, m), 2.08-2.19 (2 H, m), 2.35 (2 H, qt, J = 6.8, 1.3 Hz), 3.09-3.19<br>(2 H, m), 3.32-3.41 (1 H, m), 3.46-3.64 (3 H, m), 3.73-3.92 (1 H, m),<br>4.42 (1 H, dddd, J = 10.7, 10.7, 4.2, 4.2 Hz), 4.94-5.11 (2 H, m), 5.79-5.89<br>(1 H, m), 6.89-6.97 (2 H, m), 8.26 (1 H, d, J = 6.2 Hz) |
| 89 | 13 | ESI+: 452.4 |
| 90 | 13 | ESI+: 364.2 |
| 91 | 13 | ESI+: 418.3 |
| 92 | 14 | ESI+: 387.3<br>$^1$H NMR (400 MHz, DMSO-d$_6$) δ ppm:<br>0.85 (3 H, d, J = 6.6 Hz), 0.92 (3 H, d, J = 6.6 Hz), 1.29-1.40 (4 H, m), 1.56-<br>1.69 (1 H, m), 1.74-1.90 (1 H, m), 2.96-3.11 (2 H, m), 3.17-3.59 (3 H,<br>m), 5.07-5.16 (1 H, m), 7.19-7.27 (1 H, m), 7.27-7.35 (5 H, m), 7.41 (1<br>H, dd, J = 7.0, 2.4 Hz), 8.34 (2 H, brs), 8.61 (1 H, d, J = 7.0 Hz) |
| 93 | 14 | ESI+: 443.1 |
| 94 | 14 | ESI+: 393.1, 395.1 |
| 95 | 14 | ESI+: 379.3 |
| 96 | 15 | ESI+: 389.3 |
| 97 | 15 | ESI+: 395.2 |
| 98 | 15 | ESI+: 403.1 |
| 99 | 15 | APCI/ESI+: 380.3 |
| 100 | 15 | ESI+: 353.3 |
| 101 | 19 | ESI+: 375.3 |
| 102 | — | ESI+: 500.3 |
| 103 | — | ESI+: 369.2<br>$^1$H NMR (500 MHz, DMSO-d$_6$) δ ppm: 0.89 (3 H, d, J = 6.4 Hz), 1.04-1.16<br>(2 H, m), 1.31-1.44 (3 H, m), 1.69-1.75 (2 H, m), 1.97 (3 H, s), 2.01-2.07<br>(2 H, m), 2.32 (1 H, dd, J = 14.2, 10.5 Hz), 2.89 (1 H, d, J = 13.8 Hz), 2.93 (1<br>H, dd, J = 14.2, 2.4 Hz), 3.03 (1 H, dd, J = 10.5, 2.4 Hz), 3.12 (1 H, d, J = 13.8<br>Hz), 4.35 (1 H, dddd, J = 10.8, 10.8, 4.0, 4.0 Hz), 6.81 (1 H, dd, J = 5.8, 2.5<br>Hz), 6.83 (1 H, d, J = 2.5 Hz), 8.23 (1 H, d, J = 5.8 Hz) |
| 104 | — | ESI+: 399.4 |
| 105 | — | ESI+: 383.2<br>$^1$H NMR (500 MHz, DMSO-d$_6$) δ ppm: 0.89 (3 H, d, J = 6.6 Hz), 1.04-1.15<br>(5 H, m), 1.30-1.44 (3 H, m), 1.68-1.75 (2 H, m), 2.01-2.08 (2 H, m),<br>2.30 (1 H, dd, J = 14.5, 10.8 Hz), 2.42 (2 H, qd, J = 7.4, 2.8 Hz), 2.88 (1 H, d,<br>J = 13.8 Hz), 2.96-3.06 (2 H, m), 3.12 (1 H, d, J = 13.8 Hz), 4.35 (1 H, dddd,<br>J = 10.6, 10.6, 4.0, 4.0 Hz), 6.79-6.86 (2 H, m), 8.23 (1 H, d, J = 5.7 Hz) |
| 106 | 103 | ESI+: 397.2 |
| 107 | 103 | ESI+: 409.2 |
| 108 | 103 | ESI+: 423.3 |
| 109 | 5 | ESI+: 367.3 |
| 110 | 5 | ESI+: 379.2<br>$^1$H NMR (400 MHz, MeOH-d$_4$) δ ppm: 0.02-0.08 (2 H, m), 0.12-0.18 (2<br>H, m), 0.40-0.46 (2 H, m), 0.46-0.53 (2 H, m), 0.70-0.82 (1 H, m), 0.82-<br>0.93 (1 H, m), 1.50 (2 H, td, J = 6.8, 6.8 Hz), 1.71 (2 H, td, J = 6.6, 6.6 Hz),<br>3.17, 3.19 (2 H, ABq, J = 13.8 Hz), 3.42 (1 H, dd, J = 9.0, 3.7 Hz), 3.55-3.62<br>(3 H, m), 3.88 (1 H, dd, J = 10.3, 3.6 Hz), 4.18-4.28 (2 H, m), 7.04 (1 H, dd,<br>J = 6.2, 2.6 Hz), 7.07 (1 H, d, J = 2.4 Hz), 8.33 (1 H, d, J = 6.4 Hz) |
| 111 | 5 | ESI+: 353.2<br>$^1$H NMR (400 MHz, MeOH-d$_4$) δ ppm: 0.12-0.16 (2 H, m), 0.47-0.52 (2<br>H, m), 0.82-0.91 (4 H, m), 0.96 (3 H, d, J = 6.4 Hz), 1.48 (1 H, ddd, J = 13.9,<br>10.0, 3.4 Hz), 1.59-1.81 (4 H, m), 3.07-3.22 (5 H, m), 7.22 (1 H, dd, J = 5.7,<br>1.9 Hz), 7.28 (1 H, d, J = 1.8 Hz), 8.24 (1 H, d, J = 5.5 Hz) |
| 112 | 5 | ESI+: 381.1 |
| 113 | 5 | ESI+: 395.1 |
| 114 | 5 | ESI+: 369.1 |
| 115 | 5 | ESI+: 381.1 |
| 116 | 5 | ESI+: 409.4 |
| 117 | 5 | ESI+: 435.2 |
| 118 | 5 | ESI+: 381.3 |
| 119 | 5 | ESI+: 381.2<br>$^1$H NMR (400 MHz, MeOH-d$_4$) δ ppm: 0.86 (3 H, d, J = 6.2 Hz), 0.93 (3 H,<br>d, J = 6.6 Hz), 0.96 (3 H, d, J = 6.4 Hz), 1.10-1.24 (2 H, m), 1.35-1.51 (4 H,<br>m), 1.63-1.84 (4 H, m), 2.07-2.17 (2 H, m), 3.09 (1 H, d, J = 14.1 Hz), 3.11<br>(1 H, dd, J = 9.8, 2.5 Hz), 3.19 (1 H, d, J = 13.7 Hz), 3.34-3.43 (1 H, m), 7.17<br>(1 H, dd, J = 5.6, 1.9 Hz), 7.25 (1 H, d, J = 1.5 Hz), 8.23 (1 H, d, J = 5.5 Hz) |
| 120 | 5 | ESI+: 407.2 |
| 121 | 5 | ESI+: 381.1 |
| 122 | 5 | ESI+: 419.3 |
| 123 | 5 | APCI/ESI+: 377.2 |
| 124 | 5 | ESI+: 379.3 |
| 125 | 5 | ESI+: 383.3 |

TABLE 6-continued
| Ex | Syn | DATA |
|---|---|---|
| 126 | 5 | ESI+: 395.2 |
| 127 | 5 | ESI+: 409.3 |
| 128 | 6 | ESI+: 411.2 |
| 129 | 9 | ESI+: 353.3 |
| 130 | 9 | ESI+: 377.1 |
| 131 | 9 | ESI+: 375.3 |
| 132 | 9 | ESI+: 377.2 |
| 133 | 9 | ESI+: 401.2 |
| 134 | 9 | ESI+: 415.2 |
| 135 | 9 | ESI+: 399.1 |
| 136 | 103 | ESI+: 409.2 |
| 137 | 103 | ESI+: 409.2 |
| 138 | 103 | ESI+: 397.3 |
| 139 | 103 | ESI+: 409.3<br>$^1$H NMR (400 MHz, DMSO-d$_6$) δ ppm: −0.03-0.08 (4 H, m), 0.33-0.45 (4 H, m), 0.67-0.81 (2 H, m), 1.30-1.41 (4 H, m), 1.79-1.88 (2 H, m), 2.29-2.37 (1 H, m), 2.46-2.51 (2 H, m), 2.91 (1 H, d, J = 13.7 Hz), 2.98-3.08 (2 H, m), 3.16 (1 H, d, J = 13.7 Hz), 4.08 (2 H, t, J = 6.5 Hz), 6.82-6.89 (2 H, m), 8.26-8.30 (1 H, m) |
| 140 | 103 | ESI+: 371.3 |
| 141 | 103 | ESI+: 355.3 |
| 142 | 103 | ESI+: 369.3 |
| 143 | 103 | ESI+: 369.3<br>$^1$H NMR (400 MHz, DMSO-d$_6$) δ ppm: 0.00-0.05 (2 H, m), 0.37-0.44 (2 H, m), 0.66-0.78 (1 H, m), 1.13 (3 H, t, J = 7.4 Hz), 1.28-1.36 (2 H, m), 1.77-1.86 (2 H, m), 2.35 (1 H, dd, J = 14.1, 10.1 Hz), 2.44 (2 H, qd, J = 7.4, 1.8 Hz), 2.94 (1 H, d, J = 13.9 Hz), 3.04 (1 H, dd, J = 14.3, 2.4 Hz), 3.08 (1 H, dd, J = 10.4, 2.4 Hz), 3.14 (1 H, d, J = 13.9 Hz), 4.06 (2 H, t, J = 6.5 Hz), 6.83-6.87 (2 H, m), 8.24-8.30 (1 H, m) |
| 144 | 103 | ESI+: 383.2 |
| 145 | 103 | ESI+: 397.2 |
| 146 | 104 | ESI+: 411.4 |
TABLE 7
| PEx | Str |
|---|---|
| 1 | 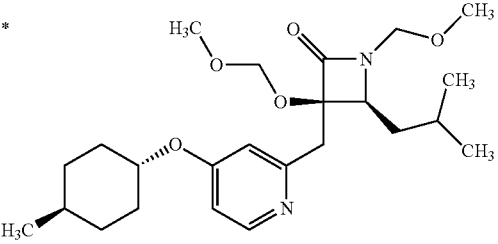 [SMILES: COCO[C@@]1(Cc2cc(O[C@H]3CC[C@H](C)CC3)ccn2)C(=O)N(COC)[C@H]1CC(C)C] |
| 2 | 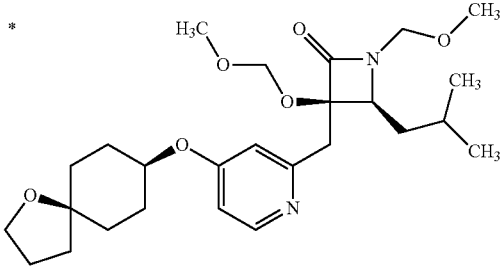 [SMILES: COCO[C@@]1(Cc2cc(O[C@H]3CC[C@]4(CCCO4)CC3)ccn2)C(=O)N(COC)[C@H]1CC(C)C] |
| 3 | 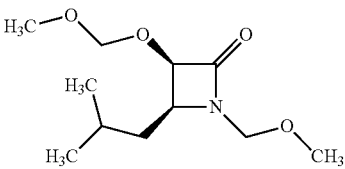 |

TABLE 7-continued
| PEx | Str |
|---|---|
| 4 | 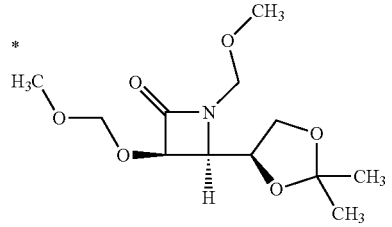 |
| 5 | 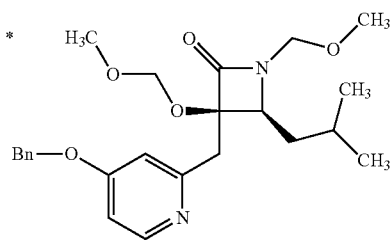 [SMILES: COCO[C@@]1(Cc2cc(OCc3ccccc3)ccn2)C(=O)N(COC)[C@H]1CC(C)C] |
| 6 | 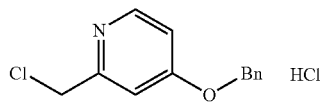 [SMILES: ClCc1cc(OCc2ccccc2)ccn1 ; Cl] |
| 7 | 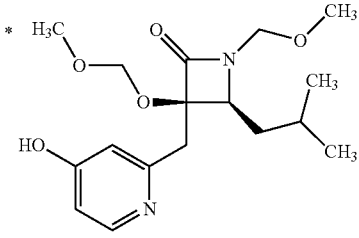 [SMILES: COCO[C@@]1(Cc2cc(O)ccn2)C(=O)N(COC)[C@H]1CC(C)C] |
| 8 | 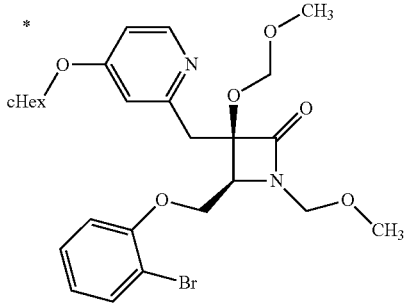 |
| 9 | 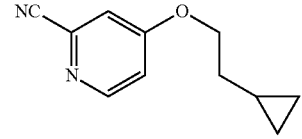 [SMILES: N#Cc1cc(OCCC2CC2)ccn1] |
| 10 | 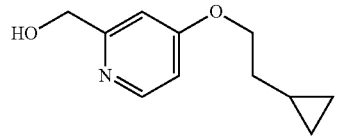 [SMILES: OCc1cc(OCCC2CC2)ccn1] |

TABLE 7-continued

| PEx | Str |
|---|---|
| 11 | (structure) |
| 12 | (structure) |
| 13 | (structure) |
| 14 | (structure) |
| 15 | (structure) |
| 16 | (structure) |

TABLE 7-continued

| PEx | Str |
|---|---|
| 17 | (structure) |
| 18 | (structure) |
| 19 | (structure) |
| 20 | (structure) |
| 21 | (structure) |
| 22 | (structure) |
| 23 | (structure) |

TABLE 7-continued
| PEx | Str |
|---|---|
| 24 | 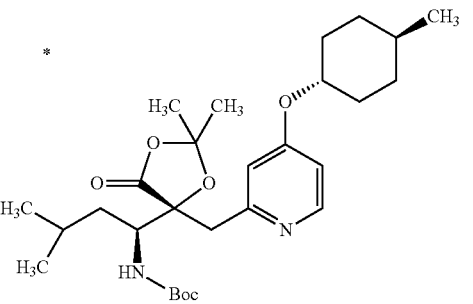 [SMILES: CC(C)C[C@H](NC(=O)OC(C)(C)C)[C@@]1(Cc2cc(O[C@H]3CC[C@H](C)CC3)ccn2)OC(C)(C)OC1=O] |
| 25 | 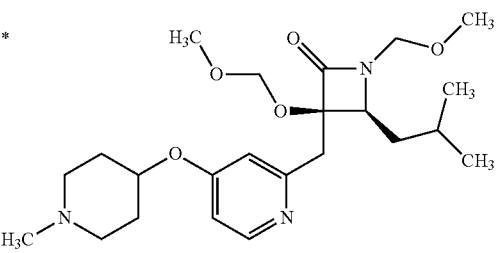 [SMILES: COCO[C@@]1(Cc2cc(OC3CCN(C)CC3)ccn2)C(=O)N(COC)[C@H]1CC(C)C] |
| 26 | 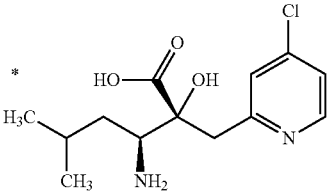 [SMILES: CC(C)C[C@H](N)[C@](O)(Cc1cc(Cl)ccn1)C(=O)O] |
| 27 | 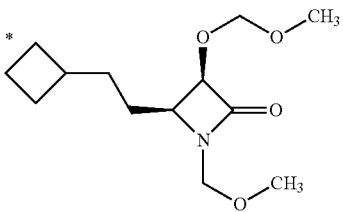 [SMILES: COCO[C@H]1C(=O)N(COC)[C@H]1CCC1CCC1] |
| 28 | 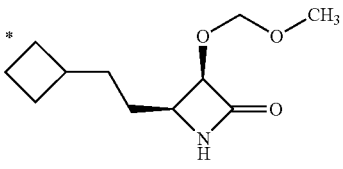 |
| 29 | 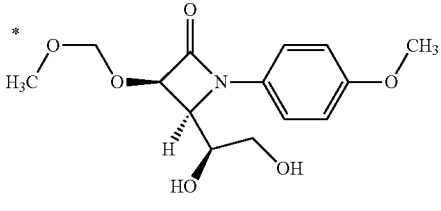 |
| 30 | 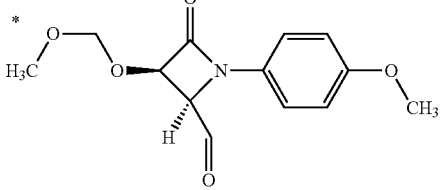 |

TABLE 7-continued

| PEx | Str |
|---|---|
| 31 | |
| 32 | |
| 33 | |
| 34 | |
| 35 | |
| 36 | |

TABLE 7-continued

| PEx | Str |
|---|---|
| 37 | |
| 38 | |
| 39 | |
| 40 | |
| 41 | |
| 42 | |

TABLE 7-continued
| PEx | Str |
|---|---|
| 43 | 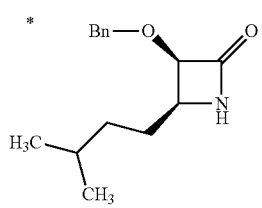 |
| 44 | 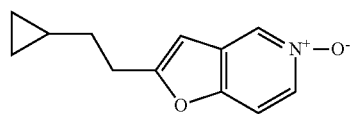 [SMILES: [O-][n+]1ccc2oc(CCC3CC3)cc2c1] |
| 45 | 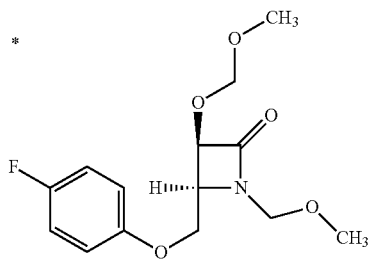 [SMILES: COCO[C@H]1C(=O)N(COC)[C@H]1COc1ccc(F)cc1] |
| 46 | 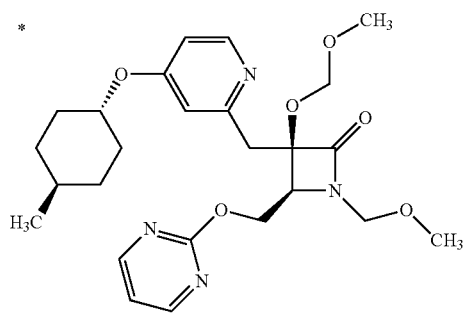 [SMILES: COCO[C@@]1(Cc2cc(O[C@H]3CC[C@H](C)CC3)ccn2)C(=O)N(COC)[C@H]1COc1ncccn1] |
| 47 | 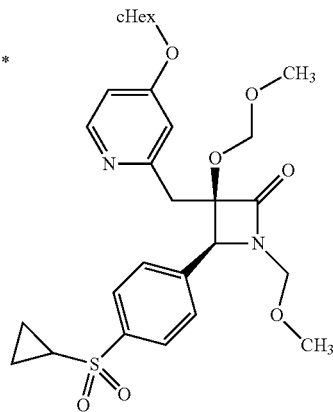 |

TABLE 7-continued
| PEx | Str |
|---|---|
| 48 | 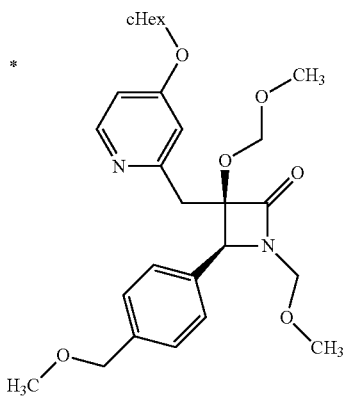 |
| 49 | 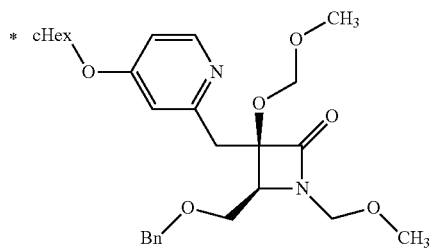 |
| 50 | 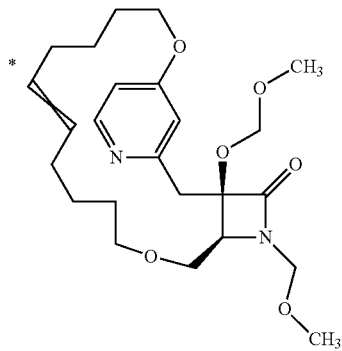 |
| 51 | 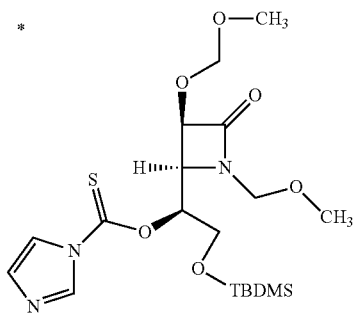 |

TABLE 7-continued

| PEx | Str |
|---|---|
| 52 | |
| 53(1) | |
| 53(2) | |
| 54 | |
| 55 | |
| 56(1) | |

TABLE 7-continued
| PEx | Str |
|---|---|
| 56(2) | 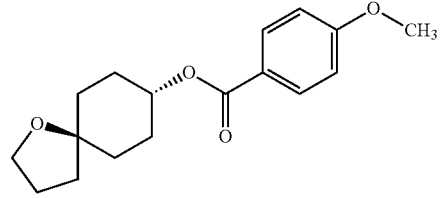 [SMILES: COc1ccc(C(=O)O[C@H]2CC[C@@]3(CCCO3)CC2)cc1] |
| 57 | 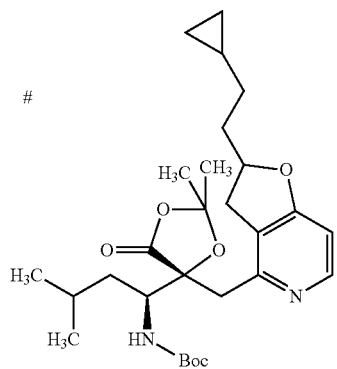 [SMILES: CC(C)C[C@H](NC(=O)OC(C)(C)C)[C@@]1(Cc2nccc3c2CC(CCC2CC2)O3)OC(C)(C)OC1=O] |
| 58 |  |
| 59(1) | 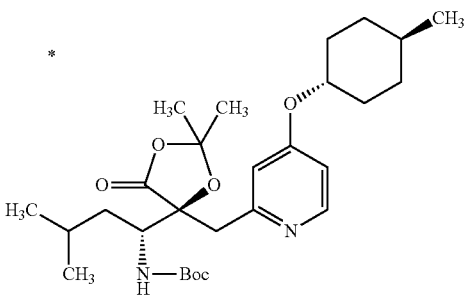 [SMILES: CC(C)C[C@@H](NC(=O)OC(C)(C)C)[C@]1(Cc2cc(O[C@H]3CC[C@H](C)CC3)ccn2)OC(C)(C)OC1=O] |
| 59(2) | 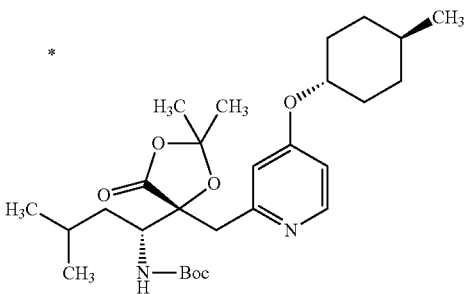 [SMILES: CC(C)C[C@@H](NC(=O)OC(C)(C)C)[C@@]1(Cc2cc(O[C@H]3CC[C@H](C)CC3)ccn2)OC(C)(C)OC1=O] |
| 60 | 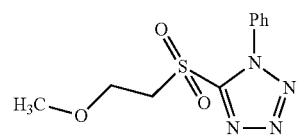 [SMILES: COCCS(=O)(=O)c1nnnn1-c1ccccc1] |

TABLE 7-continued
| PEx | Str |
|---|---|
| 61 | 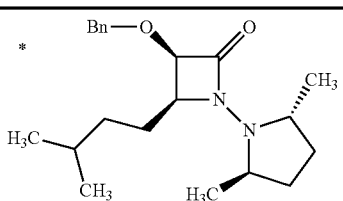 |
| 62 | 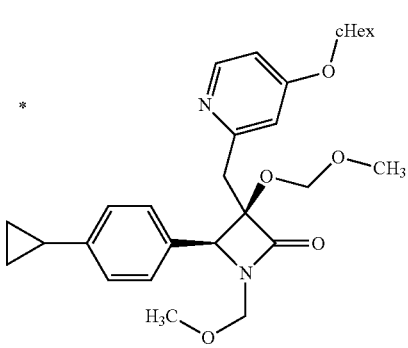 |
| 63 | 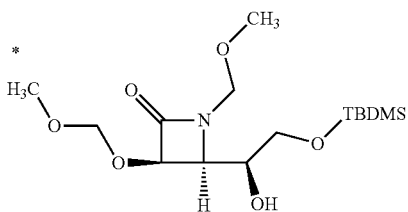 |
| 64 | 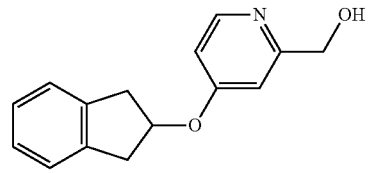 [SMILES: OCc1cc(OC2Cc3ccccc3C2)ccn1] |
| 65 | 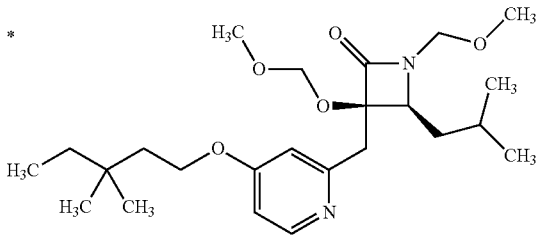 [SMILES: CCC(C)(C)CCOc1ccnc(C[C@]2(OCOC)C(=O)N(COC)[C@H]2CC(C)C)c1] |
| 66 | 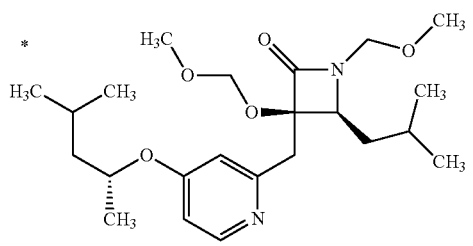 [SMILES: COCO[C@@]1(Cc2cc(O[C@H](C)CC(C)C)ccn2)C(=O)N(COC)[C@H]1CC(C)C] |
| 67 | 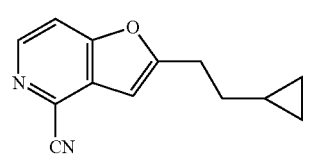 [SMILES: N#Cc1nccc2oc(CCC3CC3)cc12] |

TABLE 7-continued
| PEx | Str |
|---|---|
| 68 | 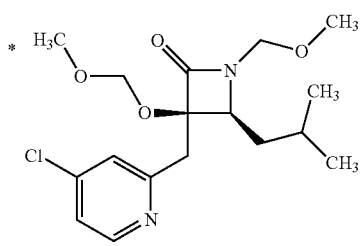 [SMILES: COCO[C@@]1(Cc2cc(Cl)ccn2)C(=O)N(COC)[C@H]1CC(C)C] |
| 69 | 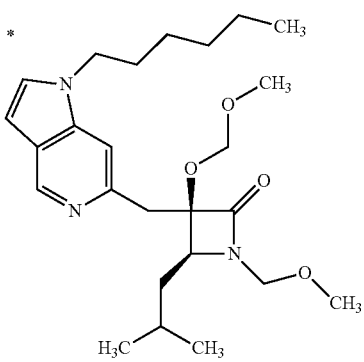 [SMILES: CCCCCCn1ccc2cnc(C[C@]3(OCOC)C(=O)N(COC)[C@H]3CC(C)C)cc21] |
| 70 | 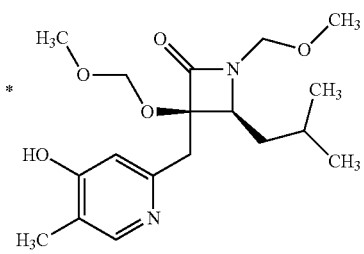 [SMILES: COCO[C@@]1(Cc2cc(O)c(C)cn2)C(=O)N(COC)[C@H]1CC(C)C] |
| 71 | 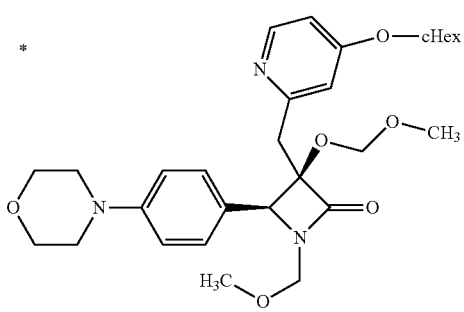 |
| 72 | 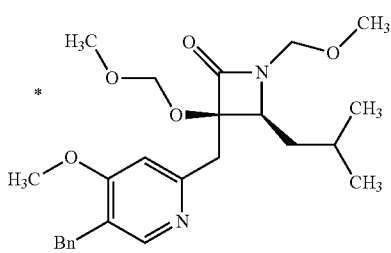 |

TABLE 7-continued

| PEx | Str |
|---|---|
| 73 | |
| 74 | |
| 75 | |
| 76 | |
| 77 | |
| 78 | |

TABLE 7-continued
| PEx | Str |
|---|---|
| 79 | 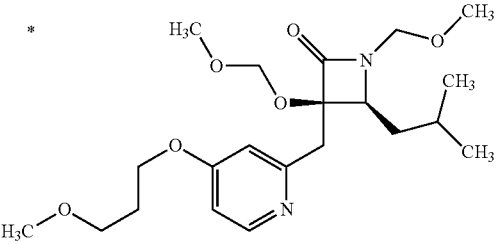 [SMILES: COCCCOc1ccnc(C[C@]2(OCOC)C(=O)N(COC)[C@H]2CC(C)C)c1] |
| 80 | 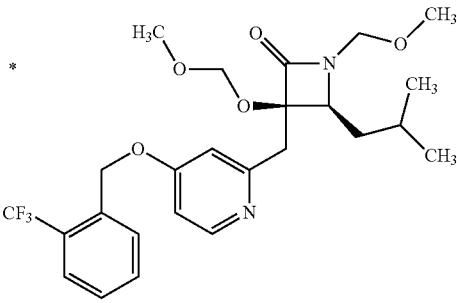 [SMILES: COCO[C@@]1(Cc2cc(OCc3ccccc3C(F)(F)F)ccn2)C(=O)N(COC)[C@H]1CC(C)C] |
| 81 | 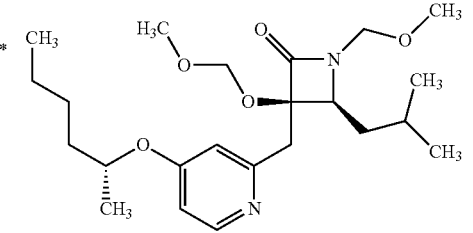 [SMILES: CCCC[C@@H](C)Oc1ccnc(C[C@]2(OCOC)C(=O)N(COC)[C@H]2CC(C)C)c1] |
| 82 | 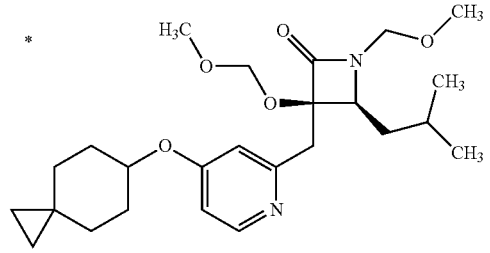 [SMILES: COCO[C@@]1(Cc2cc(OC3CCC4(CC3)CC4)ccn2)C(=O)N(COC)[C@H]1CC(C)C] |
| 83 | 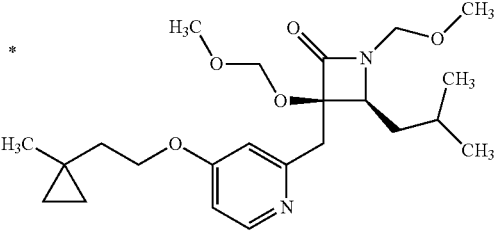 [SMILES: COCO[C@@]1(Cc2cc(OCCC3(C)CC3)ccn2)C(=O)N(COC)[C@H]1CC(C)C] |
| 84 | 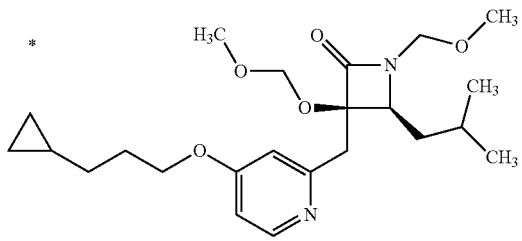 [SMILES: COCO[C@@]1(Cc2cc(OCCCC3CC3)ccn2)C(=O)N(COC)[C@H]1CC(C)C] |

TABLE 7-continued
| PEx | Str |
|---|---|
| 85 | 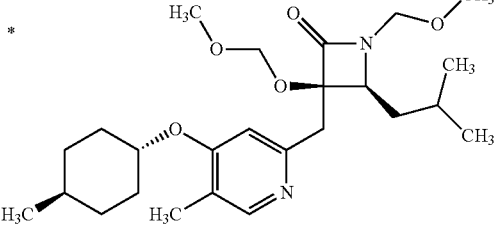 |
| 86 | 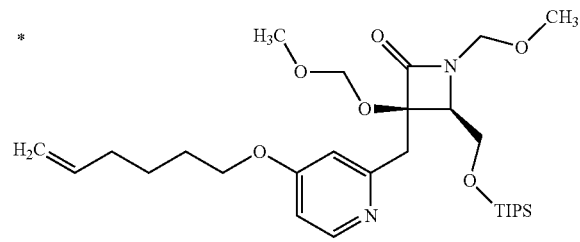 |
| 87 | 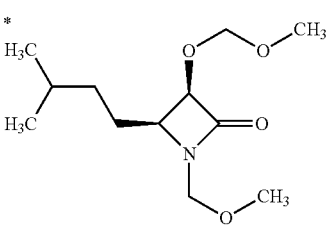 [SMILES: COCO[C@H]1C(=O)N(COC)[C@H]1CCC(C)C] |
| 88 | 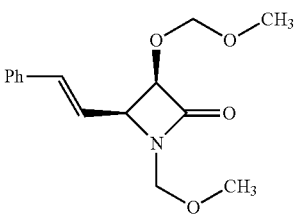 [SMILES: COCO[C@H]1C(=O)N(COC)[C@H]1/C=C/c1ccccc1] |
| 89 | 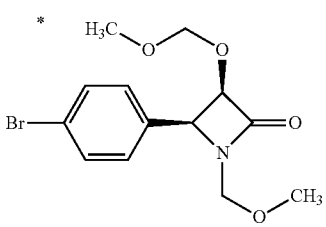 [SMILES: COCO[C@H]1C(=O)N(COC)[C@H]1c1ccc(Br)cc1] |
| 90 | 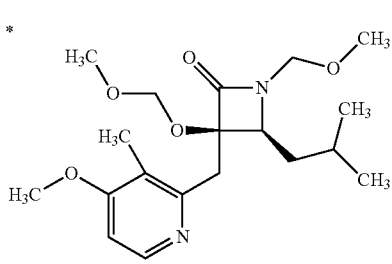 [SMILES: COCO[C@@]1(Cc2nccc(OC)c2C)C(=O)N(COC)[C@H]1CC(C)C] |

TABLE 7-continued

| PEx | Str |
|---|---|
| 91 | (structure) |
| 92 | (structure) |
| 93 | (structure) |
| 94 | (structure) |
| 95 | (structure) |
| 96 | (structure) |

TABLE 7-continued
| PEx | Str |
|---|---|
| 97 | 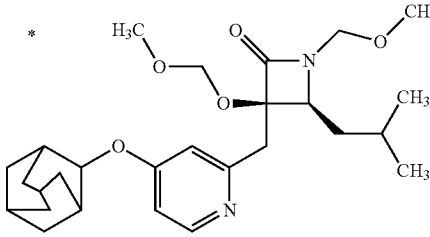 |
| 98 | 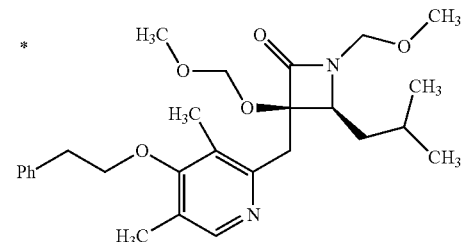 |
| 99 | 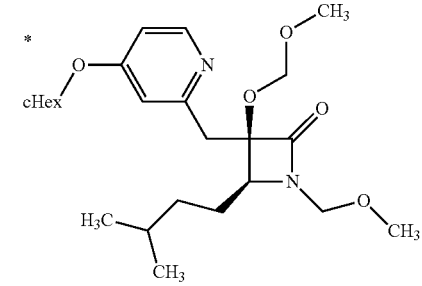 |
| 100 | 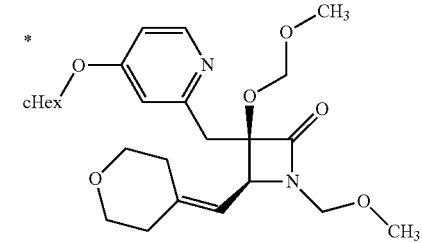 |
| 101 | 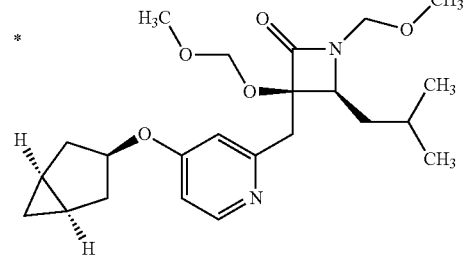 |
| 102 | 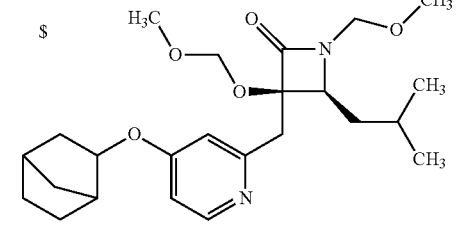 |

TABLE 7-continued
| PEx | Str |
|---|---|
| 103 | 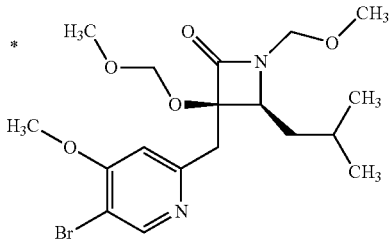 |
| 104 | 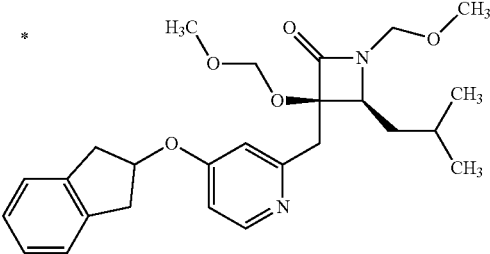 [SMILES: COCO[C@@]1(Cc2cc(OC3Cc4ccccc4C3)ccn2)C(=O)N(COC)[C@H]1CC(C)C] |
| 105 | 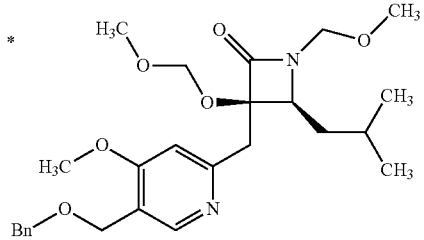 [SMILES: COCO[C@@]1(Cc2cc(OC)c(COCc3ccccc3)cn2)C(=O)N(COC)[C@H]1CC(C)C] |
| 106 | 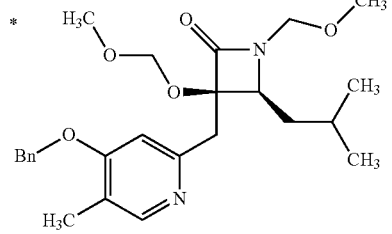 |
| 107 | 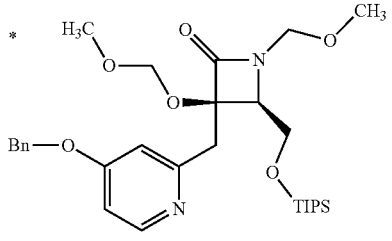 |
| 108 | 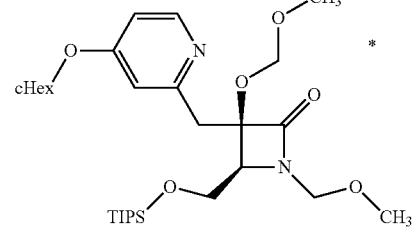 |

TABLE 7-continued
| PEx | Str |
|---|---|
| 109 | 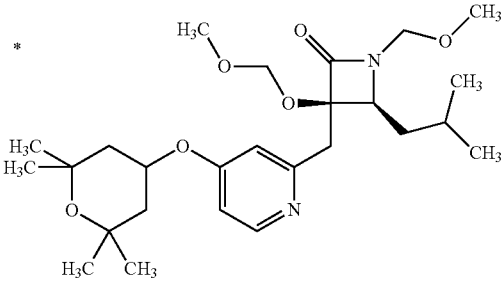 [SMILES: COCO[C@@]1(Cc2cc(OC3CC(C)(C)OC(C)(C)C3)ccn2)C(=O)N(COC)[C@H]1CC(C)C] |
| 110 | 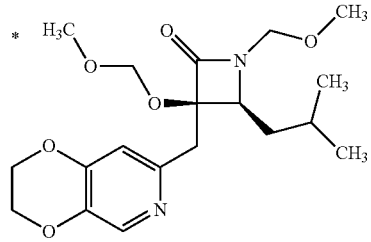 [SMILES: COCO[C@@]1(Cc2cc3c(cn2)OCCO3)C(=O)N(COC)[C@H]1CC(C)C] |
| 111 | 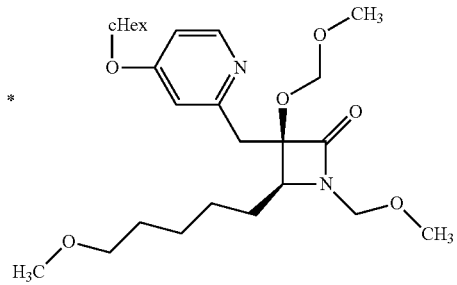 |
| 112 | 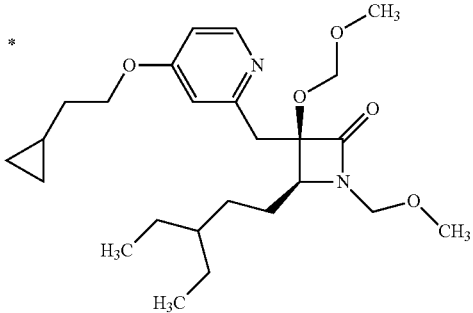 [SMILES: CCC(CC)CC[C@@H]1N(COC)C(=O)[C@]1(Cc1cc(OCCC2CC2)ccn1)OCOC] |
| 113 | 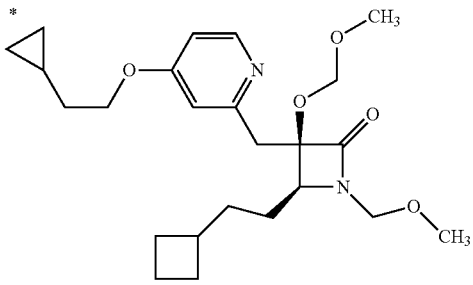 [SMILES: COCO[C@@]1(Cc2cc(OCCC3CC3)ccn2)C(=O)N(COC)[C@H]1CCC1CCC1] |
| 114 | 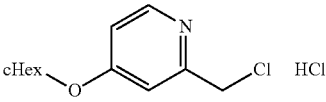 |

TABLE 7-continued
| PEx | Str |
|---|---|
| 115 | 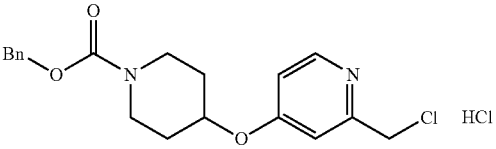 [SMILES: O=C(OCc1ccccc1)N1CCC(Oc2ccnc(CCl)c2)CC1 ; Cl] HCl |
| 116 | 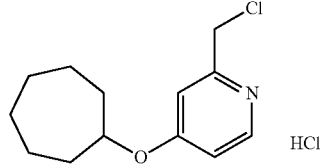 [SMILES: ClCc1cc(OC2CCCCCC2)ccn1 ; Cl] HCl |
| 117 | 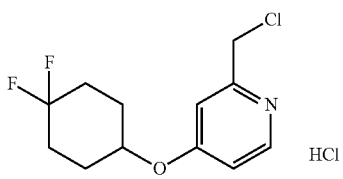 [SMILES: FC1(F)CCC(Oc2ccnc(CCl)c2)CC1 ; Cl] HCl |
| 118 | 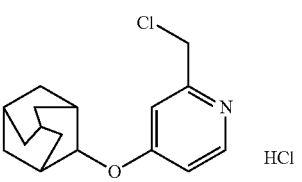 [SMILES: ClCc1cc(OC2C3CC4CC(C3)CC2C4)ccn1 ; Cl] HCl |
| 119 | 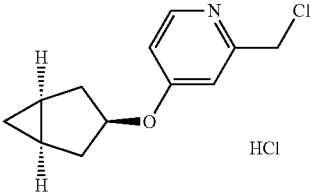 [SMILES: ClCc1cc(O[C@@H]2C[C@@H]3C[C@@H]3C2)ccn1 ; Cl] HCl |
| 120 | 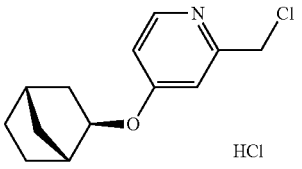 [SMILES: ClCc1cc(O[C@@H]2C[C@H]3CC[C@@H]2C3)ccn1 ; Cl] HCl |
| 121 | 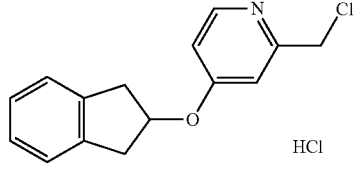 [SMILES: ClCc1cc(OC2Cc3ccccc3C2)ccn1 ; Cl] HCl |
| 122 | 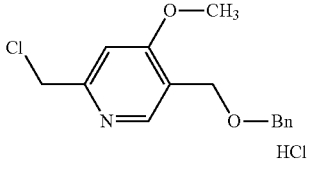 [SMILES: COc1cc(CCl)ncc1COCc1ccccc1 ; Cl] HCl |
| 123 | 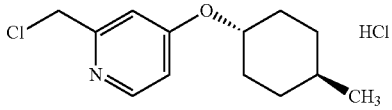 [SMILES: C[C@H]1CC[C@H](Oc2ccnc(CCl)c2)CC1 ; Cl] HCl |

TABLE 7-continued
| PEx | Str |
|---|---|
| 124 | 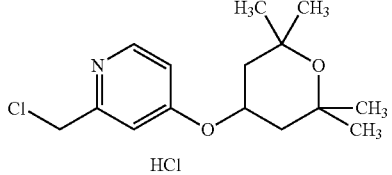 [SMILES: CC1(C)CC(Oc2ccnc(CCl)c2)CC(C)(C)O1 ; Cl] HCl |
| 125 | 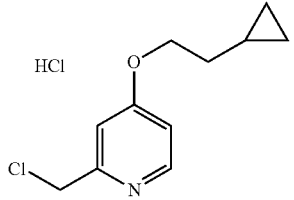 [SMILES: ClCc1cc(OCCC2CC2)ccn1 ; Cl] HCl |
| 126 | 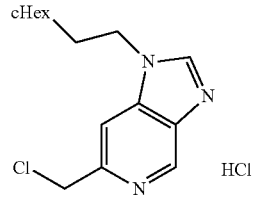 HCl |
| 127 | 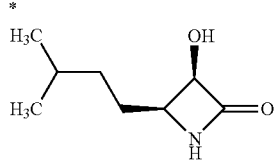 |
| 128 | 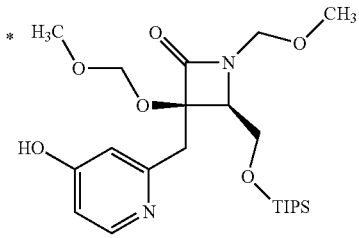 |
| 129 | 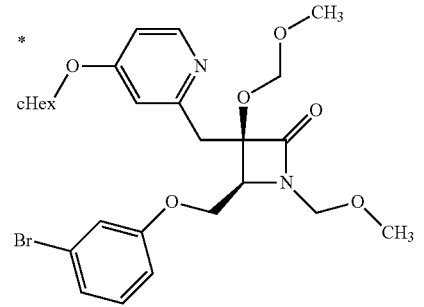 |

TABLE 7-continued
| PEx | Str |
|---|---|
| 130 | 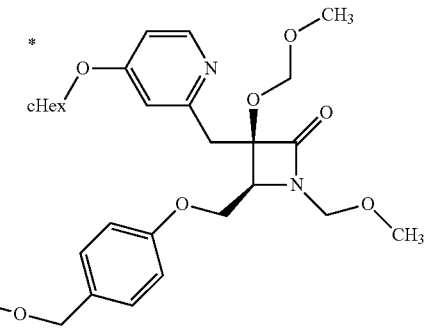 |
| 131 | 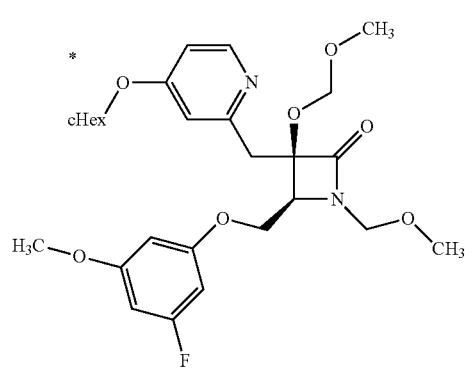 |
| 132 | 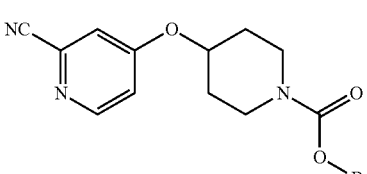 |
| 133 | 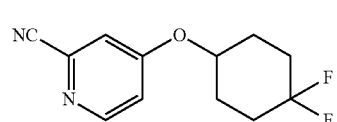 |
| 134 | 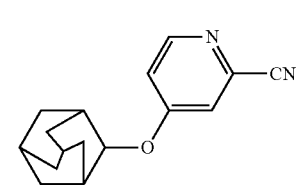 [SMILES: N#Cc1cc(OC2C3CC4CC(C3)CC2C4)ccn1] |
| 135 | 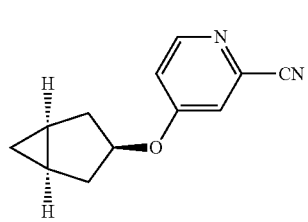 [SMILES: N#Cc1cc(O[C@@H]2C[C@@H]3C[C@@H]3C2)ccn1] |
| 136 | 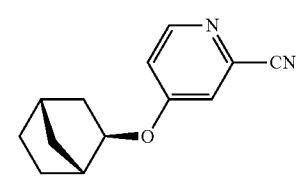 [SMILES: N#Cc1cc(O[C@@H]2C[C@H]3CC[C@@H]2C3)ccn1] |

TABLE 7-continued

| PEx | Str |
|---|---|
| 137 | |
| 138 | |
| 139 | |
| 140 | |
| 141 | |
| 142 | |
| 143 | |
| 144 | |
| 145 | |

TABLE 7-continued
| PEx | Str |
|---|---|
| 146 | 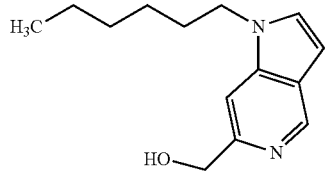 [SMILES: CCCCCCn1ccc2cnc(CO)cc21] |
| 147 | 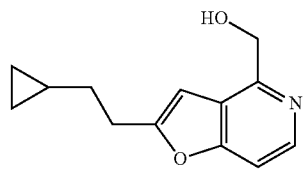 [SMILES: OCc1nccc2oc(CCC3CC3)cc12] |
| 148 | 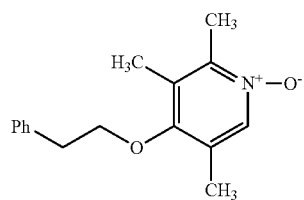 [SMILES: Cc1c[n+]([O-])c(C)c(C)c1OCCc1ccccc1] |
| 149 | 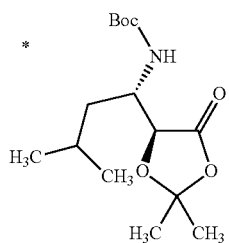 |
| 150 | 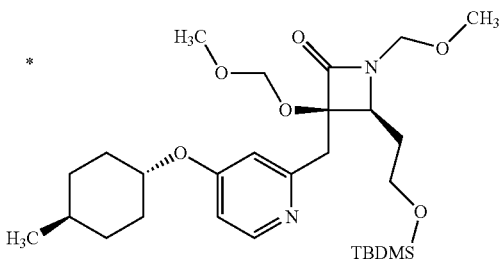 |
| 151 | 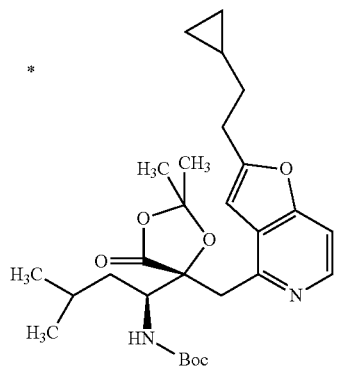 [SMILES: CC(C)C[C@H](NC(=O)OC(C)(C)C)[C@@]1(Cc2nccc3oc(CCC4CC4)cc23)OC(C)(C)OC1=O] |

TABLE 7-continued
| PEx | Str |
|---|---|
| 152 | 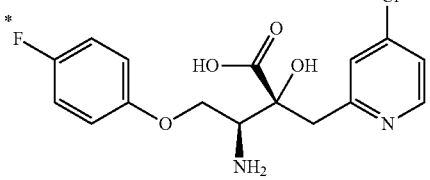 |
| 153 | 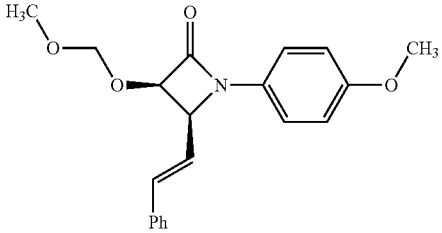 |
| 154 | 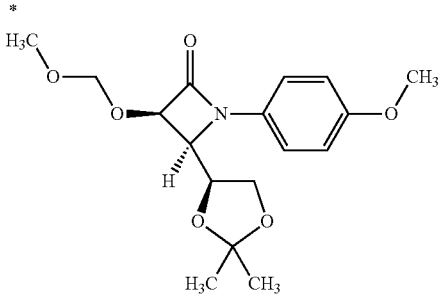 |
| 155 | 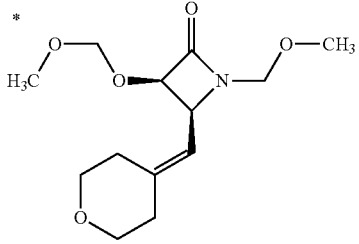 |
| 156 | 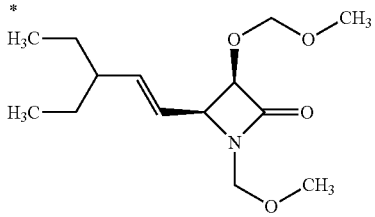 [SMILES: CCC(/C=C/[C@H]1[C@@H](OCOC)C(=O)N1COC)CC] |
| 157 | 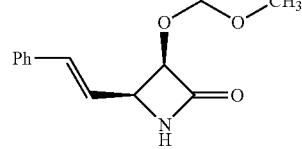 |
| 158 | 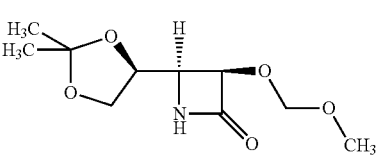 |

TABLE 7-continued
| PEx | Str |
| --- | --- |
| 159 | 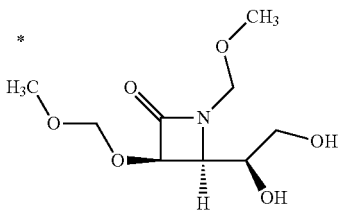 [SMILES: COCO[C@H]1C(=O)N(COC)[C@H]1[C@H](O)CO] |
| 160 | 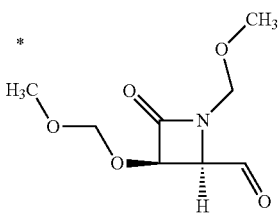 |
| 161 | 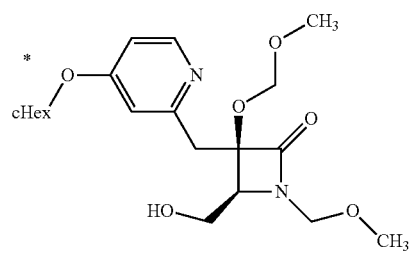 |
| 162 | 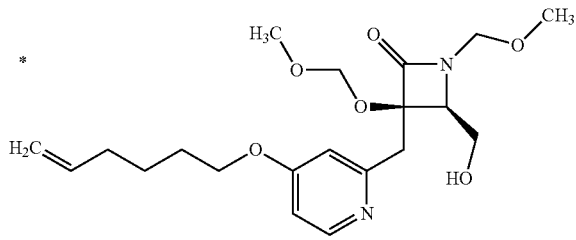 [SMILES: C=CCCCCOc1ccnc(C[C@]2(OCOC)C(=O)N(COC)[C@H]2CO)c1] |
| 163 | 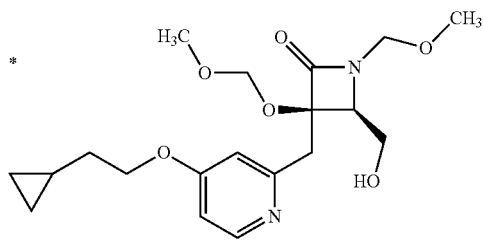 [SMILES: COCO[C@@]1(Cc2cc(OCCC3CC3)ccn2)C(=O)N(COC)[C@H]1CO] |
| 164 | 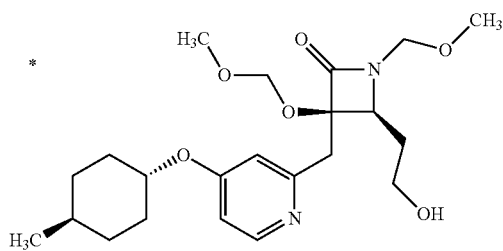 |

TABLE 7-continued
| PEx | Str |
|---|---|
| 165 | 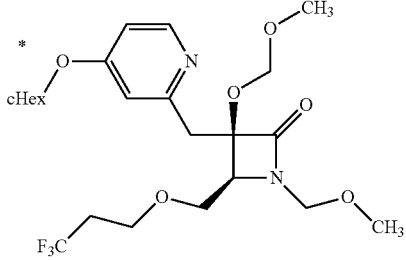 |
| 166 | 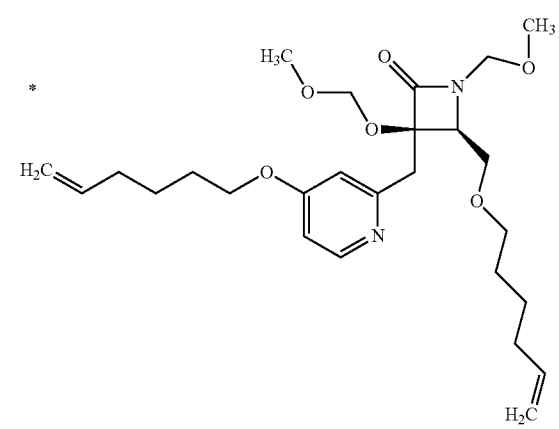 [SMILES: C=CCCCCOC[C@@H]1N(COC)C(=O)[C@]1(Cc1cc(OCCCCC=C)ccn1)OCOC] |
| 167 | 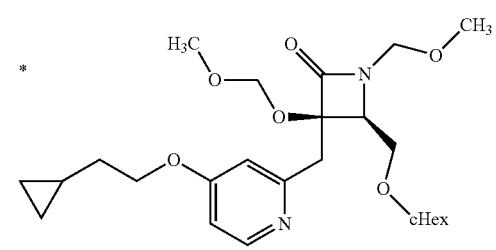 |
| 168 | 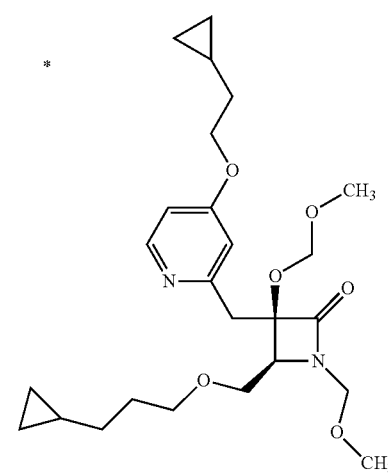 |
| 169 | 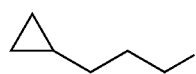 |

TABLE 7-continued

| PEx | Str |
|---|---|
| 170 | # (structure) |
| 171 | * (structure) |
| 172 | * (structure) |
| 173 | * (structure) |
| 174 | * (structure) |
| 175 | * (structure) |
| 176 | * (structure) |

TABLE 7-continued
| PEx | Str |
|---|---|
| 177 | 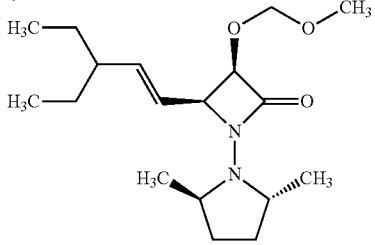 |
| 178 | 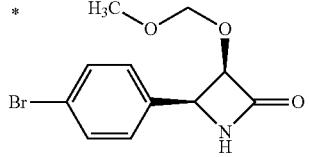 [SMILES: COCO[C@H]1C(=O)N[C@H]1c1ccc(Br)cc1] |
| 179 | 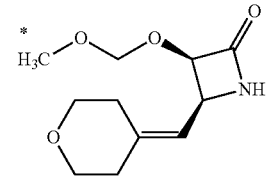 [SMILES: COCO[C@H]1C(=O)N[C@H]1C=C1CCOCC1] |
| 180 | 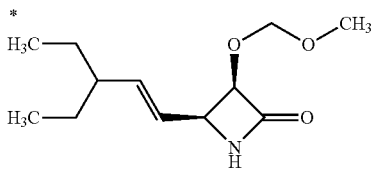 [SMILES: CCC(/C=C/[C@@H]1NC(=O)[C@@H]1OCOC)CC] |
| 181 | 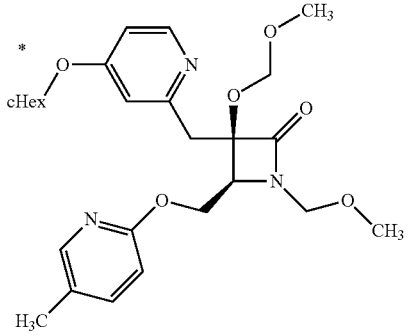 |
| 182 | 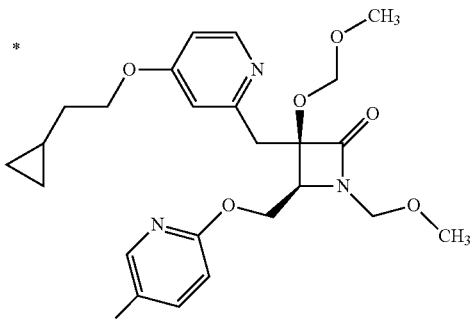 |

TABLE 7-continued
| PEx | Str |
|---|---|
| 183 | 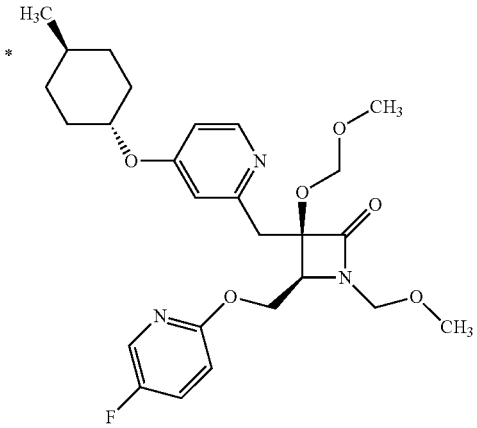 [SMILES: COCO[C@@]1(Cc2cc(O[C@H]3CC[C@H](C)CC3)ccn2)C(=O)N(COC)[C@H]1COc1ccc(F)cn1] |
| 184 | 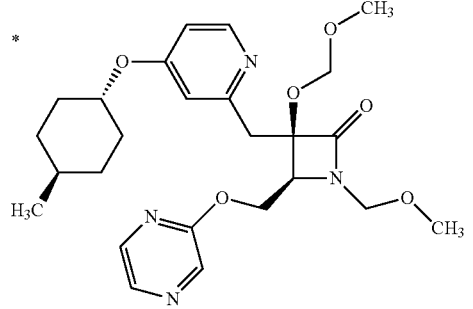 [SMILES: COCO[C@@]1(Cc2cc(O[C@H]3CC[C@H](C)CC3)ccn2)C(=O)N(COC)[C@H]1COc1cnccn1] |
| 185 | 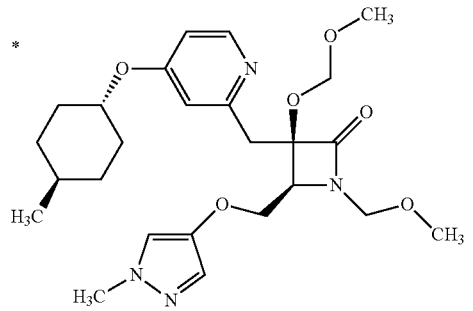 [SMILES: COCO[C@@]1(Cc2cc(O[C@H]3CC[C@H](C)CC3)ccn2)C(=O)N(COC)[C@H]1COc1cnn(C)c1] |
| 186 | 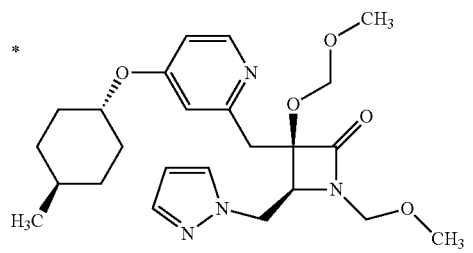 [SMILES: COCO[C@@]1(Cc2cc(O[C@H]3CC[C@H](C)CC3)ccn2)C(=O)N(COC)[C@H]1Cn1cccn1] |
| 187 | 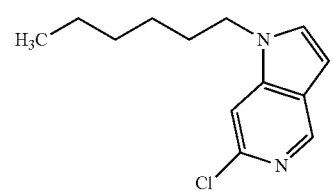 [SMILES: CCCCCCn1ccc2cnc(Cl)cc21] |

TABLE 7-continued
| PEx | Str |
|---|---|
| 188 | 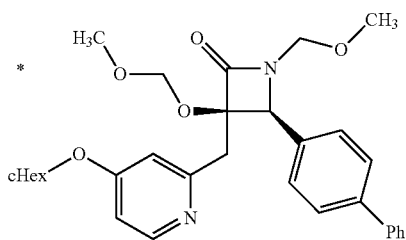 |
| 189 | 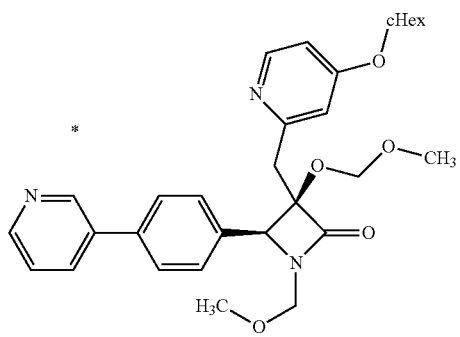 |
| 190 | 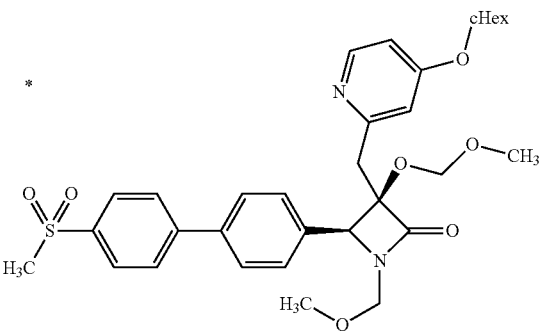 |
| 191 | 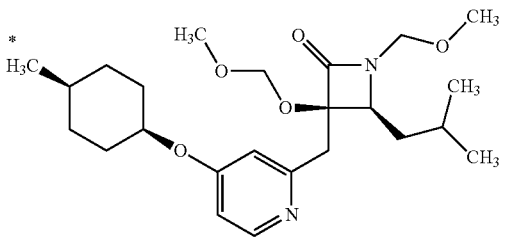 [SMILES: COCO[C@@]1(Cc2cc(O[C@H]3CC[C@@H](C)CC3)ccn2)C(=O)N(COC)[C@H]1CC(C)C] |
| 192 | 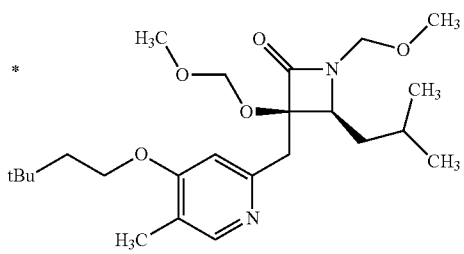 [SMILES: COCO[C@@]1(Cc2cc(OCCC(C)(C)C)c(C)cn2)C(=O)N(COC)[C@H]1CC(C)C] |

TABLE 7-continued
| PEx | Str |
|---|---|
| 193 | 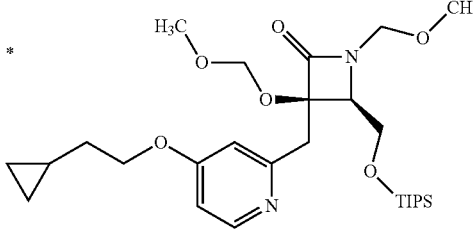 |
| 194 | 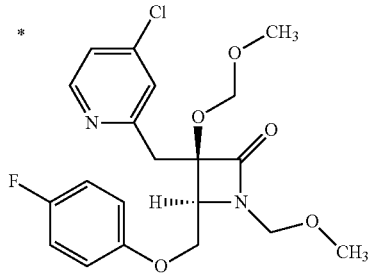 [SMILES: COCO[C@@]1(Cc2cc(Cl)ccn2)C(=O)N(COC)[C@H]1COc1ccc(F)cc1] |
| 195(1) | 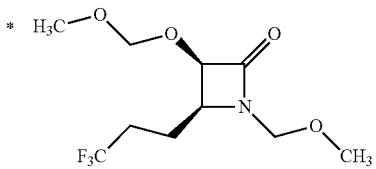 |
| 195(2) | 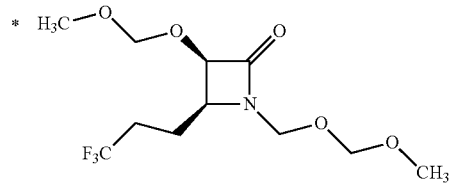 |
| 196 | 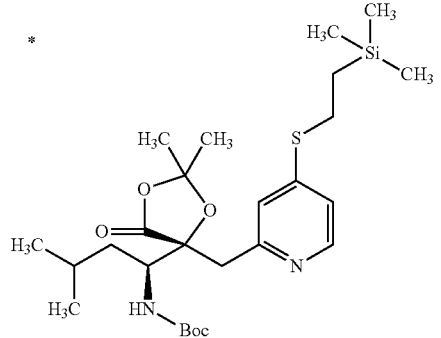 [SMILES: CC(C)C[C@H](NC(=O)OC(C)(C)C)[C@@]1(Cc2cc(SCC[Si](C)(C)C)ccn2)OC(C)(C)OC1=O] |
| 197 | 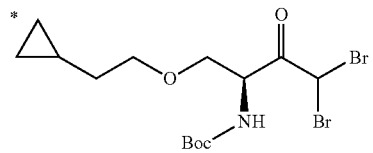 [SMILES: CC(C)(C)OC(=O)N[C@@H](COCCC1CC1)C(=O)C(Br)Br] |
| 198 | 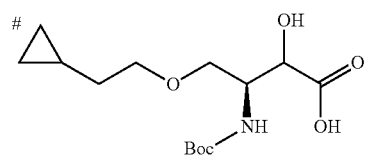 [SMILES: CC(C)(C)OC(=O)N[C@@H](COCCC1CC1)C(O)C(=O)O] |

TABLE 7-continued
| PEx | Str |
|---|---|
| 199 | 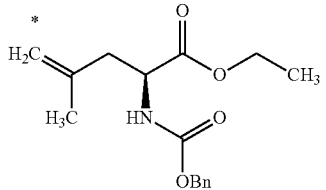 [SMILES: C=C(C)C[C@H](NC(=O)OCc1ccccc1)C(=O)OCC] |
| 200 | 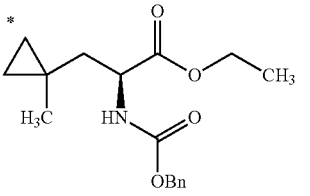 [SMILES: CCOC(=O)[C@H](CC1(C)CC1)NC(=O)OCc1ccccc1] |
| 201 | 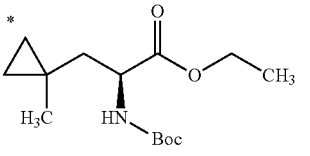 [SMILES: CCOC(=O)[C@H](CC1(C)CC1)NC(=O)OC(C)(C)C] |
| 202 | 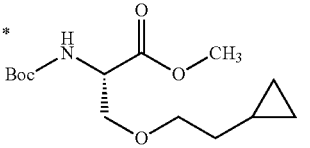 [SMILES: COC(=O)[C@H](COCCC1CC1)NC(=O)OC(C)(C)C] |
| 203 | #2 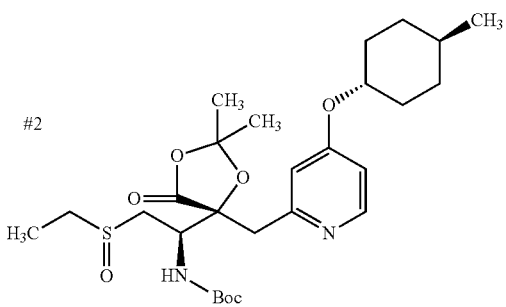 [SMILES: CCS(=O)C[C@H](NC(=O)OC(C)(C)C)[C@@]1(Cc2cc(O[C@H]3CC[C@H](C)CC3)ccn2)OC(C)(C)OC1=O] |
| 204 | 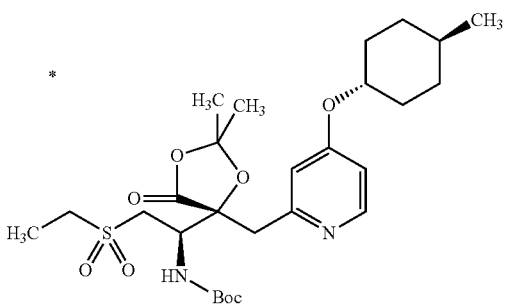 [SMILES: CCS(=O)(=O)C[C@H](NC(=O)OC(C)(C)C)[C@@]1(Cc2cc(O[C@H]3CC[C@H](C)CC3)ccn2)OC(C)(C)OC1=O] |

TABLE 7-continued
| PEx | Str |
|---|---|
| 205 | 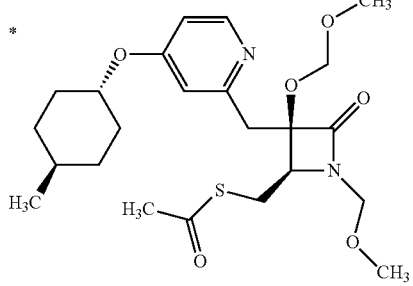 |
| 206 | 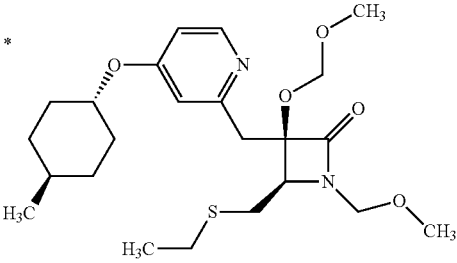 [SMILES: CCSC[C@@H]1N(COC)C(=O)[C@]1(Cc1cc(O[C@H]2CC[C@H](C)CC2)ccn1)OCOC] |
| 207 | 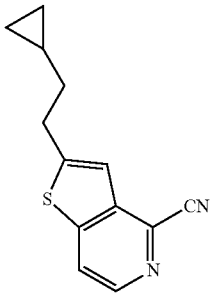 [SMILES: N#Cc1nccc2sc(CCC3CC3)cc12] |
| 208 | 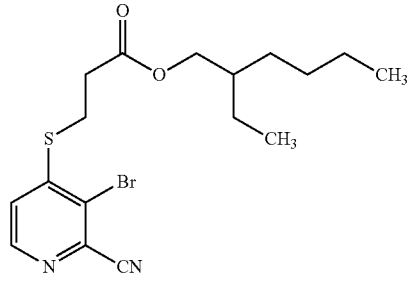 [SMILES: CCCCC(CC)COC(=O)CCSc1ccnc(C#N)c1Br] |
| 209 | 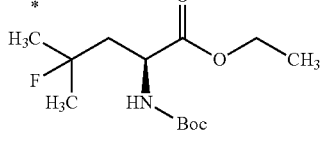 |
| 210 | 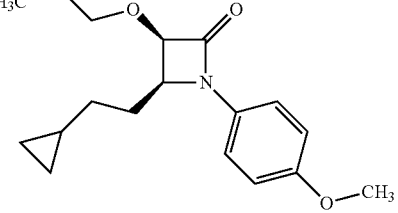 |

TABLE 7-continued
| PEx | Str |
|---|---|
| 211 | 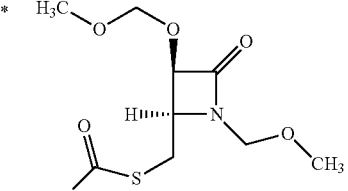 |
| 212 | 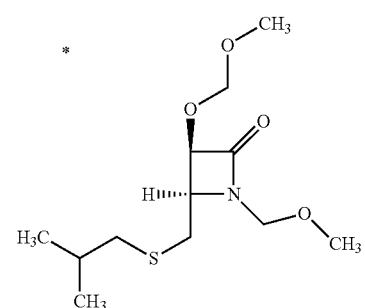 |
| 213 | 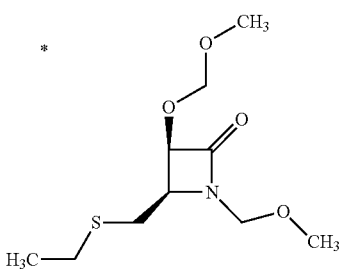 [SMILES: CCSC[C@H]1[C@@H](OCOC)C(=O)N1COC] |
| 214 | 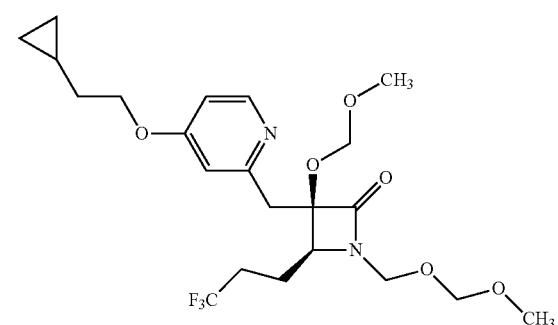 |
| 215 | 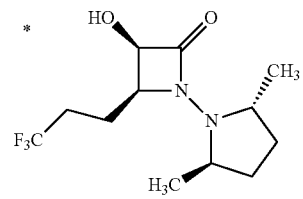 [SMILES: C[C@@H]1CC[C@@H](C)N1N1C(=O)[C@H](O)[C@@H]1CCC(F)(F)F] |
| 216 | 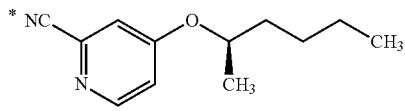 |

TABLE 7-continued
| PEx | Str |
|---|---|
| 217 | 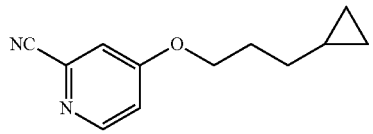 [SMILES: N#Cc1cc(OCCCC2CC2)ccn1] |
| 218 | 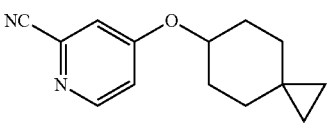 [SMILES: N#Cc1cc(OC2CCC3(CC2)CC3)ccn1] |
| 219 | 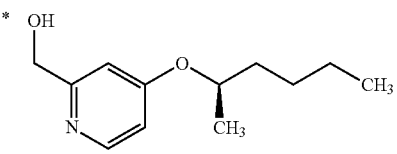 |
| 220 | 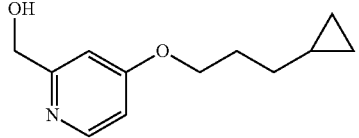 [SMILES: OCc1cc(OCCCC2CC2)ccn1] |
| 221 | 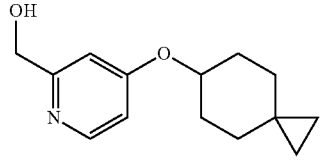 [SMILES: OCc1cc(OC2CCC3(CC2)CC3)ccn1] |
| 222 | 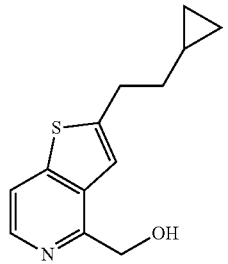 [SMILES: OCc1nccc2sc(CCC3CC3)cc12] |
| 223 | 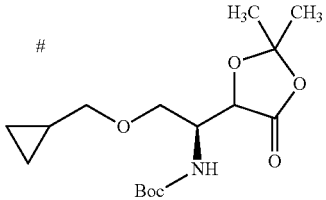 [SMILES: CC(C)(C)OC(=O)N[C@@H](COCC1CC1)C1OC(C)(C)OC1=O] |
| 224 | 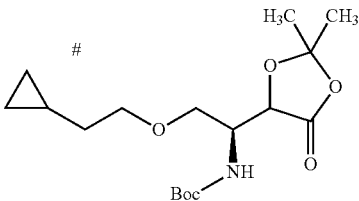 [SMILES: CC(C)(C)OC(=O)N[C@@H](COCCC1CC1)C1OC(C)(C)OC1=O] |

TABLE 7-continued

| PEx | Str |
|---|---|
| 225 | |
| 226 | |
| 227 | |
| 228 | |
| 229 | |

TABLE 7-continued
| PEx | Str |
|---|---|
| 230 | 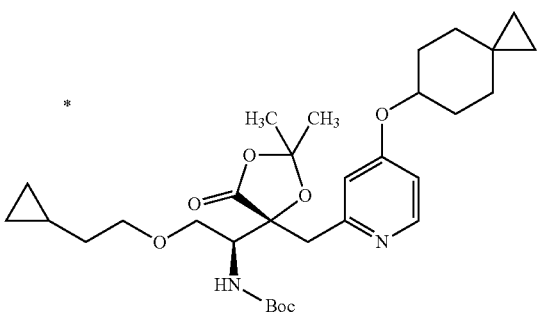 [SMILES: CC(C)(C)OC(=O)N[C@@H](COCCC1CC1)[C@@]1(Cc2cc(OC3CCC4(CC3)CC4)ccn2)OC(C)(C)OC1=O] |
| 231 | 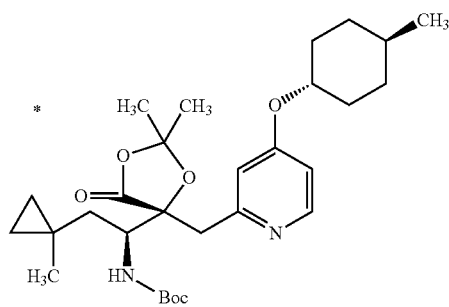 [SMILES: CC1(C[C@H](NC(=O)OC(C)(C)C)[C@@]2(Cc3cc(O[C@H]4CC[C@H](C)CC4)ccn3)OC(C)(C)OC2=O)CC1] |
| 232 | 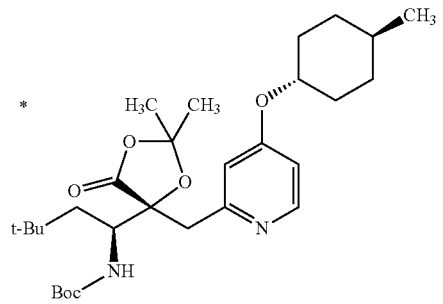 [SMILES: CC(C)(C)C[C@H](NC(=O)OC(C)(C)C)[C@@]1(Cc2cc(O[C@H]3CC[C@H](C)CC3)ccn2)OC(C)(C)OC1=O] |
| 233 | 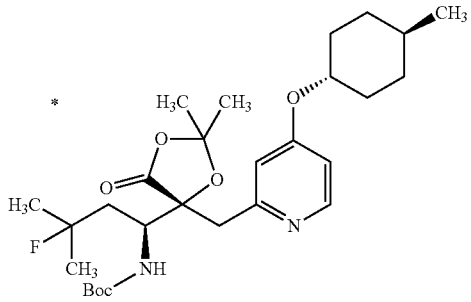 [SMILES: CC(C)(F)C[C@H](NC(=O)OC(C)(C)C)[C@@]1(Cc2cc(O[C@H]3CC[C@H](C)CC3)ccn2)OC(C)(C)OC1=O] |
| 234 | 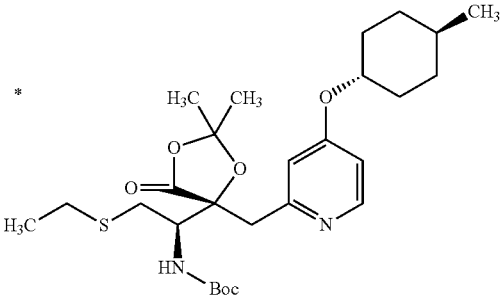 [SMILES: CCSC[C@H](NC(=O)OC(C)(C)C)[C@@]1(Cc2cc(O[C@H]3CC[C@H](C)CC3)ccn2)OC(C)(C)OC1=O] |

TABLE 7-continued
| PEx | Str |
|---|---|
| 235 | 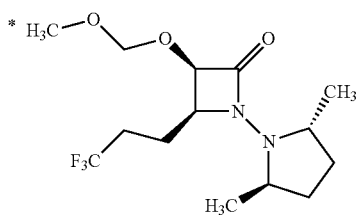 [SMILES: COCO[C@H]1C(=O)N(N2[C@H](C)CC[C@H]2C)[C@H]1CCC(F)(F)F] |
| 236 | 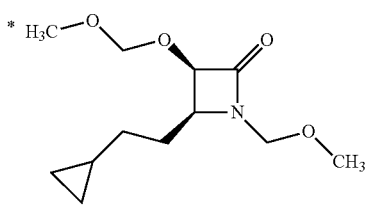 |
| 237 | 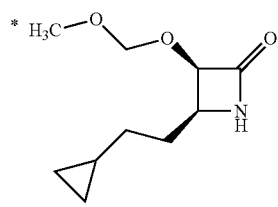 |
| 238 | 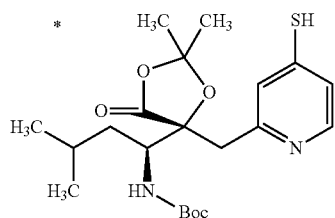 |
| 239 | 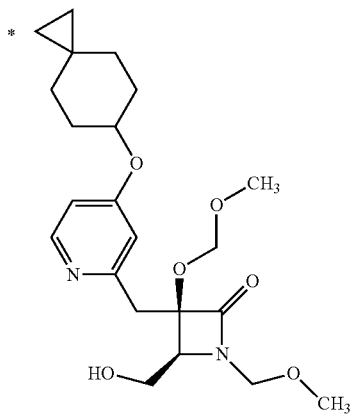 [SMILES: COCO[C@@]1(Cc2cc(OC3CCC4(CC3)CC4)ccn2)C(=O)N(COC)[C@H]1CO] |

TABLE 7-continued
| PEx | Str |
|---|---|
| 240 | 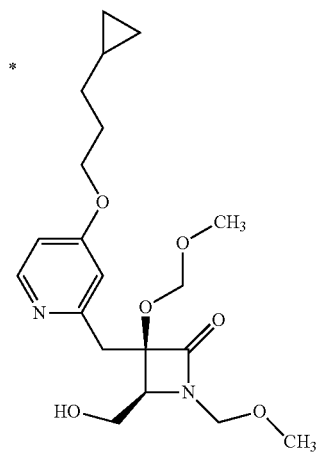 [SMILES: COCO[C@@]1(Cc2cc(OCCCC3CC3)ccn2)C(=O)N(COC)[C@H]1CO] |
| 241 | 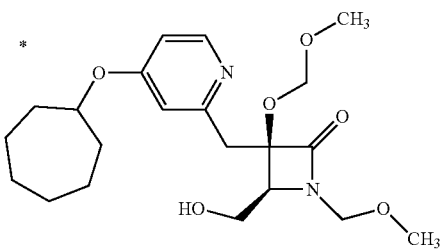 [SMILES: COCO[C@@]1(Cc2cc(OC3CCCCCC3)ccn2)C(=O)N(COC)[C@H]1CO] |
| 242 | 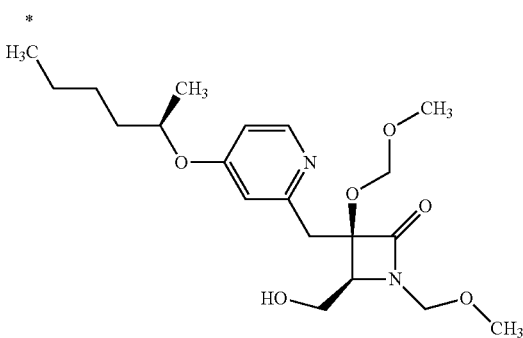 [SMILES: CCCC[C@@H](C)Oc1ccnc(C[C@]2(OCOC)C(=O)N(COC)[C@H]2CO)c1] |
| 243 | 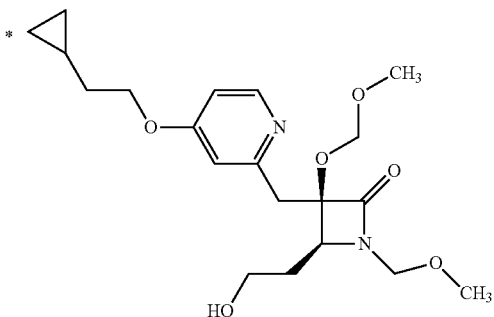 [SMILES: COCO[C@@]1(Cc2cc(OCCC3CC3)ccn2)C(=O)N(COC)[C@H]1CCO] |

TABLE 7-continued
| PEx | Str |
|---|---|
| 244 | 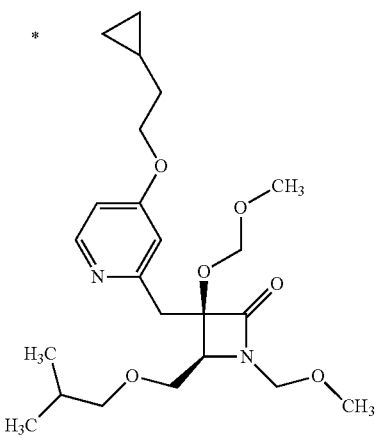 [SMILES: COCO[C@@]1(Cc2cc(OCCC3CC3)ccn2)C(=O)N(COC)[C@H]1COCC(C)C] |
| 245 | 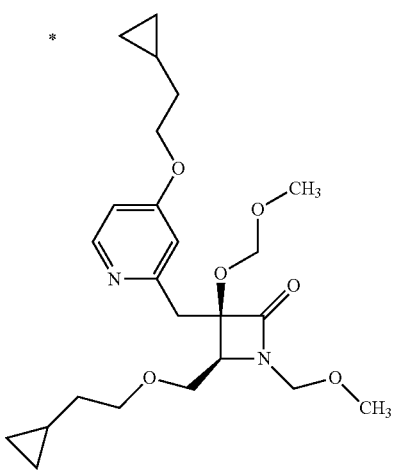 [SMILES: COCO[C@@]1(Cc2cc(OCCC3CC3)ccn2)C(=O)N(COC)[C@H]1COCCC1CC1] |
| 246 | 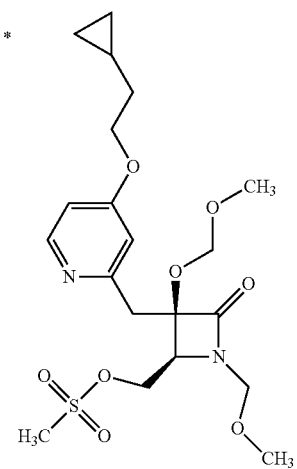 |

TABLE 7-continued
| PEx | Str |
|---|---|
| 247 | 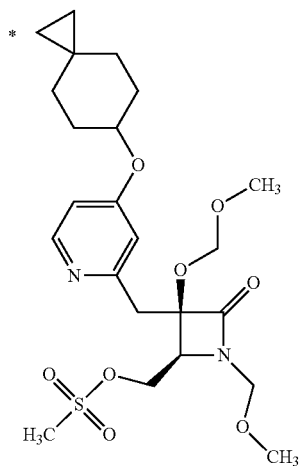 [SMILES: COCO[C@@]1(Cc2cc(OC3CCC4(CC3)CC4)ccn2)C(=O)N(COC)[C@H]1COS(C)(=O)=O] |
| 248 | 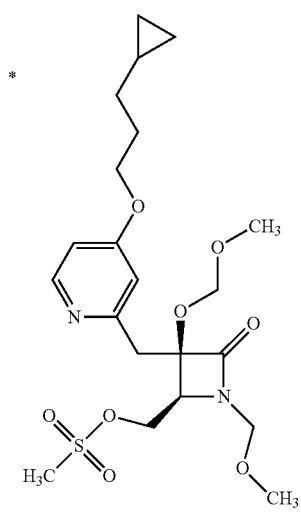 |
| 249 | 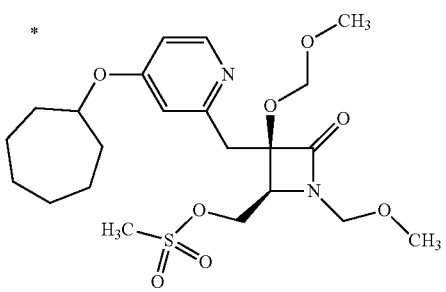 [SMILES: COCO[C@@]1(Cc2cc(OC3CCCCCC3)ccn2)C(=O)N(COC)[C@H]1COS(C)(=O)=O] |

TABLE 7-continued
| PEx | Str |
|---|---|
| 250 | 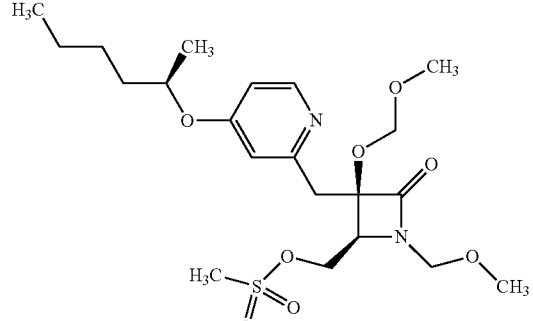 |
| 251 | 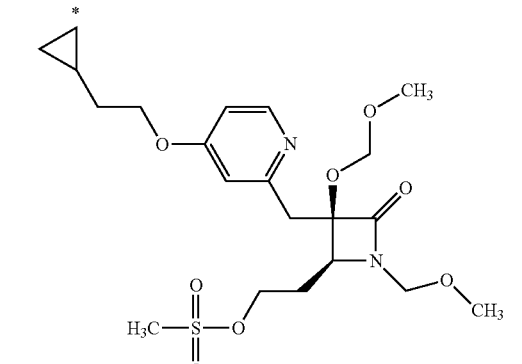 |
| 252 | 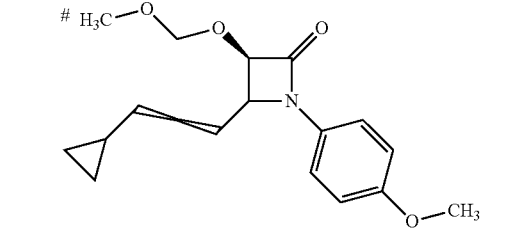 |
| 253 | 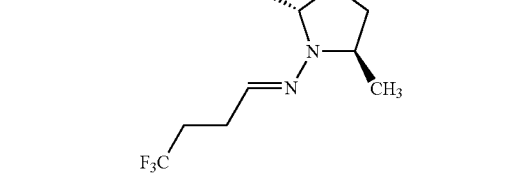 |
| 254 | 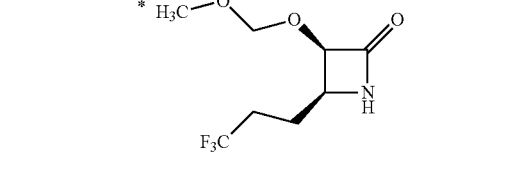 |
| 255 | 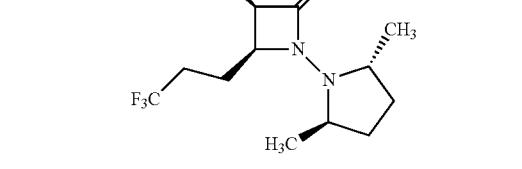 |

TABLE 7-continued

| PEx | Str |
|---|---|
| 256 | |
| 257 | |
| 258 | |
| 259 | |
| 260 | |

US 10,975,091 B2
235    236
TABLE 7-continued
| PEx | Str |
|---|---|
| 261 | 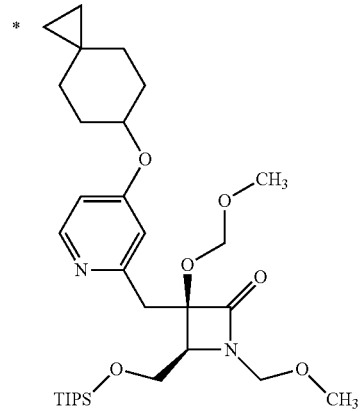 |
| 262 | 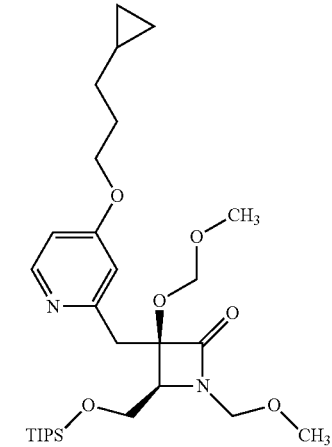 |
| 263 | 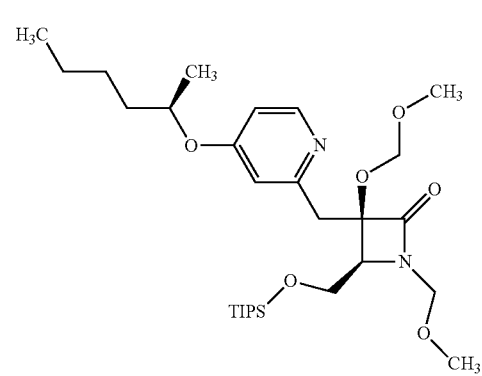 |

TABLE 7-continued
| PEx | Str |
|---|---|
| 264 | 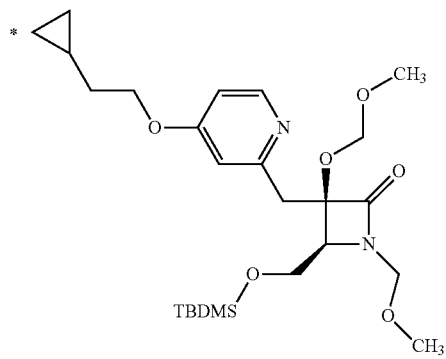 |
| 265 | 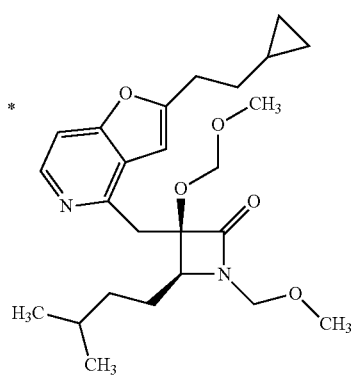 [SMILES: COCO[C@@]1(Cc2nccc3oc(CCC4CC4)cc23)C(=O)N(COC)[C@H]1CCC(C)C] |
| 266 | 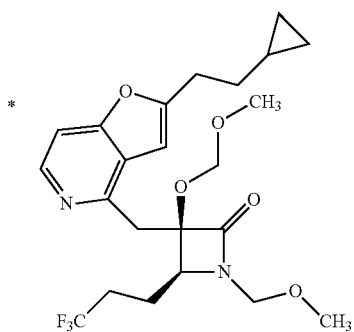 [SMILES: COCO[C@@]1(Cc2nccc3oc(CCC4CC4)cc23)C(=O)N(COC)[C@H]1CCC(F)(F)F] |
| 267 | 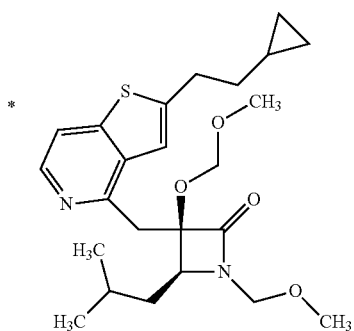 |
| 268 | 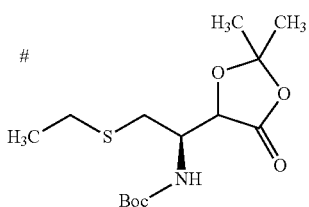 [SMILES: CCSC[C@H](NC(=O)OC(C)(C)C)C1OC(C)(C)OC1=O] |

TABLE 7-continued
| PEx | Str |
|---|---|
| 269 | 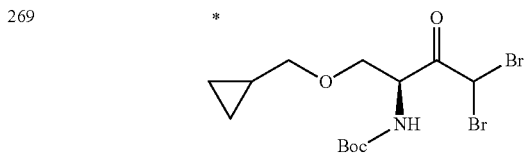 |
| 270 | 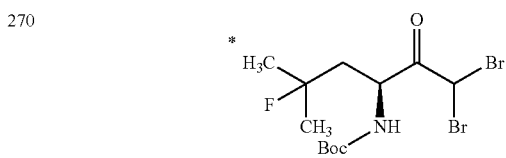 |
| 271 | 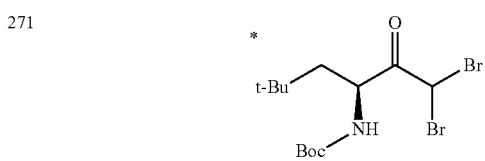 |
| 272 | 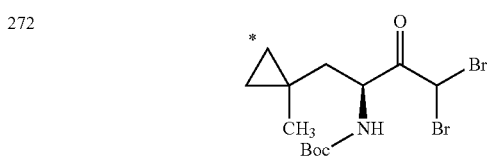 |
| 273 | 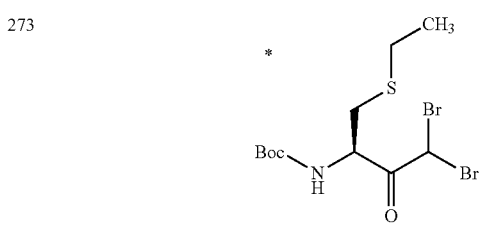 |
| 274 | 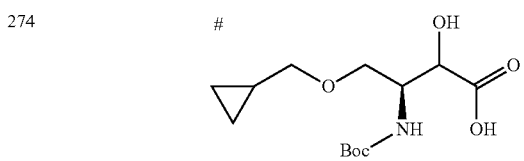 |
| 275 | 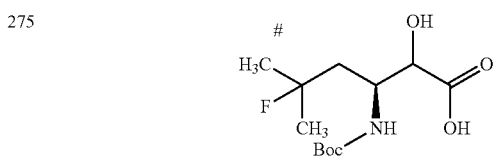 |
| 276 | 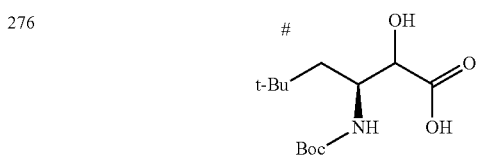 |
| 277 | 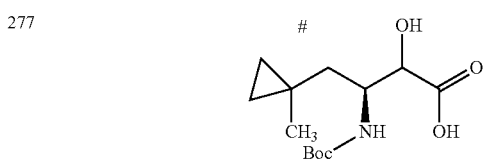 |

TABLE 7-continued
| PEx | Str |
|---|---|
| 278 | 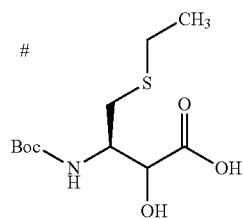 [SMILES: CCSC[C@H](NC(=O)OC(C)(C)C)C(O)C(=O)O] |
| 279 | 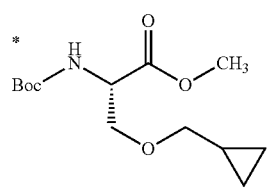 [SMILES: COC(=O)[C@H](COCC1CC1)NC(=O)OC(C)(C)C] |
| 280 | 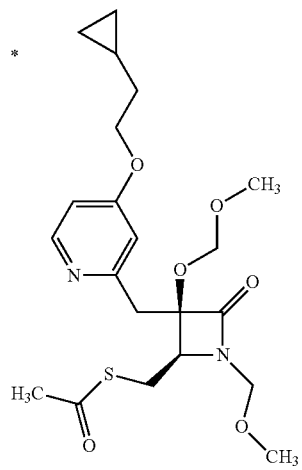 [SMILES: COCO[C@@]1(Cc2cc(OCCC3CC3)ccn2)C(=O)N(COC)[C@H]1CSC(C)=O] |
| 281 | 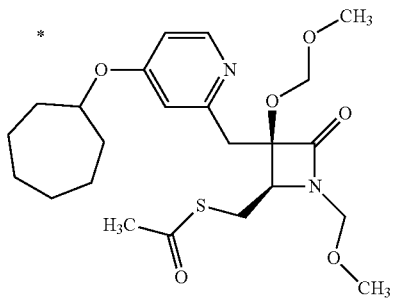 [SMILES: COCO[C@@]1(Cc2cc(OC3CCCCCC3)ccn2)C(=O)N(COC)[C@H]1CSC(C)=O] |

TABLE 7-continued
| PEx | Str |
|---|---|
| 282 | 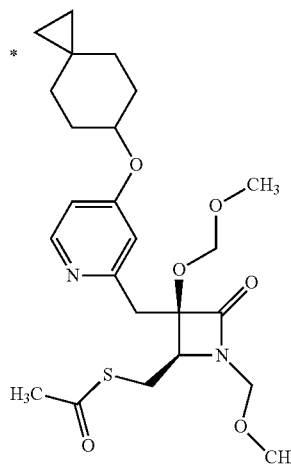 |
| 283 | 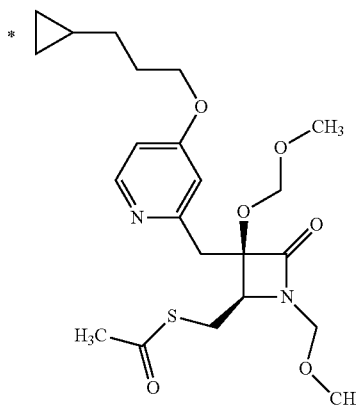 |
| 284 | 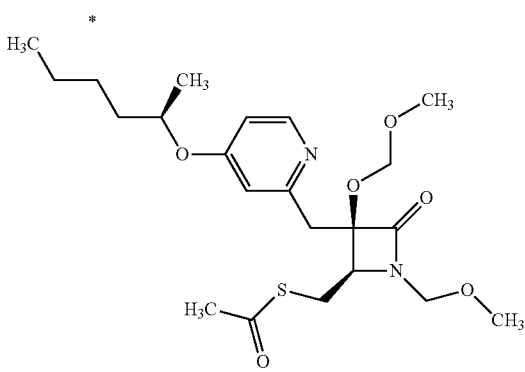 [SMILES: CCCC[C@@H](C)Oc1ccnc(C[C@]2(OCOC)C(=O)N(COC)[C@H]2CSC(C)=O)c1] |
| 285 | 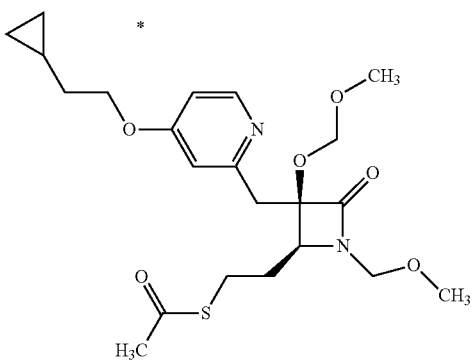 [SMILES: COCO[C@@]1(Cc2cc(OCCC3CC3)ccn2)C(=O)N(COC)[C@H]1CCSC(C)=O] |

TABLE 7-continued
| PEx | Str |
|---|---|
| 286 | 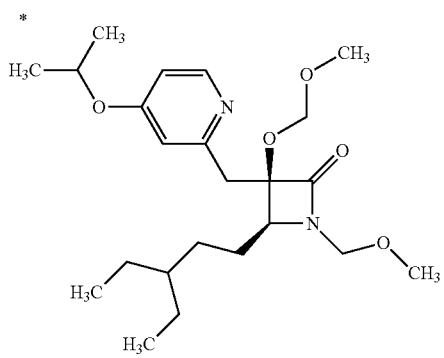 [SMILES: CCC(CC)CC[C@@H]1N(COC)C(=O)[C@]1(Cc1cc(OC(C)C)ccn1)OCOC] |
| 287 | 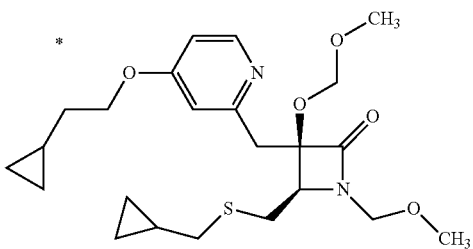 [SMILES: COCO[C@@]1(Cc2cc(OCCC3CC3)ccn2)C(=O)N(COC)[C@H]1CSCC1CC1] |
| 288 | 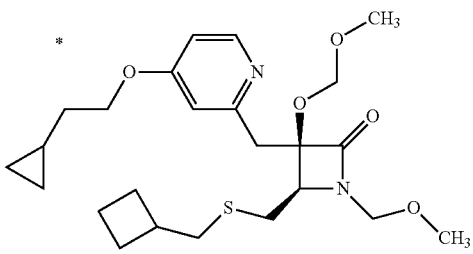 [SMILES: COCO[C@@]1(Cc2cc(OCCC3CC3)ccn2)C(=O)N(COC)[C@H]1CSCC1CCC1] |
| 289 | 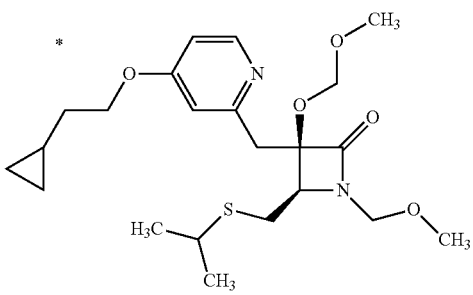 [SMILES: COCO[C@@]1(Cc2cc(OCCC3CC3)ccn2)C(=O)N(COC)[C@H]1CSC(C)C] |
| 290 | 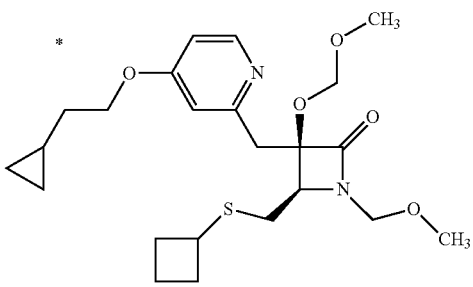 [SMILES: COCO[C@@]1(Cc2cc(OCCC3CC3)ccn2)C(=O)N(COC)[C@H]1CSC1CCC1] |

TABLE 7-continued
| PEx | Str |
|---|---|
| 291 | 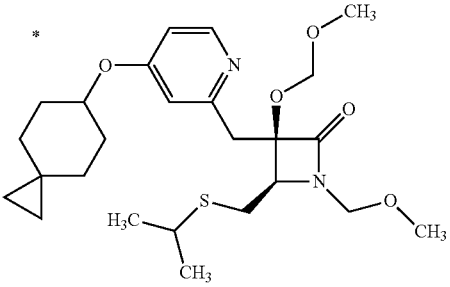 [SMILES: COCO[C@@]1(Cc2cc(OC3CCC4(CC3)CC4)ccn2)C(=O)N(COC)[C@H]1CSC(C)C] |
| 292 | 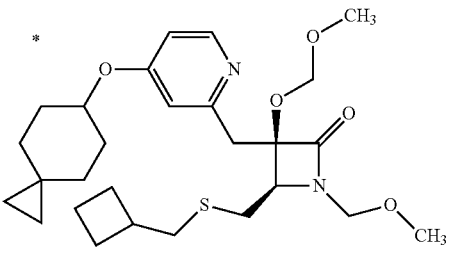 [SMILES: COCO[C@@]1(Cc2cc(OC3CCC4(CC3)CC4)ccn2)C(=O)N(COC)[C@H]1CSCC1CCC1] |
| 293 | 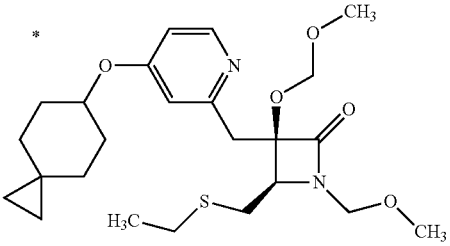 [SMILES: CCSC[C@@H]1N(COC)C(=O)[C@]1(Cc1cc(OC2CCC3(CC2)CC3)ccn1)OCOC] |
| 294 | 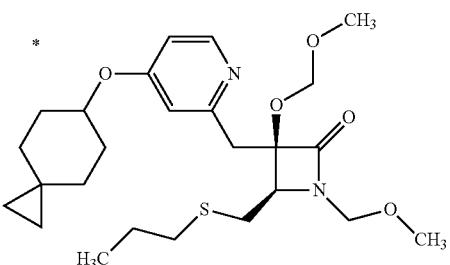 |
TABLE 8
| PEx | PSyn | DATA |
|---|---|---|
| 1 | — | ESI+: 435.2 |
| 2 | — | ESI+: 477.2 |
| 3 | — | ESI+: 254.2 [M + Na]+ |
| 4 | — | ESI+: 298.2 [M + Na]+ |
| 5 | — | ESI+: 429.1 |
| 6 | — | ESI+: 234.0, 236.0 |
| 7 | — | ESI+: 339.3 |
| 8 | — | ESI+: 551.1 |
| 9 | — | ESI+: 189.1 |
| 10 | — | ESI+: 194.1 |
| 11 | — | ESI+: 479.3 |
| 12 | — | ESI+: 464.4 |
| 13 | — | ESI+: 462.3 |
| 14 | — | ESI+: 230.1 |
| 15 | — | ESI+: 248.1, 250.1 |
| 16 | — | $^1$H NMR (400 MHz, CDCl$_3$) δ ppm: 3.89 (3 H, s), 4.56 (2 H, s), 4.60 (2 H, s), 4.73 (2 H, s), 6.75 (1 H, s), 7.27-7.40 (5 H, m), 8.41 (1 H, s) |
| 17 | — | ESI+: 422.3 |
| 18 | — | ESI+: 276.2, 278.2 |

TABLE 8-continued

| PEx | PSyn | DATA |
|---|---|---|
| 19 | — | ESI+: 244.0 |
| 20 | — | ESI+: 260.2 |
| 21 | — | ESI+: 324.3 [M + Na]+ |
| 22 | — | ESI+: 284.1, 286.1 |
| 23 | — | ESI+: 565.5 |
| 24 | — | ESI+: 505.4 |
| 25 | — | ESI+: 436.4 |
| 26 | — | ESI+: 287.1, 289.1 |
| 27 | — | ESI+: 258.1 |
| 28 | — | ESI+: 214.1 |
| 29 | — | ESI+: 298.2 |
| 30 | — | CI+: 266.1 |
| 31 | — | ESI+: 206.1 |
| 32 | — | ESI+: 384.3 [M + Na]+ |
| 33 | — | ESI+: 409.2 |
| 34 | — | ESI+: 479.3 |
| 35 | — | ESI+: 487.3 |
| 36 | — | ESI+: 519.2 |
| 37 | — | ESI+: 425.3 |
| 38 | — | CI+: 230.1 |
| 39 | — | ESI+: 318.2 |
| 40 | — | ESI+: 320.3 |
| 41 | — | ESI+: 197.1 |
| 42 | — | ESI+: 383.2, 385.2 |
| 43 | — | ESI+: 248.1 |
| 44 | — | ESI+: 204.0 |
| 45 | — | ESI+: 300.2 |
| 46 | — | ESI+: 487.4 |
| 47 | — | ESI+: 545.1 |
| 48 | — | ESI+: 485.4 |
| 49 | — | ESI+: 485.2 |
| 50 | — | ESI+: 449.3 |
| 51 | — | ESI+: 460.2 |
| 52 | — | ESI+: 356.1 [M + Na]+ |
| 53(1) | — | ESI+: 288.2 |
| 53(2) | — | ESI+: 288.2 |
| 54 | — | ESI+: 228.2 |
| 55 | — | ESI+: 543.5 |
| 56(1) | — | ESI+: 313.2 [M + Na]+ |
| 56(2) | — | ESI+: 313.2 [M + Na]+ |
| 57 | — | ESI+: 503.3 |
| 58 | — | ESI+: 157.0 |
| 59(1) | — | ESI+: 505.4 |
| 59(2) | — | ESI+: 505.4 |
| 60 | — | ESI+: 269.1 |
| 61 | — | ESI+: 345.2 |
| 62 | — | ESI+: 481.4 |
| 63 | — | ESI+: 372.2 [M + Na]+ |
| 64 | — | ESI+: 242.1 |
| 65 | — | ESI+: 437.4 |
| 66 | — | ESI+: 423.4 |
| 67 | — | ESI+: 213.1 |
| 68 | — | ESI+: 357.2, 359.2 |
| 69 | — | ESI+: 446.4 |
| 70 | — | ESI+: 353.3 |
| 71 | — | ESI+: 526.2 |
| 72 | — | ESI+: 443.4 |
| 73 | — | ESI+: 463.2 |
| 74 | — | CI+: 167.1 |
| 75 | — | ESI+: 188.1 |
| 76 | 5 | ESI+: 481.3 |
| 77 | 1 | ESI+: 443.3 |
| 78 | 1 | ESI+: 459.3 |
| 79 | 1 | ESI+: 411.2 |
| 80 | 1 | ESI+: 497.1 |
| 81 | 1 | ESI+: 423.2 |
| 82 | 1 | ESI+: 447.2 |
| 83 | 1 | ESI+: 421.3 |
| 84 | 1 | ESI+: 421.4 |
| 85 | 2 | ESI+: 449.4 |
| 86 | 2 | ESI+: 551.4 |
| 87 | 3 | ESI+: 246.1 |
| 88 | 4 | ESI+: 278.1 |
| 89 | 4 | ESI+: 330.0, 332.0 |
| 90 | 5 | ESI+: 367.2 |
| 91 | 5 | ESI+: 421.3 |
| 92 | 5 | ESI+: 556.3 |
| 93 | 5 | ESI+: 467.3 |

TABLE 8-continued

| PEx | PSyn | DATA |
|---|---|---|
| 94 | 5 | ESI+: 435.3 |
| 95 | 5 | ESI+: 457.4 |
| 96 | 5 | ESI+: 519.1, 521.1 |
| 97 | 5 | ESI+: 473.4 |
| 98 | 5 | ESI+: 471.2 |
| 99 | 5 | ESI+: 435.2 |
| 100 | 5 | ESI+: 461.2 |
| 101 | 5 | ESI+: 419.2 |
| 102 | 5 | ESI+: 433.3 |
| 103 | 5 | ESI+: 431.2, 433.2 |
| 104 | 5 | ESI+: 455.2 |
| 105 | 5 | ESI+: 473.4 |
| 106 | 5 | ESI+: 443.3 |
| 107 | 5 | ESI+: 559.2 |
| 108 | 5 | ESI+: 551.4 |
| 109 | 5 | ESI+: 479.4 |
| 110 | 5 | ESI+: 381.3 |
| 111 | 5 | ESI+: 465.3 |
| 112 | 5 | ESI+: 449.3 |
| 113 | 5 | ESI+: 433.3 |
| 114 | 6 | ESI+: 226.1, 228.1 |
| 115 | 6 | ESI+: 361.2, 363.2 |
| 116 | 6 | ESI+: 240.2, 242.2 |
| 117 | 6 | ESI+: 262.2, 264.1 |
| 118 | 6 | ESI+: 278.2, 280.2 |
| 119 | 6 | ESI+: 224.1, 226.1 |
| 120 | 6 | ESI+: 238.0, 240.0 |
| 121 | 6 | ESI+: 260.0, 262.0 |
| 122 | 6 | ESI+: 278.1, 280.1 |
| 123 | 6 | ESI+: 240.0, 242.0 |
| 124 | 6 | ESI+: 284.2, 286.2 |
| 125 | 6 | ESI+: 212.0, 214.0 |
| 126 | 6 | ESI+: 278.2, 280.2 |
| 127 | 7 | ESI+: 158.0 |
| 128 | 7 | ESI+: 469.2 |
| 129 | 8 | ESI+: 549.3, 551.3 |
| 130 | 8 | ESI+: 515.4 |
| 131 | 8 | ESI+: 519.2 |
| 132 | 9 | ESI+: 338.2 |
| 133 | 9 | ESI+: 239.1 |
| 134 | 9 | ESI+: 255.1 |
| 135 | 9 | ESI+: 201.1 |
| 136 | 9 | ESI+: 215.1 |
| 137 | 9 | ESI+: 217.2 |
| 138 | 9 | ESI+: 261.1 |
| 139 | 10 | ESI+: 343.2 |
| 140 | 10 | ESI+: 244.0 |
| 141 | 10 | ESI+: 260.1 |
| 142 | 10 | ESI+: 206.0 |
| 143 | 10 | ESI+: 220.1 |
| 144 | 10 | ESI+: 222.1 |
| 145 | 10 | ESI+: 266.1 |
| 146 | 10 | ESI+: 233.2 |
| 147 | 10 | ESI+: 218.1 |
| 148 | 14 | ESI+: 258.1 |
| 149 | 21 | ESI+: 324.2 [M + Na]+ |
| 150 | 23 | ESI+: 537.3 |
| 151 | 24 | ESI+: 501.4 |
| 152 | 26 | APCI/ESI+: 355.1, 357.1 |
| 153 | 27 | ESI+: 340.2 |
| 154 | 27 | ESI+: 338.2 |
| 155 | 27 | ESI+: 272.1 |
| 156 | 27 | ESI+: 272.3 |
| 157 | 28 | ESI+: 234.1 |
| 158 | 28 | ESI+: 232.2 |
| 159 | 29 | ESI+: 258.1 [M + Na]+ |
| 160 | 30 | ESI+: 204.1 |
| 161 | 33 | ESI+: 395.1 |
| 162 | 33 | ESI+: 395.1 |
| 163 | 33 | ESI+: 381.2 |
| 164 | 33 | ESI+: 423.3 |
| 165 | 34 | ESI+: 491.3 |
| 166 | 34 | ESI+: 477.4 |
| 167 | 34 | ESI+: 463.2 |
| 168 | 34 | ESI+: 463.4 |
| 169 | 36 | EI: 209.8 |
| 170 | 39 | ESI+: 272.2 |
| 171 | 40 | ESI+: 276.3 |

TABLE 8-continued

| PEx | PSyn | DATA |
|---|---|---|
| 172 | 40 | ESI+: 274.3 |
| 173 | 41 | ESI+: 223.2 |
| 174 | 41 | ESI+: 281.1, 283.1 |
| 175 | 41 | ESI+: 223.1 |
| 176 | 42 | ESI+: 325.3 |
| 177 | 42 | ESI+: 325.2 |
| 178 | 43 | ESI+: 286.0, 288.0 |
| 179 | 43 | ESI+: 228.1 |
| 180 | 43 | ESI+: 228.1 |
| 181 | 45 | ESI+: 486.3 |
| 182 | 45 | ESI+: 526.3 |
| 183 | 45 | ESI+: 504.2 |
| 184 | 46 | ESI+: 487.2 |
| 185 | 46 | ESI+: 489.3 |
| 186 | 46 | $^1$H NMR (400 MHz, CDCl$_3$) δ ppm: 0.93 (3 H, d, J = 6.3 Hz), 1.01-1.17 (2 H, m), 1.38-1.49 (3 H, m), 1.73-1.87 (2 H, m), 2.06-2.14 (2 H, m), 3.11 (3 H, s), 3.28-3.32 (2 H, m), 3.38 (3 H, s), 4.15-4.26 (2 H, m), 4.36-4.60 (4 H, m), 5.00 (1 H, d, J = 6.7 Hz), 5.14 (1 H, d, J = 6.7 Hz), 6.19 (1 H, t, J = 2.1 Hz), 6.62 (1 H, dd, J = 5.9, 2.2 Hz), 6.70 (1 H, d, J = 2.2 Hz), 7.40 (1 H, d, J = 2.1 Hz), 7.47-7.50 (1 H, m), 8.25 (1 H, d, J = 5.9 Hz) |
| 187 | 53 | ESI+: 237.1, 239.1 |
| 188 | 62 | ESI+: 517.3 |
| 189 | 62 | ESI+: 518.4 |
| 190 | 62 | ESI+: 595.4 |
| 191 | 65 | ESI+: 435.4 |
| 192 | 65 | ESI+: 437.4 |
| 193 | 65 | ESI+: 537.4 |
| 194 | 68 | APCI/ESI+: 425.1, 427.1 |
| 195(1) | — | ESI+: 272.1 |
| 195(2) | — | ESI+: 302.1 |
| 196 | — | ESI+: 525.3 |
| 197 | — | ESI+: 450.0, 451.9, 454.0 [M + Na]$^+$ |
| 198 | — | ESI−: 302.1 [M − H]$^−$ |
| 199 | — | ESI+: 314.0 [M + Na]$^+$ |
| 200 | — | ESI+: 328.2 [M + Na]$^+$ |
| 201 | — | ESI+: 294.1 [M + Na]$^+$ |
| 202 | — | ESI+: 288.1 |
| 203 | — | ESI+: 539.4 |
| 204 | — | ESI+: 555.3 |
| 205 | — | ESI+: 467.1 |
| 206 | — | ESI+: 453.3 |
| 207 | — | ESI+: 229.1 |
| 208 | — | ESI+: 399.0, 401.0 |
| 209 | — | ESI+: 278.1 |
| 210 | — | ESI+: 306.2 |
| 211 | — | ESI+: 264.0 |
| 212 | — | ESI+: 300.1 [M + Na]$^+$ |
| 213 | — | ESI+: 272.0 [M + Na]$^+$ |
| 214 | 5 | ESI+: 477.2 |
| 215 | 7 | ESI+: 281.1 |
| 216 | 9 | ESI+: 205.1 |
| 217 | 9 | ESI+: 203.1 |
| 218 | 9 | ESI+: 229.2 |
| 219 | 10 | ESI+: 210.1 |
| 220 | 10 | ESI+: 208.1 |
| 221 | 10 | ESI+: 234.1 |
| 222 | 10 | ESI+: 234.0 |
| 223 | 21 | ESI+: 330.1 |
| 224 | 21 | ESI+: 366.2 [M + Na]$^+$ |
| 225 | 21 | ESI+: 342.1 [M + Na]$^+$ |
| 226 | 21 | ESI+: 338.1 [M + Na]$^+$ |
| 227 | 21 | ESI+: 336.1 [M + Na]$^+$ |
| 228 | 24 | ESI+: 521.3 |
| 229 | 24 | ESI+: 547.3 |
| 230 | 24 | ESI+: 559.3 |
| 231 | 24 | ESI+: 517.4 |
| 232 | 24 | ESI+: 519.4 |
| 233 | 24 | ESI+: 523.3 |
| 234 | 24 | ESI+: 523.4 |
| 235 | 27 | ESI+: 325.2 |
| 236 | 27 | ESI+: 244.2 |
| 237 | 28 | ESI+: 200.1 |
| 238 | 33 | ESI+: 425.3 |
| 239 | 33 | ESI+: 421.3 |
| 240 | 33 | ESI+: 395.3 |
| 241 | 33 | ESI+: 409.3 |
| 242 | 33 | ESI+: 397.4 |

TABLE 8-continued

| PEx | PSyn | DATA |
|---|---|---|
| 243 | 33 | ESI+: 395.2 |
| 244 | 34 | ESI+: 437.3 |
| 245 | 34 | ESI+: 449.3 |
| 246 | 35 | ESI+: 459.2 |
| 247 | 35 | ESI+: 499.2 |
| 248 | 35 | ESI+: 473.2 |
| 249 | 35 | ESI+: 487.4 |
| 250 | 35 | ESI+: 475.1 |
| 251 | 35 | ESI+: 473.1 |
| 252 | 39 | ESI+: 304.1 |
| 253 | 41 | ESI+: 223.1 |
| 254 | 43 | ESI+: 228.1 |
| 255 | 61 | ESI+: 371.2 |
| 256 | 65 | ESI+: 493.3 |
| 257 | 66 | ESI+: 521.3 |
| 258 | 66 | ESI+: 521.3 |
| 259 | 68 | ESI+: 427.2 |
| 260 | 5 | ESI+: 565.5 |
| 261 | 69 | ESI+: 577.4 |
| 262 | 69 | ESI+: 551.4 |
| 263 | 69 | ESI+: 553.4 |
| 264 | 69 | ESI+: 509.3 |
| 265 | 69 | ESI+: 445.4 |
| 266 | 69 | ESI+: 471.3 |
| 267 | 69 | ESI+: 447.3 |
| 268 | 21 | ESI+: 342.1 [M + Na]+ |
| 269 | 197 | ESI+: 436.0, 438.0, 440.0 [M + Na]+ |
| 270 | 197 | ESI+: 426.0, 428.0, 430.0 [M + Na]+ |
| 271 | 197 | ESI−: 397.9, 399.9, 401.9 [M − H]− |
| 272 | 197 | ESI+: 419.9, 421.9, 423.9 [M + Na]+ |
| 273 | 197 | ESI+: 425.9, 427.9, 429.9 [M + Na]+ |
| 274 | 198 | ESI+: 290.1 |
| 275 | 198 | ESI+: 302.1 [M + Na]+ |
| 276 | 198 | ESI+: 298.2 [M + Na]+ |
| 277 | 198 | ESI+: 296.2 [M + Na]+ |
| 278 | 198 | ESI−: 278.0 [M − H]− |
| 279 | 202 | ESI+: 296.2 [M + Na]+ |
| 280 | 205 | ESI+: 439.2 |
| 281 | 205 | ESI+: 467.3 |
| 282 | 205 | ESI+: 479.3 |
| 283 | 205 | ESI+: 453.3 |
| 284 | 205 | ESI+: 455.3 |
| 285 | 205 | ESI+: 453.1 |
| 286 | 5 | ESI+: 423.2 |
| 287 | 212 | ESI+: 451.2 |
| 288 | 212 | ESI+: 465.3 |
| 289 | 212 | ESI+: 439.3 |
| 290 | 212 | ESI+: 451.2 |
| 291 | 212 | ESI+: 479.3 |
| 292 | 212 | ESI+: 505.4 |
| 293 | 212 | ESI+: 465.3 |
| 294 | 212 | ESI+: 479.3 |

TABLE 9

| REx | Str | DATA |
|---|---|---|
| 1 | 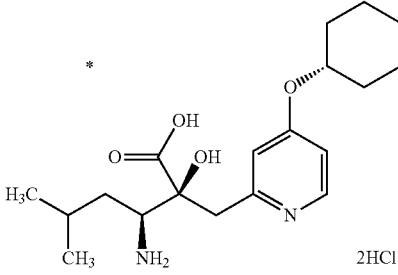 2HCl | ESI+: 365.2 |
| 2 | 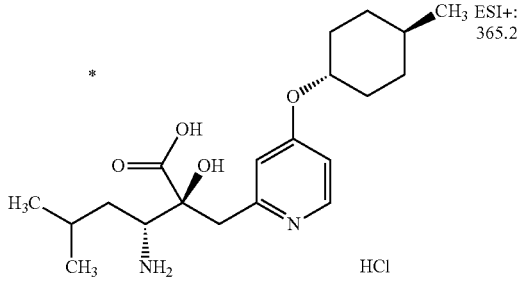 HCl | ESI+: 365.2 |

INDUSTRIAL APPLICABILITY

The compound represented by Formula (I) or a salt thereof has inhibitory activity against P-LAP, i.e. the AVP-metabolizing enzyme, and maintains and/or increases an endogenous AVP level to reduce urine production. Such a compound thus is expected to be used as an agent for treating nocturia, and is also expected to be used as an agent for treating any other voiding dysfunction or polyuria associated with a decreased AVP level, such as pollakiuria, urinary incontinence, and nocturnal enuresis.

The invention claimed is:

1. A method of treating nocturia comprising administering to a subject an effective amount of a compound represented by Formula (I) or a salt thereof:

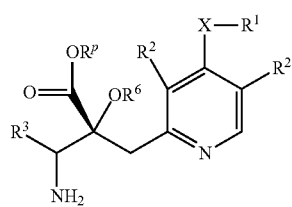

(I)

wherein, X is O, S or $NR^4$;

$R^4$ is H, lower alkyl which optionally has one to five substituents selected from the Group $G^1$, $C_{3-12}$ cycloalkyl which optionally has one to five substituents selected from the Group $G^2$, -(lower alkylene)-($C_{3-12}$ cycloalkyl which optionally has one to five substituents selected from the Group $G^2$), —C(O)-(lower alkyl which optionally has one to five substituents selected from the Group $G^1$), —C(O)—($C_{3-12}$ cycloalkyl which optionally has one to five substituents selected from the Group $G^2$), or —C(O)-(lower alkylene)-($C_{3-12}$ cycloalkyl which optionally has one to five substituents selected from the Group $G^2$), or $R^4$ forms together with neighboring —$NR^1$, as —$NR^1R^4$, a 4- to 8-membered nitrogen-containing saturated heterocyclic group, wherein the nitrogen-containing saturated heterocyclic group may be condensed with a benzene ring and optionally has one to five substituents selected from the Group $G^4$;

$R^1$ is H, $C_{1-10}$ alkyl which optionally has one to five substituents selected from the Group $G^1$, -(lower alkylene)-$X^{11}$-(lower alkyl which optionally has one to five substituents selected from the Group $G^1$), $R^{11}$, -(lower alkylene)-$R^{11}$, -(lower alkylene)-$X^{11}$—$R^{11}$, or -(lower alkylene)-$X^{11}$-(lower alkylene)-$R^{11}$;

$R^2$'s are the same or different from each other, and are H, lower alkyl which optionally has one to five substituents selected from the Group $G^1$, halogen, OH, SH, —O-(lower alkyl), —O-(lower alkylene)-aryl, —O-aryl, —S-(lower alkyl), —S-(lower alkylene)-aryl, —S-aryl, —O-(lower halogenoalkyl), —C(O)-(lower alkyl), —S(O)$_2$-(lower alkyl), —S(O)-(lower alkyl), $NO_2$, —$NH_2$, —NH-(lower alkyl), —N(lower alkyl)$_2$, —NH-aryl, —N(lower alkyl)-aryl, —C(O)OH, —C(O)O-(lower alkyl), —CHO, —C(O)$NH_2$, —C(O)NH-(lower alkyl), —C(O)N(lower alkyl)$_2$, CN, -(lower alkylene)-$X^{21}$-(lower alkyl which optionally has one to five substituents selected from the Group $G^1$), $C_{3-12}$ cycloalkyl which optionally has one to five substituents selected from the Group $G^2$, $C_{3-12}$ cycloalkenyl which optionally has one to five substituents selected from the Group $G^2$ and which may be condensed with a benzene ring optionally having one to four substituents selected from the Group $G^3$, aryl which optionally has one to five substituents selected from the Group $G^5$, -(lower alkylene)-$R^{21}$, -(lower alkylene)-$X^{21}$—$R^{21}$, or -(lower alkylene)-$X^{21}$-(lower alkylene)-$R^{21}$;

$R^3$ is $R^{32}$, -(lower alkylene)-$X^{31}$—$R^{32}$, -(lower alkenylene)-$X^{31}$—$R^{32}$, $R^{31}$, -(lower alkylene)-$R^{31}$, -(lower alkylene)-$X^{31}$—$R^{31}$, -(lower alkylene)-$X^{31}$-(lower alkylene)-$R^{31}$, -(lower alkenylene)-$R^{31}$, -(lower alkynylene)-$R^{31}$ or —CH=(saturated monocyclic heterocycle);

$X^{11}$, $X^{21}$ and $X^{31}$ are the same or different from each other, and are O or S(O), wherein n is 0, 1, or 2;

$R^{11}$, $R^{21}$, and $R^{31}$ are the same or different from each other, and are $C_{3-12}$ cycloalkyl which optionally has one to five substituents selected from the Group $G^2$, $C_{3-12}$ cycloalkenyl which optionally has one to five substituents selected from the Group $G^2$ and which may be condensed with a benzene ring optionally having one to four substituents selected from the Group $G^3$, aryl which optionally has one to five substituents selected from the Group $G^5$, or mono- or bi-cyclic heterocyclic group which optionally has one to five substituents selected from the Group $G^5$;

$R^{32}$ is $C_{1-10}$ alkyl which optionally has one to five substituents selected from the Group $G^1$, lower alkenyl which optionally has one to five substituents selected from the Group $G^1$, or lower alkynyl which optionally has one to five substituents selected from the Group $G^1$;

$R^P$ is H or an ester group and $R^6$ is H; or $R^P$ and $R^6$ are linked to each other to form, together with —O—C(=O)—C—O— to which they are attached, 2,2-di(lower alkyl)-4-oxo-1,3-dioxolane-5,5-diyl;

if $R^3$ is $C_{1-10}$ alkyl which is optionally substituted by one to five halogens, —X—$R^1$ is optionally linked to any one of $R^2$'s attached to a pyridine ring to which —X—$R^1$ is also attached, to constitute a group represented by any one of formulae —$X^b$—$(CH_2)_m$—Y—, —$X^b$—CH=CH—, —$X^b$—CH=N—, and —$X^b$—N=CH—, and form a heterocycle condensed with the pyridine ring, wherein m is an integer of 1 to 3, $X^b$ is O, S or NH, Y is $CH_2$, O, S or NH, and the heterocycle optionally has one to four substituents selected from the group consisting of: $C_{3-12}$ cycloalkyl which optionally has one to five substituents selected from the Group $G^2$; -(lower alkylene)-($C_{3-12}$ cycloalkyl which optionally has one to five substituents selected from the Group $G^2$); and the substituents defined in the Group $G^3$; in replacement of one or more H atoms attached to the ring atom(s) of the heterocycle;

—X—$R^1$ is optionally linked to $R^3$ to form a group represented by formula —X—($C_{5-15}$ carbon chain)-, wherein the $C_{5-15}$ carbon chain optionally has one to two O or S atoms in replacement of C atom(s), optionally has one to five unsaturated bonds, and optionally has one to five substituents selected from the Group $G^4$;

Group $G^1$ consists of halogen, OH, SH, —O-(lower alkyl), —O-(lower alkylene)-aryl, —O-aryl, —S-(lower alkyl), —S-(lower alkylene)-aryl, —S-aryl, —O-(lower halogenoalkyl), —C(O)-(lower alkyl), —C(O)-aryl, —S(O)$_2$-(lower alkyl), —S(O)-(lower alkyl), $NO_2$, —$NH_2$, —NH-(lower alkyl), —N(lower alkyl)$_2$, —NH-aryl, —N(lower alkyl)-aryl, —C(O)OH, —C(O)O-(lower alkyl), —CHO, —C(O)NH$_2$, —C(O)NH-(lower alkyl), —C(O)N(lower alkyl)$_2$, —C(O)NH-aryl, and CN;

Groups G$^2$ and G$^4$ consist of the substituents in the Group G$^1$, lower alkyl which optionally has one to five substituents selected from the Group G$^1$, —O—(C$_{2-3}$ alkylene)-O—, and —O—(C$_{3-4}$ alkylene)-;

Group G$^3$ consists of the substituents in the Group G$^1$ and lower alkyl which optionally has one to five substituents selected from the Group G$^1$; and Group G$^5$ consists of: i) the substituents in the Group G$^1$; ii) lower alkyl, lower alkenyl and lower alkynyl, each of which optionally has one to five substituents selected from the Group G$^1$; iii) -(lower alkylene)-O-(lower alkyl, lower alkenyl or lower alkynyl, which optionally has one to five substituents selected from the Group G$^1$); iv) C$_{3-12}$ cycloalkyl, and C$_{3-12}$ cycloalkenyl which may be condensed with a benzene ring optionally having one to four substituents selected from the Group G$^3$, the C$_{3-12}$ cycloalkyl and the C$_{3-12}$ cycloalkenyl optionally have one to five substituents selected from the Group G$^2$; v) aryl which optionally has one to five substituents selected from the Group G$^3$; vi) mono- or bi-cyclic heterocyclic group which optionally has one to five substituents selected from the Group G$^3$; vii) -(lower alkylene)-R$^G$; viii) -(lower alkylene)-O—R$^G$; ix) —C(O)—R$^G$; x) —C(O)—O—R$^G$; xi) —C(O)—O-(lower alkylene)-R$^G$; and xii) —S(O)$_2$—R$^G$, wherein R$^G$'s are the same or different from each other, and are C$_{3-12}$ cycloalkyl which optionally has one to five substituents selected from the Group G$^2$, C$_{3-12}$ cycloalkenyl which optionally has one to five substituents selected from the Group G$^2$ and which may be condensed with a benzene ring optionally having one to four substituents selected from the Group G$^3$, aryl which optionally has one to five substituents selected from the Group G$^3$, or a mono- or bi-cyclic heterocyclic group which optionally has one to five substituents selected from the Group G$^3$.

\* \* \* \* \*